(12) United States Patent
Liu et al.

(10) Patent No.: US 11,957,342 B2
(45) Date of Patent: Apr. 16, 2024

(54) DEVICES, SYSTEMS, AND METHODS FOR DETECTING TISSUE AND FOREIGN OBJECTS DURING A SURGICAL OPERATION

(71) Applicant: Cilag GmbH International, Zug (CH)

(72) Inventors: Zhijun Liu, Mason, OH (US); Christopher J. Waid, Cincinnati, OH (US); Patrick L. Creamer, New Orleans, LA (US); Morgan R. Hunter, Cincinnati, OH (US); Nathan P. K. Nguyen, Austin, TX (US); Kevin D. Felder, Cincinnati, OH (US); James M. McKale, Cincinnati, OH (US); Jeffrey S. Swayze, West Chester, OH (US); Simon L. Calcutt, London (GB); Elisa J. Barber, Bury St. Edmunds (GB); Matthew K. Sadler, Mildenhall (GB); Richard D. Lintern, Cambridge (GB); James Richardson, Cambridge (GB); Rita Stella, Cambridge (GB); Mikhail E. Bashtanov, Cambridge (GB)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/965,336

(22) Filed: Oct. 13, 2022

(65) Prior Publication Data
US 2023/0172604 A1 Jun. 8, 2023

Related U.S. Application Data

(60) Provisional application No. 63/330,502, filed on Apr. 13, 2022, provisional application No. 63/274,207, filed on Nov. 1, 2021.

(51) Int. Cl.
*A61B 17/072* (2006.01)
*A61B 34/30* (2016.01)
(Continued)

(52) U.S. Cl.
CPC ...... *A61B 17/072* (2013.01); *A61B 17/07207* (2013.01); *A61B 34/30* (2016.02);
(Continued)

(58) Field of Classification Search
CPC .......... A61B 17/068; A61B 17/072; A61B 17/07207; A61B 17/115;
(Continued)

(56) References Cited

U.S. PATENT DOCUMENTS 2,366,274 A  1/1945  Luth et al.
2,458,152 A  1/1949  Eakins
(Continued)

FOREIGN PATENT DOCUMENTS

CN  1634601 A  7/2005
CN  1922563 A  2/2007
(Continued)

OTHER PUBLICATIONS

Henriques. F.C., "Studies in thermal injury V. The predictability and the significance of thermally induced rate processes leading to irreversible epidermal injury." Archives of Pathology, 434, pp. 489-502 (1947).
(Continued)

*Primary Examiner* — Scott A Smith
(74) *Attorney, Agent, or Firm* — Frost Brown Todd LLP

(57) ABSTRACT

A surgical instrument is disclosed herein. The surgical instrument can include an end effector that includes jaws configured to transition between an opened condition and a closed condition, a plurality of electrodes positioned within the jaws of the end effector, a control circuit, and a memory configured to store an algorithm configured to cause the control circuit to determine an impedance signal based on signals received from the plurality of electrodes, detect a media positioned between the jaws of the end effector based
(Continued)

on the determined impedance signal, determine a position of the detected media based on the received signals, and generate an alert associated with the detected media and the determined position.

20 Claims, 54 Drawing Sheets

(51) Int. Cl.
*A61B 17/00* (2006.01)
*A61B 17/068* (2006.01)
*A61B 17/115* (2006.01)

(52) U.S. Cl.
CPC .............. *A61B 2017/00026* (2013.01); *A61B 2017/00119* (2013.01); *A61B 17/068* (2013.01); *A61B 2017/07214* (2013.01); *A61B 2017/07271* (2013.01); *A61B 17/115* (2013.01)

(58) Field of Classification Search
CPC ........... A61B 2017/00022; A61B 2017/07214; A61B 2017/07271; A61B 2017/00221; A61B 2017/00026; A61B 34/30; A61B 34/71
USPC .............. 227/19, 175.1, 175.2, 176.1, 180.1; 606/1, 139, 219
See application file for complete search history.

(56) References Cited

U.S. PATENT DOCUMENTS

| | | |
|---|---|---|
| 2,510,693 A | 6/1950 | Green |
| 2,736,960 A | 3/1956 | Armstrong |
| 2,849,788 A | 9/1958 | Creek |
| 2,867,039 A | 1/1959 | Zach |
| 3,015,961 A | 1/1962 | Roney |
| 3,043,309 A | 7/1962 | McCarthy |
| 3,166,971 A | 1/1965 | Stoecker |
| 3,358,676 A | 12/1967 | Frei et al. |
| 3,525,912 A | 8/1970 | Wallin |
| 3,526,219 A | 9/1970 | Balamuth |
| 3,580,841 A | 5/1971 | Cadotte et al. |
| 3,614,484 A | 10/1971 | Shoh |
| 3,636,943 A | 1/1972 | Balamuth |
| 3,703,651 A | 11/1972 | Blowers |
| 3,710,399 A | 1/1973 | Hurst |
| 3,776,238 A | 12/1973 | Peyman et al. |
| 3,777,760 A | 12/1973 | Essner |
| 3,805,787 A | 4/1974 | Banko |
| 3,862,630 A | 1/1975 | Balamuth |
| 3,900,823 A | 8/1975 | Sokal et al. |
| 3,906,217 A | 9/1975 | Lackore |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 3,988,535 A | 10/1976 | Hickman et al. |
| 4,005,714 A | 2/1977 | Hiltebrandt |
| 4,034,762 A | 7/1977 | Cosens et al. |
| 4,047,136 A | 9/1977 | Satto |
| 4,058,126 A | 11/1977 | Leveen |
| 4,063,561 A | 12/1977 | McKenna |
| 4,099,192 A | 7/1978 | Aizawa et al. |
| 4,156,187 A | 5/1979 | Murry et al. |
| 4,188,927 A | 2/1980 | Harris |
| 4,200,106 A | 4/1980 | Douvas et al. |
| 4,203,430 A | 5/1980 | Takahashi |
| 4,220,154 A | 9/1980 | Semm |
| 4,237,441 A | 12/1980 | van Konynenburg et al. |
| 4,278,077 A | 7/1981 | Mizumoto |
| 4,281,785 A | 8/1981 | Brooks |
| 4,304,987 A | 12/1981 | van Konynenburg |
| 4,314,559 A | 2/1982 | Allen |
| 4,384,584 A | 5/1983 | Chen |
| 4,445,063 A | 4/1984 | Smith |
| 4,463,759 A | 8/1984 | Garito et al. |
| 4,491,132 A | 1/1985 | Aikins |
| 4,492,231 A | 1/1985 | Auth |
| 4,535,773 A | 8/1985 | Yoon |
| 4,545,926 A | 10/1985 | Fouts, Jr. et al. |
| 4,550,870 A | 11/1985 | Krumme et al. |
| 4,582,236 A | 4/1986 | Hirose |
| 4,585,282 A | 4/1986 | Bosley |
| 4,597,390 A | 7/1986 | Mulhollan et al. |
| 4,617,927 A | 10/1986 | Manes |
| 4,633,874 A | 1/1987 | Chow et al. |
| 4,634,420 A | 1/1987 | Spinosa et al. |
| 4,640,279 A | 2/1987 | Beard |
| 4,655,746 A | 4/1987 | Daniels et al. |
| 4,671,287 A | 6/1987 | Fiddian-Green |
| 4,708,127 A | 11/1987 | Abdelghani |
| 4,735,603 A | 4/1988 | Goodson et al. |
| 4,761,871 A | 8/1988 | O'Connor et al. |
| 4,777,951 A | 10/1988 | Cribier et al. |
| 4,797,803 A | 1/1989 | Carroll |
| 4,798,588 A | 1/1989 | Aillon |
| 4,802,461 A | 2/1989 | Cho |
| 4,803,506 A | 2/1989 | Diehl et al. |
| 4,830,462 A | 5/1989 | Karny et al. |
| 4,832,683 A | 5/1989 | Idemoto et al. |
| 4,838,853 A | 6/1989 | Parisi |
| 4,849,133 A | 7/1989 | Yoshida et al. |
| 4,850,354 A | 7/1989 | McGurk-Burleson et al. |
| 4,860,745 A | 8/1989 | Farin et al. |
| 4,865,159 A | 9/1989 | Jamison |
| 4,878,493 A | 11/1989 | Pasternak et al. |
| 4,880,015 A | 11/1989 | Nierman |
| 4,896,009 A | 1/1990 | Pawlowski |
| 4,910,389 A | 3/1990 | Sherman et al. |
| 4,910,633 A | 3/1990 | Quinn |
| 4,911,148 A | 3/1990 | Sosnowski et al. |
| 4,919,129 A | 4/1990 | Weber, Jr. et al. |
| 4,920,978 A | 5/1990 | Colvin |
| 4,922,902 A | 5/1990 | Wuchinich et al. |
| 4,936,842 A | 6/1990 | D'Amelio et al. |
| 4,961,738 A | 10/1990 | Mackin |
| 4,967,670 A | 11/1990 | Morishita et al. |
| 4,981,756 A | 1/1991 | Rhandhawa |
| 5,007,919 A | 4/1991 | Silva et al. |
| 5,019,075 A | 5/1991 | Spears et al. |
| 5,020,514 A | 6/1991 | Heckele |
| 5,026,387 A | 6/1991 | Thomas |
| 5,061,269 A | 10/1991 | Muller |
| 5,093,754 A | 3/1992 | Kawashima |
| 5,099,216 A | 3/1992 | Pelrine |
| 5,099,840 A | 3/1992 | Goble et al. |
| 5,104,025 A | 4/1992 | Main et al. |
| 5,106,538 A | 4/1992 | Barma et al. |
| 5,108,383 A | 4/1992 | White |
| 5,112,300 A | 5/1992 | Ureche |
| 5,123,903 A | 6/1992 | Quaid et al. |
| 5,150,102 A | 9/1992 | Takashima |
| 5,150,272 A | 9/1992 | Danley et al. |
| 5,156,633 A | 10/1992 | Smith |
| 5,160,334 A | 11/1992 | Billings et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grzeszykowski |
| 5,188,102 A | 2/1993 | Idemoto et al. |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,217,460 A | 6/1993 | Knoepfler |
| 5,221,282 A | 6/1993 | Wuchinich |
| 5,226,910 A | 7/1993 | Kajiyama et al. |
| 5,234,428 A | 8/1993 | Kaufman |
| 5,241,236 A | 8/1993 | Sasaki et al. |
| 5,253,647 A | 10/1993 | Takahashi et al. |

(56) References Cited

U.S. PATENT DOCUMENTS

| | | | |
|---|---|---|---|
| 5,254,130 A | 10/1993 | Poncet et al. |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,267,091 A | 11/1993 | Chen |
| 5,282,800 A | 2/1994 | Foshee et al. |
| 5,285,945 A | 2/1994 | Brinkerhoff et al. |
| 5,290,286 A | 3/1994 | Parins |
| 5,293,863 A | 3/1994 | Zhu et al. |
| 5,304,115 A | 4/1994 | Pflueger et al. |
| D347,474 S | 5/1994 | Olson |
| 5,309,927 A | 5/1994 | Welch |
| 5,312,023 A | 5/1994 | Green et al. |
| 5,313,306 A | 5/1994 | Kuban et al. |
| 5,318,563 A | 6/1994 | Malis et al. |
| 5,318,564 A | 6/1994 | Eggers |
| 5,318,565 A | 6/1994 | Kuriloff et al. |
| 5,318,570 A | 6/1994 | Hood et al. |
| 5,318,589 A | 6/1994 | Lichtman |
| 5,322,055 A | 6/1994 | Davison et al. |
| 5,324,260 A | 6/1994 | O'Neill et al. |
| 5,324,299 A | 6/1994 | Davison et al. |
| 5,326,013 A | 7/1994 | Green et al. |
| 5,330,471 A | 7/1994 | Eggers |
| 5,330,502 A | 7/1994 | Hassler et al. |
| 5,333,624 A | 8/1994 | Tovey |
| 5,339,723 A | 8/1994 | Huitema |
| 5,342,359 A | 8/1994 | Rydell |
| 5,344,420 A | 9/1994 | Hilal et al. |
| 5,346,502 A | 9/1994 | Estabrook et al. |
| 5,352,219 A | 10/1994 | Reddy |
| 5,359,992 A | 11/1994 | Hori et al. |
| 5,361,583 A | 11/1994 | Huitema |
| 5,366,466 A | 11/1994 | Christian et al. |
| 5,370,640 A | 12/1994 | Kolff |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,389,098 A | 2/1995 | Tsuruta et al. |
| 5,395,033 A | 3/1995 | Byrne et al. |
| 5,395,312 A | 3/1995 | Desai |
| 5,395,331 A | 3/1995 | O'Neill et al. |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,409,483 A | 4/1995 | Campbell et al. |
| D358,887 S | 5/1995 | Feinberg |
| 5,411,481 A | 5/1995 | Allen et al. |
| 5,413,575 A | 5/1995 | Haenggi |
| 5,417,709 A | 5/1995 | Slater |
| 5,419,761 A | 5/1995 | Narayanan et al. |
| 5,421,829 A | 6/1995 | Olichney et al. |
| 5,428,504 A | 6/1995 | Bhatla |
| 5,429,131 A | 7/1995 | Scheinman et al. |
| 5,431,640 A | 7/1995 | Gabriel |
| 5,443,463 A | 8/1995 | Stern et al. |
| 5,445,615 A | 8/1995 | Yoon |
| 5,445,638 A | 8/1995 | Rydell et al. |
| 5,449,370 A | 9/1995 | Vaitekunas |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,472,443 A | 12/1995 | Cordis et al. |
| 5,476,479 A | 12/1995 | Green et al. |
| 5,477,788 A | 12/1995 | Morishita |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,489,256 A | 2/1996 | Adair |
| 5,496,317 A | 3/1996 | Goble et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,509,922 A | 4/1996 | Aranyi et al. |
| 5,511,556 A | 4/1996 | DeSantis |
| 5,520,704 A | 5/1996 | Castro et al. |
| 5,522,839 A | 6/1996 | Pilling |
| 5,531,744 A | 7/1996 | Nardella et al. |
| 5,540,648 A | 7/1996 | Yoon |
| 5,540,681 A | 7/1996 | Strul et al. |
| 5,542,916 A | 8/1996 | Hirsch et al. |
| 5,542,938 A | 8/1996 | Avellanet et al. |
| 5,558,671 A | 9/1996 | Yates |
| 5,562,609 A | 10/1996 | Brumbach |
| 5,562,610 A | 10/1996 | Brumbach |
| 5,562,657 A | 10/1996 | Griffin |
| 5,563,179 A | 10/1996 | Stone et al. |
| 5,569,164 A | 10/1996 | Lurz |
| 5,571,121 A | 11/1996 | Heifetz |
| 5,573,534 A | 11/1996 | Stone |
| 5,584,830 A | 12/1996 | Ladd et al. |
| 5,599,350 A | 2/1997 | Schulze et al. |
| 5,601,601 A | 2/1997 | Tal et al. |
| 5,604,531 A | 2/1997 | Iddan et al. |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,307 A | 4/1997 | Donlon et al. |
| 5,618,492 A | 4/1997 | Auten et al. |
| 5,624,452 A * | 4/1997 | Yates ................ A61B 18/1447 606/139 |
| 5,626,578 A | 5/1997 | Tihon |
| 5,628,760 A | 5/1997 | Knoepfler |
| 5,630,420 A | 5/1997 | Vaitekunas |
| 5,632,432 A | 5/1997 | Schulze et al. |
| D381,077 S | 7/1997 | Hunt |
| 5,643,175 A | 7/1997 | Adair |
| 5,645,065 A | 7/1997 | Shapiro et al. |
| 5,647,871 A | 7/1997 | Levine et al. |
| 5,651,780 A | 7/1997 | Jackson et al. |
| 5,653,677 A | 8/1997 | Okada et al. |
| 5,653,713 A | 8/1997 | Michelson |
| 5,657,697 A | 8/1997 | Murai |
| 5,658,281 A | 8/1997 | Heard |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,681,260 A | 10/1997 | Ueda et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,700,243 A | 12/1997 | Narciso, Jr. |
| 5,700,261 A | 12/1997 | Brinkerhoff |
| 5,704,900 A | 1/1998 | Dobrovolny et al. |
| 5,709,680 A | 1/1998 | Yates et al. |
| 5,711,472 A | 1/1998 | Bryan |
| 5,713,896 A | 2/1998 | Nardella |
| 5,716,366 A | 2/1998 | Yates |
| 5,720,742 A | 2/1998 | Zacharias |
| 5,720,744 A | 2/1998 | Eggleston et al. |
| 5,722,326 A | 3/1998 | Post |
| 5,722,426 A | 3/1998 | Kolff |
| 5,732,636 A | 3/1998 | Wang et al. |
| 5,733,074 A | 3/1998 | Stock et al. |
| 5,735,848 A | 4/1998 | Yates et al. |
| 5,738,652 A | 4/1998 | Boyd et al. |
| 5,741,226 A | 4/1998 | Strukel et al. |

(56) References Cited

U.S. PATENT DOCUMENTS

| | | |
|---|---|---|
| 5,741,305 A | 4/1998 | Vincent et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,776,130 A | 7/1998 | Buysse et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,796,188 A | 8/1998 | Bays |
| 5,797,941 A | 8/1998 | Schulze et al. |
| 5,800,432 A | 9/1998 | Swanson |
| 5,800,449 A | 9/1998 | Wales |
| 5,805,140 A | 9/1998 | Rosenberg et al. |
| 5,807,393 A | 9/1998 | Williamson, IV et al. |
| 5,810,718 A | 9/1998 | Akiba et al. |
| 5,810,811 A | 9/1998 | Yates et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,827,323 A | 10/1998 | Klieman et al. |
| 5,828,160 A | 10/1998 | Sugishita |
| 5,836,867 A | 11/1998 | Speier et al. |
| 5,836,909 A | 11/1998 | Cosmescu |
| 5,836,943 A | 11/1998 | Miller, III |
| 5,836,990 A | 11/1998 | Li |
| 5,843,109 A | 12/1998 | Mehta et al. |
| 5,853,412 A | 12/1998 | Mayenberger |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,454 A | 3/1999 | Hones et al. |
| 5,887,018 A | 3/1999 | Bayazitoglu et al. |
| 5,891,142 A | 4/1999 | Eggers et al. |
| 5,893,835 A | 4/1999 | Witt et al. |
| 5,897,569 A | 4/1999 | Kellogg et al. |
| 5,902,239 A | 5/1999 | Buurman |
| 5,904,147 A | 5/1999 | Conlan et al. |
| 5,906,579 A | 5/1999 | Vander Salm et al. |
| 5,906,625 A | 5/1999 | Bito et al. |
| 5,910,129 A | 6/1999 | Koblish et al. |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,298 A | 8/1999 | Koike |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,849 A | 9/1999 | Munro |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,984,938 A | 11/1999 | Yoon |
| 5,989,182 A | 11/1999 | Hori et al. |
| 5,989,274 A | 11/1999 | Davison et al. |
| 5,989,275 A | 11/1999 | Estabrook et al. |
| 5,993,972 A | 11/1999 | Reich et al. |
| 6,003,517 A | 12/1999 | Sheffield et al. |
| 6,007,484 A | 12/1999 | Thompson |
| 6,013,052 A | 1/2000 | Durman et al. |
| 6,014,580 A | 1/2000 | Blume et al. |
| 6,024,741 A | 2/2000 | Williamson, IV et al. |
| 6,024,744 A | 2/2000 | Kese et al. |
| 6,033,375 A | 3/2000 | Brumbach |
| 6,033,399 A | 3/2000 | Gines |
| 6,039,734 A | 3/2000 | Goble |
| 6,050,996 A | 4/2000 | Schmaltz et al. |
| 6,053,172 A | 4/2000 | Hovda et al. |
| 6,063,098 A | 5/2000 | Houser et al. |
| 6,066,132 A | 5/2000 | Chen et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,152 A | 6/2000 | Nardella et al. |
| 6,083,151 A | 7/2000 | Renner et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,093,186 A | 7/2000 | Goble |
| 6,099,483 A | 8/2000 | Palmer et al. |
| 6,099,550 A | 8/2000 | Yoon |
| 6,109,500 A | 8/2000 | Alli et al. |
| 6,113,594 A | 9/2000 | Savage |
| 6,113,598 A | 9/2000 | Baker |
| 6,123,466 A | 9/2000 | Persson et al. |
| H1904 H | 10/2000 | Yates et al. |
| 6,127,757 A | 10/2000 | Swinbanks |
| 6,132,368 A | 10/2000 | Cooper |
| 6,139,320 A | 10/2000 | Hahn |
| 6,144,402 A | 11/2000 | Norsworthy et al. |
| 6,152,902 A | 11/2000 | Christian et al. |
| 6,152,923 A | 11/2000 | Ryan |
| 6,154,198 A | 11/2000 | Rosenberg |
| 6,159,160 A | 12/2000 | Hsei et al. |
| 6,159,175 A | 12/2000 | Strukel et al. |
| 6,162,208 A | 12/2000 | Hipps |
| 6,173,199 B1 | 1/2001 | Gabriel |
| 6,173,715 B1 | 1/2001 | Sinanan et al. |
| 6,174,309 B1 | 1/2001 | Wrublewski et al. |
| 6,176,857 B1 | 1/2001 | Ashley |
| 6,190,386 B1 | 2/2001 | Rydell |
| 6,193,709 B1 | 2/2001 | Miyawaki et al. |
| 6,206,844 B1 | 3/2001 | Reichel et al. |
| 6,206,876 B1 | 3/2001 | Levine et al. |
| 6,206,877 B1 | 3/2001 | Kese et al. |
| 6,210,403 B1 | 4/2001 | Klicek |
| 6,214,023 B1 | 4/2001 | Whipple et al. |
| 6,219,572 B1 | 4/2001 | Young |
| 6,221,007 B1 | 4/2001 | Green |
| 6,228,080 B1 | 5/2001 | Gines |
| 6,228,084 B1 | 5/2001 | Kirwan, Jr. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,248,074 B1 | 6/2001 | Ohno et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,258,086 B1 | 7/2001 | Ashley et al. |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,273,887 B1 | 8/2001 | Yamauchi et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,283,981 B1 | 9/2001 | Beaupre |
| 6,292,700 B1 | 9/2001 | Morrison et al. |
| 6,309,400 B2 | 10/2001 | Beaupre |
| 6,315,789 B1 | 11/2001 | Cragg |
| 6,319,221 B1 | 11/2001 | Savage et al. |
| 6,325,799 B1 | 12/2001 | Goble |
| 6,325,811 B1 | 12/2001 | Messerly |
| 6,328,751 B1 | 12/2001 | Beaupre |
| 6,340,878 B1 | 1/2002 | Oglesbee |
| 6,352,532 B1 | 3/2002 | Kramer et al. |
| 6,364,888 B1 | 4/2002 | Niemeyer et al. |
| 6,371,952 B1 | 4/2002 | Madhani et al. |
| 6,379,320 B1 | 4/2002 | Lafon et al. |
| 6,379,351 B1 | 4/2002 | Thapliyal et al. |
| D457,958 S | 5/2002 | Dycus et al. |

(56) References Cited

U.S. PATENT DOCUMENTS

| | | |
|---|---|---|
| 6,383,194 B1 | 5/2002 | Pothula |
| 6,387,094 B1 | 5/2002 | Eitenmuller |
| 6,387,109 B1 | 5/2002 | Davison et al. |
| 6,388,657 B1 | 5/2002 | Natoli |
| 6,391,026 B1 | 5/2002 | Hung et al. |
| 6,391,042 B1 | 5/2002 | Cimino |
| 6,398,779 B1 | 6/2002 | Buysse et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,443,968 B1 | 9/2002 | Holthaus et al. |
| 6,443,969 B1 | 9/2002 | Novak et al. |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,464,703 B2 | 10/2002 | Bartel |
| 6,471,172 B1 | 10/2002 | Lemke et al. |
| 6,475,211 B2 | 11/2002 | Chess et al. |
| 6,475,216 B2 | 11/2002 | Mulier et al. |
| 6,480,796 B2 | 11/2002 | Wiener |
| 6,485,490 B2 | 11/2002 | Wampler et al. |
| 6,491,690 B1 | 12/2002 | Goble et al. |
| 6,491,691 B1 | 12/2002 | Morley et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,503,248 B1 | 1/2003 | Levine |
| 6,506,208 B2 | 1/2003 | Hunt et al. |
| 6,511,480 B1 | 1/2003 | Tetzlaff et al. |
| 6,514,252 B2 | 2/2003 | Nezhat et al. |
| 6,517,565 B1 | 2/2003 | Whitman et al. |
| 6,520,960 B2 | 2/2003 | Blocher et al. |
| 6,522,909 B1 | 2/2003 | Garibaldi et al. |
| 6,524,316 B1 | 2/2003 | Nicholson et al. |
| 6,531,846 B1 | 3/2003 | Smith |
| 6,533,784 B2 | 3/2003 | Truckai et al. |
| 6,537,196 B1 | 3/2003 | Creighton, IV et al. |
| 6,537,272 B2 | 3/2003 | Christopherson et al. |
| 6,537,291 B2 | 3/2003 | Friedman et al. |
| 6,540,693 B2 | 4/2003 | Burbank et al. |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,037 B2 | 5/2003 | Paton et al. |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,451 B1 | 6/2003 | Marucci et al. |
| 6,584,360 B2 | 6/2003 | Francischelli et al. |
| 6,585,735 B1 | 7/2003 | Frazier et al. |
| 6,589,200 B1 | 7/2003 | Schwemberger et al. |
| 6,589,239 B2 | 7/2003 | Khandkar et al. |
| 6,594,517 B1 | 7/2003 | Nevo |
| 6,599,321 B2 | 7/2003 | Hyde, Jr. |
| 6,602,252 B2 | 8/2003 | Mollenauer |
| 6,610,060 B2 | 8/2003 | Mulier et al. |
| 6,616,450 B2 | 9/2003 | Mossle et al. |
| 6,616,600 B2 | 9/2003 | Pauker |
| 6,619,529 B2 | 9/2003 | Green et al. |
| 6,620,129 B2 | 9/2003 | Stecker et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,817 B2 | 11/2003 | Schara et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,662,127 B2 | 12/2003 | Wiener et al. |
| 6,663,941 B2 | 12/2003 | Brown et al. |
| 6,669,690 B1 | 12/2003 | Okada et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,695,840 B2 | 2/2004 | Schulze |
| 6,696,844 B2 | 2/2004 | Wong et al. |
| 6,716,215 B1 | 4/2004 | David et al. |
| 6,719,684 B2 | 4/2004 | Kim et al. |
| 6,719,765 B2 | 4/2004 | Bonutti |
| 6,722,552 B2 | 4/2004 | Fenton, Jr. |
| 6,723,094 B1 | 4/2004 | Desinger |
| 6,726,686 B2 | 4/2004 | Buysse et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,743,229 B2 | 6/2004 | Buysse et al. |
| 6,746,443 B1 | 6/2004 | Morley et al. |
| 6,752,815 B2 | 6/2004 | Beaupre |
| 6,762,535 B2 | 7/2004 | Take et al. |
| 6,766,202 B2 | 7/2004 | Underwood et al. |
| 6,767,349 B2 | 7/2004 | Ouchi |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,165 B2 | 8/2004 | Jin |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,216 B1 | 9/2004 | Ishikawa |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,806,317 B2 | 10/2004 | Morishita et al. |
| 6,808,491 B2 | 10/2004 | Kortenbach et al. |
| 6,811,842 B1 | 11/2004 | Ehrnsperger et al. |
| 6,814,731 B2 | 11/2004 | Swanson |
| 6,817,974 B2 | 11/2004 | Cooper et al. |
| 6,821,273 B2 | 11/2004 | Mollenauer |
| 6,828,712 B2 | 12/2004 | Battaglin et al. |
| 6,832,998 B2 | 12/2004 | Goble |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,869,439 B2 | 3/2005 | White et al. |
| 6,875,220 B2 | 4/2005 | Du et al. |
| 6,877,647 B2 | 4/2005 | Green et al. |
| 6,893,435 B2 | 5/2005 | Goble |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |

(56) References Cited

U.S. PATENT DOCUMENTS

| | | |
|---|---|---|
| 6,926,716 B2 | 8/2005 | Baker et al. |
| 6,929,622 B2 | 8/2005 | Chian |
| 6,929,632 B2 | 8/2005 | Nita et al. |
| 6,929,644 B2 | 8/2005 | Truckai et al. |
| 6,936,003 B2 | 8/2005 | Iddan |
| D509,589 S | 9/2005 | Wells |
| 6,939,347 B2 | 9/2005 | Thompson |
| 6,945,981 B2 | 9/2005 | Donofrio et al. |
| 6,953,461 B2 | 10/2005 | McClurken et al. |
| D511,145 S | 11/2005 | Donofrio et al. |
| 6,959,852 B2 | 11/2005 | Shelton, IV et al. |
| 6,974,462 B2 | 12/2005 | Sater |
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 6,986,738 B2 | 1/2006 | Glukhovsky et al. |
| 6,986,780 B2 | 1/2006 | Rudnick et al. |
| 6,994,709 B2 | 2/2006 | Iida |
| 7,000,818 B2 | 2/2006 | Shelton, IV et al. |
| 7,004,951 B2 | 2/2006 | Gibbens, III |
| 7,011,657 B2 | 3/2006 | Truckai et al. |
| 7,029,435 B2 | 4/2006 | Nakao |
| 7,039,453 B2 | 5/2006 | Mullick et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,352 B2 | 5/2006 | Shelton, IV et al. |
| 7,044,937 B1 | 5/2006 | Kirwan et al. |
| 7,052,496 B2 | 5/2006 | Yamauchi |
| 7,055,731 B2 | 6/2006 | Shelton, IV et al. |
| 7,056,284 B2 | 6/2006 | Martone et al. |
| 7,063,699 B2 | 6/2006 | Hess et al. |
| 7,066,879 B2 | 6/2006 | Fowler et al. |
| 7,066,936 B2 | 6/2006 | Ryan |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,579 B2 | 8/2006 | Yokoi et al. |
| 7,083,617 B2 | 8/2006 | Kortenbach et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,094,235 B2 | 8/2006 | Francischelli |
| 7,096,560 B2 | 8/2006 | Oddsen, Jr. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,118,570 B2 | 10/2006 | Tetzlaff et al. |
| 7,120,498 B2 | 10/2006 | Imran et al. |
| 7,124,932 B2 | 10/2006 | Isaacson et al. |
| 7,125,409 B2 | 10/2006 | Truckai et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,147,638 B2 | 12/2006 | Chapman et al. |
| 7,147,650 B2 | 12/2006 | Lee |
| 7,153,315 B2 | 12/2006 | Miller |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,296 B2 | 1/2007 | Pearson et al. |
| 7,160,298 B2 | 1/2007 | Lawes et al. |
| 7,163,548 B2 | 1/2007 | Stulen et al. |
| 7,169,104 B2 | 1/2007 | Ueda et al. |
| 7,169,146 B2 | 1/2007 | Truckai et al. |
| 7,169,156 B2 | 1/2007 | Hart |
| 7,170,823 B2 | 1/2007 | Fabricius et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,199,545 B2 | 4/2007 | Oleynikov et al. |
| 7,204,820 B2 | 4/2007 | Akahoshi |
| 7,207,471 B2 | 4/2007 | Heinrich et al. |
| 7,208,005 B2 | 4/2007 | Frecker et al. |
| 7,211,094 B2 | 5/2007 | Gannoe et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,064 B2 | 6/2007 | Hopper et al. |
| 7,235,073 B2 | 6/2007 | Levine et al. |
| 7,241,290 B2 | 7/2007 | Doyle et al. |
| 7,241,294 B2 | 7/2007 | Reschke |
| 7,241,296 B2 | 7/2007 | Buysse et al. |
| 7,246,734 B2 | 7/2007 | Shelton, IV |
| 7,251,531 B2 | 7/2007 | Mosher et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,267,685 B2 | 9/2007 | Butaric et al. |
| 7,270,658 B2 | 9/2007 | Woloszko et al. |
| 7,270,664 B2 | 9/2007 | Johnson et al. |
| 7,273,483 B2 | 9/2007 | Wiener et al. |
| 7,276,065 B2 | 10/2007 | Morley et al. |
| 7,282,048 B2 | 10/2007 | Goble et al. |
| 7,282,773 B2 | 10/2007 | Li et al. |
| 7,287,682 B1 | 10/2007 | Ezzat et al. |
| 7,297,145 B2 | 11/2007 | Woloszko et al. |
| 7,297,149 B2 | 11/2007 | Vitali et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,344,533 B2 | 3/2008 | Pearson et al. |
| 7,353,068 B2 | 4/2008 | Tanaka et al. |
| 7,354,440 B2 | 4/2008 | Truckai et al. |
| 7,357,287 B2 | 4/2008 | Shelton, IV et al. |
| 7,360,542 B2 | 4/2008 | Nelson et al. |
| 7,364,577 B2 | 4/2008 | Wham et al. |
| 7,367,973 B2 | 5/2008 | Manzo et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,416,101 B2 | 8/2008 | Shelton, IV et al. |
| D576,725 S | 9/2008 | Shumer et al. |
| 7,422,139 B2 | 9/2008 | Shelton, IV et al. |
| 7,422,586 B2 | 9/2008 | Morris et al. |
| 7,422,592 B2 | 9/2008 | Morley et al. |
| 7,429,259 B2 | 9/2008 | Cadeddu et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,435,249 B2 | 10/2008 | Buysse et al. |

(56) References Cited

U.S. PATENT DOCUMENTS

| | | |
|---|---|---|
| 7,435,582 B2 | 10/2008 | Zimmermann et al. |
| 7,439,732 B2 | 10/2008 | LaPlaca |
| 7,441,684 B2 | 10/2008 | Shelton, IV et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,448,993 B2 | 11/2008 | Yokoi et al. |
| 7,449,004 B2 | 11/2008 | Yamada et al. |
| 7,450,998 B2 | 11/2008 | Zilberman et al. |
| 7,451,904 B2 | 11/2008 | Shelton, IV |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,479,148 B2 | 1/2009 | Beaupre |
| 7,479,160 B2 | 1/2009 | Branch et al. |
| 7,487,899 B2 | 2/2009 | Shelton, IV et al. |
| 7,488,319 B2 | 2/2009 | Yates |
| 7,491,201 B2 | 2/2009 | Shields et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,503,893 B2 | 3/2009 | Kucklick |
| 7,505,812 B1 | 3/2009 | Eggers et al. |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,511,733 B2 | 3/2009 | Takizawa et al. |
| 7,513,025 B2 | 4/2009 | Fischer |
| 7,517,349 B2 | 4/2009 | Truckai et al. |
| 7,520,877 B2 | 4/2009 | Lee, Jr. et al. |
| 7,524,320 B2 | 4/2009 | Tierney et al. |
| 7,534,243 B1 | 5/2009 | Chin et al. |
| D594,983 S | 6/2009 | Price et al. |
| 7,540,872 B2 | 6/2009 | Schechter et al. |
| 7,543,730 B1 | 6/2009 | Marczyk |
| 7,544,200 B2 | 6/2009 | Houser |
| 7,550,216 B2 | 6/2009 | Ofer et al. |
| 7,553,309 B2 | 6/2009 | Buysse et al. |
| 7,559,452 B2 | 7/2009 | Wales et al. |
| 7,566,318 B2 | 7/2009 | Haefner |
| 7,567,012 B2 | 7/2009 | Namikawa |
| 7,582,086 B2 | 9/2009 | Privitera et al. |
| 7,582,087 B2 | 9/2009 | Tetzlaff et al. |
| 7,586,289 B2 | 9/2009 | Andruk et al. |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,599,743 B2 | 10/2009 | Hassler, Jr. et al. |
| 7,601,119 B2 | 10/2009 | Shahinian |
| 7,604,150 B2 | 10/2009 | Boudreaux |
| 7,608,083 B2 | 10/2009 | Lee et al. |
| 7,611,512 B2 | 11/2009 | Ein-Gal |
| 7,617,961 B2 | 11/2009 | Viola |
| 7,621,910 B2 | 11/2009 | Sugi |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,640,447 B2 | 12/2009 | Qiu |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,678,043 B2 | 3/2010 | Gilad |
| 7,678,069 B1 | 3/2010 | Baker et al. |
| 7,678,105 B2 | 3/2010 | McGreevy et al. |
| 7,686,804 B2 | 3/2010 | Johnson et al. |
| 7,691,095 B2 | 4/2010 | Bednarek et al. |
| 7,691,098 B2 | 4/2010 | Wallace et al. |
| 7,691,103 B2 | 4/2010 | Fernandez et al. |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,717,312 B2 | 5/2010 | Beetel |
| 7,717,914 B2 | 5/2010 | Kimura |
| 7,717,915 B2 | 5/2010 | Miyazawa |
| 7,722,527 B2 | 5/2010 | Bouchier et al. |
| 7,722,607 B2 | 5/2010 | Dumbauld et al. |
| 7,725,214 B2 | 5/2010 | Diolaiti |
| D618,797 S | 6/2010 | Price et al. |
| 7,726,537 B2 | 6/2010 | Olson et al. |
| 7,744,615 B2 | 6/2010 | Couture |
| 7,751,115 B2 | 7/2010 | Song |
| 7,753,904 B2 | 7/2010 | Shelton, IV et al. |
| 7,753,908 B2 | 7/2010 | Swanson |
| 7,753,909 B2 | 7/2010 | Chapman et al. |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,775,972 B2 | 8/2010 | Brock et al. |
| 7,776,036 B2 | 8/2010 | Schechter et al. |
| 7,776,037 B2 | 8/2010 | Odom |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,663 B2 | 8/2010 | Shelton, IV |
| 7,789,283 B2 | 9/2010 | Shah |
| 7,789,878 B2 | 9/2010 | Dumbauld et al. |
| 7,789,883 B2 | 9/2010 | Takashino et al. |
| 7,793,814 B2 | 9/2010 | Racenet et al. |
| 7,799,027 B2 | 9/2010 | Hafner |
| 7,803,156 B2 | 9/2010 | Eder et al. |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,872 B2 | 10/2010 | Johnson et al. |
| D627,066 S | 11/2010 | Romero |
| 7,824,401 B2 | 11/2010 | Manzo et al. |
| 7,832,408 B2 | 11/2010 | Shelton, IV et al. |
| 7,832,612 B2 | 11/2010 | Baxter, III et al. |
| 7,837,699 B2 | 11/2010 | Yamada et al. |
| 7,845,537 B2 | 12/2010 | Shelton, IV et al. |
| 7,846,159 B2 | 12/2010 | Morrison et al. |
| 7,846,160 B2 | 12/2010 | Payne et al. |
| 7,850,688 B2 | 12/2010 | Hafner |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| D631,965 S | 2/2011 | Price et al. |
| 7,877,852 B2 | 2/2011 | Unger et al. |
| 7,877,853 B2 | 2/2011 | Unger et al. |
| 7,879,035 B2 | 2/2011 | Garrison et al. |
| 7,879,070 B2 | 2/2011 | Ortiz et al. |
| 7,887,535 B2 | 2/2011 | Lands et al. |
| 7,892,606 B2 | 2/2011 | Thies et al. |
| 7,896,875 B2 | 3/2011 | Heim et al. |
| 7,896,878 B2 | 3/2011 | Johnson et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,919,184 B2 | 4/2011 | Mohapatra et al. |
| 7,922,061 B2 | 4/2011 | Shelton, IV et al. |

(56) References Cited

U.S. PATENT DOCUMENTS

| | | | |
|---|---|---|---|
| 7,922,651 B2 | 4/2011 | Yamada et al. |
| 7,922,953 B2 | 4/2011 | Guerra |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,942,303 B2 | 5/2011 | Shah |
| 7,942,868 B2 | 5/2011 | Cooper |
| 7,947,039 B2 | 5/2011 | Sartor |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,976,544 B2 | 7/2011 | McClurken et al. |
| 7,980,443 B2 | 7/2011 | Scheib et al. |
| 7,981,113 B2 | 7/2011 | Truckai et al. |
| 7,988,567 B2 | 8/2011 | Kim et al. |
| 7,997,278 B2 | 8/2011 | Utley et al. |
| 8,020,743 B2 | 9/2011 | Shelton, IV |
| 8,033,173 B2 | 10/2011 | Ehlert et al. |
| 8,038,612 B2 | 10/2011 | Paz |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,056,787 B2 | 11/2011 | Boudreaux et al. |
| 8,057,498 B2 | 11/2011 | Robertson |
| 8,058,771 B2 | 11/2011 | Giordano et al. |
| 8,061,014 B2 | 11/2011 | Smith et al. |
| 8,062,211 B2 | 11/2011 | Duval et al. |
| 8,066,167 B2 | 11/2011 | Measamer et al. |
| 8,070,036 B1 | 12/2011 | Knodel |
| 8,070,748 B2 | 12/2011 | Hixson et al. |
| 8,075,555 B2 | 12/2011 | Truckai et al. |
| 8,075,558 B2 | 12/2011 | Truckai et al. |
| 8,092,475 B2 | 1/2012 | Cotter et al. |
| 8,100,894 B2 | 1/2012 | Mucko et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,114,119 B2 | 2/2012 | Spivey et al. |
| 8,118,206 B2 * | 2/2012 | Zand ............ A61B 5/0086 227/176.1 |
| 8,128,624 B2 | 3/2012 | Couture et al. |
| 8,128,657 B2 | 3/2012 | Shiono et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,825 B2 | 4/2012 | Madan et al. |
| 8,157,145 B2 * | 4/2012 | Shelton, IV ..... A61B 17/07207 227/19 |
| 8,161,977 B2 | 4/2012 | Shelton, IV et al. |
| 8,162,940 B2 | 4/2012 | Johnson et al. |
| 8,177,784 B2 | 5/2012 | Van Wyk et al. |
| 8,177,794 B2 | 5/2012 | Cabrera et al. |
| 8,182,502 B2 | 5/2012 | Stulen et al. |
| 8,186,560 B2 | 5/2012 | Hess et al. |
| 8,187,166 B2 | 5/2012 | Kuth et al. |
| 8,187,267 B2 | 5/2012 | Pappone et al. |
| 8,192,433 B2 | 6/2012 | Johnson et al. |
| 8,197,472 B2 | 6/2012 | Lau et al. |
| 8,197,479 B2 | 6/2012 | Olson et al. |
| 8,197,494 B2 | 6/2012 | Jaggi et al. |
| 8,197,502 B2 | 6/2012 | Smith et al. |
| 8,206,212 B2 | 6/2012 | Iddings et al. |
| 8,221,415 B2 | 7/2012 | Francischelli |
| 8,221,416 B2 | 7/2012 | Townsend |
| 8,226,675 B2 | 7/2012 | Houser et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,244,368 B2 | 8/2012 | Sherman |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,252,012 B2 | 8/2012 | Stulen |
| 8,257,352 B2 | 9/2012 | Lawes et al. |
| 8,257,377 B2 | 9/2012 | Wiener et al. |
| 8,262,563 B2 | 9/2012 | Bakos et al. |
| 8,267,300 B2 | 9/2012 | Boudreaux |
| 8,267,854 B2 | 9/2012 | Asada et al. |
| 8,267,935 B2 | 9/2012 | Couture et al. |
| 8,273,085 B2 | 9/2012 | Park et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,292,888 B2 | 10/2012 | Whitman |
| 8,298,228 B2 | 10/2012 | Buysse et al. |
| 8,298,232 B2 | 10/2012 | Unger |
| 8,303,583 B2 | 11/2012 | Hosier et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,322,455 B2 | 12/2012 | Shelton, IV et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,158 B2 | 1/2013 | McKenna et al. |
| 8,361,569 B2 | 1/2013 | Saito et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,377,053 B2 | 2/2013 | Orszulak |
| 8,377,059 B2 | 2/2013 | Deville et al. |
| 8,377,085 B2 | 2/2013 | Smith et al. |
| 8,382,754 B2 | 2/2013 | Odom et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,094 B2 | 3/2013 | Edwards et al. |
| 8,394,115 B2 | 3/2013 | Houser et al. |
| 8,397,971 B2 | 3/2013 | Yates et al. |
| 8,398,633 B2 | 3/2013 | Mueller |
| 8,403,926 B2 | 3/2013 | Nobis et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,076 B2 | 4/2013 | Pang et al. |
| 8,414,577 B2 | 4/2013 | Boudreaux et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |

(56) References Cited

U.S. PATENT DOCUMENTS

| | | |
|---|---|---|
| 8,430,898 B2 | 4/2013 | Wiener et al. |
| 8,435,257 B2 | 5/2013 | Smith et al. |
| 8,439,911 B2 | 5/2013 | Mueller |
| 8,439,939 B2 | 5/2013 | Deville et al. |
| 8,444,662 B2 | 5/2013 | Palmer et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,956 B2 | 6/2013 | McKenna et al. |
| 8,469,981 B2 | 6/2013 | Robertson et al. |
| 8,475,361 B2 | 7/2013 | Barlow et al. |
| 8,475,453 B2 | 7/2013 | Marczyk et al. |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,625 B2 | 7/2013 | Horner |
| 8,496,682 B2 | 7/2013 | Guerra et al. |
| 8,512,336 B2 | 8/2013 | Couture |
| 8,512,364 B2 | 8/2013 | Kowalski et al. |
| 8,512,365 B2 | 8/2013 | Wiener et al. |
| 8,523,889 B2 | 9/2013 | Stulen et al. |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,542,501 B2 | 9/2013 | Kyono |
| 8,553,430 B2 | 10/2013 | Melanson et al. |
| 8,562,516 B2 | 10/2013 | Saadat et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,412 B2 | 10/2013 | Brandt et al. |
| 8,569,997 B2 | 10/2013 | Lee |
| 8,574,187 B2 | 11/2013 | Marion |
| 8,574,231 B2 | 11/2013 | Boudreaux et al. |
| 8,579,176 B2 | 11/2013 | Smith et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| D695,407 S | 12/2013 | Price et al. |
| 8,596,513 B2 | 12/2013 | Olson et al. |
| 8,597,182 B2 | 12/2013 | Stein et al. |
| 8,597,297 B2 | 12/2013 | Couture et al. |
| 8,608,044 B2 | 12/2013 | Hueil et al. |
| 8,613,383 B2 | 12/2013 | Beckman et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,632,539 B2 | 1/2014 | Twomey et al. |
| 8,636,648 B2 | 1/2014 | Gazdzinski |
| 8,636,736 B2 | 1/2014 | Yates et al. |
| 8,636,761 B2 | 1/2014 | Cunningham et al. |
| 8,638,428 B2 | 1/2014 | Brown |
| 8,640,788 B2 | 2/2014 | Dachs, II et al. |
| 8,641,712 B2 | 2/2014 | Couture |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,155 B2 | 2/2014 | Houser et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,668,691 B2 | 3/2014 | Heard |
| RE44,834 E | 4/2014 | Dumbauld et al. |
| 8,684,253 B2 | 4/2014 | Giordano et al. |
| 8,685,020 B2 | 4/2014 | Weizman et al. |
| 8,685,056 B2 | 4/2014 | Evans et al. |
| 8,696,662 B2 | 4/2014 | Eder et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,708,213 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,734,443 B2 | 5/2014 | Hixson et al. |
| 8,745,840 B2 | 6/2014 | Hempstead et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,758,342 B2 | 6/2014 | Bales et al. |
| 8,764,747 B2 | 7/2014 | Cummings et al. |
| 8,770,459 B2 | 7/2014 | Racenet et al. |
| 8,784,418 B2 | 7/2014 | Romero |
| 8,789,740 B2 | 7/2014 | Baxter, III et al. |
| 8,790,342 B2 | 7/2014 | Stulen et al. |
| 8,795,274 B2 | 8/2014 | Hanna |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,752 B2 | 8/2014 | Fortier et al. |
| 8,807,414 B2 | 8/2014 | Ross et al. |
| 8,808,319 B2 | 8/2014 | Houser et al. |
| 8,814,856 B2 | 8/2014 | Elmouelhi et al. |
| 8,814,865 B2 | 8/2014 | Reschke |
| 8,814,870 B2 | 8/2014 | Paraschiv et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,488 B2 | 9/2014 | Farritor et al. |
| 8,834,518 B2 | 9/2014 | Faller et al. |
| 8,845,630 B2 | 9/2014 | Mehta et al. |
| 8,851,354 B2 | 10/2014 | Swensgard et al. |
| 8,852,184 B2 | 10/2014 | Kucklick |
| 8,864,757 B2 | 10/2014 | Klimovitch et al. |
| 8,864,761 B2 | 10/2014 | Johnson et al. |
| 8,870,867 B2 | 10/2014 | Walberg et al. |
| 8,876,858 B2 | 11/2014 | Braun |
| 8,882,766 B2 | 11/2014 | Couture et al. |
| 8,882,791 B2 | 11/2014 | Stulen |
| 8,887,373 B2 | 11/2014 | Brandt et al. |
| 8,888,776 B2 | 11/2014 | Dietz et al. |
| 8,888,783 B2 | 11/2014 | Young |
| 8,888,809 B2 | 11/2014 | Davison et al. |
| 8,906,012 B2 | 12/2014 | Conley et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,414 B2 | 12/2014 | Stone et al. |
| 8,926,607 B2 | 1/2015 | Norvell et al. |
| 8,926,608 B2 | 1/2015 | Bacher et al. |
| 8,929,888 B2 | 1/2015 | Rao et al. |
| 8,931,682 B2 | 1/2015 | Timm et al. |
| 8,939,287 B2 | 1/2015 | Markovitch |
| 8,939,974 B2 | 1/2015 | Boudreaux et al. |
| 8,939,975 B2 | 1/2015 | Twomey et al. |
| 8,944,997 B2 | 2/2015 | Fernandez et al. |
| 8,945,125 B2 | 2/2015 | Schechter et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |

(56) References Cited

U.S. PATENT DOCUMENTS

| | | |
|---|---|---|
| 8,961,547 B2 | 2/2015 | Dietz et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,332 B2 | 3/2015 | Farritor et al. |
| 8,974,453 B2 | 3/2015 | Wang |
| 8,978,845 B2 | 3/2015 | Kim |
| 8,979,838 B2 | 3/2015 | Woloszko et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,302 B2 | 3/2015 | Aldridge et al. |
| 8,989,855 B2 | 3/2015 | Murphy et al. |
| 8,992,422 B2 | 3/2015 | Spivey et al. |
| 8,992,520 B2 | 3/2015 | Van Wyk et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,017,326 B2 | 4/2015 | DiNardo et al. |
| 9,017,372 B2 | 4/2015 | Artale et al. |
| 9,023,035 B2 | 5/2015 | Allen, IV et al. |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,983 B2 | 5/2015 | Takashino et al. |
| 9,039,695 B2 | 5/2015 | Giordano et al. |
| 9,039,705 B2 | 5/2015 | Takashino |
| 9,039,731 B2 | 5/2015 | Joseph |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,113 B2 | 6/2015 | Bloom et al. |
| 9,055,961 B2 | 6/2015 | Manzo et al. |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,066,723 B2 | 6/2015 | Beller et al. |
| 9,072,535 B2 | 7/2015 | Shelton, IV et al. |
| 9,072,536 B2 | 7/2015 | Shelton, IV et al. |
| 9,078,664 B2 | 7/2015 | Palmer et al. |
| 9,089,327 B2 | 7/2015 | Worrell et al. |
| 9,089,360 B2 | 7/2015 | Messerly et al. |
| 9,094,006 B2 | 7/2015 | Gravati et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,672 B2 | 8/2015 | Tetzlaff et al. |
| 9,113,889 B2 | 8/2015 | Reschke |
| 9,113,900 B2 | 8/2015 | Buysse et al. |
| 9,119,630 B2 | 9/2015 | Townsend et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,138,289 B2 | 9/2015 | Conley et al. |
| 9,149,324 B2 | 10/2015 | Huang et al. |
| 9,149,325 B2 | 10/2015 | Worrell et al. |
| 9,155,585 B2 | 10/2015 | Bales, Jr. et al. |
| 9,161,803 B2 | 10/2015 | Yates et al. |
| 9,168,054 B2 | 10/2015 | Turner et al. |
| 9,168,082 B2 | 10/2015 | Evans et al. |
| 9,168,085 B2 | 10/2015 | Juzkiw et al. |
| 9,168,089 B2 | 10/2015 | Buysse et al. |
| 9,179,912 B2 | 11/2015 | Yates et al. |
| 9,186,204 B2 | 11/2015 | Nishimura et al. |
| 9,187,758 B2 | 11/2015 | Cai et al. |
| 9,192,380 B2 | 11/2015 | (Tarinelli) Racenet et al. |
| 9,192,421 B2 | 11/2015 | Garrison |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,716 B2 | 12/2015 | Masuda et al. |
| 9,204,879 B2 | 12/2015 | Shelton, IV |
| 9,204,919 B2 | 12/2015 | Brandt et al. |
| 9,216,050 B2 | 12/2015 | Condie et al. |
| 9,220,559 B2 | 12/2015 | Worrell et al. |
| 9,226,751 B2 | 1/2016 | Shelton, IV et al. |
| 9,226,767 B2 | 1/2016 | Stulen et al. |
| 9,237,891 B2 | 1/2016 | Shelton, IV |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,571 B2 | 2/2016 | Twomey et al. |
| 9,265,926 B2 | 2/2016 | Strobl et al. |
| 9,271,784 B2 | 3/2016 | Evans et al. |
| 9,274,988 B2 | 3/2016 | Hsu et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,308,014 B2 | 4/2016 | Fischer |
| 9,314,292 B2 | 4/2016 | Trees et al. |
| 9,326,788 B2 | 5/2016 | Batross et al. |
| 9,326,812 B2 | 5/2016 | Waaler et al. |
| 9,333,025 B2 | 5/2016 | Monson et al. |
| 9,339,323 B2 | 5/2016 | Eder et al. |
| 9,339,326 B2 | 5/2016 | McCullagh et al. |
| 9,344,042 B2 | 5/2016 | Mao |
| 9,345,481 B2 | 5/2016 | Hall et al. |
| 9,345,900 B2 | 5/2016 | Wu et al. |
| 9,351,754 B2 | 5/2016 | Vakharia et al. |
| 9,358,061 B2 | 6/2016 | Plascencia, Jr. et al. |
| 9,358,065 B2 | 6/2016 | Ladtkow et al. |
| 9,364,225 B2 | 6/2016 | Sniffin et al. |
| 9,364,230 B2 | 6/2016 | Shelton, IV et al. |
| 9,375,232 B2 | 6/2016 | Hunt et al. |
| 9,375,256 B2 | 6/2016 | Cunningham et al. |
| 9,375,267 B2 | 6/2016 | Kerr et al. |
| 9,381,060 B2 | 7/2016 | Artale et al. |
| 9,386,983 B2 | 7/2016 | Swensgard et al. |
| 9,393,037 B2 | 7/2016 | Olson et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,880 B2 | 8/2016 | Monson et al. |
| 9,421,060 B2 | 8/2016 | Monson et al. |
| 9,456,863 B2 | 10/2016 | Moua |
| 9,456,864 B2 | 10/2016 | Witt et al. |
| 9,456,876 B2 | 10/2016 | Hagn |
| 9,468,490 B2 | 10/2016 | Twomey et al. |
| 9,492,224 B2 | 11/2016 | Boudreaux et al. |
| 9,504,524 B2 | 11/2016 | Behnke, II |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,549,663 B2 | 1/2017 | Larkin |
| 9,554,845 B2 | 1/2017 | Arts |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,585,709 B2 | 3/2017 | Krapohl |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,810 B2 | 4/2017 | Hart et al. |
| 9,627,120 B2 | 4/2017 | Scott et al. |
| 9,629,629 B2 | 4/2017 | Leimbach et al. |
| 9,642,669 B2 | 5/2017 | Takashino et al. |
| 9,649,111 B2 | 5/2017 | Shelton, IV et al. |
| 9,649,144 B2 | 5/2017 | Aluru et al. |
| 9,649,151 B2 | 5/2017 | Goodman et al. |
| 9,662,131 B2 | 5/2017 | Omori et al. |
| 9,668,806 B2 | 6/2017 | Unger et al. |
| 9,687,295 B2 | 6/2017 | Joseph |

(56) References Cited

U.S. PATENT DOCUMENTS

| | | |
|---|---|---|
| 9,700,339 B2 | 7/2017 | Nield |
| 9,707,005 B2 | 7/2017 | Strobl et al. |
| 9,707,027 B2 | 7/2017 | Ruddenklau et al. |
| 9,707,030 B2 | 7/2017 | Davison et al. |
| 9,713,489 B2 | 7/2017 | Woloszko et al. |
| 9,713,491 B2 | 7/2017 | Roy et al. |
| 9,724,118 B2 | 8/2017 | Schulte et al. |
| 9,724,152 B2 | 8/2017 | Horlle et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,757,128 B2 | 9/2017 | Baber et al. |
| 9,757,142 B2 | 9/2017 | Shimizu |
| 9,757,186 B2 | 9/2017 | Boudreaux et al. |
| 9,775,665 B2 | 10/2017 | Ellman |
| 9,775,669 B2 | 10/2017 | Marczyk et al. |
| 9,782,214 B2 | 10/2017 | Houser et al. |
| 9,782,220 B2 | 10/2017 | Mark et al. |
| 9,788,891 B2 | 10/2017 | Christian et al. |
| 9,795,436 B2 | 10/2017 | Yates et al. |
| 9,802,033 B2 | 10/2017 | Hibner et al. |
| 9,808,244 B2 | 11/2017 | Leimbach et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,833,239 B2 | 12/2017 | Yates et al. |
| 9,848,937 B2 | 12/2017 | Trees et al. |
| 9,848,939 B2 | 12/2017 | Mayer et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,877,782 B2 | 1/2018 | Voegele et al. |
| 9,888,954 B2 | 2/2018 | Van Wyk et al. |
| 9,888,958 B2 | 2/2018 | Evans et al. |
| 9,901,359 B2 | 2/2018 | Faller et al. |
| 9,901,390 B2 | 2/2018 | Allen, IV et al. |
| 9,901,754 B2 | 2/2018 | Yamada |
| 9,907,563 B2 | 3/2018 | Germain et al. |
| 9,913,680 B2 | 3/2018 | Voegele et al. |
| 9,918,730 B2 | 3/2018 | Trees et al. |
| 9,918,773 B2 | 3/2018 | Ishikawa et al. |
| 9,931,157 B2 | 4/2018 | Strobl et al. |
| 9,937,001 B2 | 4/2018 | Nakamura |
| 9,943,357 B2 | 4/2018 | Cunningham et al. |
| 9,949,620 B2 | 4/2018 | Duval et al. |
| 9,949,785 B2 | 4/2018 | Price et al. |
| 9,949,788 B2 | 4/2018 | Boudreaux |
| 9,974,539 B2 | 5/2018 | Yates et al. |
| 9,993,289 B2 | 6/2018 | Sobajima et al. |
| 10,010,339 B2 | 7/2018 | Witt et al. |
| 10,016,207 B2 | 7/2018 | Suzuki et al. |
| 10,022,142 B2 | 7/2018 | Aranyi et al. |
| 10,034,707 B2 | 7/2018 | Papaioannou et al. |
| 10,041,822 B2 | 8/2018 | Zemlok |
| 10,052,044 B2 | 8/2018 | Shelton, IV et al. |
| 10,058,376 B2 | 8/2018 | Horner et al. |
| 10,070,916 B2 | 9/2018 | Artale |
| 10,080,606 B2 | 9/2018 | Kappus et al. |
| 10,092,310 B2 | 10/2018 | Boudreaux et al. |
| 10,092,348 B2 | 10/2018 | Boudreaux |
| 10,092,350 B2 | 10/2018 | Rothweiler et al. |
| 10,105,174 B2 | 10/2018 | Krapohl |
| 10,111,699 B2 | 10/2018 | Boudreaux |
| 10,117,702 B2 | 11/2018 | Danziger et al. |
| 10,130,410 B2 | 11/2018 | Strobl et al. |
| 10,130,414 B2 | 11/2018 | Weiler et al. |
| 10,135,242 B2 | 11/2018 | Baber et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,194,911 B2 | 2/2019 | Miller et al. |
| 10,194,972 B2 | 2/2019 | Yates et al. |
| 10,194,976 B2 | 2/2019 | Boudreaux |
| 10,194,977 B2 | 2/2019 | Yang |
| 10,211,586 B2 | 2/2019 | Adams et al. |
| 10,231,776 B2 | 3/2019 | Artale et al. |
| 10,231,777 B2 | 3/2019 | Brandt et al. |
| 10,238,387 B2 | 3/2019 | Yates et al. |
| 10,245,095 B2 | 4/2019 | Boudreaux |
| 10,258,404 B2 | 4/2019 | Wang |
| 10,265,118 B2 | 4/2019 | Gerhardt |
| 10,278,721 B2 | 5/2019 | Dietz et al. |
| 10,307,203 B2 | 6/2019 | Wyatt |
| 10,314,638 B2 | 6/2019 | Gee et al. |
| 10,321,950 B2 | 6/2019 | Yates et al. |
| 10,342,602 B2 | 7/2019 | Strobl et al. |
| 10,413,352 B2 | 9/2019 | Thomas et al. |
| 10,420,601 B2 | 9/2019 | Marion et al. |
| 10,420,607 B2 | 9/2019 | Woloszko et al. |
| 10,426,873 B2 | 10/2019 | Schultz |
| 10,433,900 B2 | 10/2019 | Harris et al. |
| 10,441,345 B2 | 10/2019 | Aldridge et al. |
| 10,463,421 B2 | 11/2019 | Boudreaux et al. |
| 10,478,243 B2 | 11/2019 | Couture et al. |
| 10,485,607 B2 | 11/2019 | Strobl et al. |
| 10,524,852 B1 | 1/2020 | Cagle et al. |
| 10,524,854 B2 | 1/2020 | Woodruff et al. |
| 10,568,682 B2 | 2/2020 | Dycus et al. |
| 10,575,868 B2 | 3/2020 | Hall et al. |
| 10,595,929 B2 | 3/2020 | Boudreaux et al. |
| 10,603,103 B2 | 3/2020 | Thomas et al. |
| 10,603,117 B2 | 3/2020 | Schings et al. |
| 10,639,092 B2 | 5/2020 | Corbett et al. |
| 10,646,269 B2 | 5/2020 | Worrell et al. |
| 10,675,082 B2 | 6/2020 | Shelton, IV et al. |
| 10,702,329 B2 | 7/2020 | Strobl et al. |
| 10,716,614 B2 | 7/2020 | Yates et al. |
| 10,751,109 B2 | 8/2020 | Yates et al. |
| 10,751,110 B2 | 8/2020 | Ding |
| 10,751,117 B2 | 8/2020 | Witt et al. |
| 10,758,294 B2 | 9/2020 | Jones |
| 10,779,876 B2 | 9/2020 | Monson et al. |
| 10,799,284 B2 | 10/2020 | Renner et al. |
| 10,813,640 B2 | 10/2020 | Adams et al. |
| 10,820,938 B2 | 11/2020 | Fischer et al. |
| 10,828,028 B2 * | 11/2020 | Harris .................... G16H 20/40 |
| 10,856,934 B2 | 12/2020 | Trees et al. |
| 10,881,449 B2 | 1/2021 | Boudreaux et al. |
| 10,903,685 B2 | 1/2021 | Yates et al. |
| 10,912,600 B2 | 2/2021 | Kitagawa et al. |
| 10,959,771 B2 | 3/2021 | Boudreaux et al. |
| 10,959,806 B2 | 3/2021 | Hibner et al. |
| 10,966,779 B2 | 4/2021 | Hart et al. |
| 10,987,156 B2 | 4/2021 | Trees et al. |
| 11,013,528 B2 | 5/2021 | Isosaki et al. |
| 11,033,323 B2 | 6/2021 | Witt et al. |
| 11,033,325 B2 | 6/2021 | Yates et al. |
| 11,090,103 B2 | 8/2021 | Ruddenklau et al. |
| 11,266,430 B2 | 3/2022 | Clauda et al. |
| 11,484,358 B2 | 11/2022 | Witt et al. |
| 11,490,951 B2 | 11/2022 | Davison et al. |
| 11,497,546 B2 | 11/2022 | Nott et al. |
| 11,564,686 B2 | 1/2023 | Yates et al. |
| 11,642,125 B2 * | 5/2023 | Harris ............ A61B 17/320068 227/180.1 |
| 11,653,920 B2 | 5/2023 | Shelton, IV et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0077550 A1 | 6/2002 | Rabiner et al. |
| 2002/0095175 A1 | 7/2002 | Brock et al. |
| 2002/0107517 A1 | 8/2002 | Witt et al. |
| 2002/0133149 A1 | 9/2002 | Bessette |
| 2002/0156493 A1 | 10/2002 | Houser et al. |
| 2003/0014053 A1 | 1/2003 | Nguyen et al. |
| 2003/0055443 A1 | 3/2003 | Spotnitz |
| 2003/0066938 A1 | 4/2003 | Zimmerman |

(56) References Cited

U.S. PATENT DOCUMENTS

| | | |
|---|---|---|
| 2003/0109875 A1 | 6/2003 | Tetzlaff et al. |
| 2003/0114731 A1 | 6/2003 | Cadeddu et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144660 A1 | 7/2003 | Mollenauer |
| 2003/0158548 A1 | 8/2003 | Phan et al. |
| 2003/0171747 A1 | 9/2003 | Kanehira et al. |
| 2003/0181910 A1 | 9/2003 | Dycus et al. |
| 2003/0204199 A1 | 10/2003 | Novak et al. |
| 2003/0212332 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |
| 2004/0054364 A1 | 3/2004 | Aranyi et al. |
| 2004/0092921 A1 | 5/2004 | Kadziauskas et al. |
| 2004/0092992 A1 | 5/2004 | Adams et al. |
| 2004/0093039 A1 | 5/2004 | Schumert |
| 2004/0097919 A1 | 5/2004 | Wellman et al. |
| 2004/0097996 A1 | 5/2004 | Rabiner et al. |
| 2004/0102804 A1 | 5/2004 | Chin |
| 2004/0133089 A1 | 7/2004 | Kilcoyne et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0199193 A1 | 10/2004 | Hayashi et al. |
| 2004/0249367 A1 | 12/2004 | Saadat et al. |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2005/0015125 A1 | 1/2005 | Mioduski et al. |
| 2005/0033278 A1 | 2/2005 | McClurken et al. |
| 2005/0033337 A1 | 2/2005 | Muir et al. |
| 2005/0090817 A1 | 4/2005 | Phan |
| 2005/0096502 A1 | 5/2005 | Khalili |
| 2005/0119640 A1 | 6/2005 | Sverduk et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0192610 A1 | 9/2005 | Houser et al. |
| 2005/0215858 A1 | 9/2005 | Vail |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0272972 A1 | 12/2005 | Iddan |
| 2005/0273139 A1 | 12/2005 | Krauss et al. |
| 2005/0288555 A1 | 12/2005 | Binmoeller |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0106379 A1 | 5/2006 | O'Brien et al. |
| 2006/0159731 A1 | 7/2006 | Shoshan |
| 2006/0190034 A1 | 8/2006 | Nishizawa et al. |
| 2006/0211943 A1 | 9/2006 | Beaupre |
| 2006/0253050 A1 | 11/2006 | Yoshimine et al. |
| 2006/0270916 A1 | 11/2006 | Skwarek et al. |
| 2006/0273135 A1* | 12/2006 | Beetel ................ A61B 17/128 227/175.1 |
| 2006/0293656 A1 | 12/2006 | Shadduck et al. |
| 2007/0008744 A1 | 1/2007 | Heo et al. |
| 2007/0010709 A1 | 1/2007 | Reinschke |
| 2007/0016235 A1 | 1/2007 | Tanaka et al. |
| 2007/0016236 A1 | 1/2007 | Beaupre |
| 2007/0020065 A1 | 1/2007 | Kirby |
| 2007/0032701 A1 | 2/2007 | Fowler et al. |
| 2007/0032704 A1 | 2/2007 | Gandini et al. |
| 2007/0032785 A1 | 2/2007 | Diederich et al. |
| 2007/0051766 A1 | 3/2007 | Spencer |
| 2007/0055228 A1 | 3/2007 | Berg et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0106317 A1 | 5/2007 | Shelton et al. |
| 2007/0118115 A1 | 5/2007 | Artale et al. |
| 2007/0123748 A1 | 5/2007 | Meglan |
| 2007/0130771 A1 | 6/2007 | Ehlert et al. |
| 2007/0135686 A1 | 6/2007 | Pruitt et al. |
| 2007/0149881 A1 | 6/2007 | Rabin |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0182842 A1 | 8/2007 | Sonnenschein et al. |
| 2007/0185474 A1 | 8/2007 | Nahen |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0270651 A1 | 11/2007 | Gilad et al. |
| 2007/0275348 A1 | 11/2007 | Lemon |
| 2007/0276424 A1 | 11/2007 | Mikkaichi et al. |
| 2007/0287933 A1 | 12/2007 | Phan et al. |
| 2008/0015413 A1 | 1/2008 | Barlow et al. |
| 2008/0015575 A1 | 1/2008 | Odom et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0082039 A1 | 4/2008 | Babaev |
| 2008/0082098 A1 | 4/2008 | Tanaka et al. |
| 2008/0103495 A1 | 5/2008 | Mihori et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208231 A1 | 8/2008 | Ota et al. |
| 2008/0214967 A1 | 9/2008 | Aranyi et al. |
| 2008/0228179 A1 | 9/2008 | Eder et al. |
| 2008/0234709 A1 | 9/2008 | Houser |
| 2008/0251568 A1* | 10/2008 | Zemlok ................ A61B 17/072 606/41 |
| 2008/0281200 A1 | 11/2008 | Voic et al. |
| 2008/0281315 A1 | 11/2008 | Gines |
| 2008/0287948 A1 | 11/2008 | Newton et al. |
| 2008/0296346 A1* | 12/2008 | Shelton, IV ........... A61B 34/71 227/180.1 |
| 2008/0300588 A1 | 12/2008 | Groth et al. |
| 2008/0312502 A1 | 12/2008 | Swain et al. |
| 2009/0012516 A1 | 1/2009 | Curtis et al. |
| 2009/0048589 A1 | 2/2009 | Takashino et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0114701 A1 | 5/2009 | Zemlok et al. |
| 2009/0143678 A1 | 6/2009 | Keast et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0248021 A1 | 10/2009 | McKenna |
| 2009/0254080 A1 | 10/2009 | Honda |
| 2009/0264879 A1 | 10/2009 | McClurken et al. |
| 2009/0270771 A1 | 10/2009 | Takahashi |
| 2009/0270853 A1 | 10/2009 | Yachi et al. |
| 2009/0287205 A1 | 11/2009 | Ingle |
| 2010/0022824 A1 | 1/2010 | Cybulski et al. |
| 2010/0036370 A1 | 2/2010 | Mirel et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |

(56) References Cited

U.S. PATENT DOCUMENTS

| | | |
|---|---|---|
| 2010/0158307 A1 | 6/2010 | Kubota et al. |
| 2010/0187283 A1 | 7/2010 | Crainich et al. |
| 2010/0204802 A1 | 8/2010 | Wilson et al. |
| 2010/0222752 A1 | 9/2010 | Collins, Jr. et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2011/0009857 A1 | 1/2011 | Subramaniam et al. |
| 2011/0028964 A1 | 2/2011 | Edwards |
| 2011/0036887 A1* | 2/2011 | Zemlok ............ A61B 17/07207 227/175.1 |
| 2011/0087224 A1 | 4/2011 | Cadeddu et al. |
| 2011/0118601 A1 | 5/2011 | Barnes et al. |
| 2011/0125151 A1 | 5/2011 | Strauss et al. |
| 2011/0257680 A1 | 10/2011 | Reschke et al. |
| 2011/0270245 A1 | 11/2011 | Homer et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0012636 A1* | 1/2012 | Beckman ......... A61B 17/07207 227/175.1 |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0041358 A1 | 2/2012 | Mann et al. |
| 2012/0059374 A1 | 3/2012 | Johnson et al. |
| 2012/0078244 A1 | 3/2012 | Worrell et al. |
| 2012/0080334 A1 | 4/2012 | Shelton, IV et al. |
| 2012/0085358 A1 | 4/2012 | Cadeddu et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0193396 A1* | 8/2012 | Zemlok ............ A61B 17/07207 227/176.1 |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0190753 A1 | 7/2013 | Garrison et al. |
| 2013/0253256 A1 | 9/2013 | Griffith et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0039493 A1 | 2/2014 | Conley et al. |
| 2014/0131419 A1 | 5/2014 | Bettuchi |
| 2014/0194864 A1 | 7/2014 | Martin et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0263541 A1 | 9/2014 | Leimbach et al. |
| 2014/0263552 A1 | 9/2014 | Hall et al. |
| 2015/0032150 A1 | 1/2015 | Ishida et al. |
| 2015/0080876 A1 | 3/2015 | Worrell et al. |
| 2015/0257819 A1 | 9/2015 | Dycus et al. |
| 2015/0272571 A1 | 10/2015 | Leimbach et al. |
| 2015/0272659 A1 | 10/2015 | Boudreaux et al. |
| 2015/0327918 A1 | 11/2015 | Sobajima et al. |
| 2016/0045248 A1 | 2/2016 | Unger et al. |
| 2016/0051316 A1 | 2/2016 | Boudreaux |
| 2016/0066916 A1* | 3/2016 | Overmyer ............ A61B 17/068 227/176.1 |
| 2016/0066980 A1 | 3/2016 | Schall et al. |
| 2016/0100747 A1 | 4/2016 | Nitsan et al. |
| 2016/0166256 A1* | 6/2016 | Baxter, III ....... A61B 17/07207 227/176.1 |
| 2016/0175029 A1 | 6/2016 | Witt et al. |
| 2016/0270842 A1 | 9/2016 | Strobl et al. |
| 2016/0296270 A1 | 10/2016 | Strobl et al. |
| 2017/0105786 A1 | 4/2017 | Scheib et al. |
| 2017/0105787 A1 | 4/2017 | Witt et al. |
| 2017/0135751 A1 | 5/2017 | Rothweiler et al. |
| 2017/0164972 A1 | 6/2017 | Johnson et al. |
| 2017/0312018 A1 | 11/2017 | Trees et al. |
| 2017/0325878 A1 | 11/2017 | Messerly et al. |
| 2017/0325886 A1 | 11/2017 | Graham et al. |
| 2017/0348043 A1 | 12/2017 | Wang et al. |
| 2018/0125571 A1 | 5/2018 | Witt et al. |
| 2018/0161034 A1 | 6/2018 | Scheib et al. |
| 2018/0235626 A1 | 8/2018 | Shelton, IV et al. |
| 2019/0000536 A1 | 1/2019 | Yates et al. |
| 2019/0059980 A1 | 2/2019 | Shelton, IV et al. |
| 2019/0099209 A1 | 4/2019 | Witt et al. |
| 2019/0200981 A1 | 7/2019 | Harris et al. |
| 2019/0200998 A1 | 7/2019 | Shelton, IV et al. |
| 2019/0314015 A1 | 10/2019 | Shelton, IV et al. |
| 2020/0352636 A1 | 11/2020 | Batchelor et al. |
| 2020/0375651 A1 | 12/2020 | Witt et al. |
| 2021/0100605 A1 | 4/2021 | Renner et al. |
| 2021/0196334 A1 | 7/2021 | Sarley et al. |
| 2021/0196346 A1 | 7/2021 | Leuck et al. |
| 2021/0196353 A1 | 7/2021 | Gee et al. |
| 2021/0338309 A1 | 11/2021 | Witt et al. |
| 2022/0167975 A1 | 6/2022 | Shelton, IV et al. |
| 2022/0168038 A1 | 6/2022 | Shelton, IV et al. |
| 2022/0395318 A1 | 12/2022 | Nott et al. |
| 2023/0027481 A1 | 1/2023 | Davison et al. |

FOREIGN PATENT DOCUMENTS

| | | |
|---|---|---|
| CN | 2868227 Y | 2/2007 |
| DE | 4300307 A1 | 7/1994 |
| DE | 29623113 U1 | 10/1997 |
| DE | 20004812 U1 | 9/2000 |
| DE | 10201569 A1 | 7/2003 |
| DE | 102005032371 A1 | 1/2007 |
| EP | 0171967 A2 | 2/1986 |
| EP | 0705571 A1 | 4/1996 |
| EP | 1862133 A1 | 12/2007 |
| EP | 2060238 A1 | 5/2009 |
| EP | 1747761 B1 | 10/2009 |
| EP | 1767164 B1 | 1/2013 |
| EP | 2578172 A2 | 4/2013 |
| EP | 3506274 A1 | 7/2019 |
| ES | 2419159 A2 | 8/2013 |
| GB | 2032221 A | 4/1980 |
| JP | S537994 A | 1/1978 |
| JP | H08229050 A | 9/1996 |
| JP | 2002186627 A | 7/2002 |
| JP | 2009213878 A | 9/2009 |
| JP | 2010057926 A | 3/2010 |
| JP | 2012019846 A | 2/2012 |
| WO | WO-8103272 A1 | 11/1981 |
| WO | WO-9314708 A1 | 8/1993 |
| WO | WO-9800069 A1 | 1/1998 |
| WO | WO-9923960 A1 | 5/1999 |
| WO | WO-0024330 A1 | 5/2000 |
| WO | WO-0128444 A1 | 4/2001 |
| WO | WO-02080794 A1 | 10/2002 |
| WO | WO-2004078051 A2 | 9/2004 |
| WO | WO-2008130793 A1 | 10/2008 |
| WO | WO-2009067649 A2 | 5/2009 |
| WO | WO-2010104755 A1 | 9/2010 |
| WO | WO-2011008672 A2 | 1/2011 |
| WO | WO-2011044343 A2 | 4/2011 |
| WO | WO-2011144911 A1 | 11/2011 |
| WO | WO-2012044606 A2 | 4/2012 |
| WO | WO-2012061638 A1 | 5/2012 |

(56) References Cited

FOREIGN PATENT DOCUMENTS

| WO | WO-2013131823 A1 | 9/2013 |
|---|---|---|
| WO | WO-2016088017 A1 | 6/2016 |

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (July/Aug. 1999).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Chen et al., "Heat-induced changes in the mechanics of a collagenous tissue: pseudoelastic behavior at 37° C," Journal of Biomechanics, 31, pp. 211-216 (1998).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Kurt Gieck & Reiner Gieck, Engineering Formulas § Z.7 (7th ed. 1997).
Leonard I. Malis, M.D., "The Value of Irrigation During Bipolar Coagulation," 1989.
Covidien Brochure, The LigaSure Precise™ Instrument, dated Mar. 2011 (2 pages).
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Glaser and Subak-Sharpe, Integrated Circuit Engineering, Addison-Wesley Publishing, Reading, MA (1979). (book--not attached).
Abbott, et al. Proceedings of the 2007 IEEEIRDJ International Conference on Intelligent Robots and Systems. 410-416, 2007.
Cadeddu et al., "Magnetic positioning system for trocarless laparoscopic instruments," American College of Surgeons Poster, 2004.
Cadeddu et al., "Novel magnetically guided intra-abdominal camera to facilitate laparoendoscopic single site surgery: initial human experience," Surgical Endoscopy, Sages Oral Manscript, 2009.
Cadeddu et al., "Transabdominal magnetic anchoring system for trocar-less laparoscopic surgery," American Urological Association Poster, 2002.
Cadeddu et al., "Transabdominal magnetic anchoring system for trocar-less laparoscopic surgery," Journal of Urology Abstract, 2002.
Castellvi et al., "Completely transvaginal Notes cholecystectomy in a porcine model using novel endoscopic instrumentation," Accepted for Poster Presentation, SAGES Annual Meeting, 2009.
Castellvi et al., "Hybrid transgastric Notes cholecystectomy in a porcine model using a magnetically anchored cautery and novel instrumentation," Submitted for Presentation, ASGE, 2009.
Castellvi et al., "Hybrid transvaginal Notes sleeve gastrectomy in a porcine model using a magnetically anchored camera and novel instrumentation," Accepted for Poster Presentation, Sages Annual Meeting, 2009.
Duchene et al., "Magnetic positioning system for trocarless laparoscopic instruments," Engineering and Urology Society Poster, 2004.
Fernandez et al., "Development of a transabdominal anchoring system for trocar-less laparoscopic surgery," ASME Proceedings of/MECE, 2004.
Gedeon et al., "Maximizing coupling strength of magnetically anchored notes instruments: How thick can we go?" Submittedfor Presentation, Poster, Sages Annual Meeting, 2008.
Gedeon et al., "Maximizing coupling strength of magnetically anchored notes instruments: How thick can we go?" SAGES Annual Meeting Poster, 2008.
Park et al., "Trocar-less Instrumentation for Laparoscopy: Magnetic Positioning of Intra-Abdominal Camera and Retractor", Annals of Surgery, vol. 245, No. 3, pp. 379-384, Mar. 2007.
Peirs et al., "A miniature manipulator for integration in self-propelling endoscope," Sensors and Actuators, 92:343-9, 2001.
Raman et al., "Complete transvaginal Notes nephrectomy using magnetically anchored instrumentation," Journal of Endourology, 23(3):, 2009.367-371,2009.
Rapaccini et al., "Gastric Wall Thickness in Normal and Neoplastic Subjects: A Prospective Study Performed by Abdominal Ultrasound", Gastrointestinal Radiology, vol. 13, pp. 197-199. 1988.
Scott et al., "A randomized comparison of laparoscopic, flexible endoscopic, and wired and wireless magnetic Notes cameras on ex-vivo and in-vivo surgical performance," Digestive Disease Week (DDW), American Society for Gastrointestinal Endoscopy (ASGE) Annual Meeting Abstract, 2008.
Scott et al., "Completely transvaginal Notes cholecystectomy using magnetically anchored instruments," Surg. Endosc., 21:2308-2316, 2007.
Scott et al., "Evaluation of a novel air seal access port for transvaginal notes cholecystectomy," Submitted for Presentation, Sages Annual Meeting, 2008.

(56) References Cited

OTHER PUBLICATIONS

Scott et al., "Magnetically anchored instruments for transgastric endoscopic surgery," Oral Presentation for Sages Annual Meeting, Emerging Technology Oral Abstract ET005, 2006.
Scott et al., "Optimizing magnetically anchored camera, light source, graspers, and cautery dissector for transvaginal notes cholecystectomy," Submitted for Presentation, SAGES Annual Meeting, 2008.
Scott et al., "Short-term survival outcomes following transvaginal Notes cholecystectomy using magnetically anchored instruments," Oral Presentation, ASGE Annual Meeting/DDW, 2007.
Scott et al., "Trans gastric, transcolonic, and transvaginal cholecystectomy using magnetically anchored instruments," SAGES Annual Meeting Poster, 2007.
Scott et al., "Transvaginal Notes cholecystectomy using magnetically anchored instruments," Abstract for Video Submission, ASGE II1h Annual Video Forum, 2007.
Scott et al., "Transvaginal single access 'pure' Notes sleeve gastrectomy using a deployable magnetically anchored video camera," Digestive Disease Week (DDW), American Society for Gastrointestinal Endoscopy (ASGE) Annual Meeting Poster, 2008.
Swain et al., "Linear stapler formation of ileo-rectal, entero-enteral and gastrojejunal anastomoses during dual and single access 'pure' Notes procedures: Methods, magnets and stapler modifications," Digestive Disease Week (DDW), American Society for Gastrointestinal Endoscopy (ASGE) Annual Meeting Abstract, 2008.
Swain et al., "Wireless endosurgery for Notes," Digestive Disease Week (DDW), American Society for Gastrointestinal Endoscopy (ASGE) Annual Meeting Abstract, 2008.
Tang et al., "Live video manipulator for endoscopy and natural orifice transluminal endoscopic surgery (with videos)," Gastrointestinal Endoscopy, 68:559-564, 2008.
Zeltser et al., "Single trocar laparoscopic nephrectomy using magnetic anchoring and guidance system in the porcine model," The Journal of Urology, 178:288-291, 2007.
Wright, et al., "Time-Temperature Equivalence of Heat-Induced Changes in Cells and Proteins," Feb. 1998. ASME Journal of Biomechanical Engineering, vol. 120, pp. 22-26.
Douglas, S.C. "Introduction to Adaptive Filter". Digital Signal Processing Handbook. Ed. Vijay K. Madisetti and Douglas B. Williams. Boca Raton: CRC Press LLC, 1999.
Jang, J. et al. "Neuro-fuzzy and Soft Computing." Prentice Hall, 1997, pp. 13-89, 199-293, 335-393, 453-496, 535-549.
Erbe Electrosurgery VIOR® 200 S, (2012), p. 7, 12 pages, accessed Mar. 31, 2014 at http://www.erbe-med.com/erbe/media/Marketing materialien/85140170 ERBE EN VIO 200 S D027541.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
F. A. Duck, "Optical Properties of Tissue Including Ultraviolet and Infrared Radiation," pp. 43-71 in Physical Properties of Tissue (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al., "Thermal Imaging in Surgery," p. 19-3, in Medical Infrared Imaging, N. A. Diakides and J. D. Bronzino, Eds. (2008).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Technology Overview, printed from www.harmonicscalpel.com, Internet site, website accessed on Jun. 13, 2007, (3 pages).
Gooch et al., "Recommended Infection-Control Practices for Dentistry, 1993," Published: May 28, 1993; [retrieved on Aug. 23, 2008]. Retrieved from the internet: URL: http/wonder.cdc.gov/wonder/prevguid/p0000191/p0000191.asp (15 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
International Search Report and Written Opinion dated Jan. 25, 2023 for Application No. PCT/IB2022/060482, 15 pgs.

\* cited by examiner

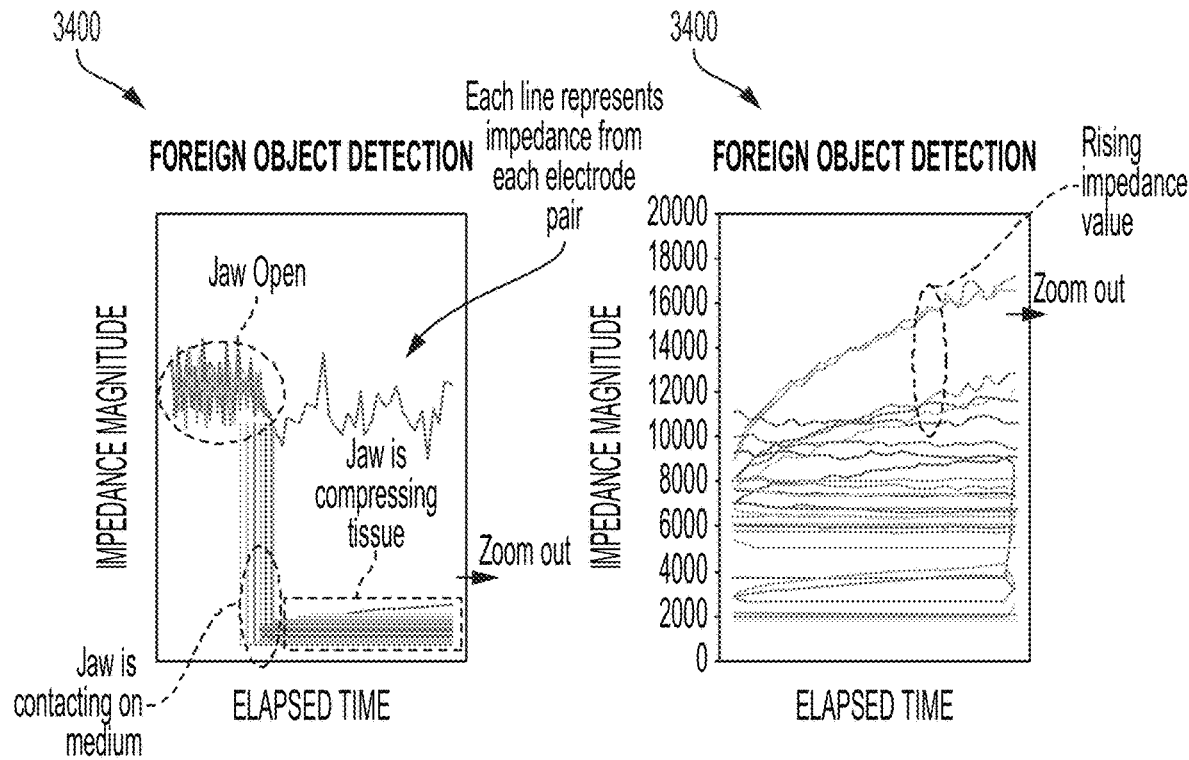
FIG. 17A
FIG. 17B
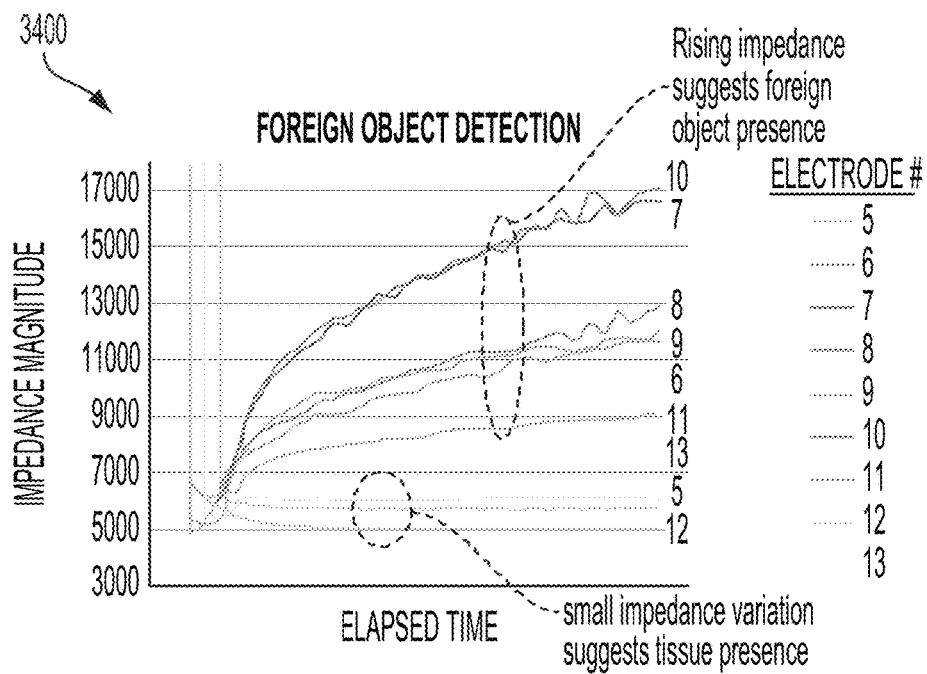
FIG. 17C

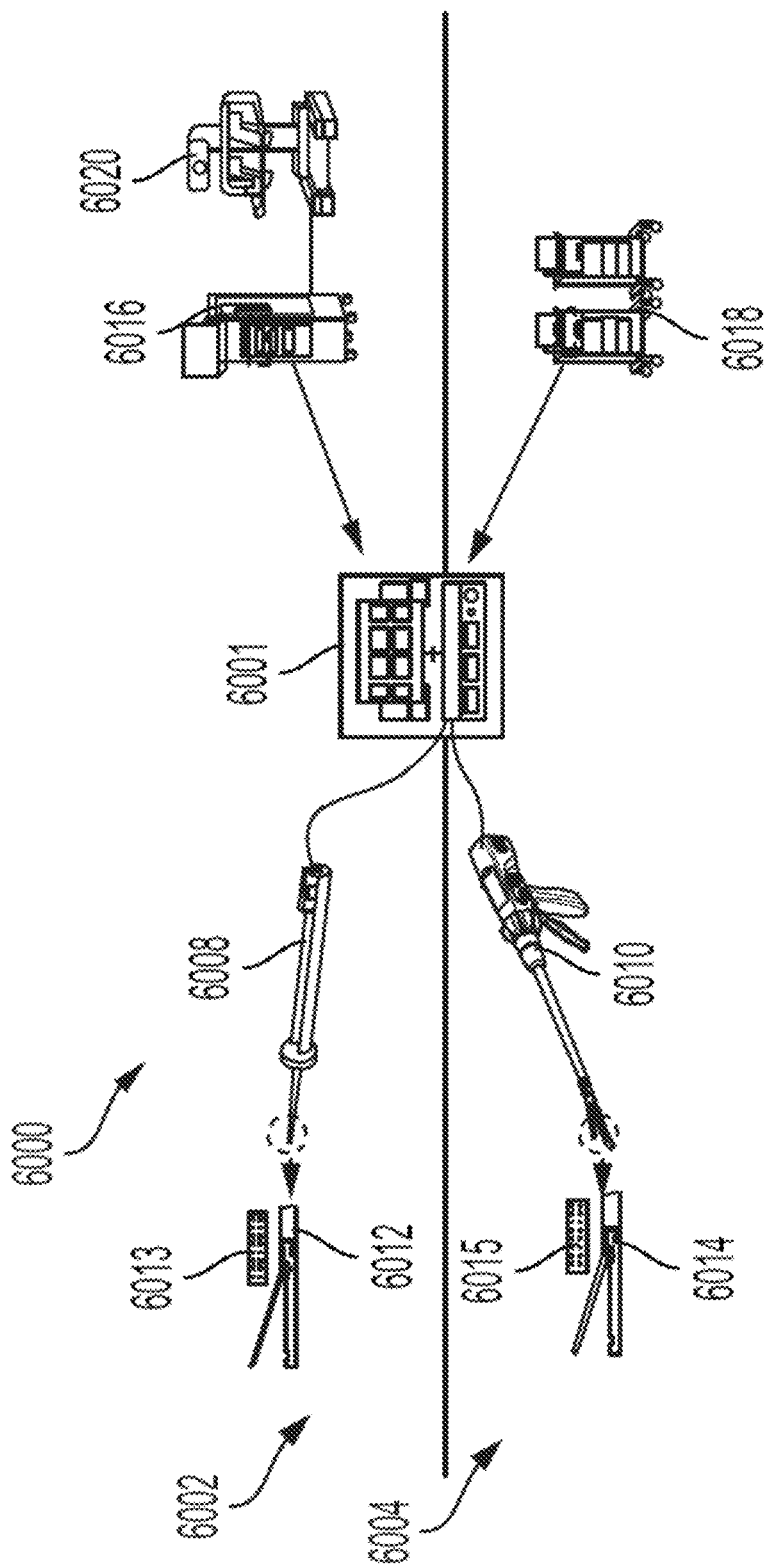

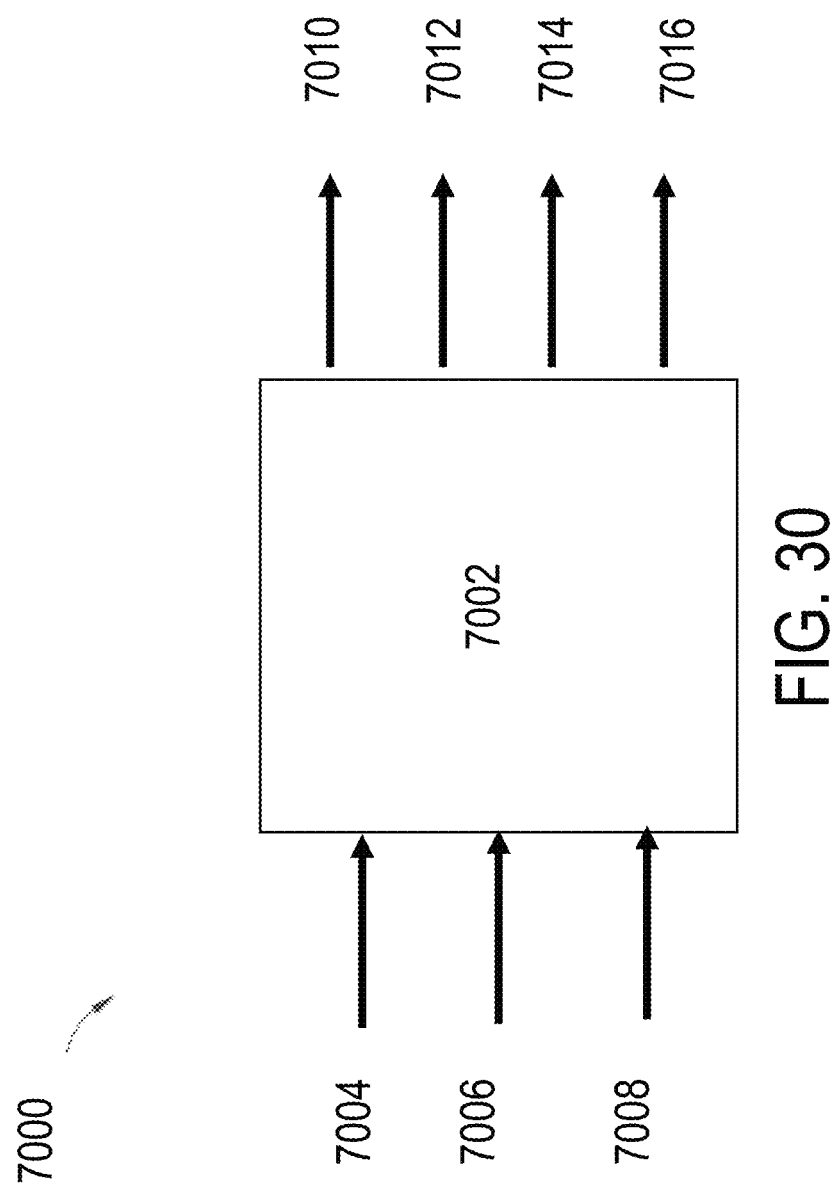

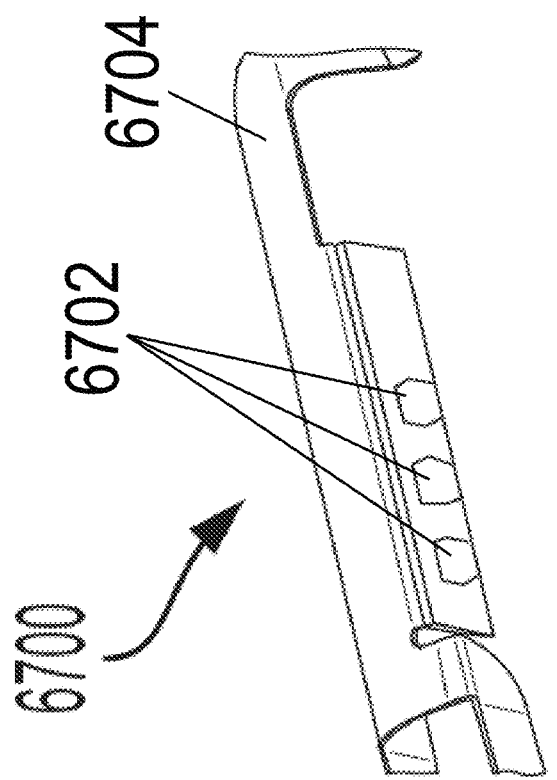

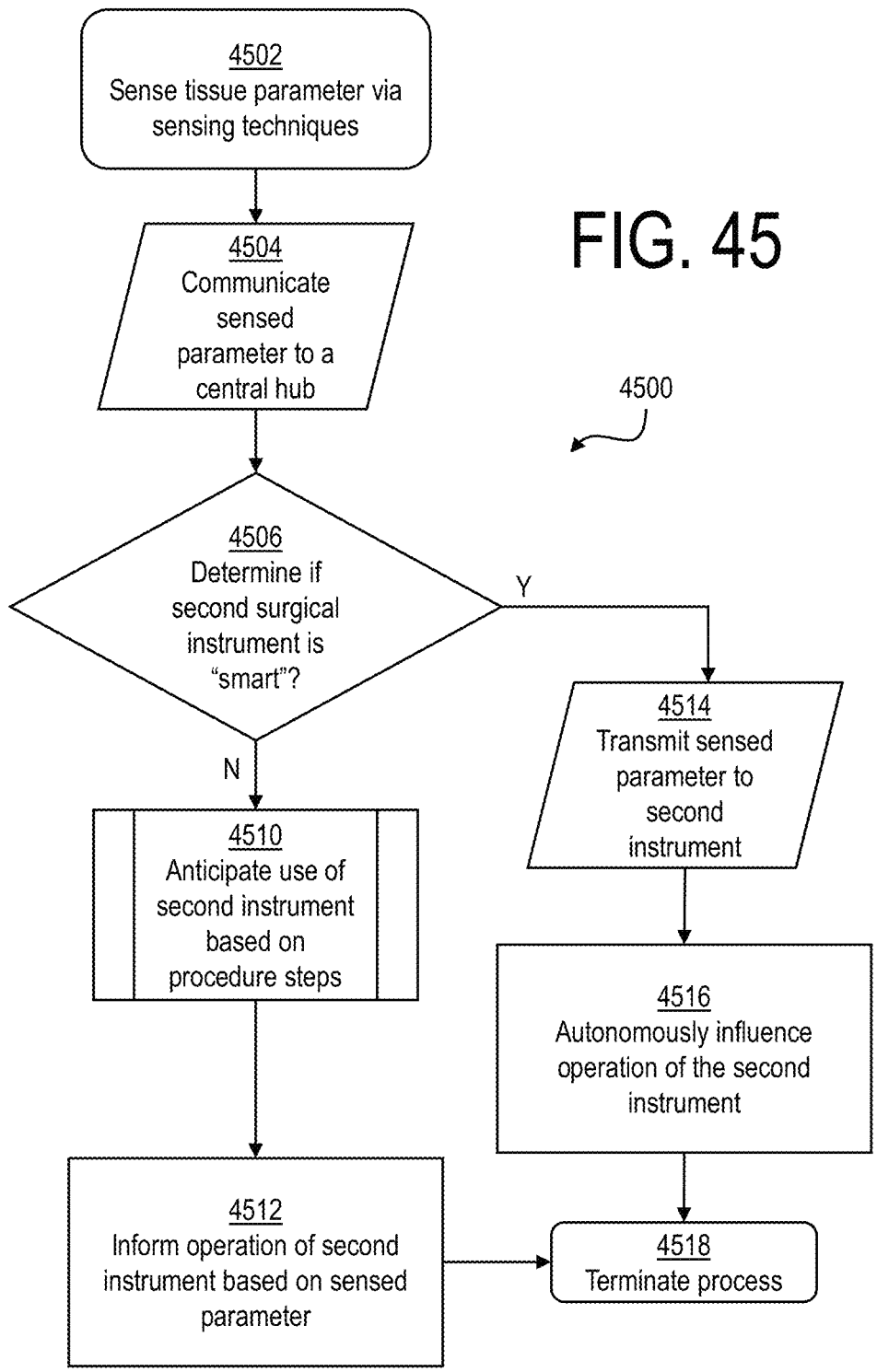

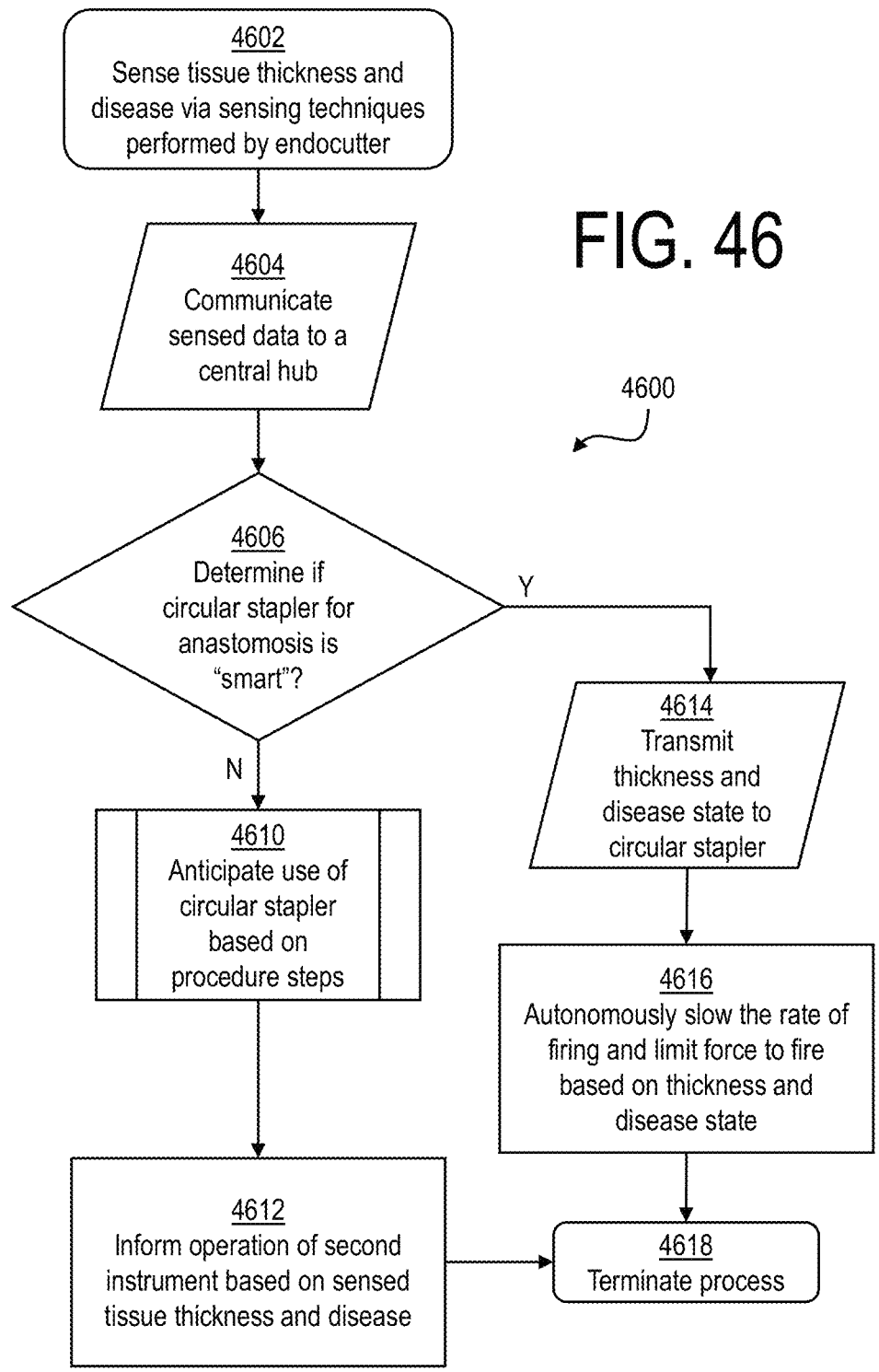

DEVICES, SYSTEMS, AND METHODS FOR DETECTING TISSUE AND FOREIGN OBJECTS DURING A SURGICAL OPERATION

CROSS-REFERENCE TO RELATED APPLICATIONS

This application claims the benefit of priority under 35 U.S.C. § 119(e) to U.S. Provisional Patent Application No. 63/274,207, titled DEVICES, SYSTEMS, AND METHODS FOR DETECTING TISSUE AND FOREIGN OBJECTS DURING A SURGICAL OPERATION, filed on Nov. 1, 2021, and U.S. Provisional Patent Application No. 63/330,502 titled DEVICES, SYSTEMS, AND METHODS FOR DETECTING TISSUE AND FOREIGN OBJECTS DURING A SURGICAL OPERATION, filed Apr. 13, 2022, the disclosures of each of which is herein incorporated by reference in its entirety.

TECHNICAL FIELD

The present invention relates to surgical instruments and, in various arrangements, to surgical stapling and cutting instruments and staple cartridges for use therewith that are designed to staple and cut tissue.

SUMMARY

In one aspect, a surgical instrument is disclosed. The surgical instrument can include an end effector that includes jaws configured to transition between an opened condition and a closed condition, a plurality of electrodes positioned within the jaws of the end effector, a control circuit, and a memory configured to store an algorithm configured to cause the control circuit to determine an impedance signal based on signals received from the plurality of electrodes, detect a media positioned between the jaws of the end effector based on the determined impedance signal, determine a position of the detected media based on the received signals, and generate an alert associated with the detected media and the determined position.

In one aspect, a surgical system is disclosed. The surgical system can include a surgical instrument including an end effector including jaws configured to transition between an opened condition and a closed condition, and a plurality of electrodes positioned within the jaws of the end effector, wherein each electrode of the plurality of electrodes is positioned about a longitudinal axis defined by the end effector, and a computer system communicably coupled to the surgical instrument, wherein the computer system includes a control circuit and a memory configured to store an algorithm configured to cause the control circuit to receive signals from the plurality of electrodes, determine an impedance signal based on the signals received from the plurality of electrodes, detect a media positioned between the jaws of the end effector based on the determined impedance signal, determine a position of the detected media along the longitudinal axis based on the signals received from the plurality of electrodes, and generate an alert associated with the detected media and the determined position.

In one aspect, a method of characterizing media positioned between jaws of an end effector of a surgical instrument is disclosed. The method can include receiving, via a control circuit of the surgical instrument, signals from a plurality of electrodes positioned within the jaws of the end effector, determining, via the control circuit, an impedance signal based on the signals received from the plurality of electrodes, detecting, via the control circuit, the media positioned between the jaws of the end effector based on the determined impedance signal, determining, via the control circuit, a position of the detected media along a longitudinal axis defined by the end effector based on the signals received from the plurality of electrodes, generating, via the control circuit, an alert associated with the detected media and the determined position, and characterizing, via the control circuit, the detected media based on the determined impedance signal.

In addition to the foregoing, various other method and/or system and/or program product aspects are set forth and described in the teachings such as text (e.g., claims and/or detailed description) and/or drawings of the present disclosure.

The foregoing is a summary and thus may contain simplifications, generalizations, inclusions, and/or omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to affect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

Further, it is understood that any one or more of the following-described forms, expressions of forms, examples, can be combined with any one or more of the other following-described forms, expressions of forms, and examples.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the described forms are set forth with particularity in the appended claims. The described forms, however, both as to organization and methods of operation, may be best understood by reference to the following description, taken in conjunction with the accompanying drawings in which:

Figure 10:
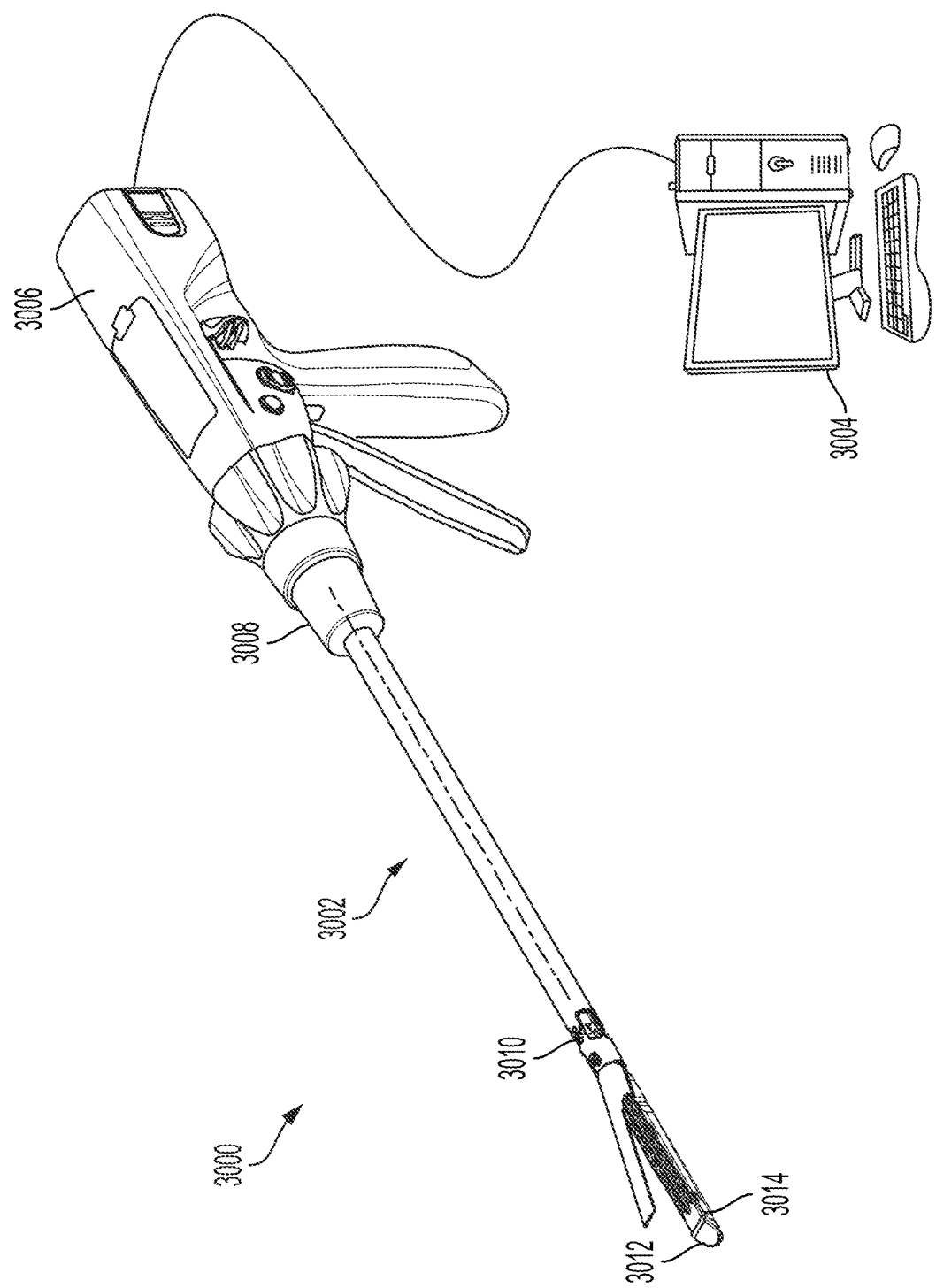
FIG. 10 illustrates a system for detecting tissue and foreign objects during a surgical operation, in accordance with at least one non-limiting aspect of the present disclosure.
Figure 13:
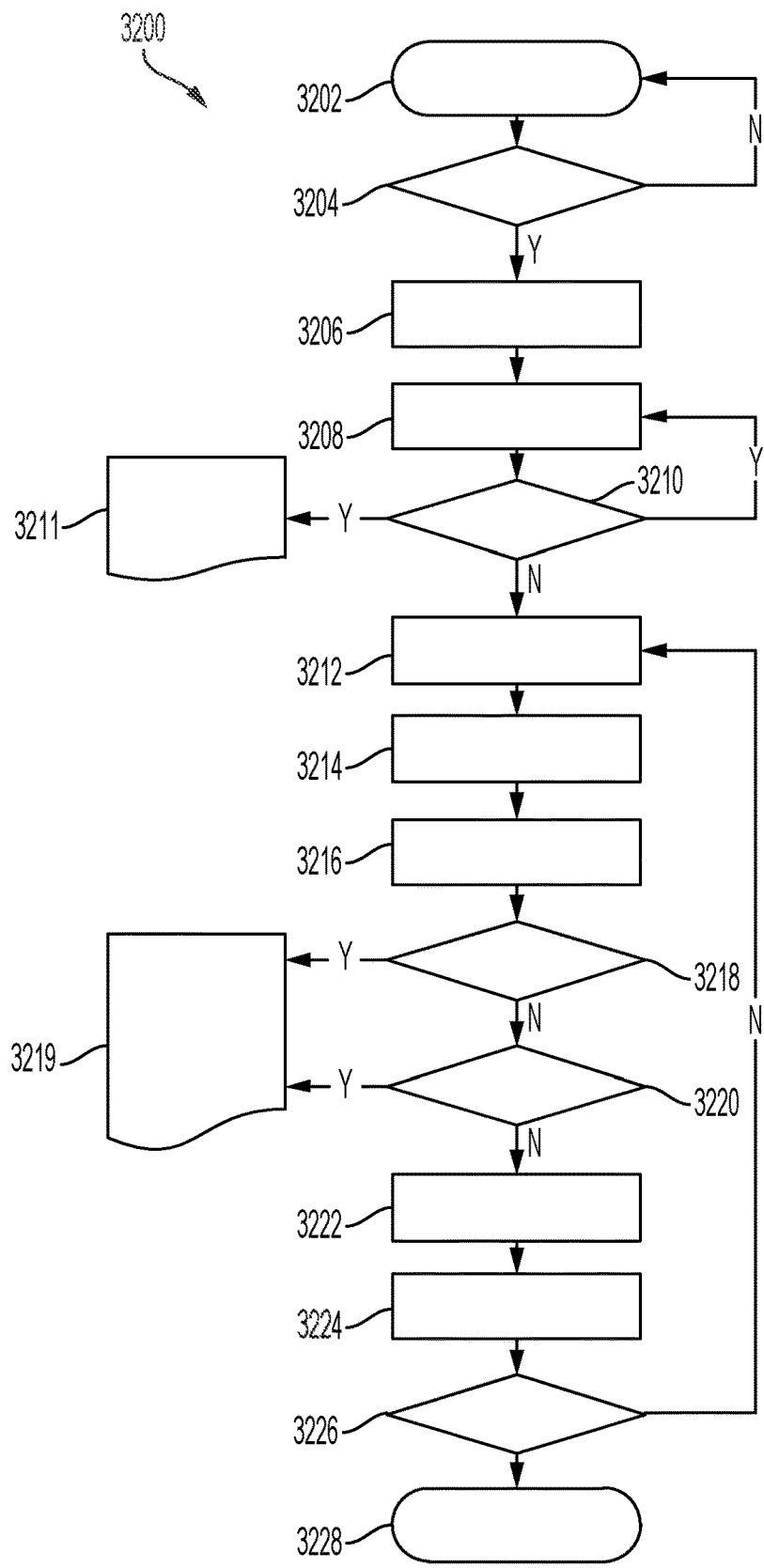
FIG. 13 illustrates a logic flow diagram of a method of detecting and locating media within jaws of an end effector of a surgical instrument of the system of FIG. 10, in accordance with at least one non-limiting aspect of the present disclosure.
Figure 14:
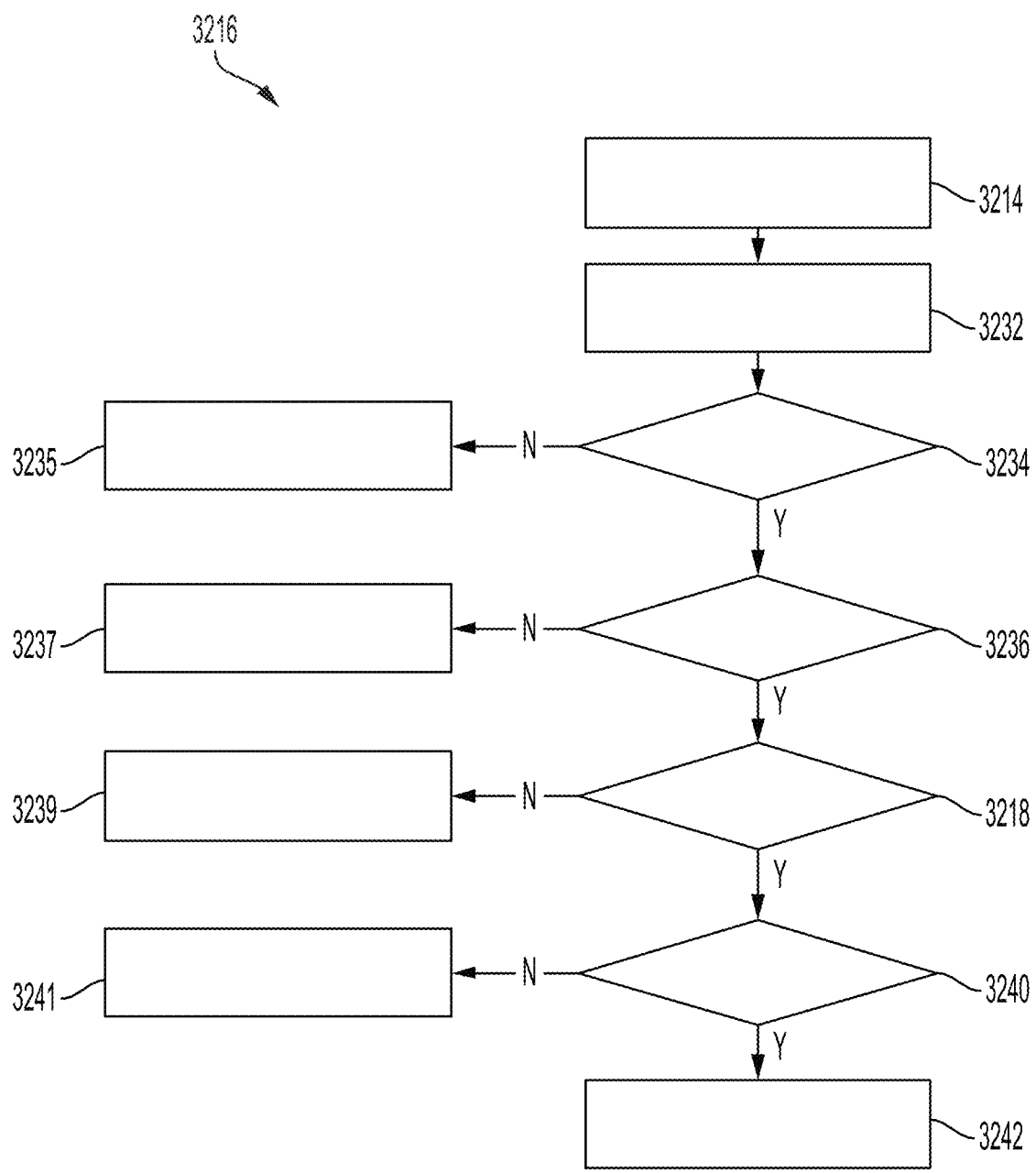
FIG. 14 illustrates a logic flow diagram of a method of detecting an anomaly as part of the method of FIG. 13, in accordance with at least one non-limiting aspect of the present disclosure.
Figure 15:
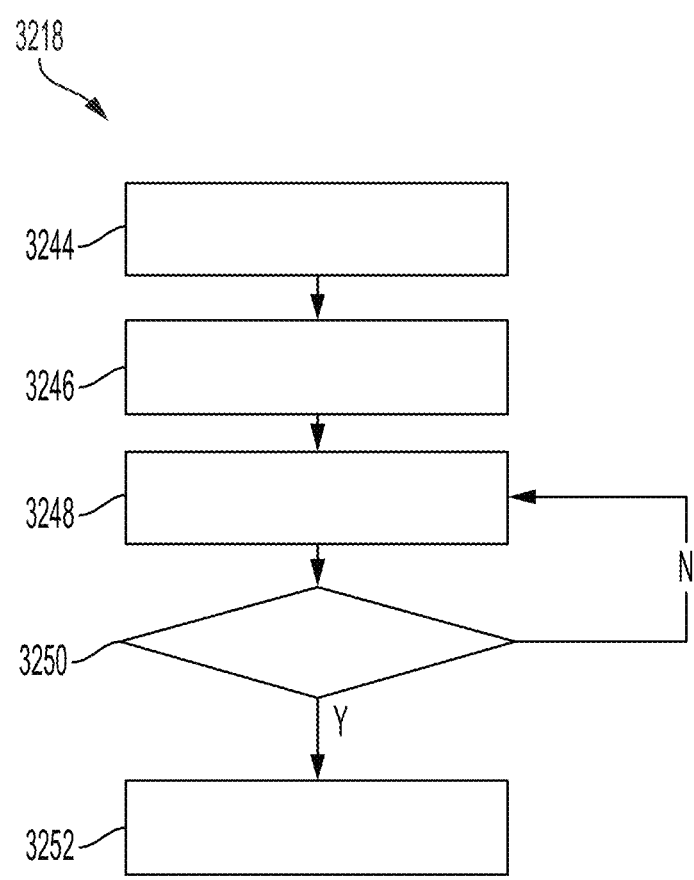
FIG. 15 illustrates a logic flow diagram of a method of detecting a presence of a foreign object within jaws of an end effector, as part of the methods of FIGS. 13 and 14, in accordance with at least one non-limiting aspect of the present disclosure.
Figure 18:
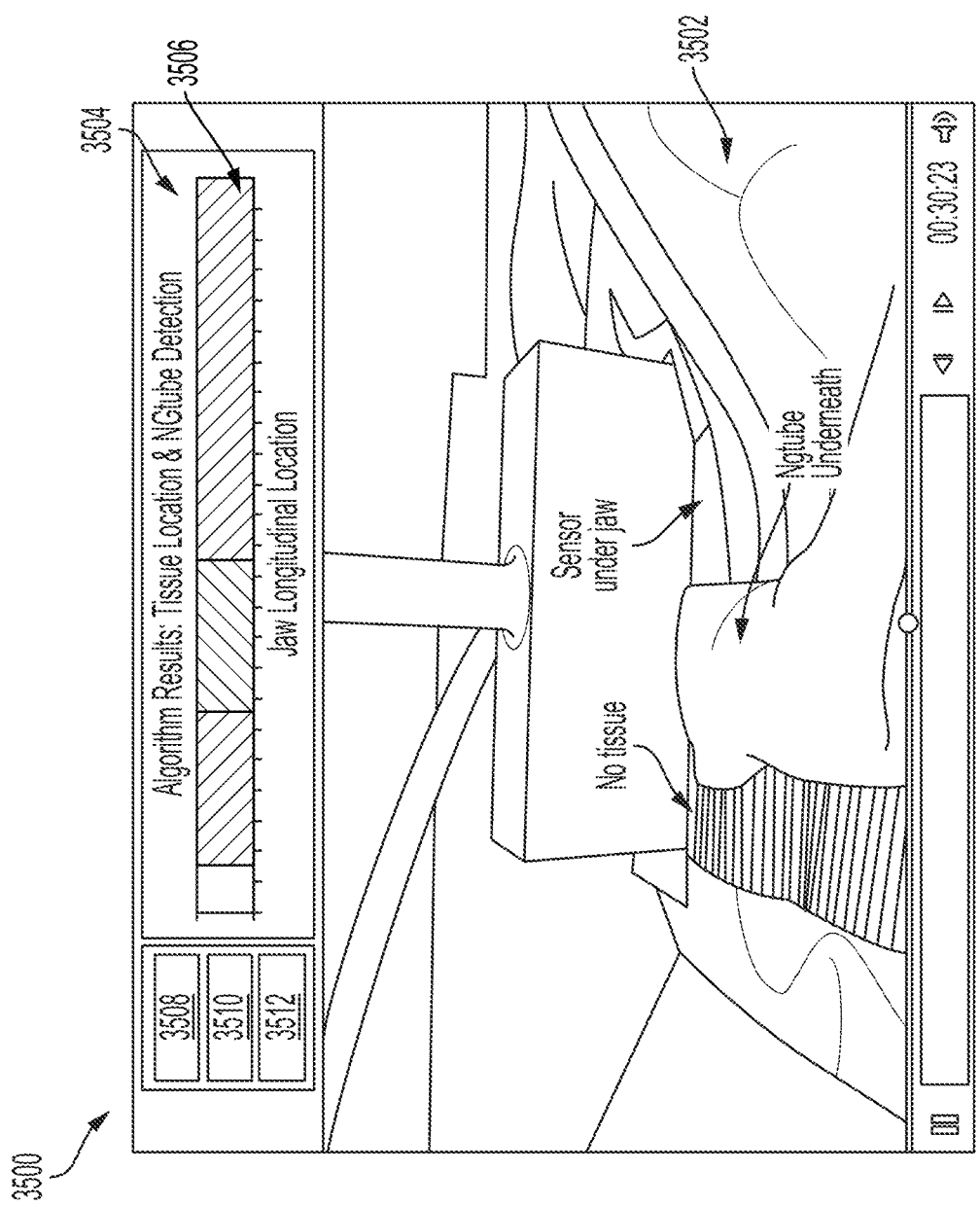
Figure 19:
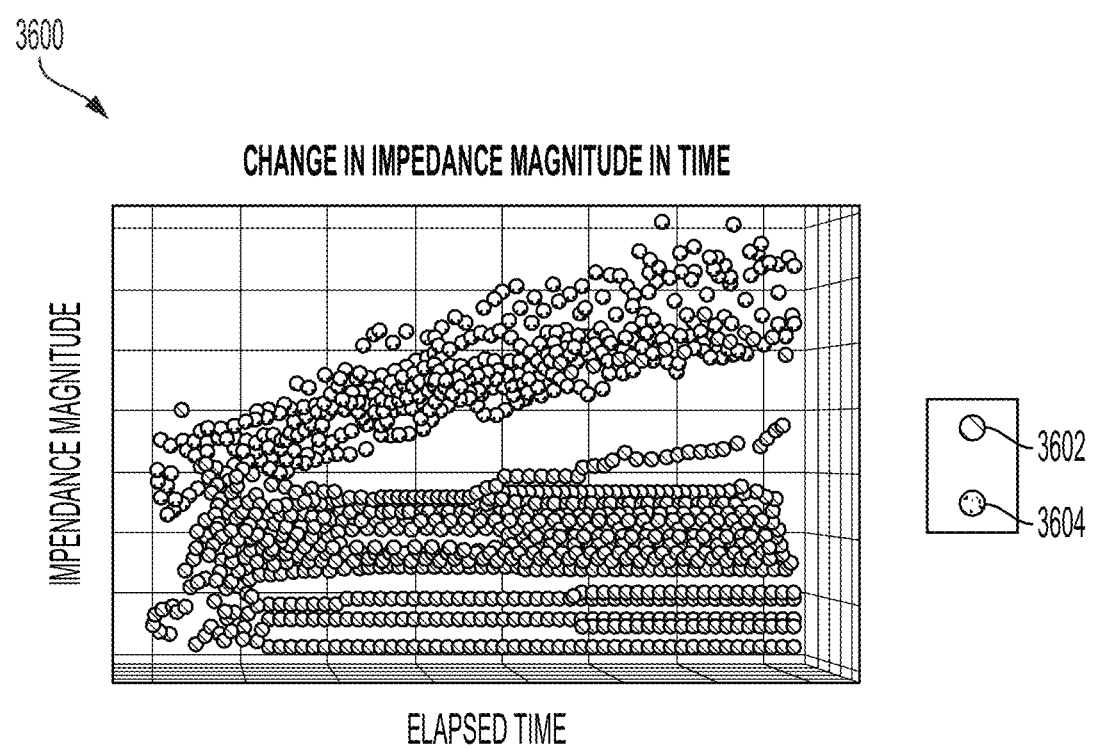
Figure 20:
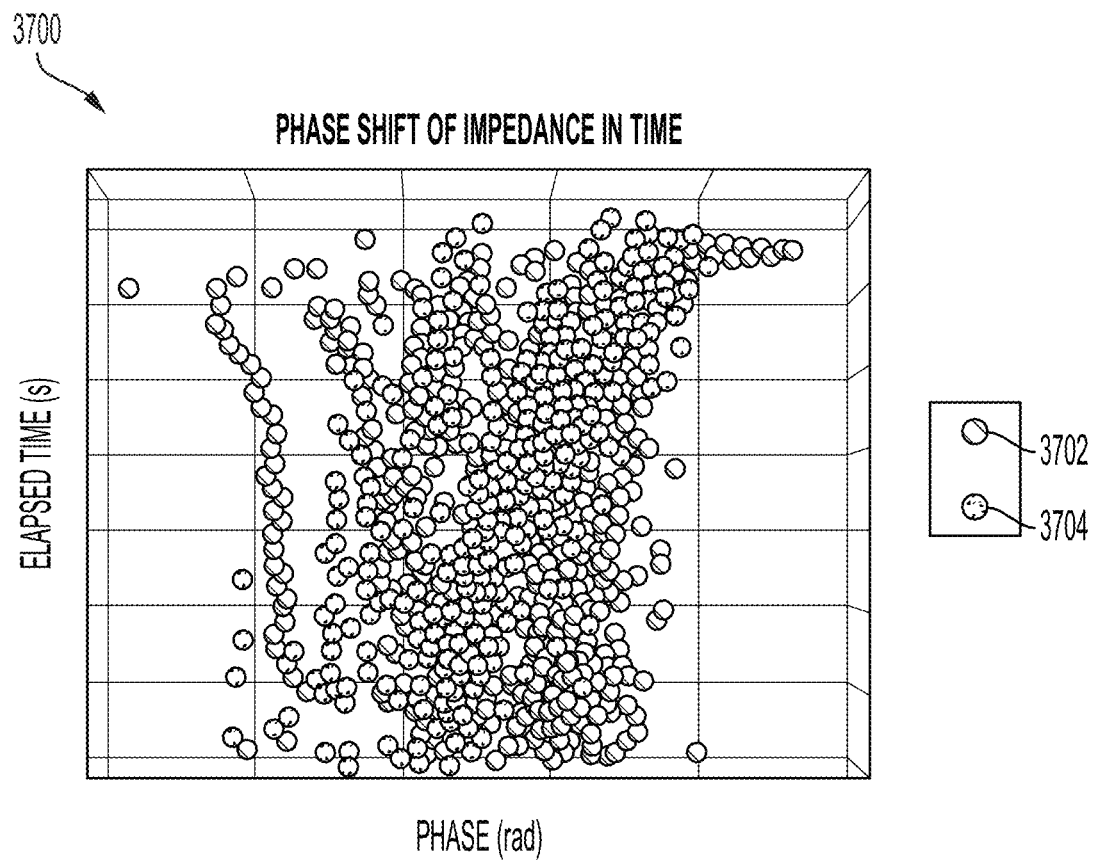
Figure 21:
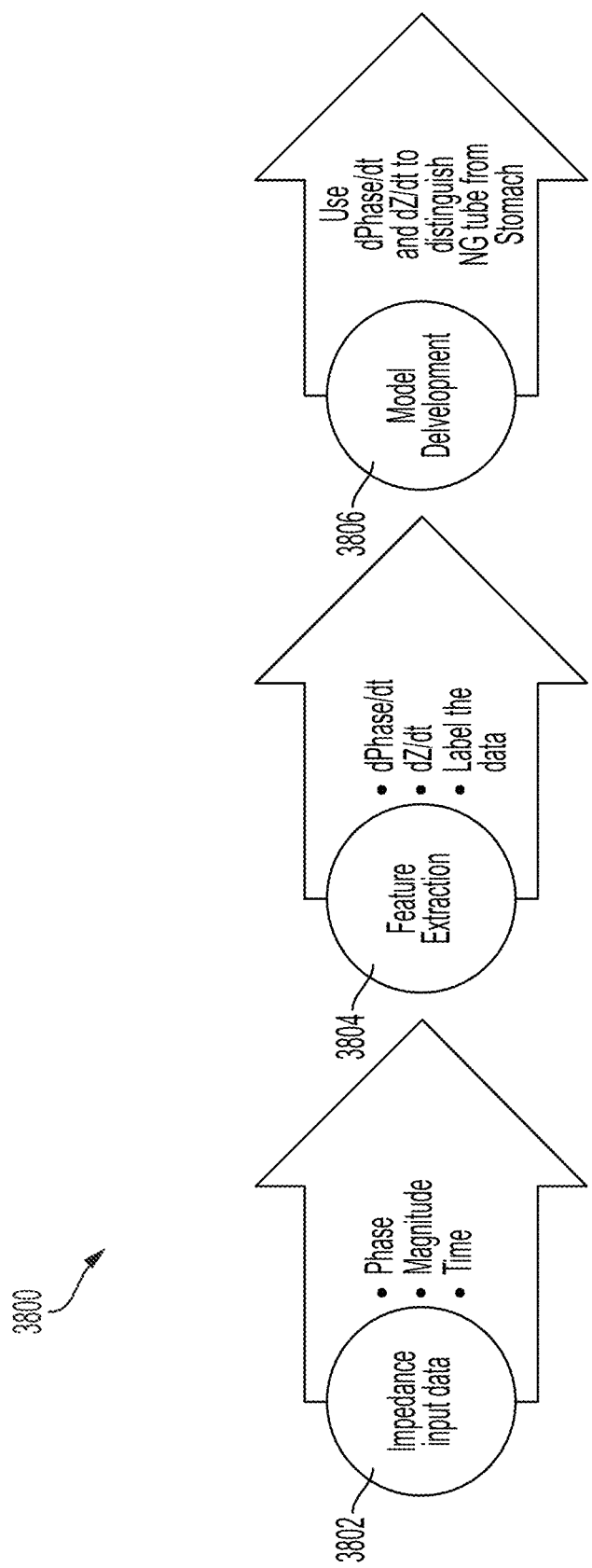
Figure 22:
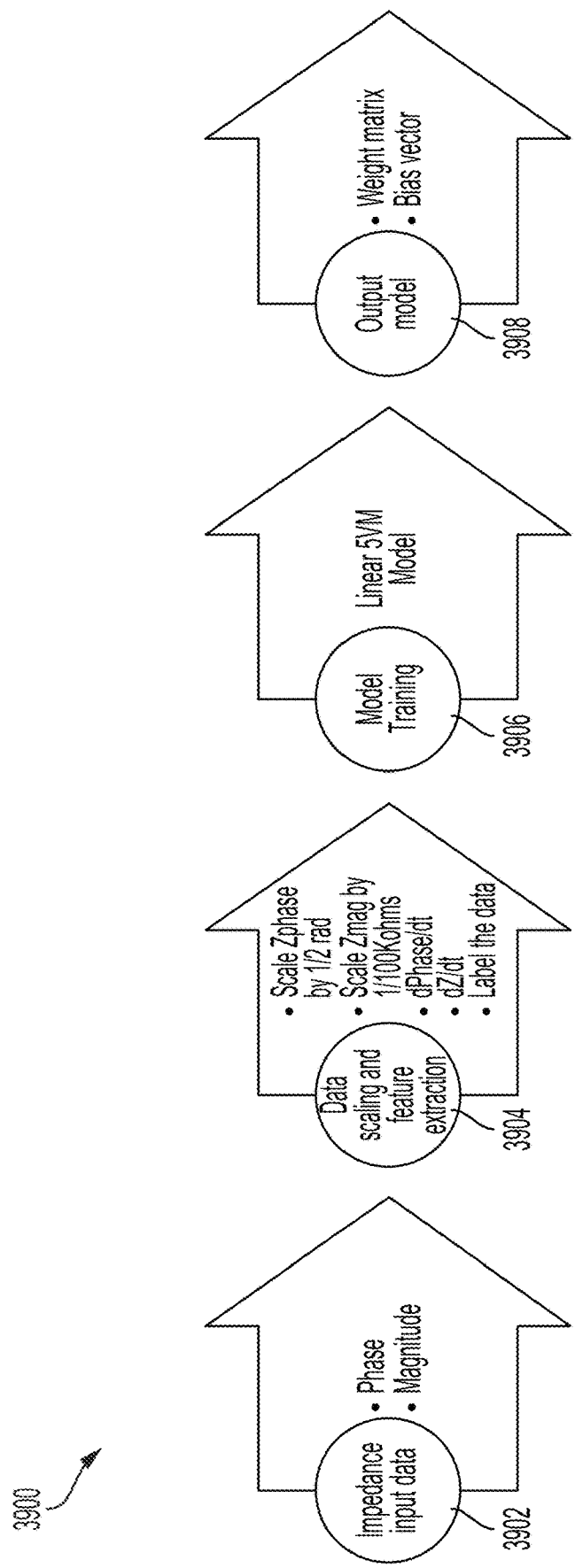
Figure 23:
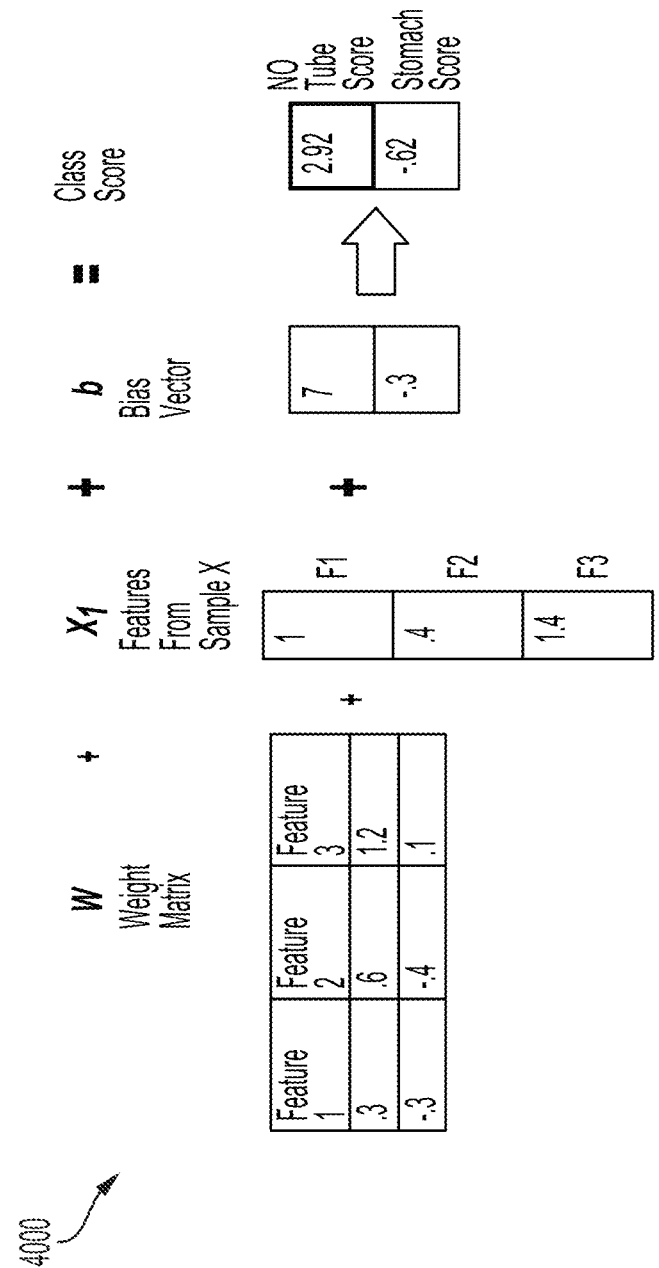
Figures 24A, 24B:
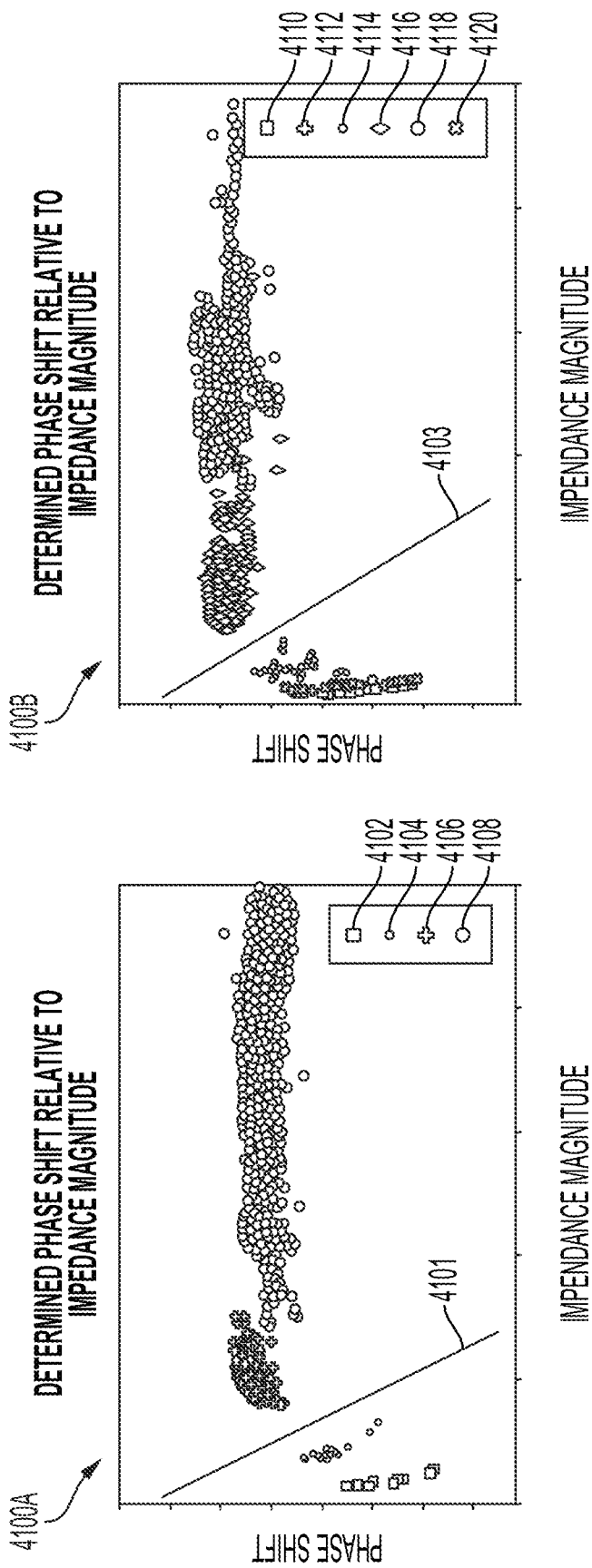
Figure 25:
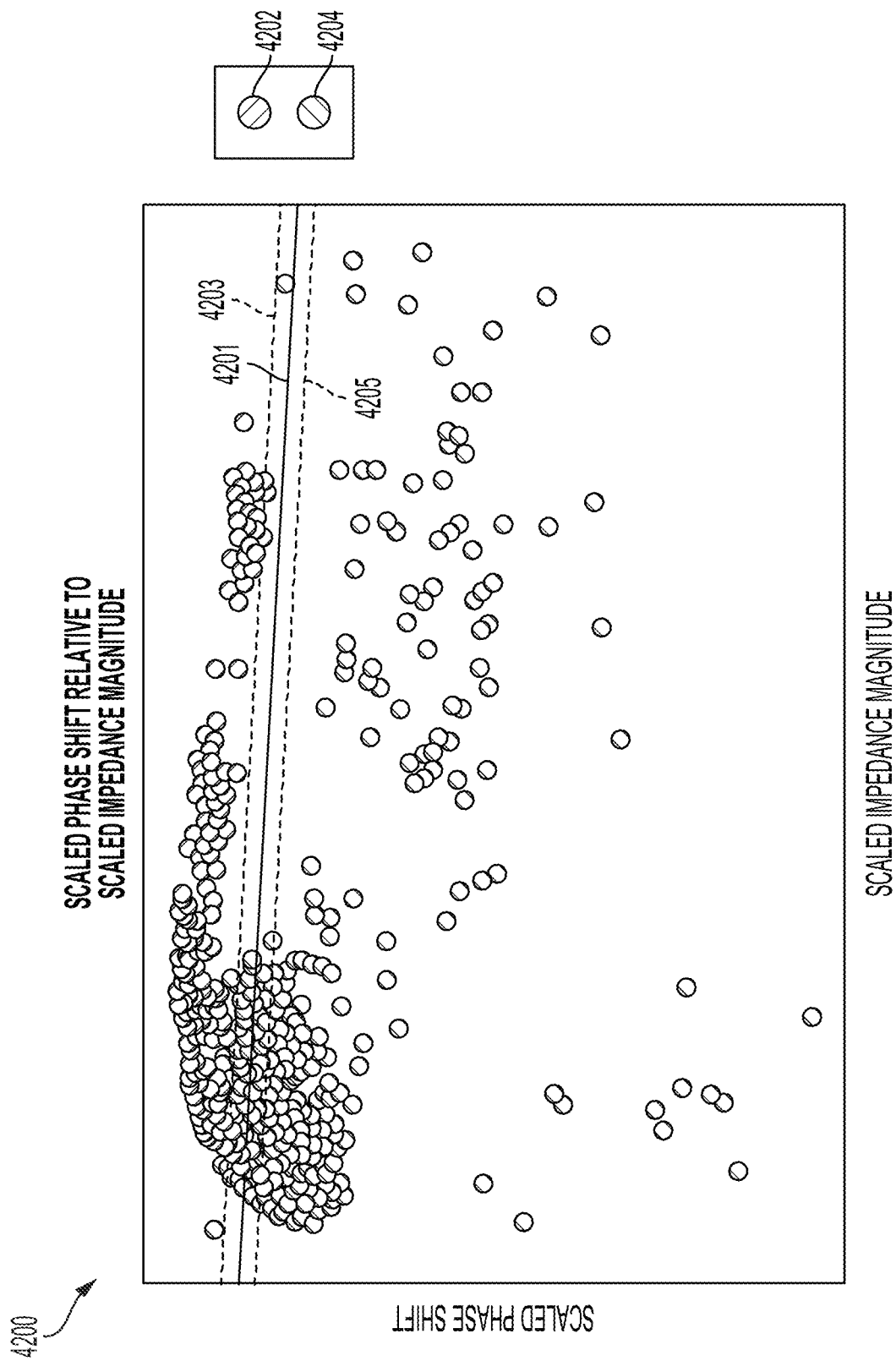
Figure 26:
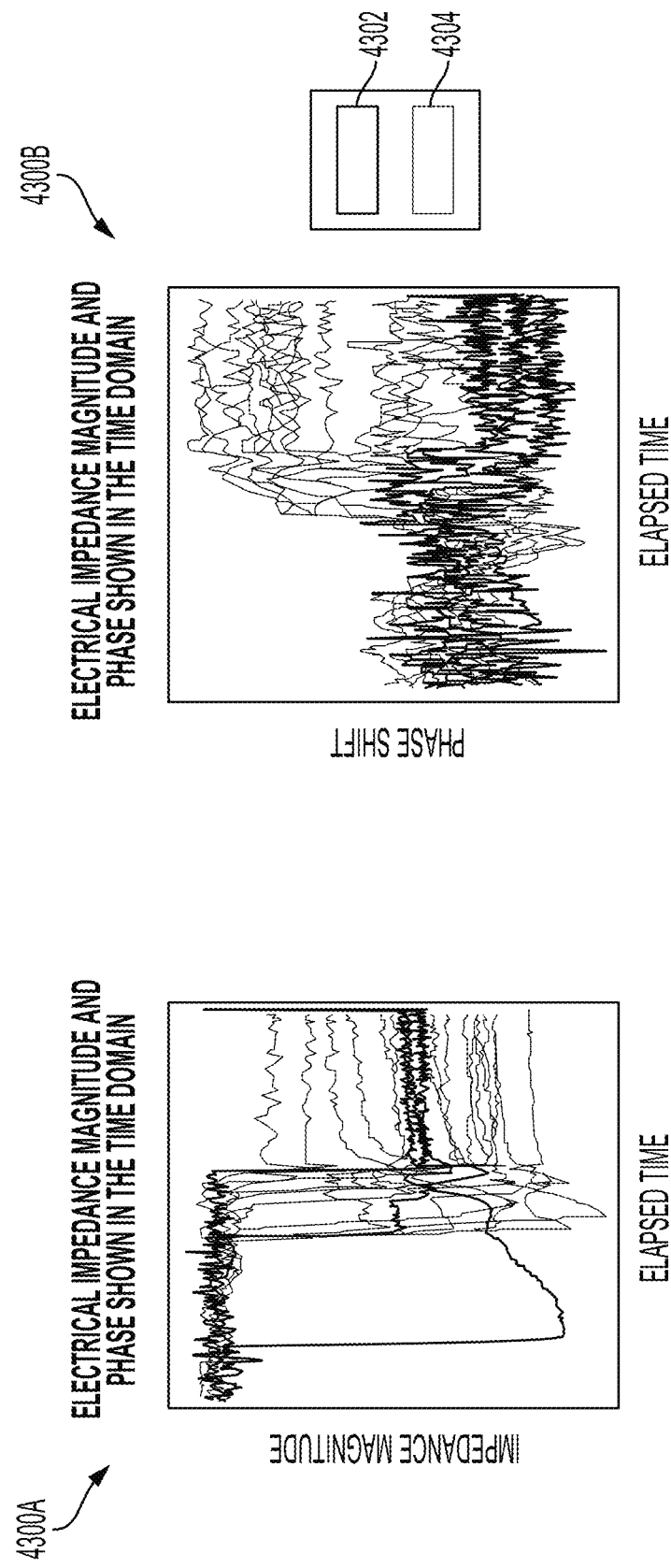
Figure 27:
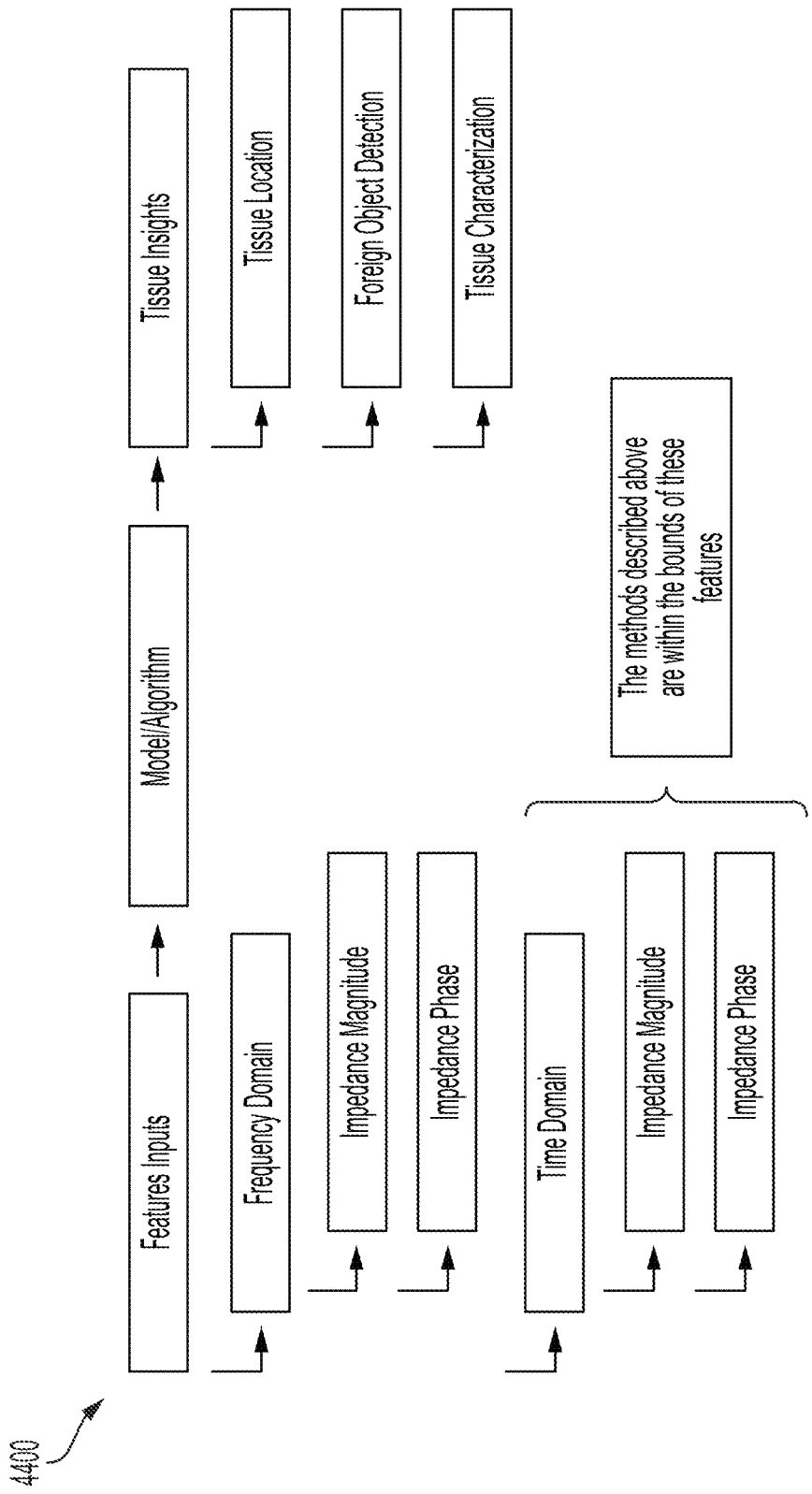
Figure 29A:
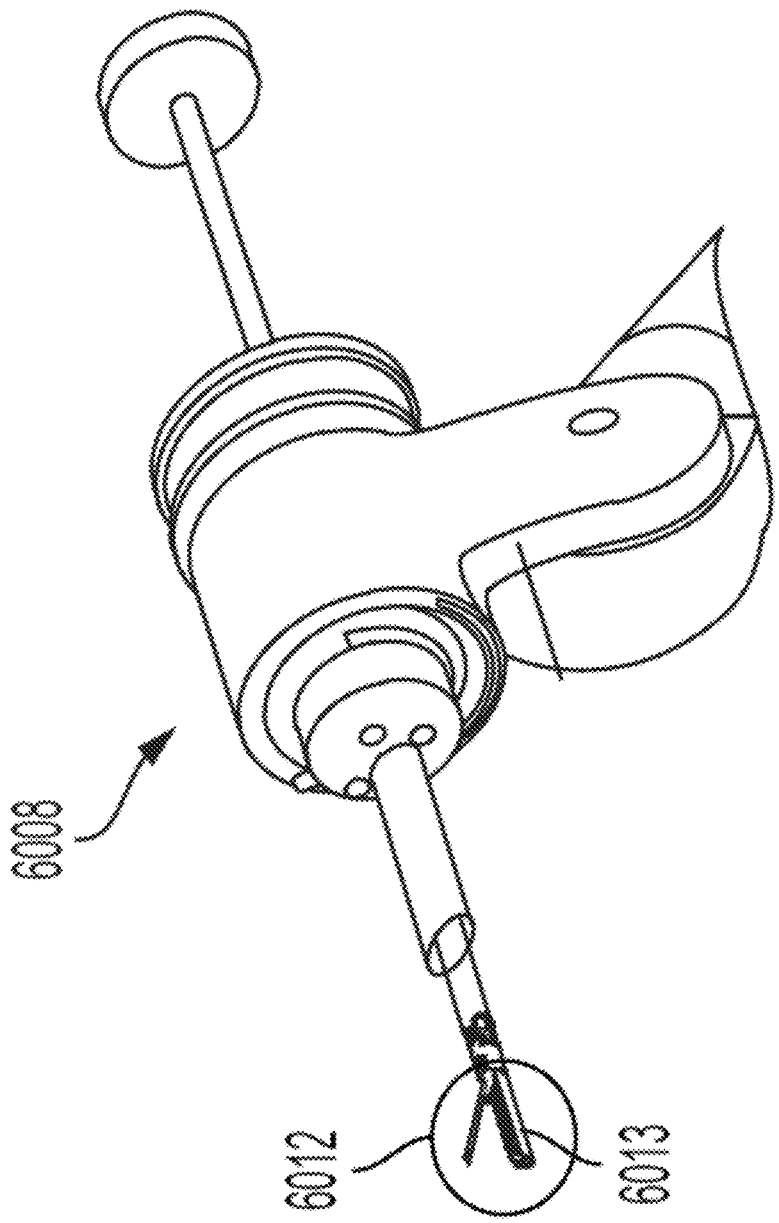
Figure 29C:
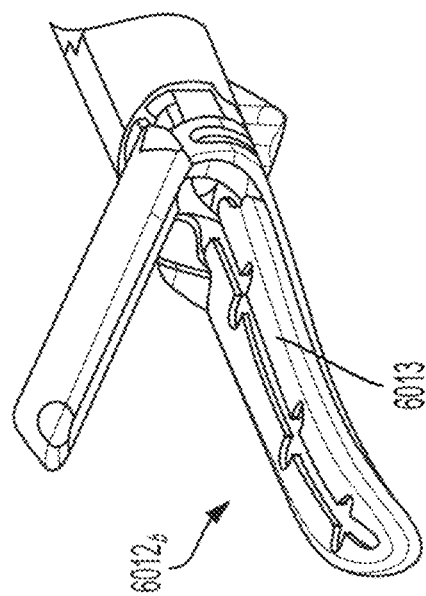
Figure 29B:
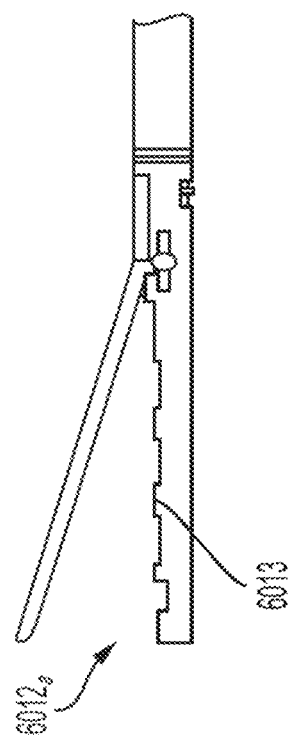
Figure 31:
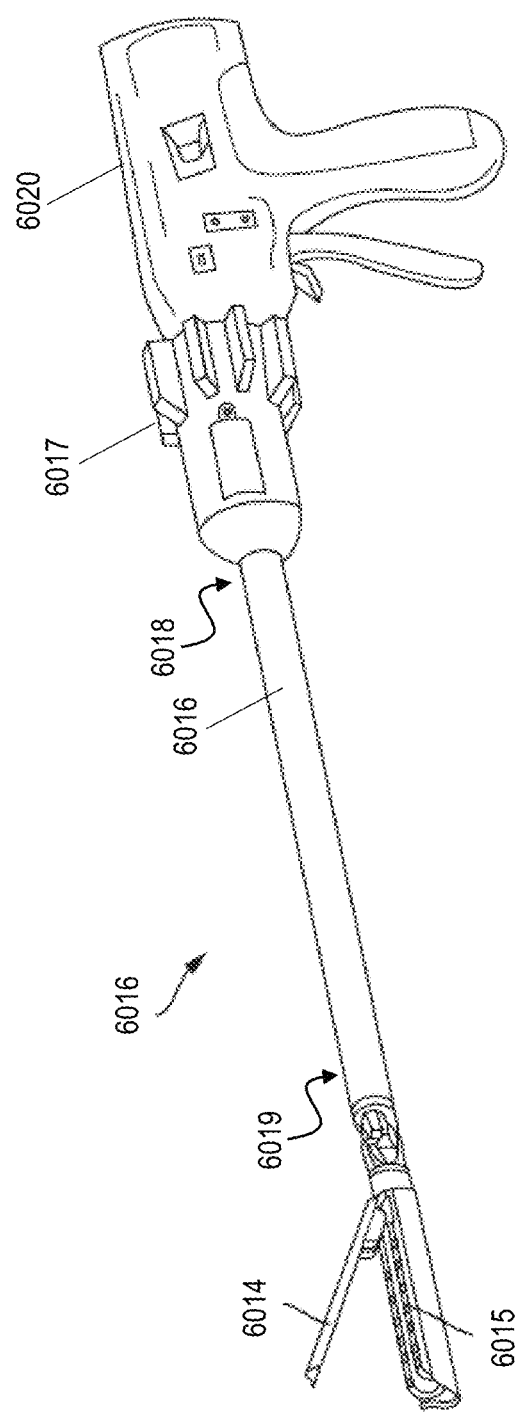
Figure 32:
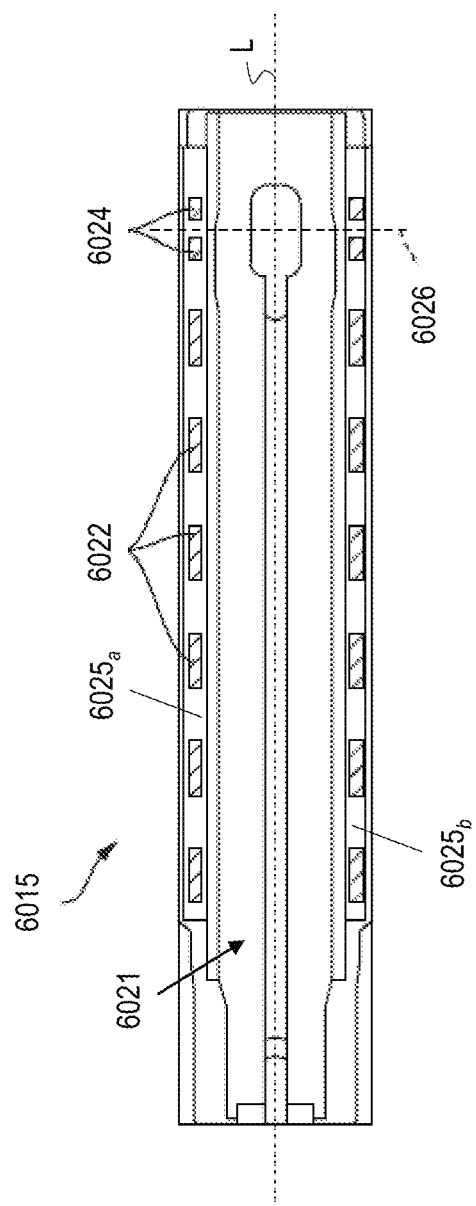
Figure 33A:
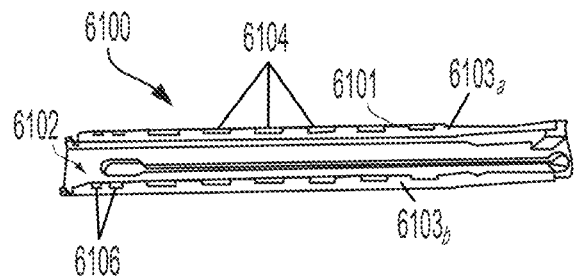
Figure 33B:
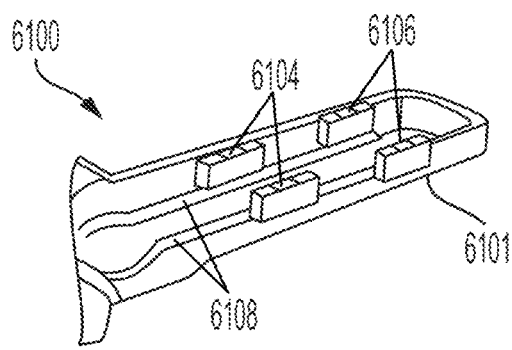
Figure 33C:
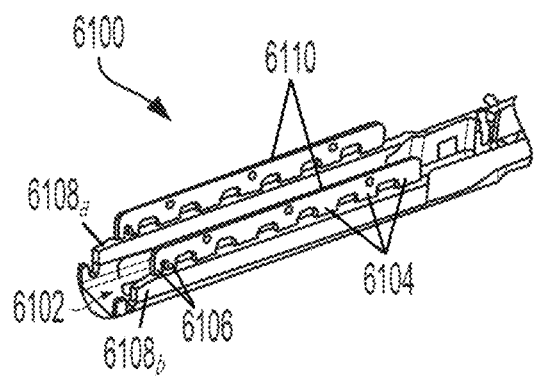
Figure 34A:
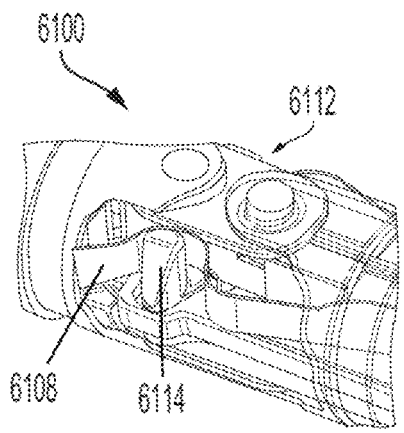
Figure 34B:
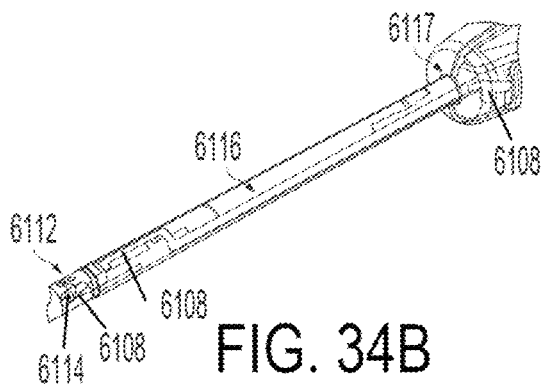
Figure 34C:
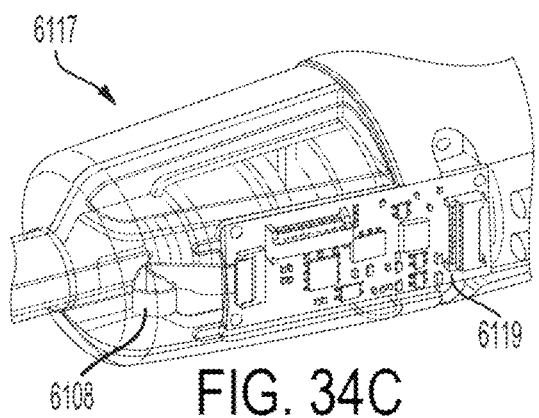
Figure 35:
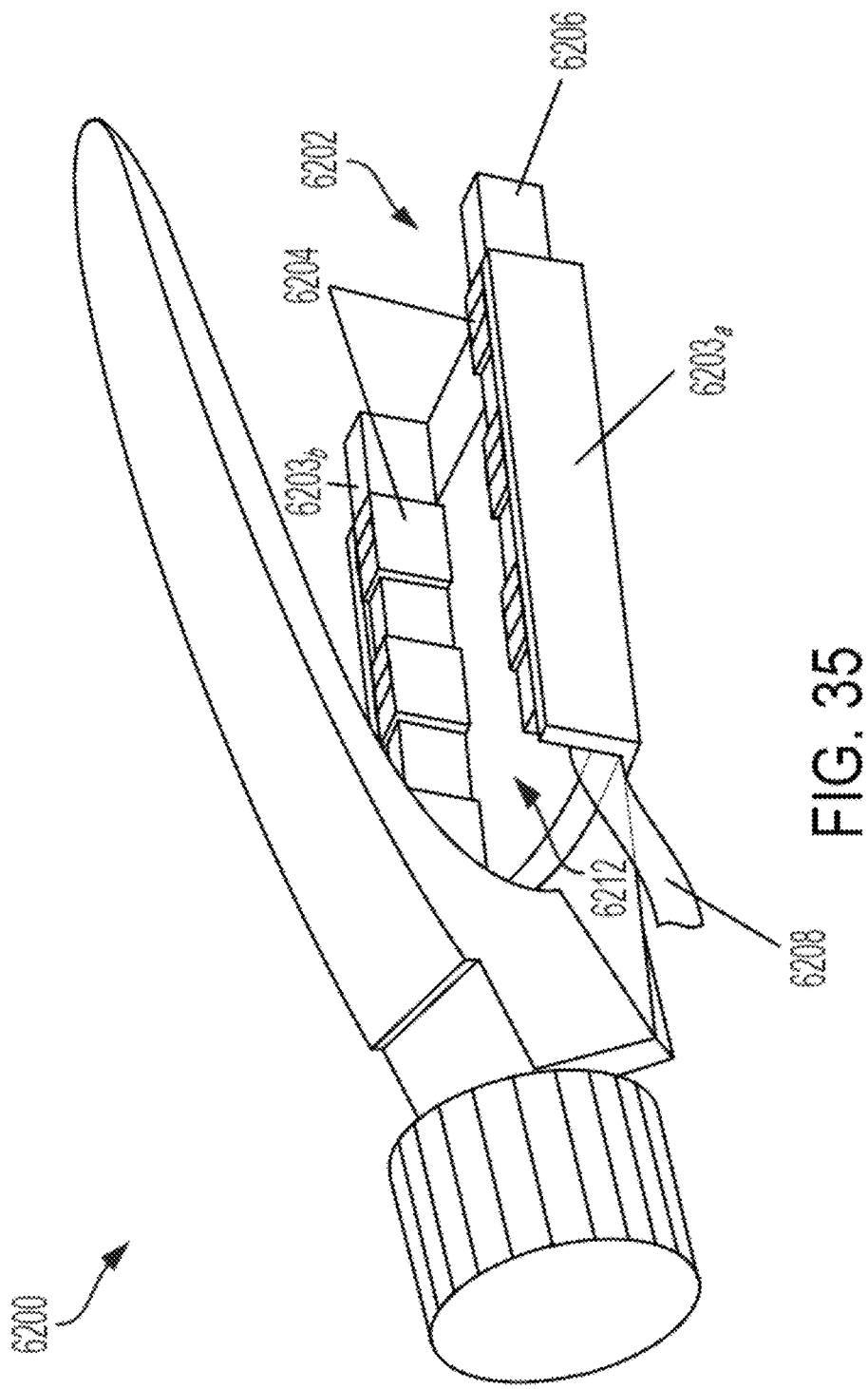
Figure 37B:
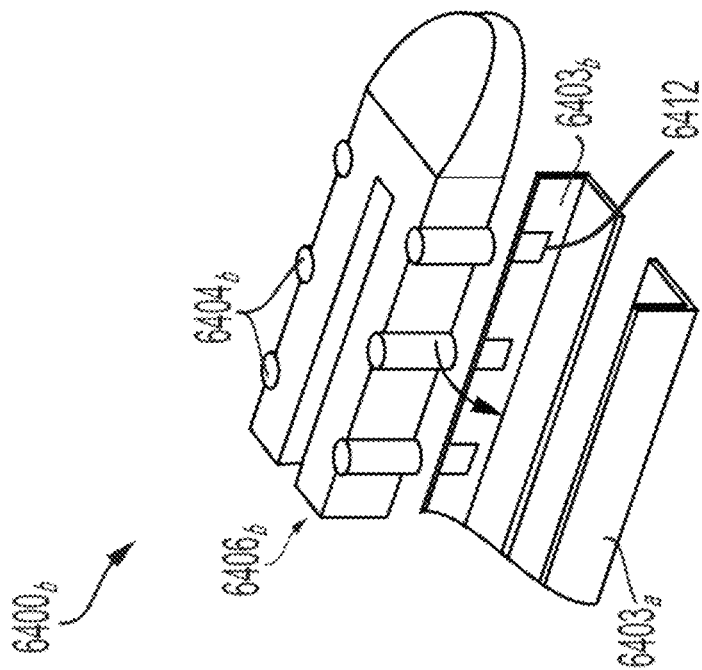
Figure 37A:
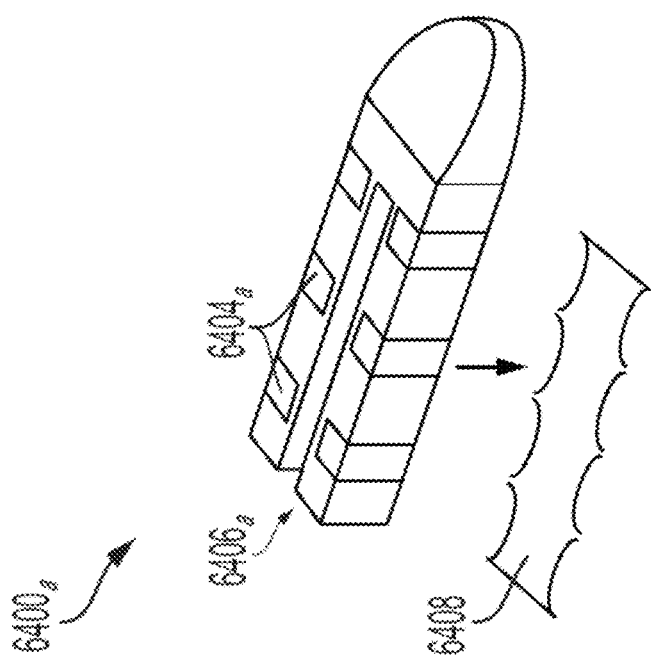
Figure 38:
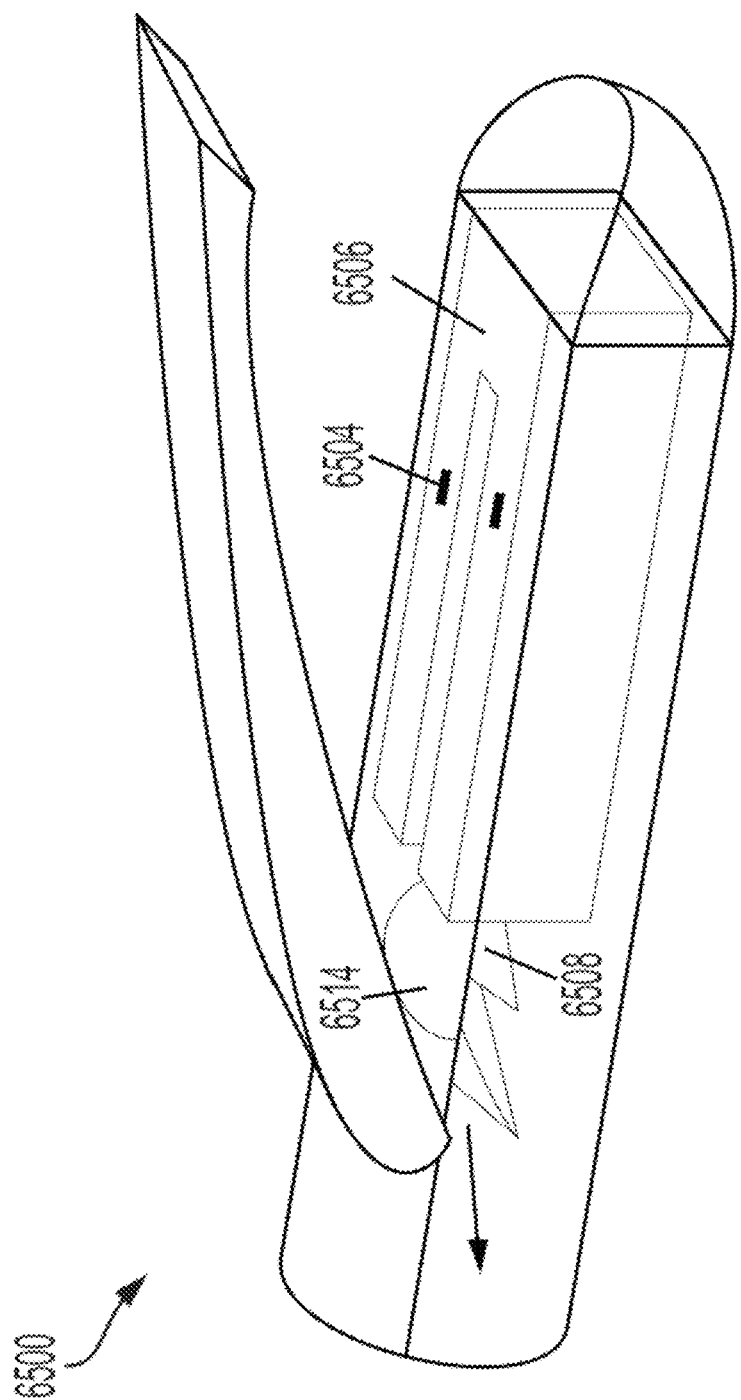
Figure 41:
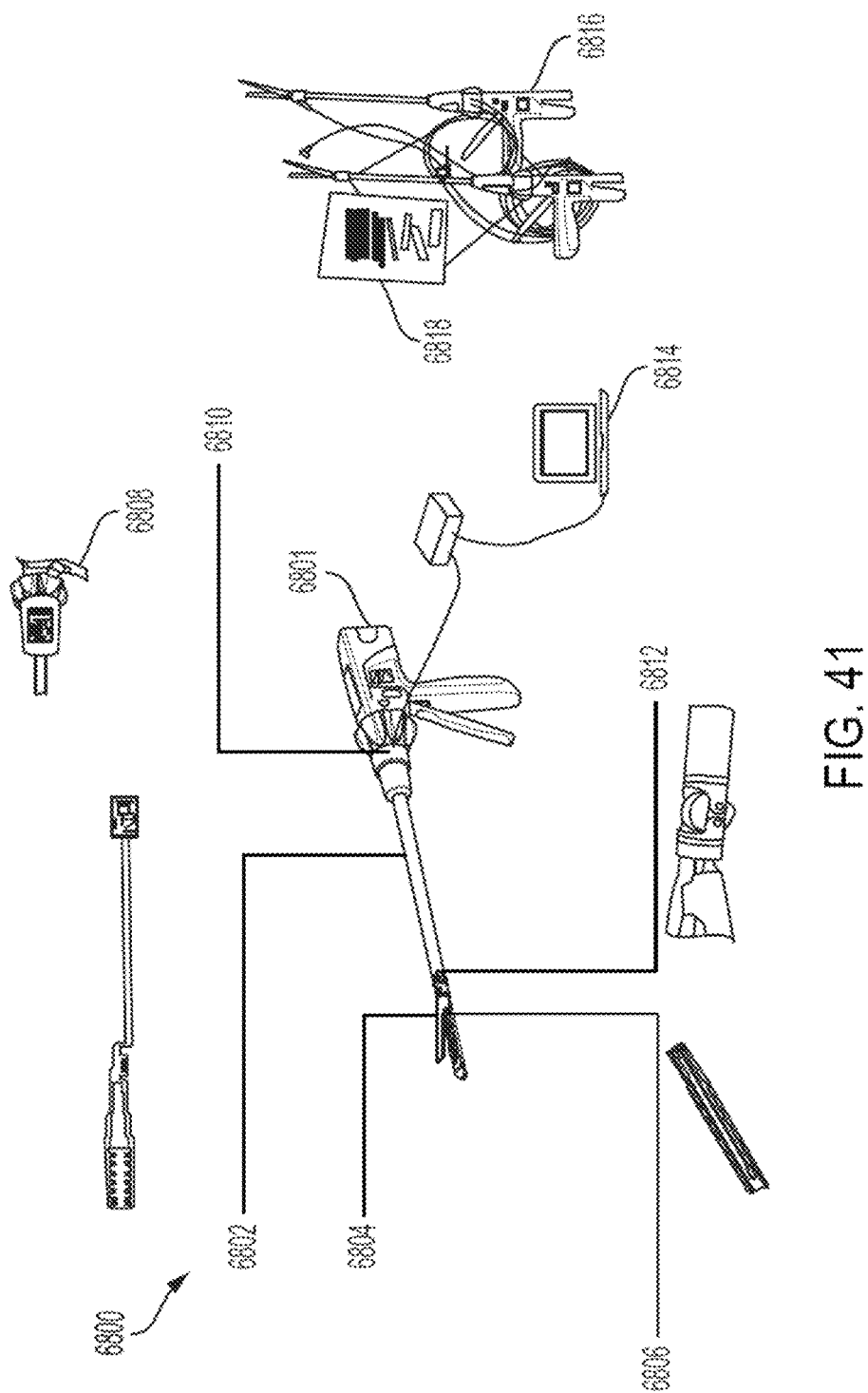
Figure 42:
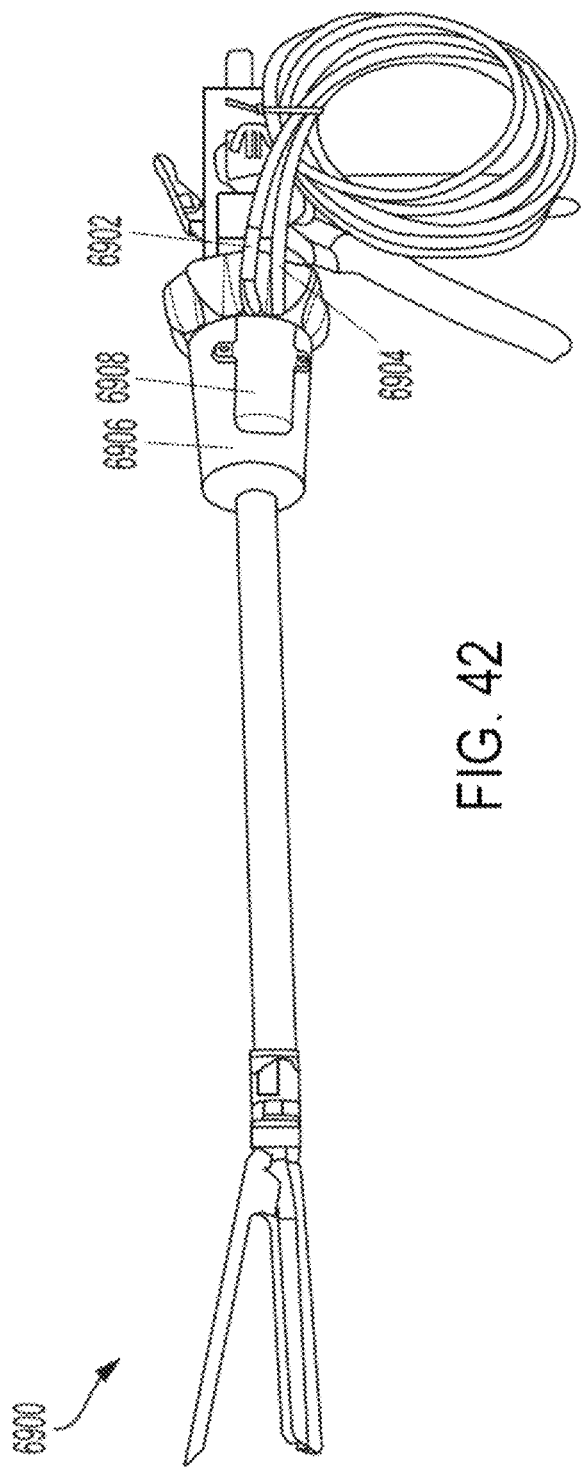
Figure 43:
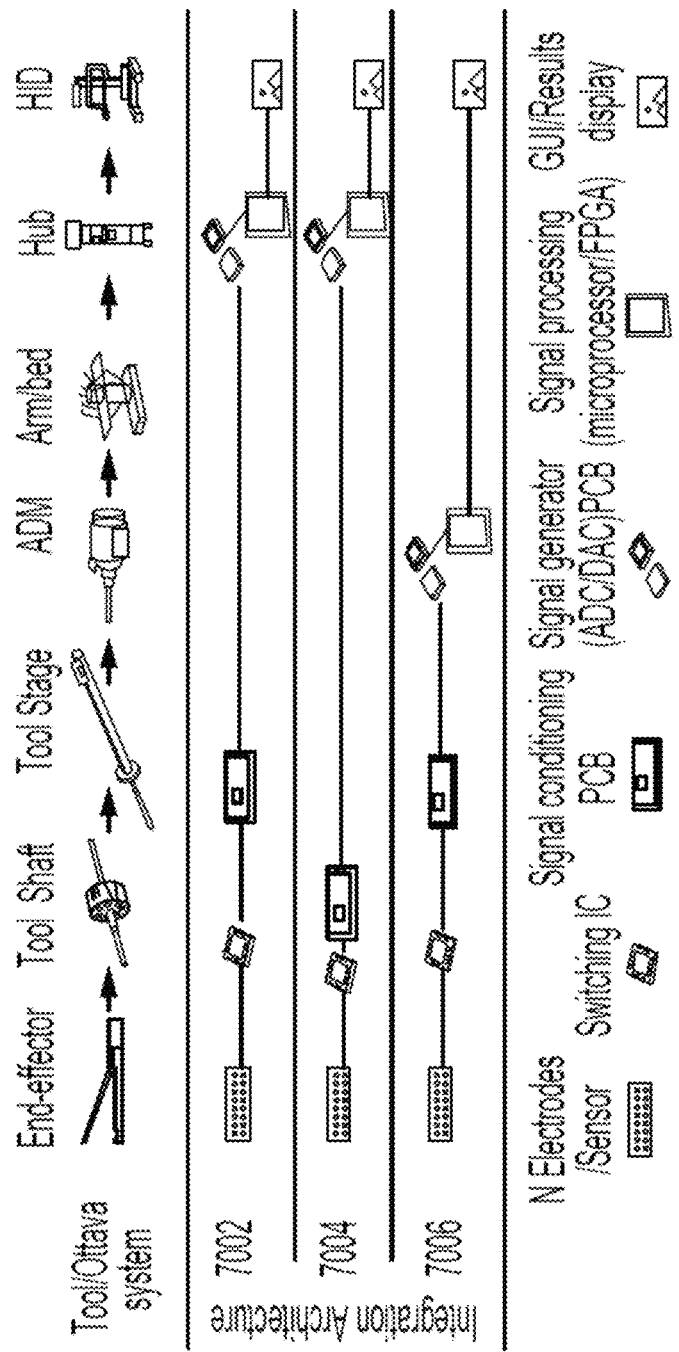
Figure 44:
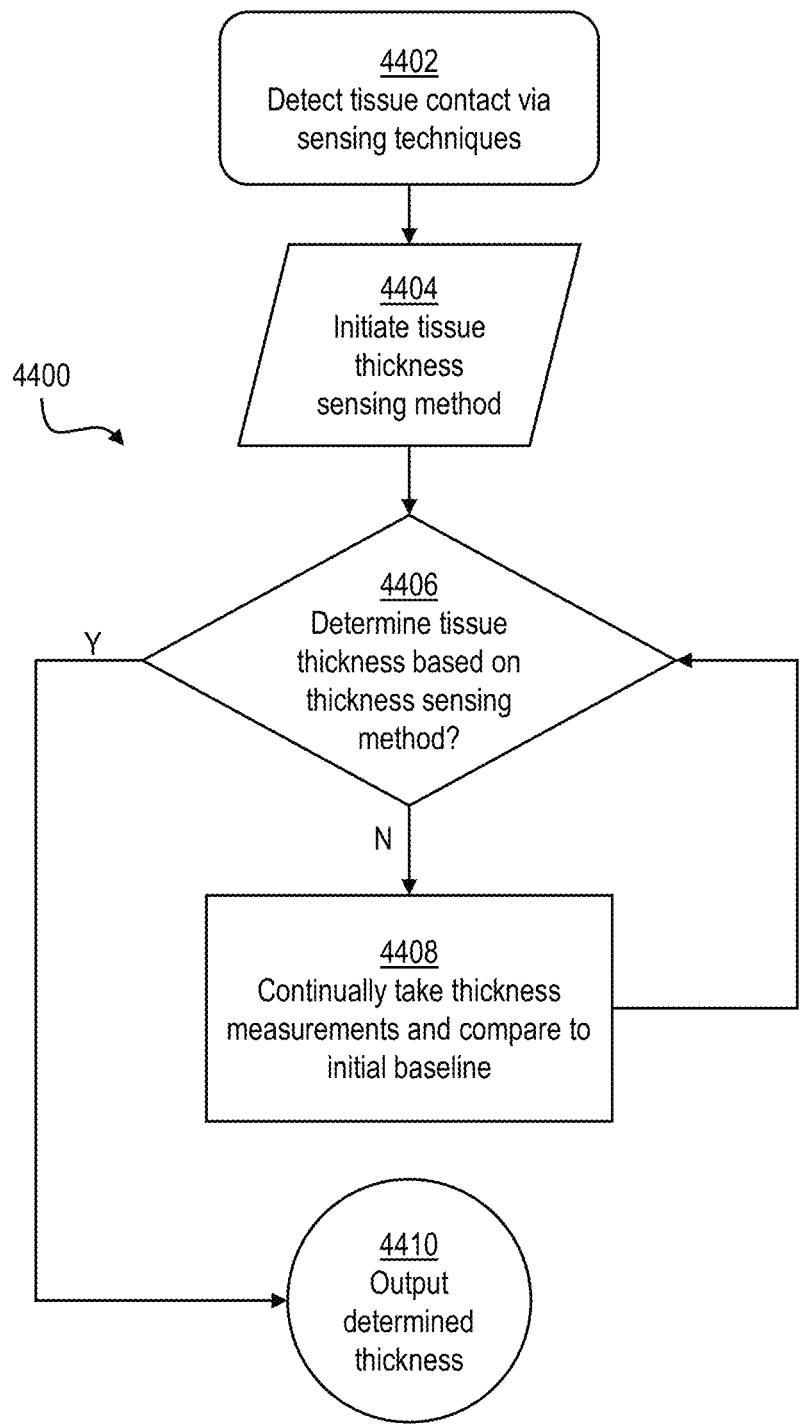

FIGS. 17A-C illustrate another chart depicting experimental results of the methods of FIGS. 13-15, in accordance with at least one non-limiting aspect of the present disclosure;

FIG. 18 illustrates another user interface displayed by a computing device of the system of FIG. 10, in accordance with at least one non-limiting aspect of the present disclosure;

FIG. 19 illustrates another chart depicting experimental results of the methods of FIGS. 13-15, in accordance with at least one non-limiting aspect of the present disclosure;

FIG. 20 illustrates another chart depicting experimental results of the methods of FIGS. 13-15, in accordance with at least one non-limiting aspect of the present disclosure;

FIG. 21 illustrates a logic flow diagram of a method that collectively implements multiple patterns to distinguish detected foreign objects from detected tissue within the jaws of an end effector, in accordance with at least one non-limiting aspect;

FIG. 22 illustrates a logic flow diagram of a method of training an algorithmic model to intelligently classify the location of media within the jaws of an end effector, in accordance with at least one non-limiting aspect;

FIG. 23 illustrates a block diagram of a method of classifying a detected media after an algorithmic model has been trained via the method of FIG. 22, in accordance with at least one non-limiting aspect of the present disclosure;

FIGS. 24A and 24B illustrate several charts depicting a distinction between various media detected within the jaws of an end effector, as determined via the method of FIG. 23, in accordance with at least one non-limiting aspect of the present disclosure;

FIG. 25 illustrates another chart depicting a distinction between various media detected within the jaws of an end effector, as determined via the method of FIG. 23, in accordance with at least one non-limiting aspect of the present disclosure;

FIGS. 26A and 26B illustrate several charts depicting a of characterizing tissue within the jaws of an end effector, in accordance with at least one non-limiting aspect of the present disclosure;

FIG. 27 illustrates a flow chart of a method of detecting media, locating media, and characterizing media positioned between the jaws of an end effector, in accordance with at least one non-limiting aspect of the present disclosure;

FIG. 28 illustrates a surgical system configured to detect, locate, and characterize media positioned between the jaws of an end effector, in accordance with at least one non-limiting aspect of the present disclosure;

FIGS. 29A-C illustrates a robotic surgical instrument configured for use with the system of FIG. 28, in accordance with at least one aspect of the present disclosure;

FIG. 30 illustrates a block diagram of an algorithmic engine employed by the surgical instrument of FIGS. 29A-C, in accordance with at least one non-limiting aspect of the present disclosure;

FIG. 31 illustrates a handheld surgical instrument configured for use with the system of FIG. 28, in accordance with at least one non-limiting aspect of the present disclosure;

FIG. 32 illustrates an exemplary electrode array, in accordance with at least one non-limiting aspect of the present disclosure;

FIGS. 33A-C illustrates another end effector configured for use with the surgical instruments disclosed herein, in accordance with at least one non-limiting aspect of the present disclosure;

FIGS. 34A-C illustrate an articulation joint, shaft, nozzle, and control circuit configured for use with the end effectors and surgical instruments disclosed herein, according to at least one non-limiting aspect of the present disclosure;

FIG. 35 illustrates another end effector, in accordance with at least one non-limiting aspect of the present disclosure;

FIGS. 36A-D illustrate another end effector, in accordance with at least one non-limiting aspect of the present disclosure;

FIGS. 37A and 37B illustrate other end effectors, in accordance with at least one non-limiting aspect of the present disclosure;

FIG. 38 illustrate another end effector, in accordance with at least one non-limiting aspect of the present disclosure;

FIGS. 39A-D illustrate another end effector, in accordance with at least one non-limiting aspect of the present disclosure;

FIG. 40 illustrates a flexible circuit configured for use with any of the end effectors disclosed herein, in accordance with at least one non-limiting aspect of the present disclosure;

FIG. 41 illustrates a system diagram of a system configured to use the surgical instruments and end effectors disclosed herein, in accordance with at least one non-limiting aspect of the present disclosure;

FIG. 42 illustrates a surgical instrument, in accordance with at least one non-limiting aspect of the present disclosure;

FIG. 43 illustrates a diagram illustrating several non-limiting surgical system configurations, in accordance with at least one non-limiting aspect of the present disclosure;

FIG. 44 illustrates a logic flow diagram of a method of identifying a particular contact between the jaws of an end effector and a media positioned within the jaws of the end effector, in accordance with at least one non-limiting aspect of the present disclosure;

FIG. 45 illustrates a logic flow diagram of a method of utilizing the sensing techniques disclosed herein to inform an operation performed by a second surgical instrument, in accordance with at least one non-limiting aspect of the present disclosure; and FIG. 46 illustrates a logic flow diagram of a specific procedure implementing the method of FIG. 45, in accordance with at least one non-limiting aspect of the present disclosure.

Corresponding reference characters indicate corresponding parts throughout the several views. The exemplifications set out herein illustrate various embodiments of the invention, in one form, and such exemplifications are not to be construed as limiting the scope of the invention in any manner.

DESCRIPTION

Applicant of the present application owns U.S. Provisional Patent Application Ser. No. 63/274,207, entitled DEVICES, SYSTEMS, AND METHODS FOR DETECTING TISSUE AND FOREIGN OBJECTS DURING A SURGICAL OPERATION, filed Nov. 1, 2021, the disclosure of which is hereby incorporated by reference in its entirety.

Applicant of the present application owns the following U.S. Provisional Patent Applications, filed on Dec. 30, 2019, the disclosure of each of which is hereby incorporated by reference in its respective entirety: U.S. Provisional Patent Application Ser. No. 62/955,294, entitled USER INTERFACE FOR SURGICAL INSTRUMENT WITH COMBINATION ENERGY MODALITY END-EFFECTOR; U.S. Provisional Patent Application Ser. No. 62/955,299, entitled ELECTROSURGICAL INSTRUMENTS FOR COMBINATION ENERGY DELIVERY; and U.S. Provisional Patent Application Ser. No. 62/955,306, entitled SURGICAL INSTRUMENTS.

Applicant of the present application owns the following U.S. Patent Applications filed on May 28, 2020, each of which is hereby incorporated by reference in its respective entirety: U.S. patent application Ser. No. 16/887,499, entitled USER INTERFACE FOR SURGICAL INSTRUMENT WITH COMBINATION ENERGY MODALITY END-EFFECTOR; U.S. patent application Ser. No. 16/887,493, entitled METHOD OF OPERATING A COMBINATION ULTRASONIC/BIPOLAR RF SURGICAL DEVICE WITH A COMBINATION ENERGY MODALITY END-EFFECTOR; U.S. patent application Ser. No. 16/887,506, entitled DEFLECTABLE SUPPORT OF RF ENERGY ELECTRODE WITH RESPECT TO OPPOSING ULTRASONIC BLADE; U.S. patent application Ser. No. 16/887,515, entitled NON-BIASED DEFLECTABLE ELECTRODE TO MINIMIZE CONTACT BETWEEN ULTRASONIC BLADE AND ELECTRODE; U.S. patent application Ser. No. 16/887,519, entitled DEFLECTABLE ELECTRODE WITH HIGHER DISTAL BIAS RELATIVE TO PROXIMAL BIAS; U.S. patent application Ser. No. 16/887,532, entitled DEFLECTABLE ELECTRODE WITH VARIABLE COMPRESSION BIAS ALONG THE LENGTH OF THE DEFLECTABLE ELECTRODE; U.S. patent application Ser. No. 16/887,554, entitled ASYMMETRIC SEGMENTED ULTRASONIC SUPPORT PAD FOR COOPERATIVE ENGAGEMENT WITH A MOVABLE RF ELECTRODE; U.S. patent application Ser. No. 16/887,561, entitled VARIATION IN ELECTRODE PARAMETERS AND DEFLECTABLE ELECTRODE TO MODIFY ENERGY DENSITY AND TISSUE INTERACTION; U.S. patent application Ser. No. 16/887,568, entitled TECHNIQUES FOR DETECTING ULTRASONIC BLADE TO ELECTRODE CONTACT AND REDUCING POWER TO ULTRASONIC BLADE; U.S. patent application Ser. No. 16/887,576, entitled CLAMP ARM JAW TO MINIMIZE TISSUE STICKING AND IMPROVE TISSUE CONTROL; U.S. patent application Ser. No. 16/887,579, entitled PARTIALLY CONDUCTIVE CLAMP ARM PAD TO ENABLE ELECTRODE WEAR THROUGH AND MINIMIZE SHORT CIRCUITING; U.S. patent application Ser. No. 10/289,787, entitled ULTRASONIC CLAMP COAGULATOR APPARATUS HAVING AN IMPROVED CLAMPING END-EFFECTOR; and U.S. patent application Ser. No. 11/243,585, entitled ULTRASONIC CLAMP COAGULATOR APPARATUS HAVING AN IMPROVED CLAMPING END-EFFECTOR.

Applicant of the present application owns the following U.S. Patent Applications filed on May 28, 2020, each of which is hereby incorporated by reference in its respective entirety: U.S. patent application Ser. No. 16/885,813, entitled METHOD FOR AN ELECTROSURGICAL PROCEDURE; U.S. patent application Ser. No. 16/885,820, entitled ARTICULATABLE SURGICAL INSTRUMENT; U.S. patent application Ser. No. 16/885,823, entitled SURGICAL INSTRUMENT WITH JAW ALIGNMENT FEATURES; U.S. patent application Ser. No. 16/885,826, entitled SURGICAL INSTRUMENT WITH ROTATABLE AND ARTICULATABLE SURGICAL END EFFECTOR; U.S. patent application Ser. No. 16/885,838, entitled ELECTROSURGICAL INSTRUMENT WITH ASYNCHRONOUS ENERGIZING ELECTRODES; U.S. patent application Ser. No. 16/885,851, entitled ELECTROSURGICAL INSTRUMENT WITH ELECTRODES BIASING SUPPORT; U.S. patent application Ser. No. 16/885,860, entitled ELECTROSURGICAL INSTRUMENT WITH FLEXIBLE WIRING ASSEMBLIES; U.S. patent application Ser. No. 16/885,866, entitled ELECTROSURGICAL INSTRUMENT WITH VARIABLE CONTROL MECHANISMS; U.S. patent application Ser. No. 16/885,870, entitled ELECTROSURGICAL SYSTEMS WITH INTEGRATED AND EXTERNAL POWER SOURCES; U.S. patent application Ser. No. 16/885,873, entitled ELECTROSURGICAL INSTRUMENTS WITH ELECTRODES HAVING ENERGY FOCUSING FEATURES; U.S. patent application Ser. No. 16/885,879, entitled ELECTROSURGICAL INSTRUMENTS WITH ELECTRODES HAVING VARI- ABLE ENERGY DENSITIES; U.S. patent application Ser. No. 16/885,881, entitled ELECTROSURGICAL INSTRUMENT WITH MONOPOLAR AND BIPOLAR ENERGY CAPABILITIES; U.S. patent application Ser. No. 16/885,888, entitled ELECTROSURGICAL END EFFECTORS WITH THERMALLY INSULATIVE AND THERMALLY CONDUCTIVE PORTIONS; U.S. patent application Ser. No. 16/885,893, entitled ELECTROSURGICAL INSTRUMENT WITH ELECTRODES OPERABLE IN BIPOLAR AND MONOPOLAR MODES; U.S. patent application Ser. No. 16/885,900, entitled ELECTROSURGICAL INSTRUMENT FOR DELIVERING BLENDED ENERGY MODALITIES TO TISSUE; U.S. patent application Ser. No. 16/885,917, entitled CONTROL PROGRAM ADAPTATION BASED ON DEVICE STATUS AND USER INPUT; U.S. patent application Ser. No. 16/885,923, entitled CONTROL PROGRAM FOR MODULAR COMBINATION ENERGY DEVICE; and U.S. patent application Ser. No. 16/885,931, entitled SURGICAL SYSTEM COMMUNICATION PATHWAYS.

Applicant of the present application owns related U.S. patent application Ser. No. 16/951,259, filed Nov. 18, 2020 and titled MULTI-LAYER CLAMP ARM PAD FOR ENHANCED VERSATILITY AND PERFORMANCE OF A SURGICAL DEVICE, the disclosure of which is hereby incorporated by reference in its respective entirety.

Applicant of the present application owns related U.S. patent application Ser. No. 16/887,493, filed May 29, 2020 and titled METHOD OF OPERATING A COMBINATION ULTRASONIC/BIPOLAR RF SURGICAL DEVICE WITH A COMBINATION ENERGY MODALITY END-EFFECTOR, the disclosure of which is hereby incorporated by reference in its respective entirety.

Applicant of the present application owns related U.S. patent application Ser. No. 16/453,343, filed Jun. 26, 2019, and titled STAPLE CARTRIDGE RETAINER SYSTEM WITH AUTHENTICATION KEYS, the disclosure of which is hereby incorporated by reference in its respective entirety.

Before explaining various forms of surgical devices in detail, it should be noted that the illustrative forms are not limited in application or use to the details of construction and arrangement of parts illustrated in the accompanying drawings and description. The illustrative forms may be implemented or incorporated in other forms, variations and modifications, and may be practiced or carried out in various ways. Further, unless otherwise indicated, the terms and expressions utilized herein have been chosen for the purpose of describing the illustrative forms for the convenience of the reader and are not for the purpose of limitation thereof. As used herein, the term "surgical device" is used interchangeably with the term "surgical instrument."

Further, it is understood that any one or more of the following-described forms, expressions of forms, examples, can be combined with any one or more of the other following-described forms, expressions of forms, and examples.

Various forms are directed to improved ultrasonic and/or electrosurgical (RF) instruments configured for effecting tissue treating, dissecting, cutting, and/or coagulation during surgical procedures. In one form, a combined ultrasonic and electrosurgical device may be configured for use in open surgical procedures, but has applications in other types of surgery, such as minimally invasive laparoscopic, orthoscopic, or thoracoscopic procedures, for example, non-invasive endoscopic procedures, either in hand held or and robotic-assisted procedures. Versatility is achieved by selective application of multiple energy modalities simultaneously, independently, sequentially, or combinations thereof. For example, versatility may be achieved by selective use of ultrasonic and electrosurgical energy (e.g., monopolar or bipolar RF energy) either simultaneously, independently, sequentially, or combinations thereof.

Although handheld and robotic surgical devices, such as surgical staplers, can provide numerous surgical benefits, it would be beneficial if such devices could be outfitted with sensing and feedback features, which could generate information regarding tissue location in jaws, tissue characteristics, and the presence of foreign objects within the jaws of a surgical device. Such features could bring high value to both hand-held and robotic surgical devices that could make surgical operations, such as stapling tasks, more efficient, precise, and safer for the patient. Electrical impedance spectroscopy ("EIS") is a powerful technique that utilizes particularly configured signals to probe the impedance characteristics of objects. Accordingly, EIS techniques can be implemented to scan a tissue sample within the jaws of a surgical device using signals with a wide range of frequencies to generate an impedance spectrum for the tissue sample. Accordingly, there is a need for improved surgical devices, systems, and methods for detecting tissue locations and foreign objects. Such surgical devices, systems, and methods can employ EIS techniques to scan and characterize a tissue sample and thus, improve the efficiency, precision, and safety of a surgical operation.

Figure 1:
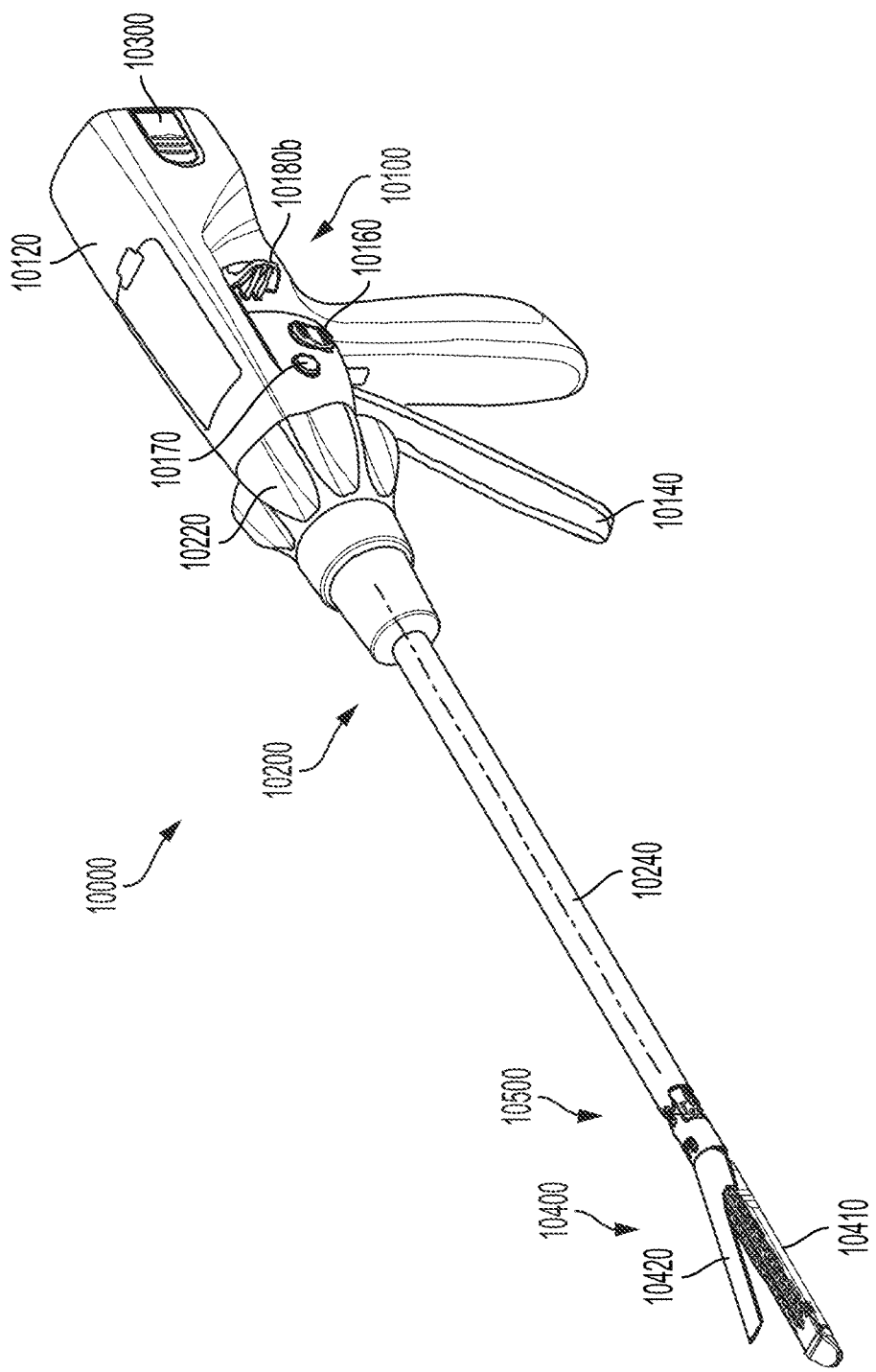
FIG. 1 illustrates a perspective view of a surgical instrument in accordance with at least one embodiment.

A surgical instrument 10000 is illustrated in FIG. 1. The surgical instrument 10000 comprises a handle 10100 including a handle housing 10120, a shaft 10200 extending from the handle 10100, and an end effector 10400. The end effector 10400 comprises a first jaw 10410 configured to receive a staple cartridge and a second jaw 10420 movable relative to the first jaw 10410. The second jaw 10420 comprises an anvil including staple forming pockets defined therein. The surgical instrument 10000 further comprises a closure actuator 10140 configured to drive a closure system of the surgical instrument 10000 and move the second jaw 10420 between an unclamped position and a clamped position. The closure actuator 10140 is operably coupled with a closure tube 10240 that is advanced distally when the closure actuator 10140 is closed. In such instances, the closure tube 10240 contacts the second jaw and cams and/or pushes the second jaw 10420 downwardly into its clamped position.

Further to the above, the second jaw 10420 is pivotably coupled to the first jaw 10410 about a pivot axis. In various embodiments, the second jaw can both translate and rotate as it is being moved into its clamped position. In various alternative embodiments, a surgical instrument comprises a staple cartridge jaw that is movable between an unclamped position and a clamped position relative to an anvil jaw. In any event, the handle 10100 comprises a lock configured to releasably hold the closure actuator 10140 in its clamped position. The handle 10100 further comprises release actuators 10180b on opposite sides thereof which, when actuated, unlock the closure actuator 10140 such that the end effector 10400 can be re-opened. In various alternative embodiments, the handle 10100 comprises an electric motor configured to move the closure tube 10240 proximally and/or distally when actuated by the clinician.

The end effector 10400 is attached to the shaft 10200 about an articulation joint 10500 and is rotatable within a plane about an articulation axis. The shaft 10200 defines a longitudinal axis and the end effector 10400 is articulatable between an unarticulated position in which the end effector 10400 is aligned with the longitudinal axis and articulated positions in which the end effector 10400 extends at a transverse angle relative to the longitudinal axis. In various embodiments, the surgical instrument 10000 comprises a first articulation joint which permits the end effector 10400 to be articulated in a first plane and a second articulation joint which permits the end effector 10400 to be articulated in a second plane which is orthogonal to the first plane, for example. The handle 10100 comprises at least one electric motor and a control system configured to control the operation of the electric motor in response to articulation actuators 10160 and 10170. The electric motor comprises a brushless DC motor; however, the electric motor can comprise any suitable motor, such as a brushed DC motor, for example.

The entire disclosure of U.S. Pat. No. 10,149,683, entitled POWERED SURGICAL CUTTING AND STAPLING APPARATUS WITH MANUALLY RETRACTABLE FIRING SYSTEM, which issued on Dec. 11, 2018, is incorporated by reference herein. The entire disclosure of U.S. Patent Application Publication No. 2018/0125481, entitled MOTOR-DRIVEN SURGICAL CUTTING INSTRUMENT, which published on May 10, 2018, is incorporated by reference herein. The handle 10100 further comprises a replaceable and/or rechargeable battery 10300 attachable to the handle housing which powers the surgical instrument 10000. The entire disclosure of U.S. Pat. No. 8,632,525, entitled POWER CONTROL ARRANGEMENTS FOR SURGICAL INSTRUMENTS AND BATTERIES, which issued on Jan. 21, 2014, is incorporated by reference herein.

Further to the above, the shaft 10200 is rotatable about a longitudinal axis extending through the shaft 10200. The shaft 10200 is rotatably connected to the handle 10100 about a rotation joint 10220 and the shaft 10200 comprises one or more finger grooves defined therein which facilitate a clinician using the stapling instrument 10000 to rotate the shaft 10200. In various embodiments, the surgical instrument 10000 comprises an electric motor and a rotation actuator that, when actuated by the clinician, powers the electric motor to rotate the shaft 10200 in a first direction or a second direction depending on the direction in which the rotation actuator is actuated.

Further to the above, the surgical instrument 10000 comprises a staple firing drive configured to eject the staples out of the staple cartridge. The staple firing drive comprises an electric motor and a firing member which is driven distally through a staple firing stroke by the electric motor. During the staple firing stroke, the firing member pushes the sled in the staple cartridge distally to eject the staples from the staple cartridge. The entire disclosure of U.S. Pat. No. 9,629,629, entitled CONTROL SYSTEMS FOR SURGICAL INSTRUMENTS, which issued on Apr. 25, 2017, is incorporated by reference herein.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein. The disclosures of International Patent Publication No. WO 2017/083125, entitled STAPLER WITH COMPOSITE CARDAN AND SCREW DRIVE, published May 18, 2017, International Patent Publication No. WO 2017/083126, entitled STAPLE PUSHER WITH LOST MOTION BETWEEN RAMPS, published May 18, 2017, International Patent Publication No. WO 2015/153642, entitled SURGICAL INSTRUMENT WITH SHIFTABLE TRANSMISSION, published Oct. 8, 2015, U.S. Patent Application Publication No. 2017/0265954, filed Mar. 17, 2017, entitled STAPLER WITH CABLE-DRIVEN ADVANCEABLE CLAMPING ELEMENT AND DUAL DISTAL PULLEYS, now U.S. Pat. No. 10,350,016, U.S. Patent Application Publication No. 2017/0265865, filed Feb. 15, 2017, entitled STAPLER WITH CABLE-DRIVEN ADVANCEABLE CLAMPING ELEMENT AND DISTAL PULLEY, now U.S. Pat. No. 10,631,858, and U.S. Patent Application Publication No. 2017/0290586, entitled STAPLING CARTRIDGE, filed on Mar. 29, 2017, now U.S. Pat. No. 10,722,233, are incorporated herein by reference in their entireties.

Figure 2:
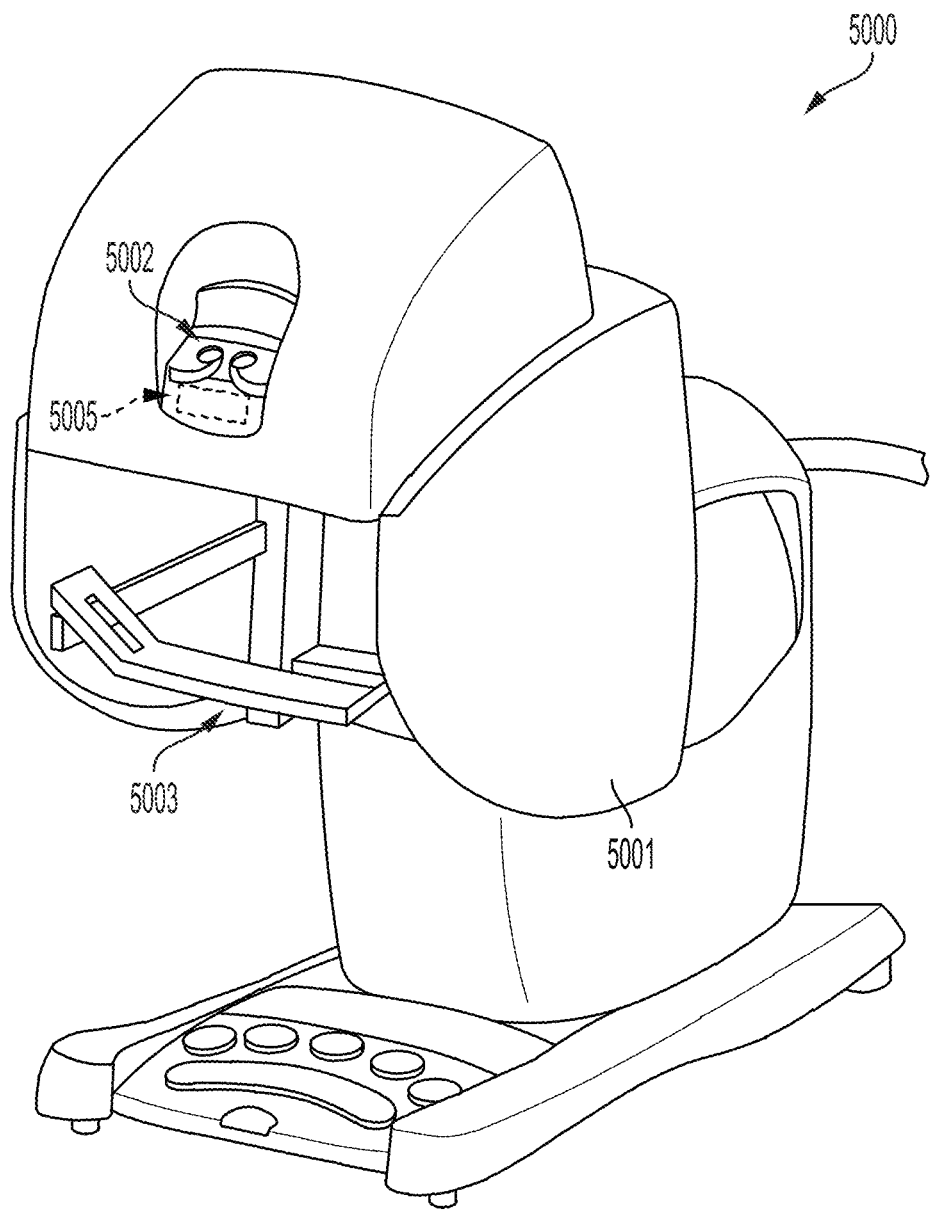
FIG. 2 illustrates a perspective view of a controller of a robotic surgical system.
Figure 3:
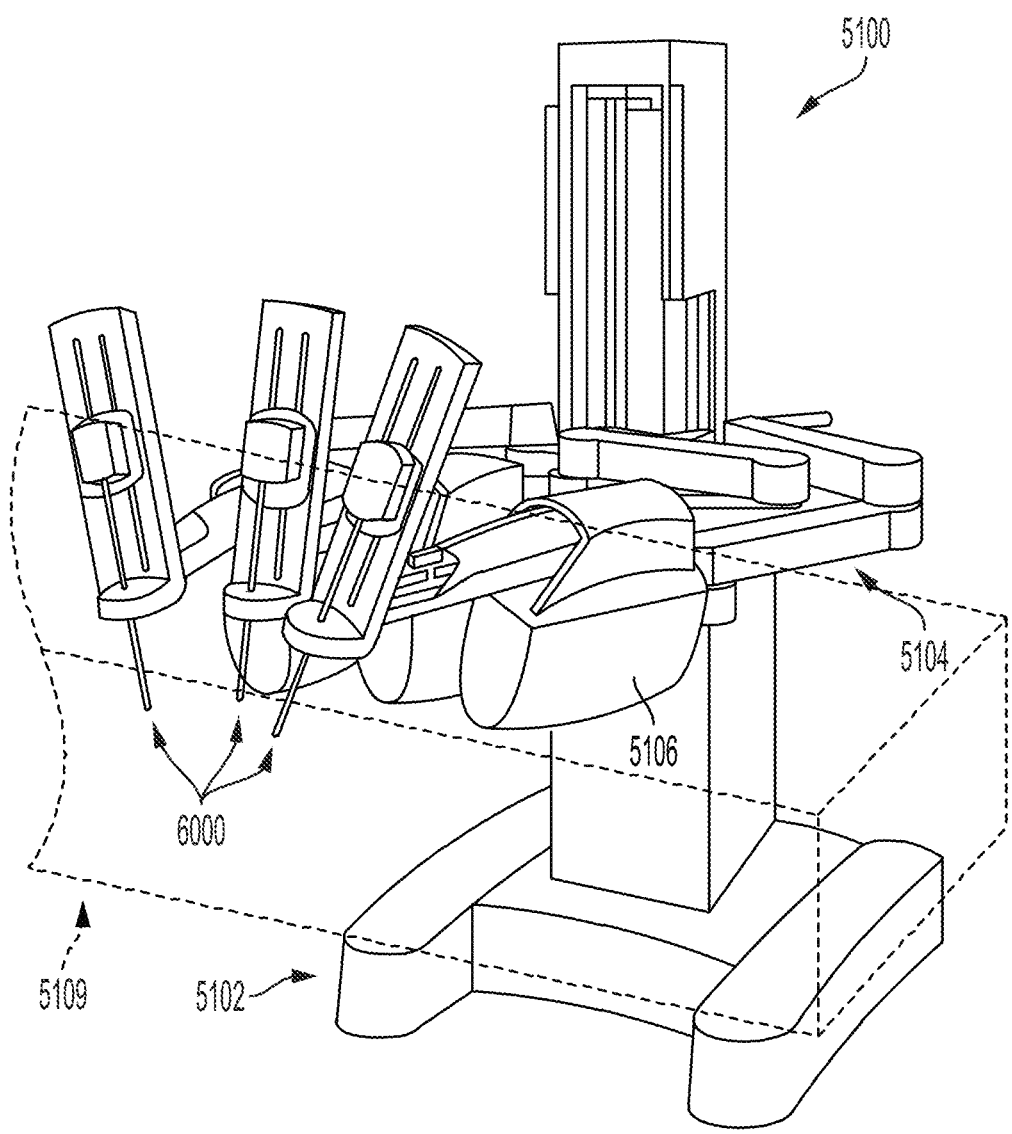
FIG. 3 illustrates a perspective view of the robotic surgical system of FIG. 2 comprising a plurality of robotic surgical arms which each operably support a surgical instrument thereon.
Figure 4:
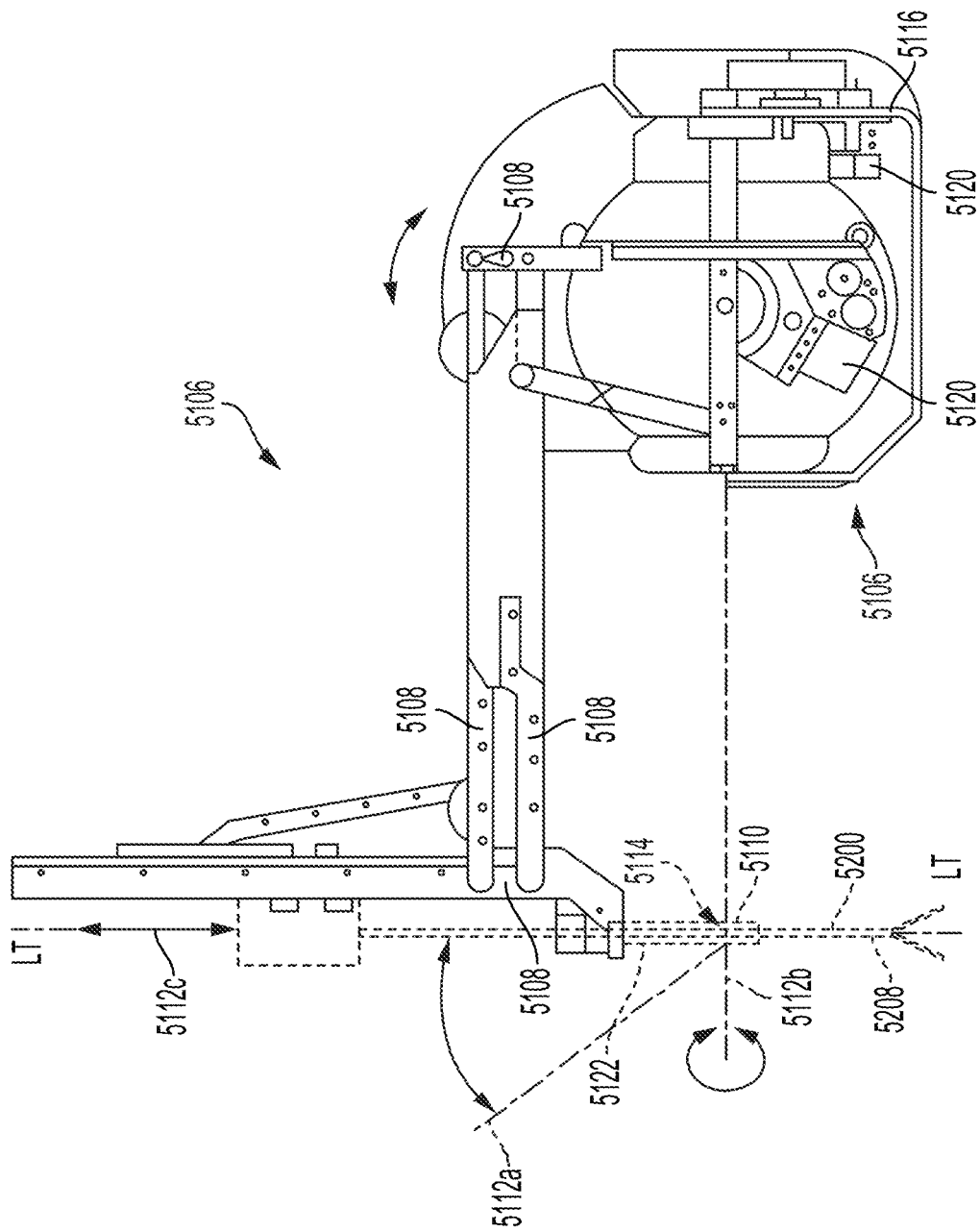
FIG. 4 illustrates a side view of a robotic surgical arm illustrated in FIG. 3.

Various embodiments disclosed herein may be employed in connection with a robotic surgical system, such as the robotic system 1000 depicted in FIGS. 1-3, for example. FIG. 1 depicts a master controller 5001 that may be used in connection with a robotic arm cart 5100 depicted in FIG. 2. The master controller 5001 and the robotic arm cart 5100, as well as their respective components and control systems, are collectively referred to herein as a robotic system 5000. Examples of such systems and devices are disclosed in U.S. Pat. No. 7,524,320, entitled MECHANICAL ACTUATOR INTERFACE SYSTEM FOR ROBOTIC SURGICAL TOOLS, as well as U.S. Pat. No. 9,072,535, entitled SURGICAL STAPLING INSTRUMENTS WITH ROTATABLE STAPLE DEPLOYMENT ARRANGEMENTS, which are each hereby incorporated by reference herein in their respective entireties. The details of such systems and devices are not repeated herein for the sake of brevity. The master controller 5001 includes controls 5003 which are grasped and manipulated by the surgeon while the surgeon views the patient via a display 1002. The controls 5003 can comprise manual input devices which move with multiple degrees of freedom, for example, and can further comprise an actuatable trigger for actuating surgical instruments, or tools, to close grasping jaws, staple and incise tissue, and/or apply an electrical potential to an electrode, for example.

With reference to FIGS. 2 and 3, the robotic arm cart 5100 is configured to actuate one or more surgical instruments, such as surgical instruments 6000, for example, in response to inputs from the master controller 5001. In various forms, the robotic arm cart 5100 includes a base 5002, arm linkages including set-up joints 5104, and instrument manipulators 5106. Such an arrangement can facilitate the rotation of a surgical instrument 6000 around a point in space, which is described in U.S. Pat. No. 5,817,084, entitled REMOTE CENTER POSITIONING DEVICE WITH FLEXIBLE DRIVE, the entire disclosure of which is hereby incorporated by reference herein. This arrangement provides for pivoting rotation of a surgical instrument 6000 about an axis 5112*a*, or pitch axis. The arrangement also provides for rotation of the surgical instrument 6000 about an axis 5112*b*, or yaw axis. The pitch and yaw axes 5112*a*, 5112*b* intersect at a remote center 5114, which is aligned along an elongate shaft of the surgical instrument 6000. A surgical instrument 6000 may have further degrees of driven freedom, including sliding motion along a longitudinal axis LT-LT. As the surgical instrument 6000 slides along the longitudinal axis LT-LT relative to the instrument manipulator 5106 (arrow 5112*c*), the remote center 5114 remains fixed relative to a base 5116 of the instrument manipulator 5106. To move the remote center 5114, linkage 5108 is driven by one or more motors 5120 which move the linkage 5108 in response to commands from the master controller 5001 to position and/or manipulate the surgical instrument 6000 within the surgical site. Various other arrangements are disclosed in U.S. Pat. No. 5,878,193, entitled AUTOMATED ENDOSCOPE SYSTEM FOR OPTIMAL POSITIONING, the entire disclosure of which is hereby incorporated by reference herein.

Additionally, while the data communication between a robotic component and the processor of the robotic surgical system is primarily described herein with reference to communication between a surgical instrument, or tool, and the master controller 5001, it should be understood that similar communication may take place between the circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like. In accordance with at least one aspect, various surgical instruments disclosed herein may be used in connection with other robotically-controlled or automated surgical systems and are not necessarily limited to use with the specific robotic system components shown in FIGS. 1-3 and described in the aforementioned references. Various robotic surgery systems and methods are disclosed in U.S. Pat. No. 6,132,368, entitled MULTI-COMPONENT TELEPRESENCE SYSTEM AND METHOD, the entire disclosure of which is hereby incorporated by reference herein.

Figure 5:
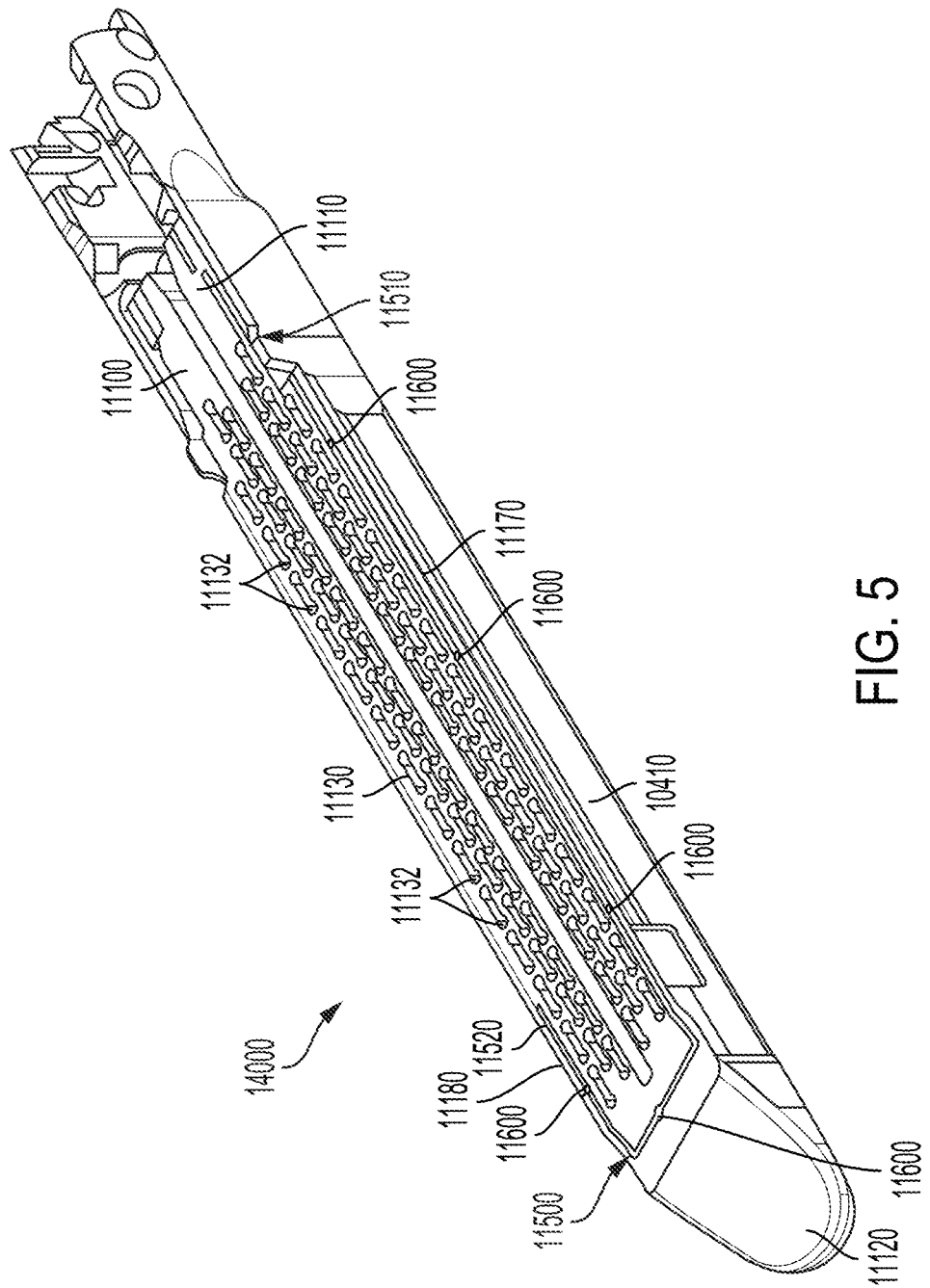
FIG. 5 illustrates a perspective view of a staple cartridge positioned in a cartridge jaw in accordance with at least one embodiment.

Referring to FIG. 5, a staple cartridge, such as staple cartridge 14000, for example, comprises a cartridge body 11100 and an electronic circuit 11500 including sensors 11600. The staple cartridge 14000 is similar to the other staple cartridges disclosed herein in many respects and such respects are not discussed herein for the sake of brevity. As discussed above, the cartridge body 11100 comprises a deck 11130 and longitudinal rows of staple cavities 11140 defined in the deck 11130. Each staple cavity 11140 comprises a staple stored therein that is driven upwardly out of the staple cavity 11140 by a staple driver during a staple firing stroke. Each staple comprises a base and two legs extending from the base such that the legs extend generally upwardly and outwardly to form a V-shape configuration. In various instances, the legs of the staple are resiliently deflected inwardly by the proximal and distal end walls of the staple cavity 11140 when the staple is stored in the staple cavity 11140. When the staple is driven upwardly out of the staple cavity 11140, the legs of the staple emerge from the staple cavity 11140 and extend above the deck 11130 while the rest of the staple is pushed upwardly out of the staple cavity 11140. The cartridge body 11100 comprises projections 11132 (FIG. 5B) extending from the deck 11130 which are configured to guide and/or control the legs of the staples as the staples are being ejected from the staple cavities 11140. A projection 11132 is positioned at the distal end of each staple cavity 11140 and at the proximal end of each staple cavity 11140. However, alternative embodiments are envisioned in which a projection 11132 is positioned at only one end of each staple cavity 11140. Moreover, various embodiments are envisioned in which some of the staple cavities 11140 do not comprise projections 11132 at the ends thereof. The projections 11132 are further configured to engage the patient tissue positioned against the deck 11130 and limit the flow or movement of the patient tissue relative to the deck 11130.

In various embodiments, the electronic circuit 11500 comprises a substrate including features engaged with the projections 11132. In at least one embodiment, the substrate comprises apertures defined therein, the sidewalls of which are engaged with the projections 11132. The apertures are in a snap-fit and/or press-fit arrangement with the projections 11132 such that the electronic circuit 11500 is held in position relative to the cartridge body 11100. In at least one embodiment, the projections 11132 comprise at least partially annular or circumferential shoulders which hold the sensor circuit 11500 against the cartridge body 11100.

In various embodiments, a sensor circuit of a staple cartridge is comprised of a conductive material printed on the deck of the cartridge body. In at least one embodiment, the conductive material is comprised of metal particles bonded to the deck which form an electrical circuit connecting the sensors. In at least one such embodiment, the printed electrical circuit is printed onto the cartridge body with a three-dimensional printer. In various embodiments, the sensor circuit comprises electrodes, or contacts, that are printed onto the cartridge body. In at least one embodiment, the sensor circuit comprises electrodes which comprise a polygonal surface configured to contact the tissue. In at least one alternative embodiment, the electrodes comprise a curved and/or tortuous path on the deck surface which, in various instances, can increase the contact area between the electrodes and the tissue. In at least one embodiment, the electrodes comprise needles extending therefrom which are configured to penetrate the tissue. In at least one embodiment, the needles comprise a diameter of about 1 μm, for example. In various instances, the needles provide parallel signal paths between the tissue and the sensor circuit within one electrode to improve the sensitivity of the sensor circuit. In at least one embodiment, a conductive grease or conductive viscous agent covers the tissue contact points of the sensor circuit which improves the contact between the electrodes and the tissue. In various embodiments, portions of the sensor circuit are embedded in the cartridge body. In at least one such embodiment, the sensor circuit comprises flat, thin conductors that are embedded into the cartridge body when a plastic material, for example, is overmolded onto portions of the conductors. Portions of the conductors, however, remain exposed to provide tissue engaging pads and/or electrically-conductive attachment points for soldering sensors thereto. In at least one embodiment, part of the cartridge sensor circuit can be defined on the lateral sidewalls of the cartridge jaw. In at least one such embodiment, a proximal portion and a distal portion of the sensor circuit are defined on the cartridge body and an intermediate portion of the sensor circuit is defined on the cartridge jaw that electrically connects the proximal portion and the distal portion of the sensor circuit. In at least one embodiment, the portions of the sensor circuit mounted to the cartridge jaw comprise conductive strips mounted to the sidewalls. When the staple cartridge is seated in the cartridge jaw, the cartridge sensor circuit engages the conductive strips to complete the circuit.

As discussed above, a sensor circuit can include conductive tissue-contacting surfaces. In various embodiments, a sensor circuit can include non-conductive tissue-contacting surfaces. In at least one embodiment, a sensor circuit comprises one or more capacitive electrodes. In various instances, projected capacitance measurement techniques are used to measure the presence of the tissue over the capacitive electrodes and/or a property of the tissue over the capacitive electrodes. In at least one embodiment, each capacitive electrode comprises an insulative covering which covers capacitive pads contained therein. In various instances, further to the above, surface capacitance measurement techniques can be used. In various embodiments, a sensor circuit comprises one or more inductive sensors. In at least one embodiment, an eddy current is induced in each of the inductive sensors which changes when the tissue contacts the sensors. In such embodiments, the changes to the sensor eddy currents are detected by the control system of the staple cartridge. In various embodiments, the sensor circuit can comprise temperature sensors which are used to detect the presence of tissue over the temperature sensors. In at least one embodiment, the sensor circuit comprises electrodes comprised of a doped polycrystalline ceramic comprising barium titanate (BaTiO3), for example. The resistance of these ceramic materials changes in response to temperature changes, such as when patient tissue is positioned against the electrodes. The cartridge processor is configured to employ an algorithm to monitor the resistance fluctuations in the ceramic materials to assess whether or not tissue was positioned against the electrodes. In various instances, the electrodes of the sensor circuit are in a parallel arrangement such that a detected resistance, capacitance, voltage, and/or current change can be directly related to the position of a sensor. With this information, the processor can assess whether and where tissue is positioned over the staple cartridge.

Figure 5A:
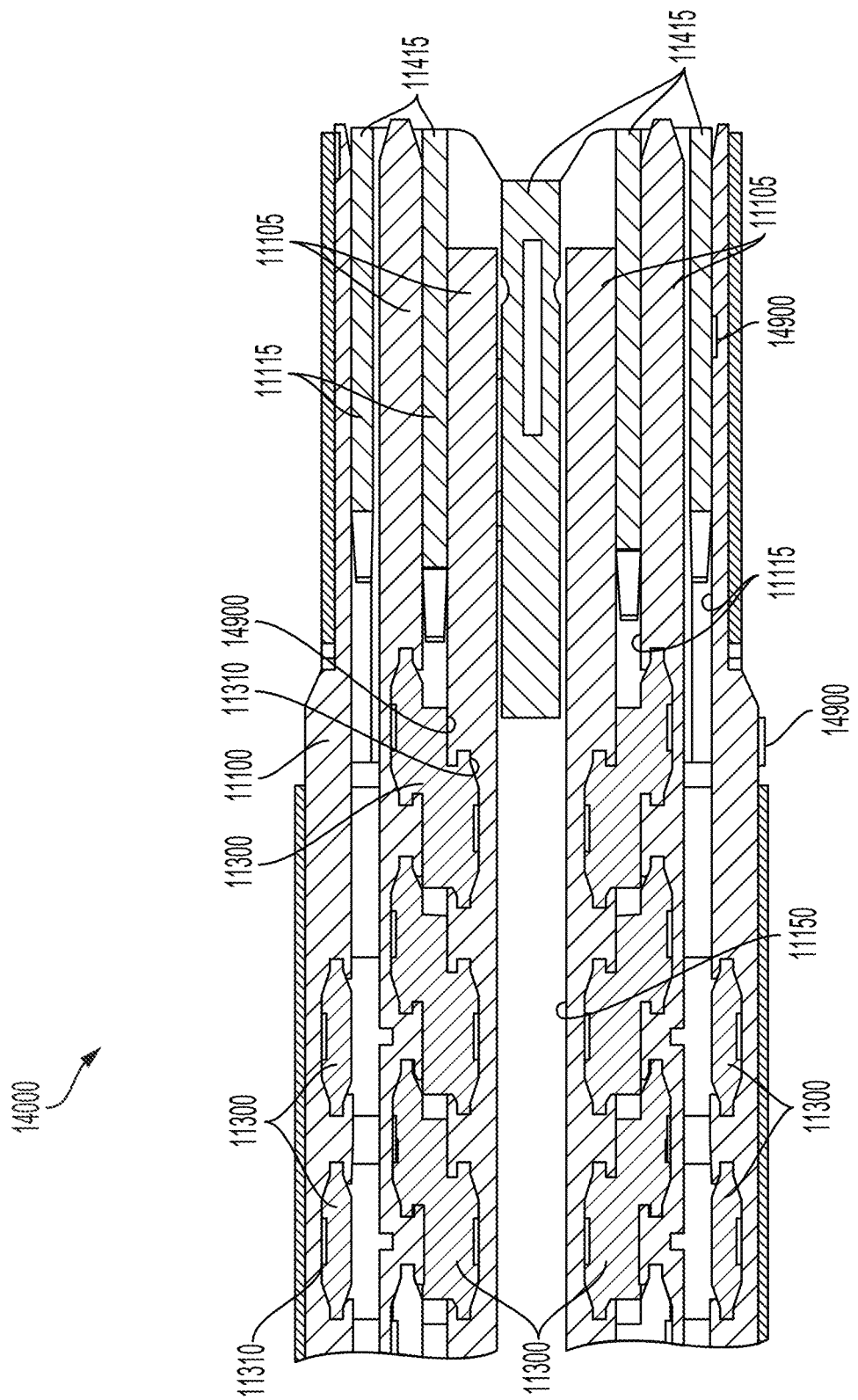
FIG. 5A illustrates a partial cross-sectional view of the staple cartridge of FIG. 5.
Figure 5B:
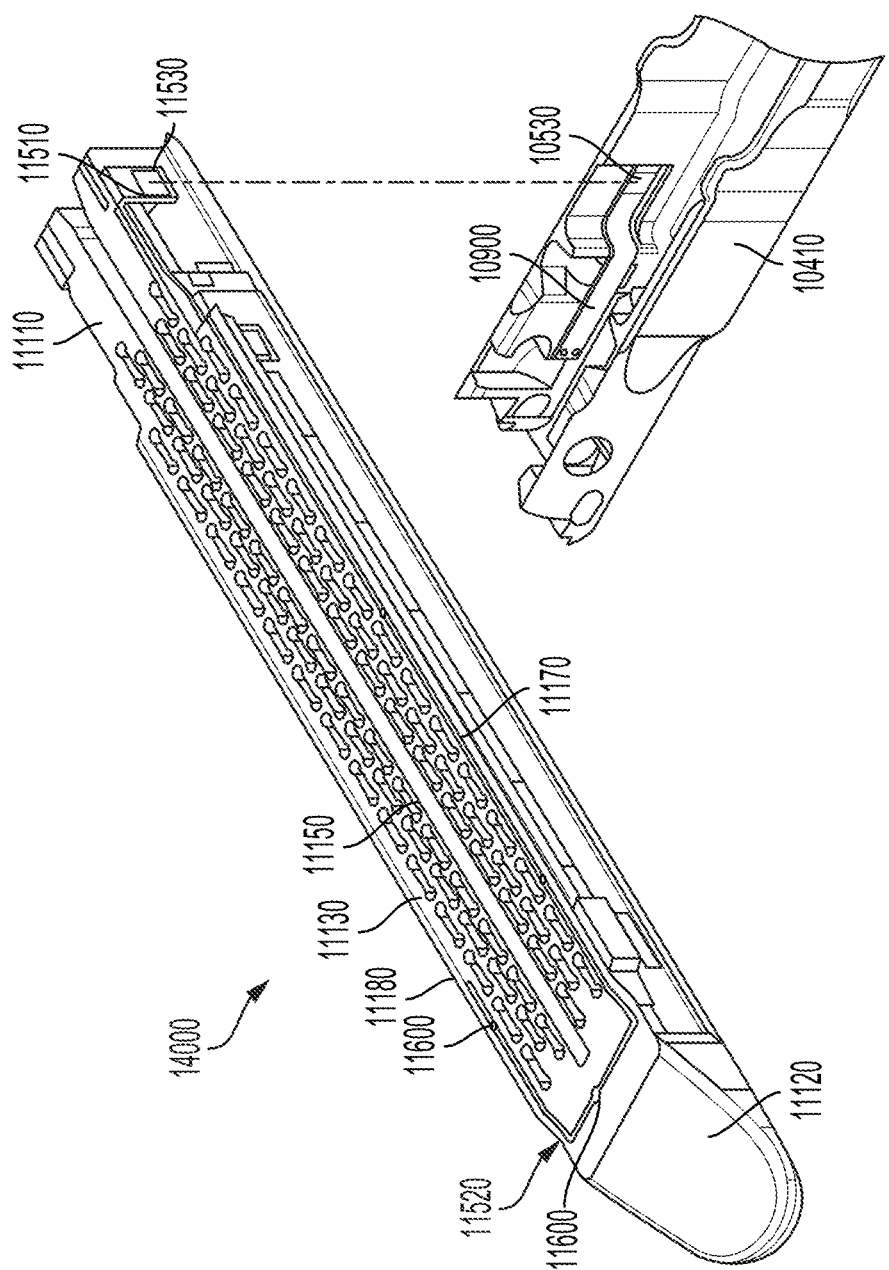
FIG. 5B illustrates a perspective view of the staple cartridge of FIG. 5 removed from the cartridge jaw.
Figure 5C:
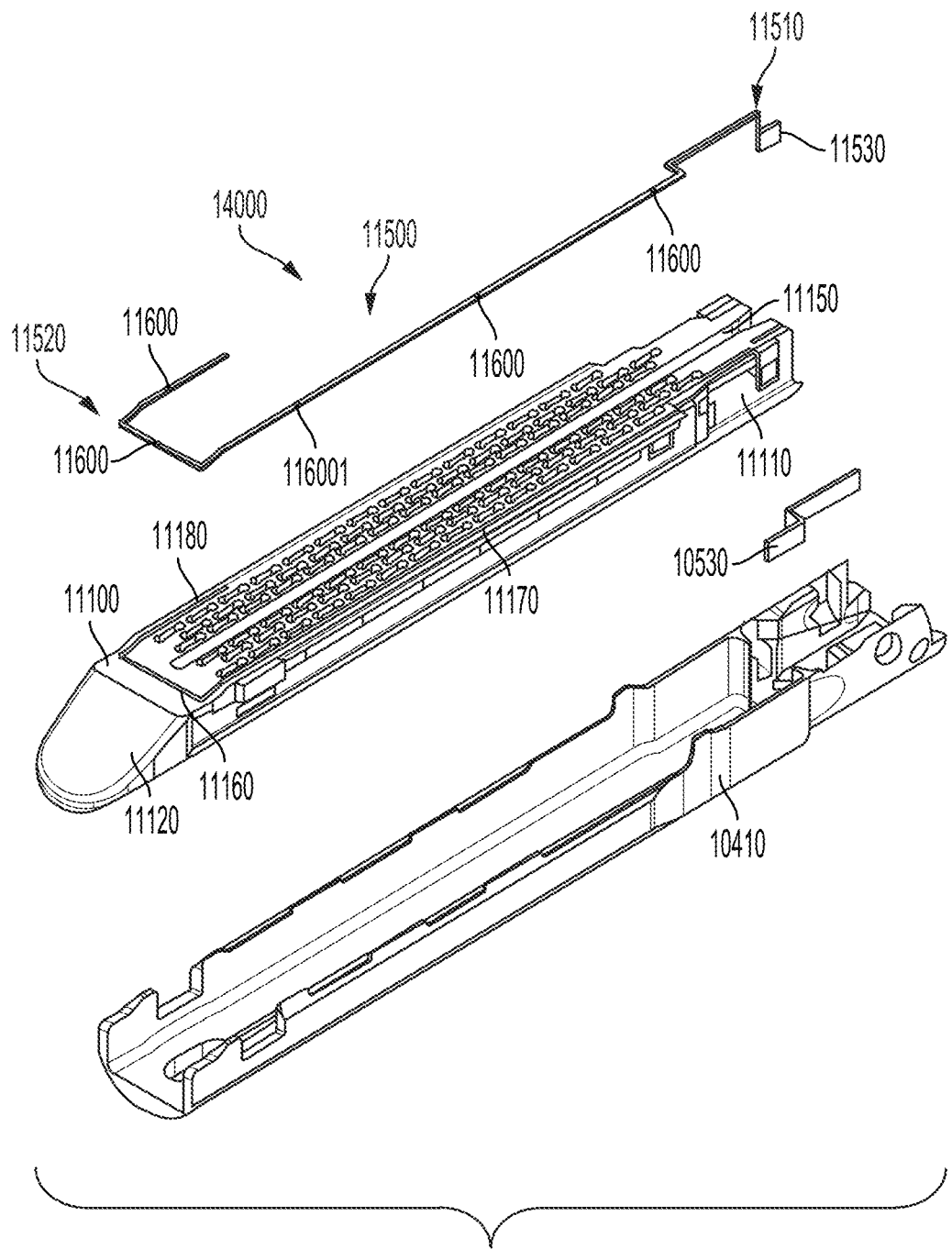
FIG. 5C illustrates an exploded view of the staple cartridge of FIG. 5.
Figure 5D:
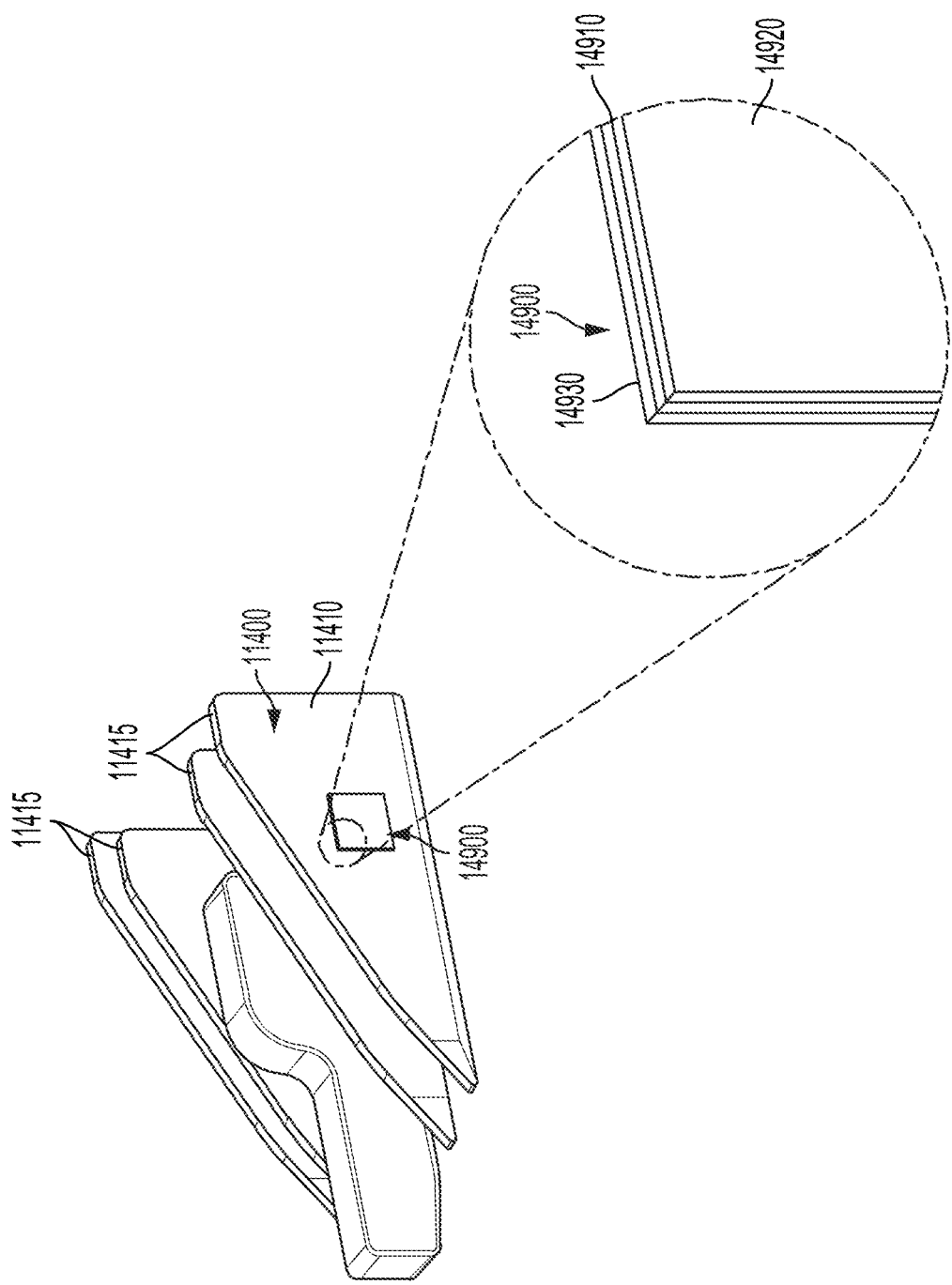
FIG. 5D illustrates a perspective view of a sled of the staple cartridge of FIG. 5.

Referring to FIGS. 5A and 5D, the staple cartridge 14000 further comprises a laminate material 14900 mounted to one or more components of the staple cartridge 14000 to control the electrical effects created within the cartridge components by the fields emitted from and/or surrounding the staple cartridge 14000. In at least one instance, the laminate material 14900 comprises a flux field directional material including at least two layers—a first layer 14910, or cover, and a second layer 14920 of magnetic material attached to the first layer 14910. The first layer 14910 is comprised of polyethylene terephthalate, for example, which protects the second layer 14920, but can be comprised of any suitable material. The second layer 14920 is comprised of a sintered ferrite sheet, for example, but can be comprised of any suitable material. In at least one instance, an adhesive layer 14930 comprised of a pressure-sensitive adhesive, for example, is bonded to the second layer 14920 and is used to attach the laminate material 14900 to one or more components of the staple cartridge 14000, as discussed further below. In at least one instance, the laminate material 14900 is a Flux Field Directional Material EM15TF manufactured by 3M, for example.

In various embodiments, further to the above, laminate material 14900 is bonded to the cartridge body 11100 and is arranged to change and/or control the shape of the fields extending from the cartridge antennas. In at least one embodiment, the laminate material 14900 focuses the fields away from the metal cartridge jaw of the surgical instrument 10000 in which the staple cartridge 14000 is seated. In at least one instance, the cartridge body 11100 is comprised of plastic and the laminate material 14900 is mounted to the cartridge body 11100 such that the laminate material 14900 surrounds, or at least substantially surrounds, the cartridge antennas. In at least one instance, laminate material 14900 is mounted to the cartridge body 11100 at a location which is intermediate the cartridge data coil 11540" and the cartridge power coil 11545" such that the cartridge coils 11540" and 11545" are separated by the laminate material 14900. In various embodiments, laminate material 14900 is bonded to the metal walls of the cartridge jaw 10410. In at least one instance, laminate material 14900 is mounted to the metal walls of the cartridge jaw 10410 at a location which is intermediate the instrument data coil 10540" and the power transmission coil 10545". In various embodiments, the laminate material 14900 bonds the cartridge data antenna 11530" and/or the cartridge power antenna 11535" to the cartridge body 11100. In at least one embodiment, the laminate material 14900 bonds the instrument data antenna 10530" and/or the instrument power antenna 10535" to the metal cartridge jaw 10410.

In various embodiments, further to the above, laminate material 14900 is mounted to the metal pan 11700. In at least one such instance, laminate material 14900 is positioned intermediate the metal pan 11700 and the cartridge data antenna 11530" and, also, intermediate the metal pan 11700 and the cartridge power antenna 11535". Such an arrangement can focus the fields created by the antennas 11530" and 11535" away from the metal pan 11700 to minimize the electrical effects that the fields have on the metal pan 11700. In various embodiments, laminate material 14900 is mounted to the movable components of the staple cartridge 14000. In at least one instance, referring to FIG. 5D, laminate material 14900 is mounted to the sled 11400. In at least one such instance, laminate material 14900 is mounted to the lateral sides 11410 of the sled 11400, for example. In at least one instance, referring to FIG. 5A, laminate material 14900 is mounted to one or more of the staple drivers 11300, for example. In at least one such instance, laminate material 14900 is mounted to the lateral sides 11310 of the staple drivers 11300. Laminate material 14900 can be mounted to all of the staple drivers 11300, or just the staple drivers 11300 adjacent the cartridge antennas 11530" and 11535", for example.

Further to the above, the fields generated by the cartridge antennas and/or instrument antennas can affect the output of the sensors 11600. Such an effect can be reduced or mitigated by the laminate material 14900, for example. In various instances, the processor of the staple cartridge 14000 is configured to electronically account for the effect that the antenna fields will have on the sensors 11600. In at least one such instance, the cartridge processor can monitor when signals are being transmitted between the antenna couples and, in such instances, modify the sensor outputs being received from the sensors 11600 before transmitting the sensor outputs to the surgical instrument processor and/or recording the sensor outputs in a memory device in the staple cartridge 14000. When signals are not being transmitted between the antenna couples, the sensor outputs may not need to be modified by the processor before being transmitted to the surgical instrument processor and/or recorded in a memory device in the staple cartridge 14000. In various instances, the processor can apply a first compensation factor to the sensor outputs when the power antenna couple is transmitting signals, a second compensation factor to the sensor outputs when the signal antenna couple is transmitting signals, and a third compensation factor to the sensor outputs when both antennas are transmitting signals. In at least one such instance, the third compensation factor is larger than the first compensation factor and the first compensation factor is larger than the second compensation factor, for example.

Further to the above, the circuit 11500 is flush with the top surface of the deck 11130 and/or recessed with respect to the top surface of the deck 11130. In various instances, the staple cartridge 11000 further comprises latches rotatably mounted thereto which are rotatable from an unlatched position to a latched position to hold the circuit 11500 in the circuit slot 11160. The latches engage the cartridge body 11100 in a press-fit and/or snap-fit manner when the latches are in their latched position. When the latches are in their latched position, the latches are flush with and/or recessed below the top surface of the deck 11130. In at least one embodiment, the projections 11132 are mounted to and/or integrally-formed with the latches and/or any other suitable restraining features. In any event, the circuit 11500 comprises one or more sensors which are held in place relative to the cartridge body 11100 as a result of the above.

Figure 6:
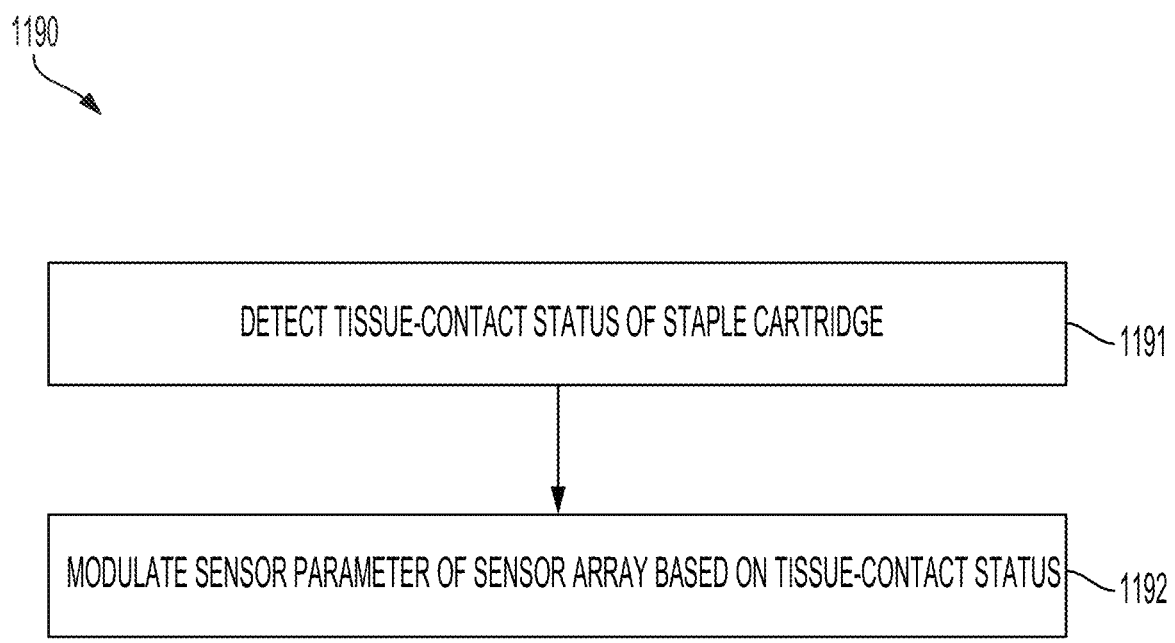
FIG. 6 illustrates a logic flow diagram of an algorithm depicting a control program or a logic configuration for modulating a sensor parameter of the sensor array, in accordance with at least one aspect of the present disclosure.

FIG. 6 is a logic flow diagram of an algorithm 1190 depicting a control program or a logic configuration for modulating a sensor parameter of the sensor array 1036, in accordance with at least one aspect of the present disclosure. In the illustrated example, the algorithm 1190 includes detecting 1191 a tissue contact status of the staple cartridge 1046. The algorithm 1190 further includes selectively modulating 1182 a sensor parameter of one or more sensors of the sensor array 1036 in accordance with the detected tissue contact status. In the illustrated example, the algorithm 1190 is implemented, or at least partially implemented, by the control circuit 1026. In other examples, various aspects of the algorithm 1190 can be implemented by other control circuits such as, for example, the control circuit 1049, or any other suitable control circuit. For brevity the following description will focus on executing various aspects of the algorithm 1190 by the control circuit 1026.

In various aspects, detecting 1191 the tissue contact status of the staple cartridge 1046 is performed at each of a plurality of closure states. As the closure of the end effector 1040 commences, the size and/or position of the tissue in contact with the sensor array 1036 of the staple cartridge 1046 may change. To optimize sensor data collection, transmission, and/or processing, the control circuit 1026 can be configured to adjust one or more sensor parameters of one or more sensors, or groups of sensors, of the sensor array 1036 based on whether tissue contact is detected at the different closure states.

Figure 7:
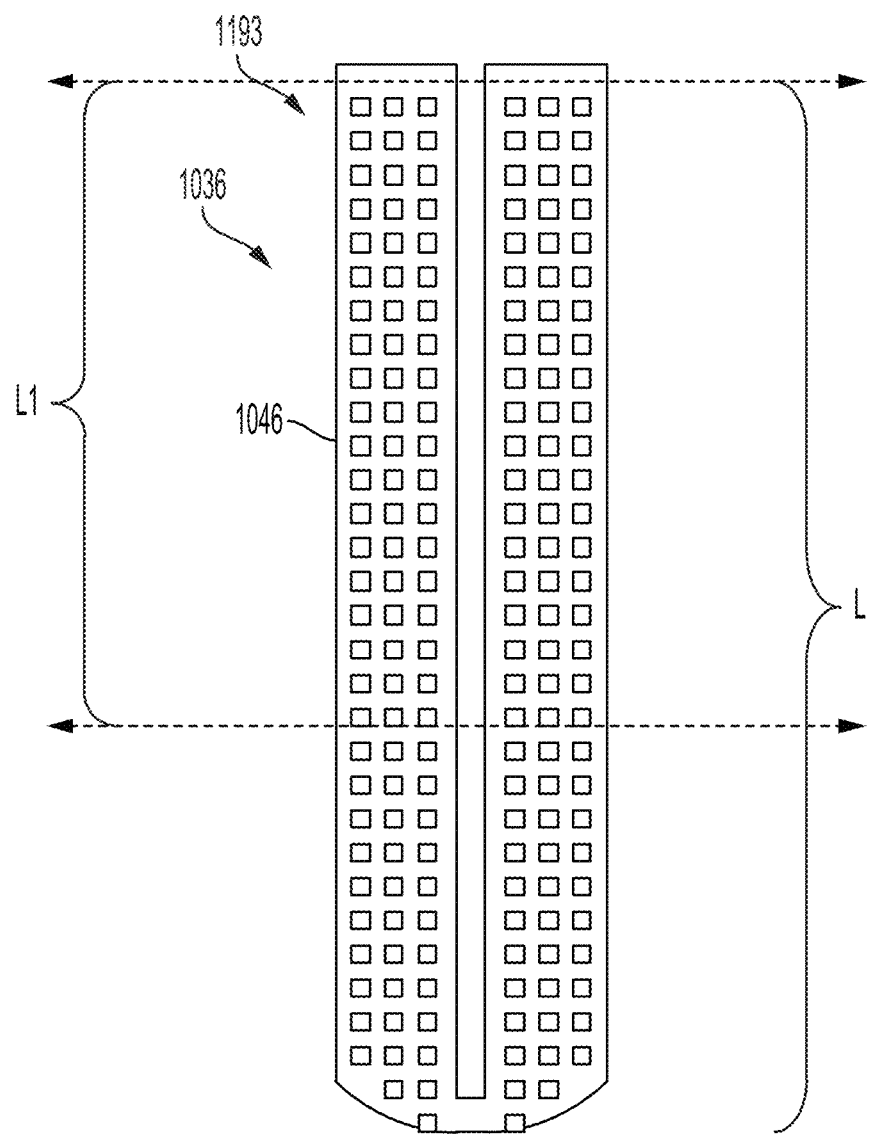
FIG. 7 illustrates a top schematic view of a staple cartridge, in accordance with at least one aspect of the present disclosure.

In certain exemplifications, as illustrated in FIG. 7, the sensor array 1036 is disposed along a length L of the staple cartridge 1046. However, the tissue grasped by the end effector 1040 may cover a region 1193 extending only along a portion of the length L, for example extending along a length L1. In such instances, sensor data from sensors beyond the region 1193 can be assigned a lower priority than sensor data from sensors within the region 1193. A control circuit 1026 can be configured to determine a priority level of the sensors of the sensor array 1036 based on their location with respect to the region 1193, for example. Furthermore, the control circuit 1026 can be configured to switch sensors of the sensor array 1036 that are within the region 1193 to an active mode 1083 and/or switch sensors of the sensor array 1136 that are outside the region 1193 to an idler mode 1084, for example.

In various aspects, tissue contact detection can be accomplished by a tissue contact circuit 2830, as described in greater detail elsewhere in the present disclosure. The tissue contact circuit 2830 is in open circuit mode with no tissue located against the sensors 2788a, 2788b. The tissue contact circuit 2830 is transitioned to a closed circuit mode by the tissue 2820. The sensors 2788a, 2788b are powered by voltage source V and a sensors circuit 2790 measures a signal generated by the sensors 2788a, 2788b. In some aspects, the sensors 2788a, 2788b may include a pair of opposing electrode plates to make electrical contact with the tissue 2820.

Any of the sensors 2788a, 2788b disclosed herein may include, but are not limited to, electrical contacts placed on an inner surface of a jaw which, when in contact with tissue, close a sensing circuit that is otherwise open. The contact sensors may also include sensitive force transducers that detect when the tissue being clamped first resists compression. Force transducers may include, and are not limited to, piezoelectric elements, piezoresistive elements, metal film or semiconductor strain gauges, inductive pressure sensors, capacitive pressure sensors, and resistive sensors.

Further to the above, a control circuit 1026, for example, may receive one or more signals from the sensor circuit 2790 and/or sensors 2788a, 2788b indicative of a tissue contact status of one or more regions along the length L of the staple cartridge 1046. In response, the adjust one or more sensor parameters of one or more sensors, or groups of sensors, the control circuit 1026 can be configured to adjust sensor parameters of one or more sensors of the sensor array 1036 in the one or more regions based on the tissue contact status.

Additional details are disclosed in U.S. Pat. No. 10,595,887, titled SYSTEMS FOR ADJUSTING END EFFECTOR PARAMETERS BASED ON PERIOPERATIVE INFORMATION, and issued Mar. 24, 2020, U.S. Pat. No. 9,724,094, titled ADJUNCT WITH INTEGRATED SENSORS TO QUANTIFY TISSUE COMPRESSION, and issued Aug. 8, 2017, and U.S. Pat. No. 9,808,246, titled METHOD OF OPERATING A POWERED SURGICAL INSTRUMENT, and issued Nov. 7, 2017, the entireties of disclosures of which are hereby incorporated by reference herein.

In one general aspect, the present disclosure provides methods of monitoring multiple sensors over time to detect moving characteristics of tissue located in the jaws of the end effector. In one aspect, the end effector comprises a cartridge. More than one sensor can be located on a cartridge to sense the motion of the tissue from one sensor towards an adjacent sensor. In a stapling cartridge, multiple sensors may be located on the stapling cartridge to sense movement of tissue by monitoring a property of the tissue. In one aspect, the tissue property could be an electrical property of the tissue such as impedance or capacitance. In another aspect, monitoring the impedance of the tissue from one time point to the next can allow the system to detect the motion of the tissue from one sensor towards the next.

In one aspect, a method of monitoring multiple sensors over time to detect moving characteristics of the tissue comprises monitoring multiple sensors over time to detect tissue movement relative to at least two sensed locations. The method provides real-time tissue flow sensing through monitoring a sensed tissue property through time.

Figure 8:
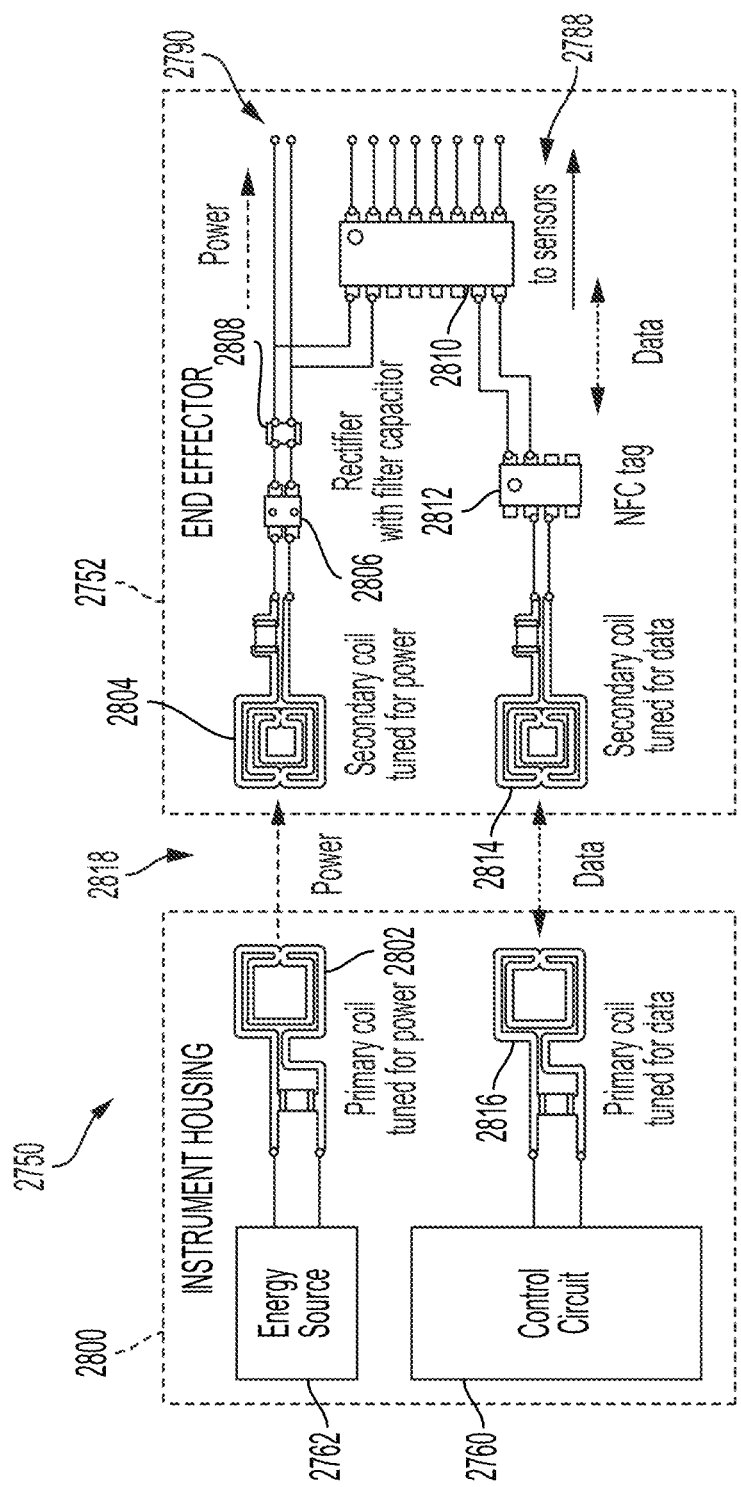
FIG. 8 illustrates a diagram of a cartridge comprising a plurality of sensors coupled to a control circuit through a set of coils to transfer power and data between the cartridge and a control circuit located in an instrument housing, in accordance with at least one aspect of the present disclosure.

Turning now to FIG. 8, which illustrates a diagram of a surgical instrument 2750 comprising an instrument housing 2800 and an end effector 2752 inductively coupled to the instrument housing 2800 via a set of coils 2818 implementing a wireless power and data communication system, in accordance with at least one aspect of the present disclosure. The instrument housing 2800 comprises an energy source 2762 and a control circuit 2760 inductively coupled to the end effector 2752. Power from the energy source 2762 is inductively coupled to the end effector 2752 from a primary coil 2802 tuned for power located in the instrument housing 2800 to a secondary coil 2804 tuned for power located in the end effector 2752. Data is transmitted between the control circuit 2760 and the end effector sensor circuits 2790 between a primary coil 2816 tuned for data located in the instrument housing 2800 and a secondary coil 2814 tuned for data located in the end effector 2752.

FIG. 8 illustrates one implementation of the transmission system 1045 for wireless transmission of power and data. In the implementation illustrated in FIG. 8, power and data are transmitted separately. In other implementations, as described supra, power and data are transmitted sequentially or simultaneously. For brevity, the following description focuses on the implementation of the transmission system 1045 that is configured to separately transmit power and data. However, it is understood that the other implementations of the transmission system 1045 can be equally utilized.

In various aspects, the end effector 2752 comprises a cartridge 2768 and an anvil 2766 pivotally coupled to the cartridge 2768. A plurality of sensors 2788 may be disposed in the cartridge 2768, the anvil 2766, or both. As described supra, the end effector 2752 comprises secondary coils 2804, 2814 to receive power from the instrument housing 2800 and communicate between the end effector 2752 circuits and the instrument housing 2800 circuits, respectively. Power from the secondary coil 2804 is rectified by a rectifier circuit 2806 and filter capacitor 2808 and is provided to a plurality of sensors 2788 via an analog multiplexer 2810 or other analog switching circuit. Signals from the sensors 2788 are transmitted through the analog multiplexer 2810, coupled to a near field communication (NFC) tag 2812, and coupled to the control circuit 2760 from the secondary coil 2814 located in the end effector 2752 and the primary coil 2816 located in the instrument housing 2800. The NFC tag 2812 is configured to transmit data from the cartridge 2768. The sensors 2788 may be configured to measure tissue impedance, tissue temperature, tissue capacitance, tissue inductance, elapsed time, among other tissue parameters explained in the following description.

In other aspects, the cartridge 2768 portion of the end effector 2752 may comprise electrodes to receive electrosurgical energy to assist or enhance the tissue sealing process. In such aspects, some or all of the plurality of sensors 2788 may act as electrodes to deliver the electrosurgical energy through the tissue clamped between the anvil 2766 and the cartridge 2768. In such aspects, the plurality of sensors 2788 may be configured to measure tissue parameters such as impedance, capacitance, among other tissue parameters explained in the following description.

In other aspects, the end effector 2752 may comprise a clamp arm assembly and an ultrasonic blade for cutting and sealing tissue clamped between the clamp arm assembly and the ultrasonic blade instead of the anvil 2766 and cartridge 2768 as shown in the example of FIG. 8. Is such aspects comprising a clamp arm assembly and ultrasonic blade, the plurality of sensors 2788 may be disposed in the clamp arm assembly and the electrical return path may be provided through the electrically conductive ultrasonic blade. The plurality of sensors 788 may be configured to measure tissue parameters such as impedance, capacitance, among other tissue parameters explained in the following description.

In other aspects, the end effector 2752 may comprise a pair of jaws configured with electrodes to deliver electrosurgical energy to seal tissue clamped between the jaws instead of the anvil 2766 and cartridge 2768 as shown in the example of FIG. 8. One of the jaws may be configured with a knife slot for cutting through the tissue after sealing. In such aspects, the plurality of sensors 2788 may be disposed in either jaw or both. The plurality of sensors 2788 may be configured to measure tissue parameters such as impedance, capacitance, among other tissue parameters explained in the following description.

In other aspects, the end effector 2752 may comprise a clamp arm assembly and an ultrasonic blade instead of the anvil 2766 and cartridge 2768 as shown in the example of FIG. 8. In such aspects, the clamp arm assembly is configured with electrodes for receiving electrosurgical energy for sealing tissue located between the clamp arm assembly and the ultrasonic blade. The electrical return path for the electrosurgical energy is provided through the electrically conductive ultrasonic blade. In such aspects, the ultrasonic blade is utilized to cut the sealed tissue clamped between the clamp arm assembly and the ultrasonic blade. The plurality of sensors 2788 may be configured to measure tissue parameters such as impedance, capacitance, among other tissue parameters explained in the following description.

In certain instances, as described in greater detail elsewhere in the present disclosure, wireless power and/or data transmission between an instrument housing 2800 and the end effector 2752 encompasses a wireless power and/or data transmission between the surgical instrument 2750 and the staple cartridge 2768. For example, the primary coils 2802, 2816 can be disposed on a cartridge channel of the end effector 2752, and the secondary coils 2804, 2814 can be disposed on the staple cartridge 2768 such that the primary coils 2802, 2816 and the secondary coils 2804, 2814 are aligned for a wireless connection when the staple cartridge 2768 is seated in the cartridge channel. In such instances, the instrument housing 2800 may encompass a proximal housing including the energy source 2762 and the control circuit 2760, a shaft extending distally from the proximal housing, and the cartridge channel.

Figure 9:
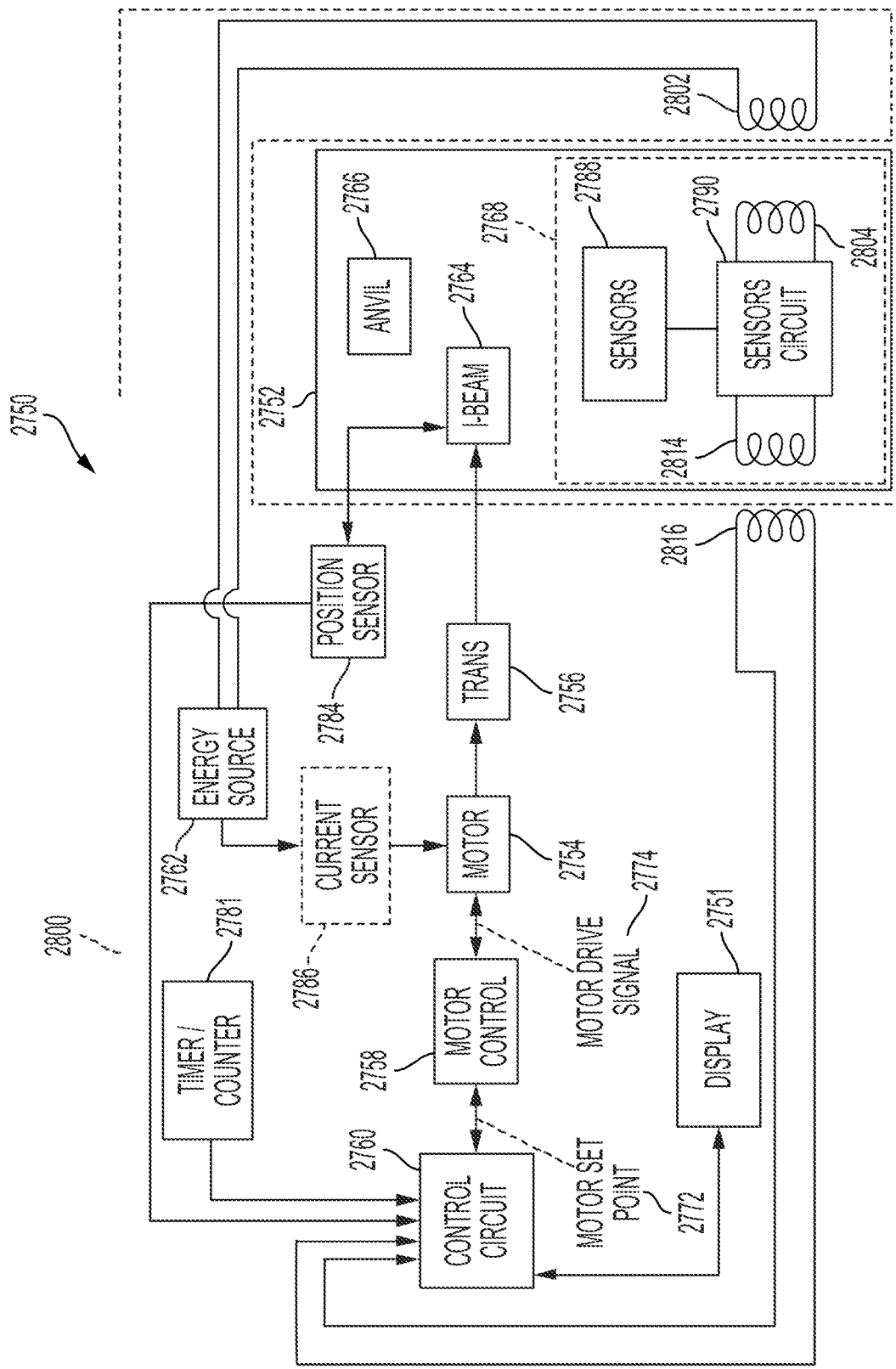
FIG. 9 illustrates a block diagram of a surgical instrument configured or programmed to control the distal translation of a displacement member, in accordance with at least one aspect of the present disclosure.

FIG. 9 illustrates a block diagram of the surgical instrument 2750 shown in FIG. 8 comprising an instrument housing 2800 and an end effector 2752 inductively coupled to the instrument housing 2800 via a set of coils 2818 implementing a wireless power and data communication system, in accordance with at least one aspect of the present disclosure. In one aspect, the surgical instrument 2750 is configured or programmed to control the distal translation of a displacement member such as the I-beam 2764. The surgical instrument 2750 comprises an end effector 2752 that may comprise an anvil 2766, an I-beam 2764 (including a sharp cutting edge), and a removable cartridge 2768. The end effector 2752 comprises sensors 2788 and a sensors circuit 2790 coupled to the sensors 2788. Power is inductively coupled to the sensor circuit 2790 and to the sensors 2788 through coils 2802, 2804 via near field communication. Signals (e.g., voltage, current, resistance, impedance, capacitance, inductance, frequency, phase, etc.) from the sensors 2788 are conditioned by the sensors circuit 2790. The signals or data corresponding to the signals are communicated between the sensors circuit 2790 in the end effector 2752 and the control circuit 2760 in the instrument housing 2800 via near field communication inductive coupling between the coils 2814, 2816.

It will be appreciated that the sensors 2788 may be located in any suitable location in the end effector 2752. In one aspect, the sensors 2788 are arranged in an array in the cartridge 2768. In another aspect, the sensors 2788 are arranged in an array in the anvil 2766. In various aspects, the sensors 2788 are arranged in arrays in the cartridge 2768 and the anvil 2766. The control circuit 2760 may be configured to monitor the sensors 2788 over time to detect moving characteristics of tissue located in the jaws of the end effector 2752. In one aspect, the jaws of the end effector 2752 may be comprised of the anvil 2766 and the cartridge 2768, for example.

The position, movement, displacement, and/or translation of a linear displacement member, such as the I-beam 2764, can be measured by an absolute positioning system, sensor arrangement, and position sensor 2784. A control circuit 2760 may be configured or programmed to control the translation of the displacement member, such as the I-beam 2764. The control circuit 2760, in some examples, may comprise one or more microcontrollers, microprocessors, or other suitable processors for executing instructions that cause the processor or processors to control the displacement member, e.g., the I-beam 2764. In other aspects, the control circuit 2760 may comprise analog or digital circuits such as, for example, programmable logic devices (PLD), field programmable gate arrays (FPGA), discrete logic, or other hardware circuits, software, and/or firmware, or other machine executable instructions to perform the functions explained in the following description.

In one aspect, the control circuit 2760 may be configured or programmed to sense multiple longitudinal and lateral locations within the end effector 2752 independently and to use these different sensed locations with a localized predetermined return path to sense changes in the impedance of tissue grasped between the anvil 2766 and the cartridge 2768 both laterally and longitudinally to be able to detect any specific tissue mid-thickness measure by triangulating at least two interconnected session combinations. For example, the sensors 2788 may comprise an array of impedance sensors distributed laterally and longitudinally along the length of the stapler jaws, i.e., the cartridge 2768 and anvil 2766. As the jaws are closing, the control circuit 2760 may track the local impedance over time during the course of the jaw closure for each sensor, based on readings from the timer/counter 2781, or using software timing techniques. This time history can be used to infer, if present, regions of heterogeneous impedance values—where there are distinct changes or anomalies that mark a particular location. These baseline location(s) are noted and tracked as firing is initiated. Once initiated, the position histories of these locations is tracked and used for feedback control of the firing process. In another example, the control circuit may be configured or programmed to modify functions of the surgical instrument 2750 to alter tissue flow during firing of the I-beam 2764 including changing the firing speed, pauses (complete stops) in firing, closure force, among other parameters.

In other aspects, the control circuit 2760 may be configured or programmed to predict an amount of tissue flow occurring in the jaws of the end effector 2752 by monitoring the sensors 2788. Knowledge of tissue type from situational awareness and/or other device sensed measures, e.g., rate of change of closure load during closure, rate of change of closure load after closure is complete, etc. can be used by the control circuit 2760 to predict tissue flow. Accordingly, in one aspect, the control circuit 2760 is configured or programmed to determine tissue type or condition by combining tissue flow during jaw closure with force feedback of the anvil 2766 closure system.

In another example, the predictions can be further refined by using the sensors 2788 to measure tissue impedance, among other parameters, detect rigid or foreign objects in the jaws, measure magnitude of tissue impedance, measure tissue flow during jaw closure, etc. In another example, the control circuit 2760 may execute a jaw closure algorithm to sense tissue movements during closure as an indicator of the potential effect of each change during firing of the I-beam 2764. For example, at a first closure rate, the control circuit 2760 estimates the magnitude/direction of tissue flow, adjusts the closure rate of the jaws, and observes or records the changes in tissue flow within the jaws. In another example, the control circuit 2760 may be configured or programmed to predict post-fire tissue position by utilizing closure flow in combination with closure force feedback prior to firing to provide feedback to surgeon and allowing an opportunity to reposition the end effector 2752 to ensure tissue is fully captured in cut the line of the end effector 2752.

In other aspects, the control circuit 2760 may be configured or programmed to receive data for various configurations of the sensors 2788 to monitor and interrogate tissue. This may include, monitoring tissue impedance, and tracking the impedance of the tissue across a single electrode or segmented electrode set configured along the length of the cartridge 2788. The control circuit 2760 may be configured or programmed to monitor spectrographic impedance by utilizing sweeps of different frequencies and monitoring the tissue impedance to the power and frequency to determine the physiological composition of the tissue, monitoring capacitance of the tissue, and determining the tissue characteristics and gap relationship of the jaws to determine the amount of tissue present within the jaws. In another aspect, the control circuit 2760 may be configured or programmed to measure light transmissivity, refractivity or Doppler effects to determine tissue characteristics. Local light refractivity analysis may be employed to determine the surface conditions of the tissue to monitor irregularities within the tissue captured between the jaws. The control circuit 2760 may be configured or programmed to monitor local moving particles of tissue using Doppler effect frequency analysis of the light.

In one aspect, a timer/counter 2781 provides an output signal, such as the elapsed time or a digital count, to the control circuit 2760 to correlate the position of the I-beam 2764 as determined by the position sensor 2784 with the output of the timer/counter 2781 such that the control circuit 2760 can determine the position of the I-beam 2764 at a specific time (t) relative to a starting position. The timer/counter 2781 may be configured to measure elapsed time, count external events, or time external events. In other aspects, the timer/counter 2781 may be employed to measure elapsed time to monitor the sensors 2788 over time to detect moving characteristics of tissue located in the jaws of the end effector 2752.

The control circuit 2760 may generate a motor set point signal 2772. The motor set point signal 2772 may be provided to a motor controller 2758. The motor controller 2758 may comprise one or more circuits configured to provide a motor drive signal 2774 to the motor 2754 to drive the motor 2754 as described herein. In some examples, the motor 2754 may be a brushed DC electric motor. For example, the velocity of the motor 2754 may be proportional to the motor drive signal 2774. In some examples, the motor 2754 may be a brushless DC electric motor and the motor drive signal 2774 may comprise a PWM signal provided to one or more stator windings of the motor 2754. Also, in some examples, the motor controller 2758 may be omitted, and the control circuit 2760 may generate the motor drive signal 2774 directly.

The motor 2754 may receive power from an energy source 2762. The energy source 2762 may be or include a battery, a super capacitor, or any other suitable energy source. The motor 2754 may be mechanically coupled to the I-beam 2764 via a transmission 2756. The transmission 2756 may include one or more gears or other linkage components to couple the motor 2754 to the I-beam 2764. A position sensor 2784 may sense a position of the I-beam 2764. The position sensor 2784 may be or include any type of sensor that is capable of generating position data that indicate a position of the I-beam 2764. In some examples, the position sensor 2784 may include an encoder configured to provide a series of pulses to the control circuit 2760 as the I-beam 2764 translates distally and proximally. The control circuit 2760 may track the pulses to determine the position of the I-beam 2764. Other suitable position sensors may be used, including, for example, a proximity sensor. Other types of position sensors may provide other signals indicating motion of the I-beam 2764. Also, in some examples, the position sensor 2784 may be omitted. Where the motor 2754 is a stepper motor, the control circuit 2760 may track the position of the I-beam 2764 by aggregating the number and direction of steps that the motor 2754 has been instructed to execute. The position sensor 2784 may be located in the end effector 2752 or at any other portion of the instrument.

The control circuit 2760 may be in communication with one or more sensors 2788 located in the end effector 2752. The sensors 2788 may be positioned in the end effector 2752 and adapted to operate with the surgical instrument 2750 to measure various derived parameters such as gap distance versus time, tissue compression versus time, anvil strain versus time, tissue movement versus time, tissue impedance, tissue capacitance, spectroscopic impedance, light transmissivity, refractivity or Doppler effects, among other parameters. The sensors 2788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 2752. The sensors 2788 may include one or more sensors.

The one or more sensors 2788 may comprise a strain gauge, such as a micro-strain gauge, configured to measure the magnitude of the strain in the anvil 2766 during a clamped condition. The strain gauge provides an electrical signal whose amplitude varies with the magnitude of the strain. The sensors 2788 may comprise a pressure sensor configured to detect a pressure generated by the presence of compressed tissue between the anvil 2766 and the cartridge 2768. The sensors 2788 may be configured to detect impedance of a tissue section located between the anvil 2766 and the cartridge 2768 that is indicative of the thickness and/or fullness of tissue located therebetween.

The sensors 2788 may be is configured to measure forces exerted on the anvil 2766 by a closure drive system. For example, one or more sensors 2788 can be at an interaction point between a closure tube and the anvil 2766 to detect the closure forces applied by a closure tube to the anvil 2766. The forces exerted on the anvil 2766 can be representative of the tissue compression experienced by the tissue section captured between the anvil 2766 and the cartridge 2768. The one or more sensors 2788 can be positioned at various interaction points along the closure drive system to detect the closure forces applied to the anvil 2766 by the closure drive system. The one or more sensors 2788 may be sampled in real time during a clamping operation by a processor of the control circuit 2760. The control circuit 2760 receives real-time sample measurements to provide and analyze time-based information and assess, in real time, closure forces applied to the anvil 2766.

A current sensor 2786 can be employed to measure the current drawn by the motor 2754. The force required to advance the I-beam 2764 corresponds to the current drawn by the motor 2754. The force is converted to a digital signal and provided to the control circuit 2760.

The drive system of the surgical instrument 2750 is configured to drive the displacement member, cutting member, or I-beam 2764, by a brushed DC motor with gearbox and mechanical links to an articulation and/or knife system. Another example is the electric motor 2754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 2754. The outside influence, such as drag, may cause the operation of the physical system to deviate from a desired operation of the physical system.

Various example aspects are directed to a surgical instrument 2750 comprising an end effector 2752 with motor-driven surgical stapling and cutting implements. For example, a motor 2754 may drive a displacement member distally and proximally along a longitudinal axis of the end effector 2752. The end effector 2752 may comprise a pivotable anvil 2766 and, when configured for use, a cartridge 2768 positioned opposite the anvil 2766. A clinician may grasp tissue between the anvil 2766 and the cartridge 2768, as described herein. When ready to use the instrument 2750, the clinician may provide a firing signal, for example by depressing a trigger of the instrument 2750. In response to the firing signal, the motor 2754 may drive the displacement member distally along the longitudinal axis of the end effector 2752 from a proximal stroke begin position to a stroke end position distal of the stroke begin position. As the displacement member translates distally, an I-beam 2764 with a cutting element positioned at a distal end, may cut the tissue between the cartridge 2768 and the anvil 2766.

In various examples, the control circuit 2760 may be configured or programmed to control the distal translation of the displacement member, such as the I-beam 2764, for example, based on one or more tissue conditions. The control circuit 2760 may be configured or programmed to sense tissue conditions, such as thickness, flow, impedance, capacitance, light transmissivity, either directly or indirectly, as described herein. The control circuit 2760 may be configured or programmed to select a firing control program based on tissue conditions. A firing control program may describe the distal motion of the displacement member. Different firing control programs may be selected to better treat different tissue conditions. For example, when thicker tissue is present, the control circuit 2760 may be configured or programmed to translate the displacement member at a lower velocity and/or with lower power. When thinner tissue is present, the control circuit 2760 may be configured or programmed to translate the displacement member at a higher velocity and/or with higher power.

The entire disclosures of U.S. Pat. No. 8,622,274, entitled MOTORIZED CUTTING AND FASTENING INSTRUMENT HAVING CONTROL CIRCUIT FOR OPTIMIZING BATTERY USAGE, U.S. Pat. No. 10,135,242, entitled SMART CARTRIDGE WAKE UP OPERATION AND DATA RETENTION, U.S. Pat. No. 10,548,504, entitled OVERLAID MULTI SENSOR RADIO FREQUENCY (RF) ELECTRODE SYSTEM TO MEASURE TISSUE COMPRESSION, U.S. Pat. No. 9,993,248, entitled SMART SENSORS WITH LOCAL SIGNAL PROCESSING, U.S. Patent Application Publication No. 2016/0256071, entitled OVERLAID MULTI SENSOR RADIO FREQUENCY (RF) ELECTRODE SYSTEM TO MEASURE TISSUE COMPRESSION, now U.S. Pat. No. 10,548,504, U.S. Patent Application No. 2018/0168625, entitled SURGICAL STAPLING INSTRUMENTS WITH SMART STAPLE CARTRIDGES, U.S.

Patent Application No. 2018/0250002, entitled POWERED SURGICAL DEVICES HAVING TISSUE SENSING FUNCTION, and International Patent Publication No. WO 2018/049206, entitled STAPLER RELOAD DETEC- TION AND IDENTIFICATION, and U.S. patent application Ser. No. 16/354,470, entitled are incorporated by reference herein.

The entire disclosures of U.S. Pat. No. 4,785,180, titled OPTOELECTRIC SYSTEM HOUSED IN A PLASTIC SPHERE, issued Nov. 15, 1988, U.S. Pat. No. 6,804,012, titled ARRANGEMENT FOR THE DETECTION OF RELATIVE MOVEMENTS OR RELATIVE POSITION OF TWO OBJECTS, issued Oct. 12, 2004, European Patent Application No. 1,850,210, titled OPTOELECTRONIC DEVICE FOR DETERMINING RELATIVE MOVEMENTS OR RELATIVE POSITIONS OF TWO OBJECTS, published Oct. 31, 2007, U.S. Patent Application Publication No. 2008/0001919, titled USER INTERFACE DEVICE, published Jan. 3, 2008; and U.S. Pat. No. 7,516,675, titled JOYSTICK SENSOR APPARATUS, issued Apr. 14, 2009 are incorporated by reference herein. Generally, these references describe multi-dimensional input devices and/or sensor arrangements.

The entire disclosures of U.S. patent application Ser. No. 16/354,470 U.S., titled SEGMENTED CONTROL INPUTS FOR SURGICAL ROBOTIC SYSTEMS, filed Mar. 15, 2019, U.S. Pat. No. 4,785,180, titled OPTOELECTRIC SYSTEM HOUSED IN A PLASTIC SPHERE, issued Nov. 15, 1988, U.S. Pat. No. 6,804,012, titled ARRANGEMENT FOR THE DETECTION OF RELATIVE MOVEMENTS OR RELATIVE POSITION OF TWO OBJECTS, issued Oct. 12, 2004, European Patent Application No. 1,850,210, titled OPTOELECTRONIC DEVICE FOR DETERMINING RELATIVE MOVEMENTS OR RELATIVE POSITIONS OF TWO OBJECTS, published Oct. 31, 2007, U.S. Patent Application Publication No. 2008/0001919, titled USER INTERFACE DEVICE, published Jan. 3, 2008; U.S. Pat. No. 7,516,675, titled JOYSTICK SENSOR APPARATUS, issued Apr. 14, 2009, and U.S. patent application Ser. No. 15/940,627, titled DRIVE ARRANGEMENTS FOR ROBOT-ASSISTED SURGICAL PLATFORMS, filed Mar. 29, 2018, are hereby incorporated by reference in their entirety. Generally, these references describe robotic surgical systems and multi-dimensional input devices and/or sensor arrangements.

Referring now to FIG. 10, a system 3000 for detecting tissue and foreign objects during a surgical operation is depicted in accordance with at least one non-limiting aspect of the present disclosure. According to the non-limiting aspect of FIG. 10, the system 3000 can include a surgical instrument 3002, which can be similarly configured to the surgical instrument 10000 of FIG. 1 and a computing device 3004. Although the surgical instrument 3002 of FIG. 1 is connected to the computing device 3002 via a cable, the surgical instrument 3002 can be configured for any form of wired and/or wireless communication with the computing device 3004. As used herein, the term "computing device" can include any server, personal computer, laptop, tablet, and/or mobile phone, amongst other devices communicably coupled to a display and capable of generating a user interface associated with use of the surgical instrument 3002. According to some non-limiting aspects, the computing device 3004 can be further configured to control the surgical instrument 3002 during the surgical operation. Although, according to the non-limiting aspect of FIG. 1, the surgical instrument 3002 is a handheld surgical stapler, the present disclosure contemplates other non-limiting aspects wherein the surgical instrument 3002 is robotically configured. Alternately, the surgical instrument 3002 can be an electrosurgical instrument configured to perform surgical operations via ultrasonic and/or RF energy.

In certain aspects, the computing device 3004 is a component of a surgical hub in wired and/or in wireless communication with the surgical instrument 3000. Various suitable surgical hubs are disclosed in U.S. patent application Ser. No. 16/209,453, titled METHOD FOR CONTROLLING SMART ENERGY DEVICES, and filed Dec. 4, 2018, which is hereby incorporated by reference herein in its entirety.

In further reference to FIG. 10, the surgical instrument 3002 can include sensors, such as one or more electrodes 3012 positioned within an end effector 3014 coupled to the distal end of a shaft 3010. However, according to other non-limiting aspects, other sensors can be utilized to achieve a similar effect. According to some non-limiting aspects, an array of electrodes 3012 can be positioned within the end effector 3014. For example, according to some non-limiting aspects, the array can include 16 electrodes 3012. According to other non-limiting aspects, the electrodes 3012 can be positioned in a segmented configuration, as previously discussed. The electrodes 3012 can be electrically coupled through the inside of a hollow cavity defined by the shaft 3010 such that they can be connected to electronics positioned within a handle portion 3008 of the surgical instrument 3002. For example, the handle portion 3008 can include processing electronics configured to process signals passed by the electrodes 3012. Such electronics can include impedance measuring electronics, which can determine an electrical impedance of media positioned between jaws of the end effector 3014 based on the signals passed by the electrodes 3012. Alternately and/or additionally, electronics within the handle portion 3008 can transmit signals received from the electrodes 3012 to a connected computing device 3004 for further processing.

Accordingly, during a surgical operation, such as an intraoperative stapling procedure, the surgical instrument 3002 can be used to generate real-time electrical impedance measurements based on signals received from the electrodes 3012. These signals can be processed along with other variables, such as selected inputs, using a model and/or algorithm, which can be used to detect media within the jaws of the end effector 3014 and determine characteristics of said media, such as a location and/or a condition of the media. Accordingly, the system 3000 of FIG. 10 can be used to detect both tissue and foreign objects (e.g., NGtubes, staples, etc.) within the jaws of the end effector 3014. The algorithmic results can be communicated to a display of a communicably coupled computing device 3004. According to some non-limiting aspects, the system 3000 does not require a computing device 3004 and the display (e.g., an LED screen, etc.) can be integrated into the handle portion 3008 of the surgical instrument 3002. According to other non-limiting aspects, the display can be a component of a console for a robotically assisted device. In still other non-limiting aspects, no display is required by the system 3000 and either the surgical instrument 3002 or the computing device 3004 can be configured to emit an audible notification associated with the algorithmic results. Furthermore, according to some non-limiting aspects, one or more depicted components of the system 3000 of FIG. 10 can include a clock circuit configured to measure passing time. Accordingly, the system 3000 of FIG. 3 can be configured to communicate the algorithmic results and thus, information associated with the detected media within the jaws of the end effector 3014 to an operating clinician.

As such, an algorithm, which will be described in further detail herein, can be used in conjunction with various surgical instruments, including the instrument 3000 of FIG.

Figure 11:
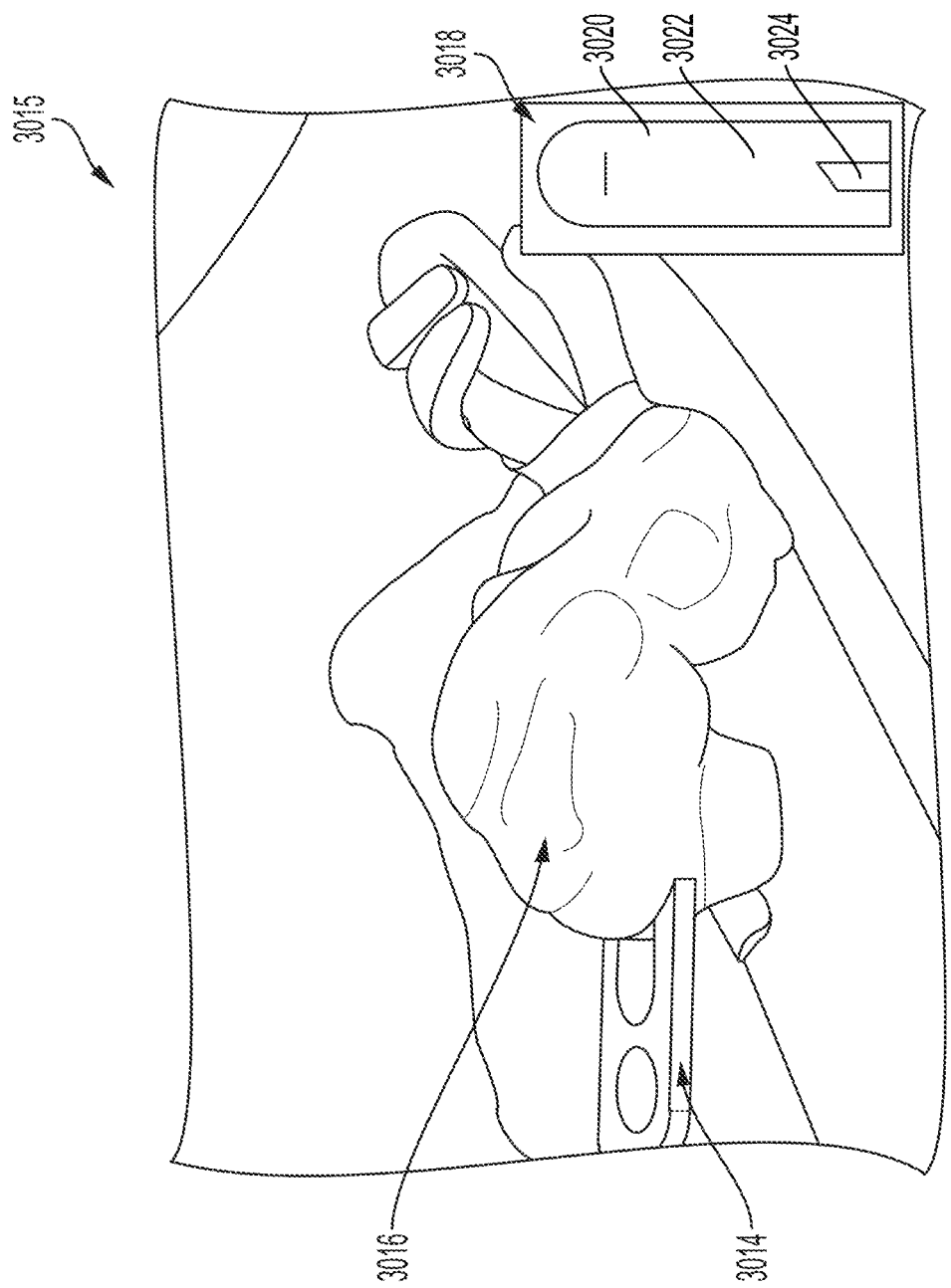
FIG. 11 illustrates a user interface displayed by a computing device of the system of FIG. 10, in accordance with at least one non-limiting aspect of the present disclosure.

10, or the robotically controlled instrument 5100 of FIG. 3, to detect and/or characterize various media (e.g., tissue, foreign objects, etc.) positioned within the jaws of an end effector in real time. Referring now to FIG. 11, a user interface 3015 displayed by the computing device 3004 of the system 3000 of FIG. 10 is depicted in accordance with at least one non-limiting aspect of the present disclosure. One or more components of the system 3000 (FIG. 10) can include a memory configured to store the algorithm. For example, according to some non-limiting aspects, the algorithm can be stored within a memory of the computing device 3004. However, according to other non-limiting aspects, the algorithm can be stored within a memory of the surgical instrument 3002. Regardless, the algorithm can be implemented to generate one or more components of the user interface 3015 of FIG. 11.

According to the non-limiting aspect of FIG. 11, the user interface 3015 can include an image of the end effector 3014 of the surgical instrument 3002 (FIG. 10) grabbing a tissue sample 3016 within a patient. For example, the image can be generated via one or more image sensors implemented by the system 3000 (FIG. 10). For example, the image sensor can be mounted on or around the surgical instrument 3002 (FIG. 10). The user interface 3015 can further include a widget 3018 overlaying the image, with a digital representation of the end effector 3020. The digital representation of the end effector 3020 can include a first portion 3022 corresponding to the tissue sample 3016 within the jaws of the end effector 3014, as detected by the electrodes 3012 (FIG. 10). The digital representation of the end effector 3020 can further include a second portion 3024 corresponding to a foreign object within the jaws of the end effector 3014, as detected by the electrodes 3012 (FIG. 10). Accordingly, the widget 3018 can visually communicate the specific composition and/or location of various media positioned within the jaws of the end effector 3014 to an operating clinician. This can enhance the surgical operation because the operating clinician can identify exactly what objects are positioned within the end effector 3014 as well as the specific location of those objects within the end effector 3014. In other words, the system 3000 of FIG. 10 can provide in-operative, real-time feedback regarding the location of tissue and/or foreign objects within the jaws of the end effector 14. This feedback can be implemented to prevent inadvertent damage and/or critical errors to surrounding structures during a surgical operation, such as a stapling procedure. Detection algorithms can be light and efficient and thus, suitable for on-board electronics deployment for both handheld and/or robotics surgical platforms.

Algorithms can generate the digital representation of the end effector 3020—including the first and second portions 3022, 3024—based on media parameters (e.g., impedance) that can be algorithmically determined based on signals received from the electrodes 3012 (FIG. 10) positioned within the end effector 3014. For example, the electrodes 3012 (FIG. 10) can be utilized to detect an electrical impedance of the media positioned within the jaws of the end effector 3014, which can vary significantly based on the material composition of the media. Accordingly, the determined electrical impedance can correspond to a particular type of media positioned within the jaws of the end effector 3014, such as different types of tissue, other biological material with varying properties (e.g., blood, blood vessels, veins, etc.), an interaction between a tool and/or tissue, a foreign object (e.g., staples, tubes, etc.), and/or varying clinical environments the end effector is placed in, amongst other forms of media.

However, it may be difficult to identify the boundaries of parameter variations, such as electrical impedance, in certain situations. Accordingly, in some non-limiting aspects, an algorithm can use signals from the electrodes 3012 (FIG. 10) to first detect non-tissue media within the jaws of the end effector 3014, which may correspond to anomalous parameters (e.g., impedances) relative to biologic media positioned within the jaws. In other words, non-tissue media between the jaws of the end effector 3014 may be more easily classified, as they may only correspond to a few categories of media. Media such as air, liquids, and/or foreign objects positioned within the end effector 3014 can result in signals that will result in different algorithmically determined parameters (e.g., impedances) relative to biologic media (e.g., tissue) positioned within the end effector 3014 and thus, such media can be easier to detect and distinguish via a user interface, such as the user interface 3015 of FIG. 11.

Figure 12:
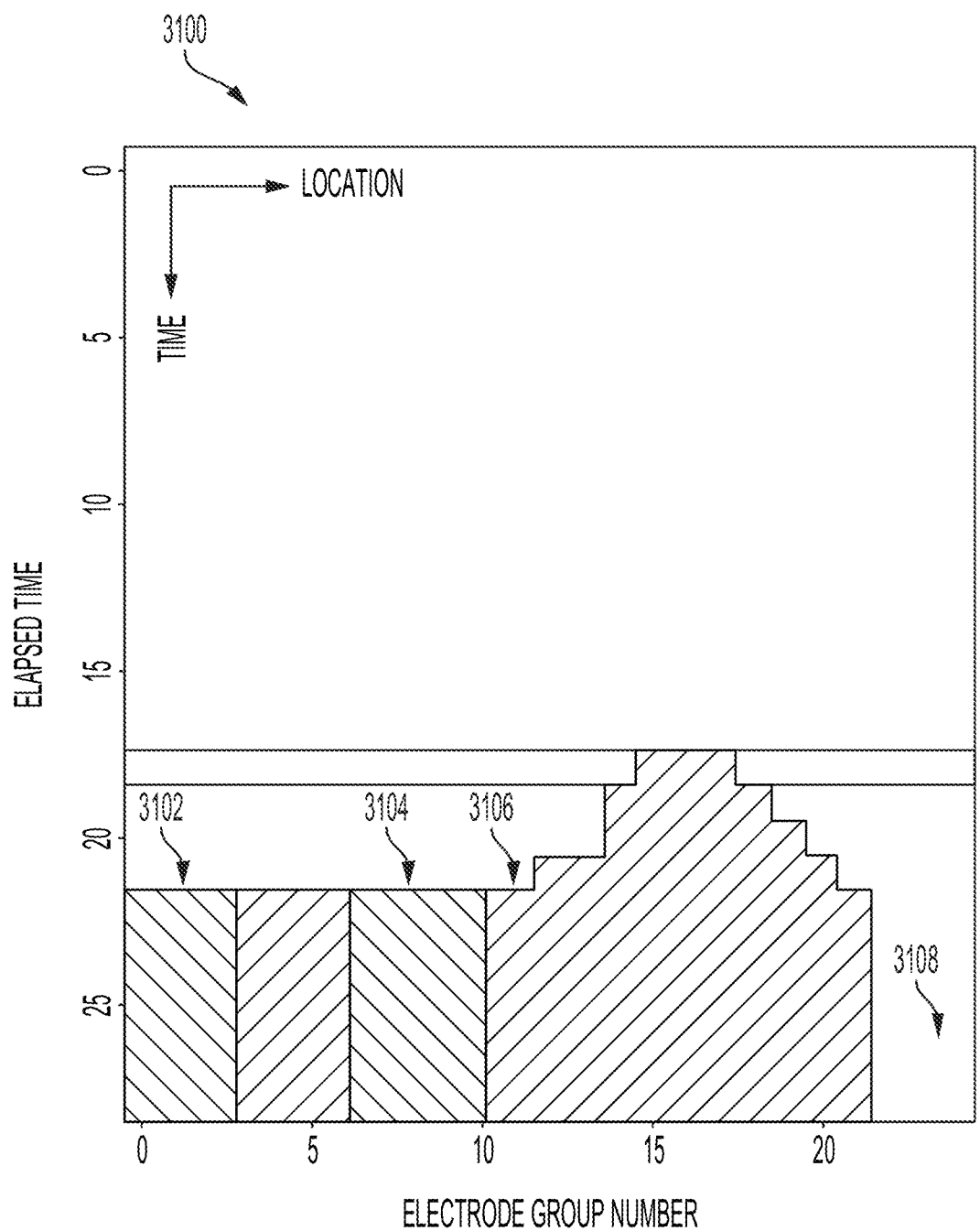
FIG. 12 illustrates a chart depicting a parameter measured by the system of FIG. 10 in time, in accordance with at least one non-limiting aspect of the present disclosure.

Referring now to FIG. 12, a chart 3100 illustrating a parameter (e.g., impedance) measured by the system 3000 of FIG. 10 in time is depicted in accordance with at least one non-limiting aspect of the present disclosure. According to the non-limiting aspect of FIG. 12, the chart 3100 can include illustrate how a magnitude of the impedance can vary by location, as illustrated by the x-axis, and time, as illustrated by the y-axis. The location can be determined via the impedance measured based on electrical parameters (e.g., voltage) generated by various groupings of electrodes 3012 (FIG. 10) installed within the end effector 3014 (FIG. 10). Time can be measured via any desired duration, though according to some aspects time can be measured in seconds to promote the real-time capabilities of the system 3000 (FIG. 10) and algorithm.

In further reference to FIG. 12, the chart 3100 conceptually illustrates the detection results, including classifications of media detected within the end effector 3014 (FIG. 10), which can be illustrated using different colors and/or patterns to enhance the visual distinction along the x-axis as time elapses, as represented along the y-axis. In other words, the chart 3000 of FIG. 12 can represent impedance detected by various groups of electrodes 3012 (FIG. 10) positioned within the end effector 3014 (FIG. 10) in time, which can be used to characterize the composition and location of various media positioned within the end effector 3014 (FIG. 10) as the jaws of the end effector 3014 (FIG. 10) open and close, clamping down on and compressing said media. As illustrated by the chart 3100 of FIG. 12, an algorithm, can be used to detect a first media 3102 positioned between electrode group numbers 0 and 5, a second media 3104 positioned between electrode group numbers 5 and 10, a third media 3106 positioned between electrode group numbers 10 and 20, and a fourth media 3108 positioned beyond electrode group number 20. For example, the algorithm may determine, based on impedance determined based on signals received from the electrodes, that the first media 3102 is a fluid (e.g., blood), the second media 3104 is a foreign object (e.g., a staple, a NGtube, etc.), the third media 3106 is a tissue sample, and the fourth media 3108 is air, meaning the end effectors are open and/or nothing is positioned between the jaws beyond electrode group number 20. In fact, the third media 3106 is identifiable as a tissue sample based upon the compression exhibited by the stepped peak of impedance signal detected between electrode group numbers 10 and 20. It shall be appreciated that, as used herein, an impedance signal can include a variety of signal parameters, including a magnitude and/or a phase, amongst others. Moreover, impedance signals and their respective parameters can be measured in the time domain and/or the frequency domain, amongst others.

Referring now to FIG. 13, a logic flow diagram of a method 3200 of detecting and locating media within the jaws of the end effector 3014 (FIG. 10) of the system 3000 of FIG. 10 is depicted in accordance with at least one non-limiting aspect of the present disclosure. According to some non-limiting aspects, the system 3000 (FIG. 10) can include a control circuit, such as the control circuit 2760 of FIG. 9, and a memory configured to control an algorithm, wherein the algorithm is configured to cause the control circuit to perform the method 3200 of FIG. 13. According to some non-limiting aspects, the control circuit and/or memory can be positioned within the surgical instrument 3002 (FIG. 10). According to other non-limiting aspects, the control circuit and/or memory can be positioned within the computing device 3004 (FIG. 10). According to still other non-limiting aspects, the memory can be positioned in a remotely located server (not shown), such as a cloud-based analytics system configured to communicate with various surgical instruments 3002 (FIG. 10) and computing devices 3004 (FIG. 10).

Specifically, FIG. 13 illustrates the main steps of data flow associated with the determination of a parameter (e.g., impedance, etc.), including recordation 3206, processing 3214, and result generation and communication 3219. The algorithm logic will allow the detection and feedback of tissue locations and foreign objects, if present, within the jaws of the end effector 3014 (FIG. 10), with block-level placeholders for the algorithmic detection of anomalies and foreign objects 3216 and the detection foreign objects 3218, which are described in more detail in reference to FIGS. 14 and 15, respectively. Of course, the method 3200 of FIG. 13 is merely illustrative, and the illustrated processes of the method 3200 are non-exclusive. According to other non-limiting aspects, the method 3200 may include more steps or fewer steps than are depicted in FIG. 13.

According to the non-limiting aspect of FIG. 13, the method 3200 can include commencing 3202 the detection process, including initiating and activating 3204 the sensors (e.g., electrodes 3012 of FIG. 10) to take measurements. If the sensors 3012 (FIG. 10) are not activated for measurements, the sensors 3012 (FIG. 10) should be activated. The method 3200 can further include recording 3206 data associated with the determined parameter (e.g., impedance, etc.) based on signals received from electrodes 3012 (FIG. 10) of the surgical instrument 3002 (FIG. 10) and checking 3208 the signal quality. If the quality exceeds a predetermined margin of error 3210, the system 3000 (FIG. 10) may issue a warning 3211 that the sensors have failed or are generating data of insufficient quality. According to some non-limiting aspects, the warning can be a visual alert provided via a display, such as a display coupled to the computing device 3004 (FIG. 10) or embedded within the surgical instrument 3002 (FIG. 10), itself. According to other non-limiting aspects, the warning can be an audible alert provided via the surgical instrument 3002 (FIG. 10) and/or computing device 3004 (FIG. 10).

Still referring to FIG. 13, the method 3200 can further include filtering and preprocessing 3212 data streams associated with the surgical instrument 3002 (FIG. 10), and processing 3214 them accordingly using an algorithm. The method 3200 can further include algorithmically detecting 3216 whether there is a foreign object 3218 and/or fluid 3220 within the jaws of the end effector 3014 (FIG. 10). If either determination is affirmative, the system 3000 (FIG. 10) can issue 3219 a warning to the operating clinician. Once again, the warning can either include a visual and/or audible alert. If not, the method 3200 can include determining 3222 if there is an open circuit at the location, or, determining 3224 if there is tissue at the location. The method 3200 can further include determining 3226 whether the detection methods should be repeated for a subsequent time period and, if the determination is affirmative, the method 3200 can be repeated from the filtering and preprocessing 3212 step. If the algorithm determines that the detection method should not be repeated, the method 3200 can be terminated 3228.

In other words, the method 3200 can include sensing that is automatically triggered/turned on by users (e.g., surgeons, operating clinicians, etc.) during a procedure, such as a surgical stapling procedure. The method 3200 can include the determination of real-time parameters, such as impedance measurements, based on signals received from sensors, such as each electrode 3012 (FIG. 10) within the end effector 3014 (FIG. 10), which are algorithmically processed to determine an impedance characteristic (or "feature") of the media positioned within the end effector 3014 (FIG. 10). According to some non-limiting aspects, the impedance feature can be the impedance magnitude at a pre-determined frequency. According to some non-limiting aspects, one or more frequencies can be selected. For example, it may be preferable to use a frequency of approximately 100 kHz. Furthermore, the method 3200 can record and track impedance features over time. Once determined, such impedance features can be used as inputs to the media detection model and/or algorithm.

A detection model, via built-in algorithmic logic, can differentiate the presence and/or location of various media, such as tissue and non-tissue mediums, positioned within the jaws of the end effector 3014 (FIG. 10), which will be described in further detail in reference to FIG. 14. Non-tissue media can be air, indicating that the jaws of the end effector 3014 (FIG. 10) are open. Alternately and/or additionally, non-tissue media can include liquids (e.g., blood) and/or foreign objects (e.g., staples, NGtubes, etc.). The non-tissue media can be detected via anomalies. The location of media such as tissue can then be detected after non-tissue mediums location are effectively identified. The algorithm can then classify the results, marking it as tissue, air, liquids, and/or foreign objects based on the determined impedances, and the classified results can be visually displayed via the system 3000 (FIG. 10). Furthermore, the method 3200 can include combining detection results from pairs of electrodes 3012 (FIG. 10) (e.g., a driven electrode and corresponding return electrode) of an array of electrodes 3012 (FIG. 10) to provide the location information of the detected tissue and non-tissue media along the jaws of the end effector 3014 (FIG. 10). According to some non-limiting aspects, some detection results can be selectively displayed in real-time, depending on a particular step of the surgical operation. As such, the system 3000 (FIG. 10) can provide critical and timely feedback to operating clinicians.

Referring now to FIG. 14, a logic flow diagram of the method 3216 of detecting an anomaly as part of the method 3200 of FIG. 13, is depicted in accordance with at least one non-limiting aspect of the present disclosure. According to the non-limiting aspect of FIG. 14, data outputs from the processing 3214 step of the method 3200 of FIG. 13 can be used to perform the anomaly detecting 3216 step of the method 3200 of FIG. 13, which begins by extracting, or algorithmically determining 3232, an impedance signal value at selected frequencies for each electrode 3012 (FIG.

10) of an electrode group positioned within the jaws of the end effector 3014 (FIG. 10) of the system 3000 of FIG. 10. Once again, according to some non-limiting aspects, one or more frequencies can be selected. The determination 3232 can be based on signals received from each electrode 3012 (FIG. 10). The determined impedance signal values can be correlated with a particular time within the time domain, illustrated along the y-axis of the chart 3100 of FIG. 12. According to other non-limiting aspects, the determined parameter can be another characteristic of the media positioned within the jaws of the end effector 3014 (FIG. 10) and can be determined based on signals received form sensors other than the electrode 3012 (FIG. 10).

According to the non-limiting aspect of FIG. 14, once the impedance value is determined, the method 316 can further include a series of comparisons 3234, 3236, 3218 of the determined impedance value to one or more predetermined thresholds. For example, according to the non-limiting aspect of FIG. 14, the method 3216 can include a determination 3234 of whether the determined impedance value is less than a predetermined threshold associated with an open circuit. If the determined impedance value is not less than the predetermined threshold associated with an open circuit, the algorithm can determine that open jaw (air media in jaw) has been detected, and classify 3235 the associated electrode 3012 (FIG. 10) group as "open." If the determined impedance value is less than the predetermined threshold associated with an open circuit, the method 3216 can further include a determination 3236 of whether the determined impedance value is greater than a predetermined threshold associated with a fluid. If the determined impedance value is not greater than the predetermined threshold associated with a fluid, the algorithm can determine that fluid has been detected, and classify 3237 the associated electrode 3012 (FIG. 10) group as "fluid." If the determined impedance value is greater than the predetermined threshold associated with a fluid, the method 3016 can proceed to a determination 3218 of whether a foreign object is present within the jaws of the end effector 3014 (FIG. 10), as illustrated in the method 3200 of FIG. 13. If the algorithm determines that no foreign object is present within the jaws of the end effector 3014 (FIG. 10), the algorithm can determine that tissue is present within the jaws of the end effector 3014 (FIG. 10) and classify 3239 the associated electrode 3012 (FIG. 10) group as "tissue." If a foreign object is detected within the jaws of the end effector 3014 (FIG. 10), the method 3016 can proceed to a determination 3240 of whether the foreign object is detected for a predetermined time and for more than two neighboring electrode 3012 (FIG. 10) groups. If the algorithm determines that the foreign object is detected for a predetermined time and for more than two neighboring electrode 3012 (FIG. 10) groups, the algorithm can determine that a foreign object is present within the jaws of the end effector 3014 (FIG. 10), classify the associated electrode 3012 (FIG. 10) groups as "foreign object," and record a location within the end effector 3014 (FIG. 10) that is associated with the foreign object. In fact, the algorithmic method 3216 can further record a location within the end effector 3014 (FIG. 10) that is associated with the open classification, the fluids classification, and/or the tissue classification, as well. If the algorithm determines that the foreign object is not detected for a predetermined time and/or that the foreign object is not detected for more than two neighboring electrode 3012 (FIG. 10) groups, the algorithm can determine 3240 that there is noise and/or a nuisance that led to the initial detection 3218 of the foreign object.

In further reference to the non-limiting aspect of FIG. 14, it may be preferable to calibrate 3242 the electrodes 3014 such that impedance signal values can be determined at a specific frequency or frequencies. According to some non-limiting aspects, one or more frequencies can be selected. For example, it may be preferable to determine the impedance signal values at frequencies ranging from 5 kHz to 500 kHz. According to some non-limiting aspect, it may be preferable to determine the impedance signal values at a frequency of 100 kHz, which would allow the threshold values considered during the various comparison steps 3234, 3236, 3218, 3240 can be empirically learned. Accordingly, the algorithm and/or models can be particularly configured to require fewer inputs, which can reduce a computational burden, maintain the simplicity and robustness of the method 3200, and therefore, enable the method 3200 to be deployed via real-time, on-board electronics. Accordingly, an algorithm and methods 3200, 3216 of FIGS. 13 and 14 represent a technological improvement over conventional methods of detecting media within the jaws of an end effector, which can require extensive processing requirements that may be prohibitive to on-board deployments. Experimental results, such as those generated in the experiment described in reference to the user interface of FIG. 18, exhibit that the algorithmic methods 3200, 3216 of FIGS. 13 and 14 can be more efficient and effective than conventional means of media detection, improve surgical outcomes, and can enhance patient safety relative to conventional means.

Referring now to FIG. 15, a logic flow diagram of the method 3218 of detecting the presence of a foreign object within the jaws of an end effector 3014 (FIG. 10), as part of the methods 3200, 3216 of FIGS. 13 and 14, is depicted in accordance with at least one non-limiting aspect of the present disclosure. As previously discussed, the algorithmic method 3216 of FIG. 14 can detect 3244 and classify air and/or a medium positioned within the jaws of the end effector 3014 (FIG. 10). For example, the algorithmic method 3216 (FIG. 14) can detect 3244 an open circuit and thus, a significant drop in the impedance value determined between one or more electrode 3012 (FIG. 10) groups. Alternately and/or additionally, the algorithmic method 3216 (FIG. 14) can detect 3244 a media that has contacted the jaws of the end effector 3014 (FIG. 10) based on a magnitude of the determined impedance value. As previously discussed, the impedance signals can be determined as a function of frequency and/or multiple frequencies, electrode 3012 (FIG. 10) group, and/or time, depending on user preference and/or intended application.

According to the non-limiting aspect of FIG. 15, the method 3218 can further include tracking 3246 the determined impedance signals over time and record certain data points of interest. For example, it may be preferable to record a minimum impedance signal value tracked during a period of time. The method 3218 can further include calculating 3248 a ratio of any determined impedance signal value relative to the data points of interest, such as a minimum impedance signal value tracked during a period of time. The method 3218 can further include determining 3250 whether the ratio is greater than a predetermined threshold, such as a predetermined threshold over a predetermined time period. If the algorithm determines that the ratio is not greater than the predetermined threshold, it will continue calculating 3248 ratio in time. However, if the algorithm determines that the ratio is greater than the predetermined threshold, it can determine 3252 that a foreign object (e.g., a staple, a bougie, an NGtube, etc.) is present within the jaws of the end effector 3014 (FIG. 10).

Still referring to FIG. 15, according to some non-limiting aspects, the featured input for the algorithmic method 3218 of foreign object detection can be a calculated ratio of impedance signal at a specific frequency relative to its minimum value marked at jaw-tissue contacting moment. For example, according to some non-limiting aspects, it may be preferable to calculate the impedance signals and rations at a frequency of 100 kHz. Additionally and/or alternately, threshold values can be empirically learned. According to the non-limiting aspect of FIG. 15, the method 3218 can be deployed to detect foreign objects such as NGtubes, and/or other tube-like objects. However, according to other non-limiting aspect, other foreign objects can be detected using similar techniques. Experimental results of the method 3218 of FIG. 15 are further described in reference to FIG. 17, including a distinct pattern of impedance responses for NGtube and/or a tissue sample positioned within the jaws of an end effector 3012 (FIG. 10). It can be possible to characterize different impedance response patterns associated with different foreign objects of interest. Correspondingly, the algorithmic logic can be altered to detect various foreign objects, while employing substantially a similar functional approach, as illustrated in FIG. 15.

Figure 16:
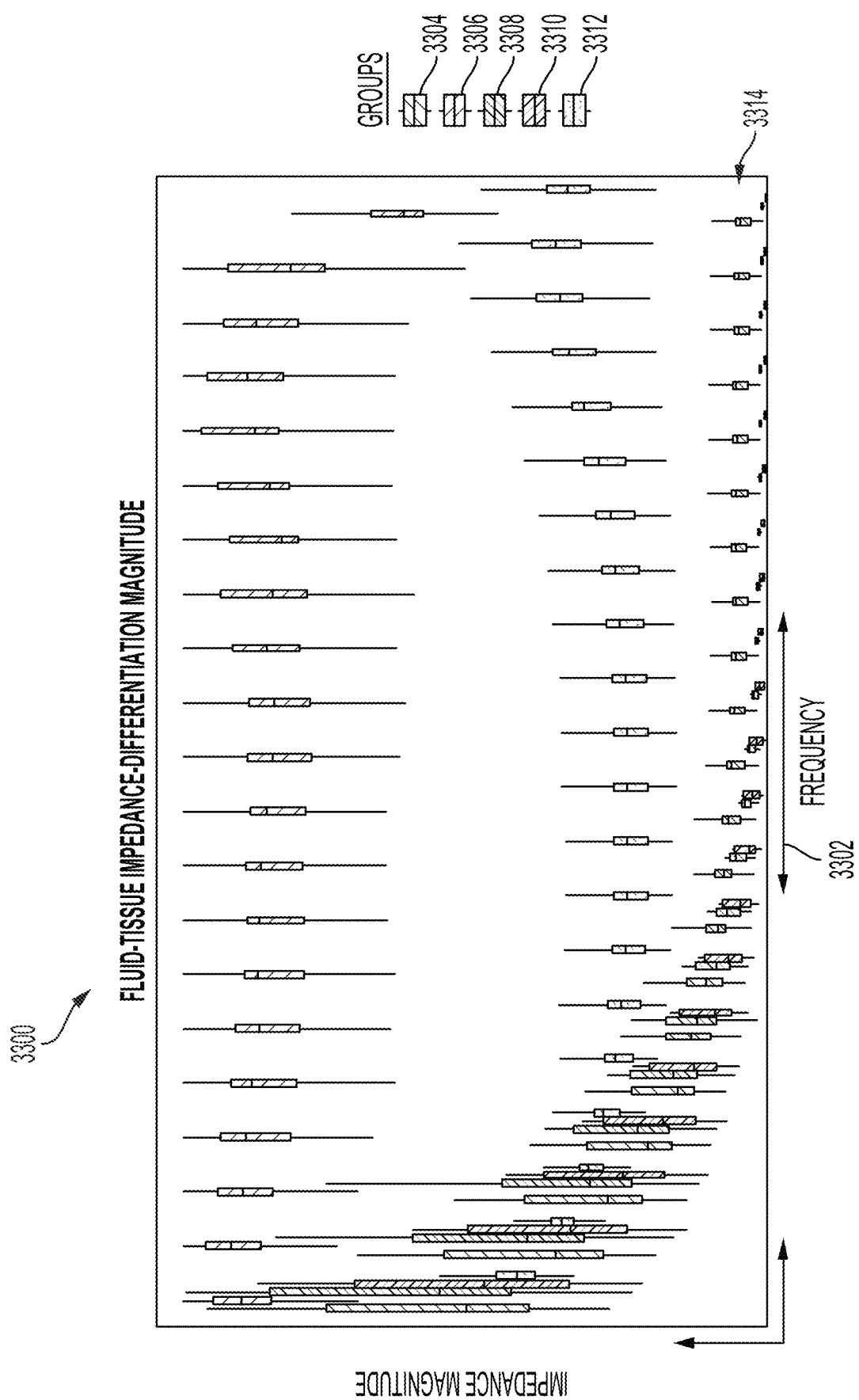
FIG. 16 illustrates a chart depicting experimental results of the methods of FIGS. 13-15, in accordance with at least one non-limiting aspect of the present disclosure.

Referring now to FIG. 16, a chart 3300 illustrating example results of the methods 3200, 3216, 3218 of FIGS. 13-15 is depicted in accordance with at least one non-limiting aspect of the present disclosure. As depicted by the chart 3300 of FIG. 16, different media 3304, 3306 3308, 3310, 3312 can have different determined impedance signals at different frequencies. For example, the chart 3300 of FIG. 16 illustrates impedance signals for blood 3304, lung tissue 3306, peritoneal fluid 3308, saline 3310, and stomach tissue 3312. Moreover, the chart of FIG. 16 depicts impedance signals taken over a particular frequency range of interest 3302. According to some non-limiting aspects, the frequency range of interest can be approximately between 10 kHz and 150 kHz. Furthermore, the chart 3300 of FIG. 16 depicts how a group of fluids 3314 can have lower determined impedance signals relative to other media detected within the jaws of the end effector 3014 (FIG. 10). In other words, non-tissue media, including the blood 3304, the peritoneal fluid 3308, and the saline 3310 can be easily differentiable from tissue, such as the lung tissue 3306 and the stomach tissue 3312, as previously discussed. Specifically, the chart 3300 of FIG. 16 is a bode (e.g., frequency vs magnitude) boxplot that summarizes impedance signal variation of all the data collected from various experiments for tissue and fluids, including pig lung 3306, pig stomach tissue 3312, saline 3310, blood 3304, and peritoneal fluids 3308. However, it is anticipated that similar results, including the distinguishable difference in impedance signals determined for the fluid 3304, 3308, 3310, would be present for human-oriented implementations.

Referring now to FIGS. 17A-C, another chart 3400 illustrating experimental results of the methods of FIGS. 13-15 is depicted in accordance with at least one non-limiting aspect of the present disclosure. Specifically, FIGS. 17B and 17C illustrate portion of interest of chart 3400 in more detail. Furthermore, the chart 3400 has been annotated to illustrate notable features of the experimental results. According to the non-limiting aspect of FIGS. 17A-C, the chart 3400 can illustrate various impedance signals determined based on signals received from different electrode 3012 (FIG. 10) groups as time elapses. FIG. 17C, specifically, illustrates how patterns of determined impedance responses in time can be quite different for electrode 3012 (FIG. 10) groups associated with locations where a NGtube is present, especially when compared to impedance responses associated with electrode 3012 (FIG. 10) groups associated with locations where a NGtube is not present and only tissue exists between the jaws of the end effector 3014 (FIG. 10). As time elapses along the domain, the jaws of the end effector 3014 (FIG. 10) are closing and thus, compressing media (e.g., NGtube, tissue) positioned between the jaws. As the jaws are compressing, particularly between 30 seconds and 40 seconds along the time-domain, the impedance signal is rising at a more dramatic rate for electrode groups 6-10, where a foreign object, such as an NGtube, is present. This pattern is demonstrably different than the relatively stable impedance signal determined at electrode groups 5 and 11-13, where only tissue is present. Accordingly, the system 3000 (FIG. 10) and more specifically, the control circuit, can generate an alert that communicates the presence and specific location of the detected foreign object to an operating clinician. According to some non-limiting aspects, the alert can be visually displayed via a user interface, such as the user interface 3015 of FIG. 11. According to other non-limiting aspects, the alert can be audibly communicated via a speaker positioned within the surgical instrument 3002 (FIG. 10) or the computing device 3004 (FIG. 10).

Referring now to FIG. 18, another user interface 3500 displayed by a computing device 3004 of the system of FIG. 10 is depicted in accordance with at least one non-limiting aspect of the present disclosure. According to the non-limiting aspect of FIG. 18, the user interface 3500 of FIG. 18 can display image data and a visual representation of the algorithmic results generated during a simulated experiment utilizing the methods 3200, 3216, 3218 of FIGS. 13-15. Specifically, the user interface 3500 can include an image portion 3502 and a digital representation 3506 of an end effector. However, according to the non-limiting aspect of FIG. 18, test equipment is simulating the jaws of an end effector. Once again, the image can be generated via one or more image sensors implemented by the system 3000 (FIG. 10). The user interface 3500 can further include a widget 3504 overlaying the image portion 3502, with a digital representation of the end effector 3506.

As illustrated in FIG. 18, the simulated end effector is compressing various media. For example, a distal portion of the simulated end effector has no media beneath it, a center portion of the simulated end effector has an NGtube beneath it, and a proximal end of the simulated end effector has tissue beneath it. As previously discussed one or more electrodes 3012 (FIG. 10) can be positioned within an end effector 3014 (FIG. 10), or in the case of FIG. 18, the simulated end effector. The widget 3504 and, more specifically, the digital representation of the end effector 3506 can be color coded, wherein each color can associated with a media detected by the algorithmic methods 3200, 3216, 3218 of FIGS. 13-15, based on calculated impedance signals based on signals passed by the one or more electrodes positioned within the simulated end effector. According to the non-limiting aspect of FIG. 18, three media have been detected, including air 3508, tissue 3510, and a foreign object, the NGtube 3512. The digital representation of the end effector 3506 includes a longitudinal scale, corresponding to the relative positions within which the electrodes 3012 (FIG. 10) span from a distal end of the end effector to a proximal end of the end effector. Accordingly, the digital representation of the end effector 3506 is segmented into four colored portions, wherein each portion corresponds to media determined by the algorithmic methods, as detected by the electrodes. For example, according to the non-limiting aspect of FIG. 18, the widget 3504 can communicate to an operating clinician that air 3508, tissue 3510, an NGtube 3512, and more tissue 3510 is positioned within the jaws of the simulated end effector, from its distal to its proximal end, in order.

As will be appreciated, the capability to consistently identify the presence of a foreign object beneath the tissue being operated on is imperative. For example, foreign objects can include NGtubes, bougies, previous staple lines, and/or additional, non-tissue objects that could obstruct and/or adversely effect the surgical operation. For example, an operating clinician needs to know whether a surgical instrument, such as the surgical instrument 3002 of FIG. 10, has accidentally clamped down upon a foreign object, prior to the firing of said surgical instrument. If a foreign object, such as an NGtube, lies beneath the tissue, it can be difficult for the operating clinician to know if the surgical instrument has actually clamped on the NGtube, which is not ideal. This lack of certainty and visibility as to what media is between the jaws of the end effector can complicate a surgical operation and lead to less desirable surgical outcomes. Accordingly, to detect and differentiate the presence of these foreign objects from the surrounding tissue, several key patterns have been observed, and an algorithm has been developed to detect the presence of foreign objects. Some of the patterns contemplated by the present disclosure will be discussed in further detail, below.

Referring now to FIG. 19, another chart 3600 illustrating experimental results of the methods of FIGS. 13-15 is depicted in accordance with at least one non-limiting aspect of the present disclosure. According to the non-limiting aspect of FIG. 19, the algorithmic methods 3200 of FIGS. 13-15 have detected stomach tissue 3602 and a foreign object 3604, such as an NGtube, between the jaws of the end effector 3014 (FIG. 10). However, as the jaws of the end effector 3014 (FIG. 10) close in time, the determined impedance signal associated with the NGtube 3604 increases whereas the determined impedance signal associated with the stomach tissue 3602 remains relative uniform. Accordingly, this pattern can be used by the algorithmic methods 3200, 3216, 3218 of FIGS. 13-15 and the system 3000 of FIG. 10 to generate a user interface, such as the user interface 3500 of FIG. 18, which can communicate to the operating clinician that a foreign object, such as the NGtube 3604, is present between the jaws of the end effector 3014 (FIG. 10), as well as the precise location of the NGtube 3604 within the jaws.

Referring now to FIG. 20, another chart 3700 illustrating experimental results of the methods of FIGS. 13-15 is depicted in accordance with at least one non-limiting aspect of the present disclosure. The chart 3700 of FIG. 20 illustrates a second identifying pattern which can be used by the algorithmic methods 3200, 3216, 3218 of FIGS. 13-15 to detect media positioned between the jaws of the end effector 3014 (FIG. 10). Specifically, the chart 3700 of FIG. 20 depicts a change in impedance phase over time, which produces a pattern that can be used to differentiate foreign objects from tissue. For example, according to the non-limiting aspect of FIG. 20, the algorithmic methods 3200 of FIGS. 13-15 have once again determined impedance signals associated with stomach tissue 3702 and a foreign object 3704, namely, a NGtube, between the jaws of the end effector 3014 (FIG. 10). However, according to the non-limiting aspect of FIG. 20, the phase of the foreign object 3704 decreases over time, while the phase for stomach tissue stays relatively constant. Accordingly, this pattern can be used by the algorithmic methods 3200, 3216, 3218 of FIGS. 13-15 and the system 3000 of FIG. 10 to generate a user interface, such as the user interface 3500 of FIG. 18, which can communicate to the operating clinician that a foreign object, such as the NGtube 3704, is present between the jaws of the end effector 3014 (FIG. 10), as well as the precise location of the NGtube 3704 within the jaws.

According to some non-limiting aspects, a combination of patterns and trends, including the patterns illustrated in FIGS. 19 and 20, can be collectively implemented to distinguish foreign objects from tissue. Referring now to FIG. 21, a logic flow diagram of a method 3800 that collectively implements multiple patterns to distinguish detected foreign objects from detected tissue within the jaws of an end effector is depicted in accordance with at least one non-limiting aspect. According to the non-limiting aspect of FIG. 21, the method 3800 can include the collection of impedance input data 3802, feature extraction 3804, and model development 3806. As previously described, the method 3800 can commence via the receipt of signals from sensors, such as electrodes 3012 (FIG. 10) positioned within the jaws of an end effector 3014 (FIG. 10). Based on such signals, an algorithm can be configured to determine parameters such as impedance signal and impedance phase in time, as illustrated by the input step 3802 of the method 3800 of FIG. 21. These determined measurements can be used to characterize, or extract features 3804, such as a phase shift in time and/or a change in impedance signal in time. These features, and other data, can also be labeled as part of the feature extraction 3804. Finally, the model can be developed 3806. Model development 3806 can include the use of the determined phase shift or change in impedance signal to distinguish various media within the jaws of the end effector 3014 (FIG. 10). As such, an output from the method 3800 of FIG. 21 can be used to identify various media, such as foreign objects, within the jaws of the end effector 3014 (FIG. 10) and thus, used by the system 3000 (FIG. 10) to provide a warning to an operating clinician.

According to other non-limiting aspects, the present disclosure contemplates a support vector machine model for classification of tissue location within the jaws of the end effector 3014 (FIG. 10). In order to provide tissue location feedback to the surgeon, a robust algorithm that can differentiate between tissue, fluid, and air must be developed. It has been observed that this distinction can be made when using Electrical Impedance Spectroscopy ("EIS") technology. Machine learning techniques and/or support vector machines can be used to provide such classifications. Such techniques can further assist an operating clinician in visualizing where tissue is located within the jaws of the end effector 3014 (FIG. 10), to ensure that an entire vessel is fully clamped before performing a surgical operation, such as cutting and/or stapling. This can be challenging to visualize when an operating clinician is operating deep within the body and cannot see the cut line at the distal tip of the device. For example, when firing a surgical instrument, such as a stapler, across a vessel or artery, it may be important to capture the vessel fully within the jaws of the device. Capturing the vessel fully within the jaws can ensure that the surgical operation, such as a cutting and/or sealing of the vessel, occurs all the way across the vessel, thereby preventing blood loss. Sometimes during a procedure, however, it can be difficult to visually identify where the tissue is located within the jaws and if it extends past the cut line.

Referring now to FIG. 22, a logic flow diagram of a method 3900 of training an algorithmic model to intelligently classify the location of media within the jaws of an end effector 3014 (FIG. 10) is depicted in accordance with at least one non-limiting aspect. Specifically, the method 3900 can include the use of a support vector machine model of classifying tissue located within the jaws of the end effector 3014 (FIG. 10). According to the non-limiting aspect of FIG. 22, the method 3900 can include the collection of impedance input data 3902, data scaling and feature extraction 3904, model training 3906, and outputting the model 3908. As previously described, the method 3900 can commence via the receipt of signals from sensors, such as electrodes 3012 (FIG. 10) positioned within the jaws of an end effector 3014 (FIG. 10). Based on such signals, an algorithm can be configured to determine parameters such as impedance signal and impedance phase in time, as illustrated by the input step 3902 of the method 3900 of FIG. 22. These determined measurements can be used to for data scaling and feature extraction 3904, such as scaling a phase shift (e.g., by ½ rad, etc.), scaling an impedance signal (e.g., by 1/100 Kohms, etc.), determining a phase shift in time, and/or determining a change in impedance signal in time. For example, the impedance phase ("Zphase") can be scaled between a range of $0.001\pi$ and $2\pi$ radians and the impedance magnitude ("Zmag") can be scaled between a range of 0.001 and 1 Mohm. The scaling can be performed using a custom scaling function. These features, and other data, can also be labeled as part of the feature extraction 3904. Calculations can be performed on the data to extract new features such as change in Z magnitude over time. However, the scaling and feature extraction 3904 can differ from a corresponding step 3804 of the method 3800 of FIG. 21 in that the data can be labeled with the appropriate tissue type and the input features with their tissue type labels are used to train 3906 a the algorithmic model. For example, the method 3900 can include training 3906 the model via a linear support vector machine algorithm using the open source Scikit Learn Python library.

The trained model produces a weight matrix and bias vector that are used for classification of future samples.

For example support vector machine models is one of the most popular supervised learning algorithms, which can be used for classification as well as regression problems. Specifically, the present disclosure contemplates implementing support vector machine modeling for classification of media within the jaw of an end effector 3014 (FIG. 10) as a means of machine learning and thus, improving the algorithmic performance. The goal of the support vector machine algorithm is to create the best line or decision boundary that can segregate n-dimensional space into classes so that new data points (e.g., impedance measurements) can be properly and efficiently categorized in the future. This best decision boundary can be called a hyperplane. Thus, the model training 3906 can choose extreme points/vectors in time that help the algorithmic model create a hyperplane. These extreme cases are called as support vectors, and hence algorithm is known as a "support vector machine" algorithm. Then, the linear support vector machine can create a novel weight matrix, which can include weights configured to determine how significant each input feature is for each class. The training 3906 can further create a bias vector, which can be used to calculate classification scores. Finally, the model can be output 3908. The output model 3908 can include weight matrix and/or a bias vector, as previously discussed. Ultimately, the training 3906 can be performed using a training dataset and, once trained, the algorithm can classify future samples using only a simple dot product and addition.

Referring now to FIG. 23, a block diagram of a method 4000 of classifying a detected media after an algorithmic model has been trained via the method 3900 of FIG. 22 is depicted in accordance with at least one non-limiting aspect of the present disclosure. According to the non-limiting aspect of FIG. 23, the mathematical operations—which can be performed algorithmically—to classify a new sample after the model has been trained are illustrated. Specifically, the weight matrix will be an "m" by "n" matrix, where "m" (#rows) represents the number of classes the model is trained on, and "n" (#columns) represents the number of input features for the model, as extracted 3902 via the method 3900 of FIG. 22. It shall be appreciated that the weight matrix can include any number of rows and/or columns as needed. The model can be trained using multiple classes and multiple inputs. According to some non-limiting aspects, there can be four classes (e.g., corresponding to tissue, fluid, air, and/or foreign objects) and four input features (e.g., corresponding to Z mag, Z phase, dZ/dt, and/or dPhase/dt). For example, according to the non-limiting aspect of FIG. 23, the model can be trained for two distinct classes, with three input features. Sample X of FIG. 23 illustrates feature data extracted from a new sample (e.g., an impedance measurement determined based on signals received from electrodes 3012 (FIG. 12)), which needs to be classified. The model consults the historical patterns, such as the relationship between determined impedance signal and impedance phase shifting in time for samples at a frequency of interest. Once classified, determined distinctions in classifications can easily be communicated to the operating clinician in accordance with any of the methods and/or means disclosed herein.

Referring now to FIGS. 24A and 24B, several charts 4100A, 4100B illustrating a distinction between various media detected within the jaws of an end effector 3014 (FIG. 10), as determined via the method 4000 of FIG. 23 is depicted in accordance with at least one non-limiting aspect of the present disclosure. According to the non-limiting aspect of FIG. 24A, the first chart 4100A illustrates a determined distinction between detected tissue and fluids, when impedance signal is considered relative to impedance phase. Specifically, the model has generated a linear boundary line 4101 between tissue, such as stomach tissue 4106 and lung tissue 4108 and fluid, such as saline 4102 and blood 4104 respectively. In other words, the model has established clear distinction between tissue 4106, 4108 and fluids 4102, 4104.

According to the non-limiting aspect of FIG. 24B, the chart 4100B once again illustrates a determined distinction between detected tissue and fluids, when impedance signal is considered relative to impedance phase. Specifically, the model has generated a linear boundary line 4103 between tissue, such as stomach tissue 4116 and lung tissue 4118 and fluid, such as saline 4110, peri-blood 4112, blood 4114, and peritoneal fluid 4120 respectively. In other words, the model has established clear distinction between tissue 4116, 4118 and fluids 4110, 4112, 4114, 4120. According to some non-limiting aspects, the algorithm can perform this classification and create the boundary line between datasets is a custom linear support vector machine.

Referring now to FIG. 25, another chart 4200 illustrating a distinction between various media detected within the jaws of an end effector 3014 (FIG. 10), as determined via the method 4000 of FIG. 23 is depicted in accordance with at least one non-limiting aspect of the present disclosure. According to the non-limiting aspect of FIG. 25, the phase shift and impedance signal can be scaled via the scaling process 3904 of FIG. 23. For example, according to the non-limiting aspect of FIG. 25, the phase shift can be scaled by ½ rad and the impedance signal can be scaled by 1/100 Kohms. Once again, the model has generated a boundary line 4201 that distinguishes tissue, such as stomach tissue 4204 from a foreign object, such as an NGtube 4202. However, according to the non-limiting aspect of FIG. 25, the model has also generated support vectors 4203, 4205 which can be used by the model to further determine and refine the boundary line 4201.

According to other non-limiting aspects of the present disclosure, devices, systems, and methods of data analysis to characterization tissue via electrical impedance spectroscopy are disclosed. During a surgical procedure, surgeons may encounter various situations where information about tissue characteristics and location within a stapler jaw becomes advantageous. The ability to know the type of tissue being fired upon as well as the position of the specimen in the jaw supports the surgeon's capacity to fire the stapling device effectively. Algorithm development needs feature inputs from data to form meaningful tissue insights from electrical impedance data using minimal computing power, which can promote processing efficiency and improve the computing performance of an intelligent surgical instrument. As part of the algorithm and model development process to extract tissue insights from electrical impedance spectroscopy sensing technology, feature inputs need to be established to identify key patterns within the data. Electrical impedance measurements are composed of impedance signal and impedance phase. These two values can be studied either through the lens of time or frequency. By studying the sensed electrical impedance profiles over the time domain, different specimens may exhibit distinct and differentiable patterns which can be used to characterize both liquids and tissues. Such features represent a technical enhancement by providing continuous, real-time tissue characterization that could not be manually performed by the operating clinician and other surgical instruments and systems are incapable of. Thus, the techniques disclosed herein represent a significant technological improvement over conventional devices.

Referring now to FIGS. 26A and 2B, several charts 4300A, 4300B illustrating a distinction a means of characterizing tissue within the jaws of an end effector 3014 (FIG. 10) are depicted in accordance with at least one non-limiting aspect of the present disclosure. The charts 4300A, 4300B illustrate the use electrical impedance signal and phase shifts, as determined in the time domain via the methods and means disclosed herein, to provide innovative tissue insights. According to the non-limiting aspects of FIGS. 26A and 26B, the charts 4300A, 4300B illustrate measured parameters determined in time, as associated with a lung lobe 4302 and a bronchus 4304. Specifically, the chart 4300A of FIG. 26A illustrates an impedance profile in the time domain of lung lobe 4302 and bronchus 4304 tissue. The chart 4300B of FIG. 26B illustrates an impedance shift in the time domain of lung lobe 4302 and bronchus 4304 tissue. In reviewing both charts 4300A, 4300B, it becomes evident that the range of values between bronchus 4304 is easily differentiable from the lung lobe 4302 due to a different range of phase values uniquely exhibited by each specimen. The charts 4300A, 4300B further illustrate how measure values can change as a function of time, and how the time domain can also offer insights into tissue characterization. For example, the measured values may change as the operating clinician closes the jaws of the end effector 3104 (FIG. 10), thereby compressing the tissue and potentially changing the measured parameters, depending on the media. Additionally, by using the time domain, a clear distinction between tissue types is possible by using only one frequency of interest. The ability to use less frequencies to obtain the necessary model inputs streamlines and thus, reduces the computing power required by the sensing modality to characterize the tissue. Furthermore, limiting the frequency range may also reduce the complexity of the sensor hardware required on the surgical instrument.

Referring now to FIG. 27, a flow chart of a method 4400 of detecting media, locating media, and characterizing media positioned between the jaws of an end effector 3104 (FIG. 10) is depicted in accordance with at least one non-limiting aspect. Notably, the method 4400 of FIG. 27 summarizes the methods and functions performed by the systems and devices described above, and illustrates how powerful the system 3000 (FIG. 10) can be when implemented in a comprehensive way.

It shall be appreciated that, the foregoing aspects illustrate devices, systems, and methods that, when implemented via the aforementioned surgical instruments, can utilize various signals and signal parameters to generate tissue insights (e.g., tissue locations, foreign body notifications, critical structure notifications, tissue characterizations, etc.). Accordingly, the foregoing aspects illustrate devices, systems, and methods can enable intraoperative instrument-tissue interactions, which can allow an operating clinician to "see the unseen," thereby augmenting surgical decision making, which can result in a safer, more efficient, and/or more precise surgical operation. However, when implemented via improved surgical instruments, the foregoing devices, systems, and methods can produce even more benefits, as will be discussed in further detail herein. For example, according to some non-limiting aspects, one or more electrodes can be electro-mechanically integrated into the jaws of an end effector, such that the surgical instrument can generate enhanced insights using a variety of methods, which shall include but not limited to electrical impedance spectroscopy ("EIS"). However, according to some non-limiting aspects, the electrodes can be implemented for alternate means of electrical sensing (e.g., monitoring voltage, current, power, impedance, or any combination of those). As such, the surgical instruments disclosed herein can be particularly configured to process motor load responses, based on programmable conditions (e.g., end effector opening, end effector closing, tissue compression, etc.) that generate tissue responses. The surgical instruments disclosed herein can include various combinations of electrode arrays and multiplexers configured to activate various electrodes in various ways, thereby enabling the electrodes and thus, the surgical instruments to generate the previously disclosed insights. It shall be appreciated that the following aspects can be implemented via a handheld surgical instrument, such as the surgical instrument 10000 of FIG. 1, or via a robotic surgical instrument, such as the surgical instrument 5100 of FIG. 3.

In order to generate those insights, the surgical instruments disclosed herein can include specifically configured electrode arrays, which are integrated into various portions of and end effector, coupled via a particular routing configuration to a system interface located proximal to the end effector and electrode array. For example, the surgical instruments disclosed herein can include electrode arrays with a variety of electrodes of varying numbers (e.g., two, four, six, eight, etc.), geometric configurations (e.g., circular, rectangular, triangular, asymmetric, etc.), materials (e.g., gold, aluminum, titanium, stainless steel, etc.), and locations (e.g., channels, cartridge, anvil). As such, the arrays of electrodes can be used for EIS measurements, which are conveyed via electrical connections that run through the surgical instrument to a connection interface. This connects the stapler to the EIS control electronics. The routing of signals within the external boundary of the stapler could be achieved using a flexible printed circuit board or via a wireless connection. As will be disclosed herein, electrodes can be integrated within a channel, a separate consumable, a cartridge, or an anvil of the end effector, amongst other locations.

Likewise, the way signals are routed to an from the electrodes for insight generation can further improve the performance of a surgical instrument. For example, the use and/or position of a multiplexer, or switching integrated circuit, can enhance the way the surgical instrument activates and utilizes each electrode of an array. Moreover, the position of the multiplexer can enhance performance. For example, according to some non-limiting aspects, it might make sense to position the multiplexer in a channel defined by the end effector, elsewhere in the jaws of the end effector, the shaft of the surgical instrument, the handle of the surgical instrument, in a consumable or cartridge configured for placement within the end effector, or within a standalone piece of capital equipment (e.g., an electrosurgical generator). Additionally, the means by which the electrodes interface (e.g., wired or wireless) with the surgical instrument can further enhance performance. Additionally, a control circuit configured to process signals from the electrode array and generate insights can be positioned within the surgical instrument, or external to the surgical instrument, and can likewise be configured for wired or wireless interfacing. Accordingly, a portion of a cable can be dedicated to signals associated with power and data communication and can be plugged into the surgical instrument's proximal end to enable sensing as needed (e.g., plug-n-play functionality). A second portion of the cable can be connected to system capital module (e.g., a surgical hub), which can provide the power, signal generation and/or computational signal processing capabilities. According to some non-limiting aspects, the control circuit can be configured to received signals from the electrode array via a wired or wireless interface, regardless of whether the control circuit is onboard or external to the surgical instrument. As such, various surgical instruments can include various degrees of system integration to generate the previously discussed insights as will be discussed in further detail herein.

For example, referring to FIG. 28, a surgical system 6000 is depicted in accordance with at least one aspect of the present disclosure. According to the non-limiting aspect of FIG. 28, the surgical system 6000 can include a hub 6001 configured to be communicably coupled to one or more modular surgical instruments 6008, 6010, which can be interchangeably connected to the hub 6001. According to some non-limiting aspects, the hub 6001 can be similar to those disclosed in U.S. patent application Ser. No. 16/562,172 titled PORT PRESENCE DETECTION SYSTEM FOR MODULAR ENERGY SYSTEM, filed on Sep. 5, 2019 and published as U.S. Patent Application Publication No. 2020/0078113 on Mar. 12, 2020, the disclosure of which is hereby incorporated by referenced in its entirety. Although the surgical instruments 6008, 6010 of FIG. 28 are wired to the hub 6001, according to some non-limiting aspects, the surgical instruments 6008, 6010 can be wirelessly coupled to the hub 6001. Regardless, the hub 6001 can communicate signals and/or commands to the surgical instruments 6008, 6010 and can receive signals and/or feedback from the surgical instruments 6008, 6010.

In further reference to FIG. 28, the surgical system 6000 can be compatibly configured for use with a robotic platform 6002 that utilizes a robotic surgical instrument 6008 and/or a handheld platform 6004 that utilizes a handheld surgical instrument 6010, depending on the intended application. For example, according to the non-limiting aspect of FIG. 28, the handheld surgical instrument 6010 can be a laparoscopic device; however, according to other non-limiting aspects, the present disclosure contemplates other handheld surgical instruments. In both platforms 6002, 6004, the hub 6001 can be positioned within a rack 6016, 6018 that includes various control units (e.g., processors, actuators, generators, etc.) configured to control the communicably coupled surgical instruments 6008, 6010. For example, the robotic platform 6002, in particular, can further include a controller of a robotic surgical system, such as the controller 5000 of FIG. 2.

Notably, the modular surgical instruments 6008, 6010 of FIG. 28 can each include an end effector 6012, 6014 configured with a first jaw that is movable relative to a second jaw, as previously disclosed. Depending on the implementing surgical instrument 6008, 6010 and/or platform 6002, 6004, each end effector 6012, 6014 can be particularly configured to perform an intended surgical operation. For example, according to some non-limiting aspects, the end effectors 6012, 6014 can be configured to perform a surgical stapling operation. According to other non-limiting aspects, the end effectors 6012, 6014 can be configured to deliver RF and/or ultrasonic energy in response to a command received from the hub 6001 and/or energy received from a generator positioned in the rack 6016, 6018. For example, according to some non-limiting aspects, the end effector 6002 can be configured for an advanced bipolar surgical operation. According to still other non-limiting aspects, the end effector 6002 can be configured for Highly Articulating Tools ("HAT"), such as end effectors configured to articulate in two or more planes. Regardless, each end effector 6012, 6014 can include an array of electrodes 6013, 6015 configured to facilitates the generation of enhanced tissue insights using a variety of methods, as will be explained in further detail herein.

Referring now to FIGS. 29A-C, a robotic surgical instrument 6008 configured for use with the system 6000 of FIG. 28 is depicted in accordance with at least one aspect of the present disclosure. According to the non-limiting aspect of FIG. 29A, the surgical instrument 6008 can include an end effector 6012 configured to perform a surgical operation. For example, according to some non-limiting aspects, the end effector 6012 can be configured for use a surgical stapling operation. According to other non-limiting aspects, the end effector 6012 can be configured to deliver RF and/or ultrasonic energy. For example, according to some non-limiting aspects, the end effector 6012 can be configured for an advanced bipolar surgical operation. According to still other non-limiting aspects, the end effector 6012 can be configured for HAT.

In reference to FIGS. 29B and 29C, certain end effectors $6012_a$, $6012_b$ and electrode configurations $6013_a$, $6013_b$ that can be coupled to the robotic surgical instrument 6008 of FIG. 29A are depicted in accordance with at least two non-limiting aspects of the present disclosure. For example, FIG. 29B illustrates an end effector 6012, that can include electrodes that traverse a longitudinal axis defined by the end effector $6012_a$ and protrude from an external wall of the end effector $6012_a$. According to FIG. 29C, electrodes can be defined from a pad that similarly traverses a longitudinal axis defined by the end effector $6012_b$, but are flush relative to an external wall of the end effector $6012_a$. As will be discussed in further detail, the electrodes $6013_a$, $6013_b$ can be integrated within the end effectors $6012_a$, $6012_b$ and/or integrated within cartridges configured to be inserted into the end effectors $6012_a$, $6012_b$.

In further reference to FIGS. 29A-C, the robotic surgical instrument 6008 can be further configured to generate data associated with the robotic surgical instrument 6008, which can enhance the feedback received from the surgical instrument 6008 and thus, improve the insights generated by a surgical hub and/or control circuit communicably coupled to the surgical instrument 6008, as illustrated and discussed in reference to FIGS. 1-27. For example, the surgical instrument 6008 of FIGS. 29A-C can generate data associated with its position, load, and/or motor via one or more internal sensors (e.g., an encoder, torque sensors, controlled motion sensors, etc.) positioned within its housing. This data, in conjunction with electrical impedance spectroscopy ("EIS") data generated by a plurality of electrodes 6013 positioned within the end effector 6012 can be used to inputs to the previously discussed algorithm engines, which can estimate, detect, and/or evaluate key outputs and/or insights regarding the tissue being operated on, the surgical instrument 6008 itself, and/or the operation, generally. Such outputs can provide high clinical values. For example, various combinations of tissue EIS data, position data, load data, and/or motor torque data generated by the surgical instrument 6008 of FIG. 29A-C can be used by the previously discussed algorithm engines to estimate a relative tissue tension, a thickness of the tissue within the jaw, tissue characteristics, and/or the position of a critical structure (e.g., a vessel).

Referring now to FIG. 30, a block diagram 7000 of an algorithmic engine 7002 employed by the surgical instrument 6008 of FIGS. 29A-C is depicted in accordance with at least one non-limiting aspect of the present disclosure. Although the algorithmic engine 7002 of FIG. 30 is discussed in specific reference to the surgical instrument 6008 of FIGS. 29A-C, it shall be appreciated that the algorithmic engine 7002 of FIG. 3 can be similarly implemented by any of the surgical instruments and/or surgical hubs disclosed herein. According to the non-limiting aspect of FIG. 30, the surgical instrument 6008 can generate several signals 7004, 7006, 7008 that can be provided to the algorithmic engine 7002 for processing and/or analysis.

For example, according to some non-limiting aspects, the surgical instrument 6008 of FIGS. 29A-C can generate signals associated with tissue EIS data 7004, position data 7006, and/or torque/load data 7008 detected by the various sensors and/or electrodes 6013 positioned within the end effector 6012 of the surgical instrument 6008. The algorithm engine 7002, employing the previously discussed methods and techniques, can process these inputs and generate one or more outputs 7010, 7012, 7014, 7016 that could provide the clinician with insights regarding the tissue, surgical instrument 6008, and/or operation being performed.

Referring now to FIG. 31, a handheld surgical instrument 6010 configured for use with the system 6000 of FIG. 28 is depicted in accordance with at least one non-limiting aspect of the present disclosure. Although it is specifically configured for manual operation, the handheld instrument 6010 of FIG. 31 can include any of the features and provide similar benefits to those discussed in reference to the robotic surgical instrument 6008 of FIGS. 29A-C. According to the non-limiting aspect of FIG. 31, the surgical instrument 6010 can include an end effector 6015 and a handle 6020. The surgical instrument 6010 can further include a shaft 6016 with a proximal portion 6018 and a distal portion 6019. The end effector 6014 can be coupled to the distal portion 6019 of the shaft 6016 via an articulation joint and the shaft 6016 can be coupled to the handle 6020 via a nozzle 6017. As previously described, the end effector 6014 can include a first jaw movable relative to a second jaw, and can be configured to accommodate a plurality of electrodes 6015.

Similar to the robotic surgical instrument 6008 of FIGS. 29A-C, the surgical instrument 6010 of FIG. 31 can also be configured to perform a surgical operation. For example, according to some non-limiting aspects, the end effector 6014 can be configured for use a surgical stapling operation. According to other non-limiting aspects, the end effector 6014 can be configured to deliver RF and/or ultrasonic energy. For example, according to some non-limiting aspects, the end effector 6014 can be configured for an advanced bipolar surgical operation. According to still other non-limiting aspects, the end effector 6014 can be configured for HAT.

Referring now to FIG. 32, an exemplary electrode array 6015 is depicted in accordance with at least one non-limiting aspect of the present disclosure. Although the electrode array 6015 of FIG. 32 is depicted as a component of the end effector 6014 of FIG. 31, it shall be appreciated that the electrode array 6015 of FIG. 32 can be implemented via any of the end effectors employed by any of the surgical instruments disclosed herein. For example, a first jaw of the end effector 6014 of FIG. 31 can define an elongate channel 6021 that traverses a longitudinal axis L of the end effector 6014 (FIG. 31). Specifically, the channel 6021 can be defined by one or more walls $6025_a$, $6025_b$ that extend along the longitudinal axis L on opposing sides of the longitudinal axis L. For example, the electrode array 6015 of FIG. 32 includes eight pairs of electrodes 6022, 6024, each having a rectangular shape and constructed from titanium. However, according to other non-limiting aspects, the array 6015 can include electrodes 6022, 6024 of varying numbers, geometries, and/or materials, depending on intended application and/or user preference. As further illustrated by FIG. 32, certain electrodes 6024 of the array 6015 can be configured different relative to other electrodes 6022. For example, certain electrodes 6024 can be positioned about a cutline 6026 can be configured such that the electrodes 6024 provide an increased resolution at either side of the cutline 6026.

According to the non-limiting aspect of FIG. 32, the electrode array 6015 can include one or more electrodes 6022, 6024 integrated into the walls $6025_a$, $6025_b$ of the channel 6021 defined by one of the jaws of the end effector 6014 (FIG. 31). Specifically, each electrode 6022, 6024 can be over-mounted, or over-molded onto the walls $6025_a$, $6025_b$ of the channel 6021. Of course, other means of integration can be employed to a achieve a similar effect. According to the non-limiting aspect of FIG. 32, certain electrodes 6024 can be positioned about a cutline 6026 of the end effector 6014 (FIG. 31), such that those electrodes 6024, when activated by a multiplexed signals conveyed via a multiplexer (as will discussed in further detail herein), can cut tissue about the cutline 6026. The multiplexed signals and multiplexer can utilize the other electrodes 6022 to generate tissue insights, as previously discussed.

Referring now to FIGS. 33A-C, another end effector 6100 configured for use with the surgical instruments disclosed herein is depicted in accordance with at least one non-limiting aspect of the present disclosure. Similar to the end effector 6014 of FIGS. 31 and 32, the end effector 6100 of FIGS. 33A-C can include a first jaw 6101 that defines a channel 6102 interspersed between two walls $6103_a$, $6103_b$ of the jaw 6101. Additionally, an array of electrodes 6104, 6106 can be integrated within each sidewall $6103_a$, $6103_b$ of the jaw 6101. In specific reference to FIG. 33B, a sectioned, isometric view of the end effector 6100 of FIG. 33A is depicted in accordance with at least one non-limiting aspect. According to the non-limiting aspect of FIG. 33A, the end effector 6100 can further include a flexible conductor 6108 capable of carrying multiplexed signals, wherein the flexible conductor 6108 traverses through the jaw 6101.

In further reference to FIG. 33B, the flexible conductor 6108 can be multiplexed and electrically coupled to the electrodes 6104, 6106 such that the electrodes 6104, 6106 can receive signals from transmitted by and/or through a control circuit positioned within the surgical instrument and/or surgical hub. The flexible conductor 6108 can accomplish this via multiple layers that provide electrical connections to the various electrodes 6104, 6106. Accordingly, the flexible conductor 6108 can be configured as a multiplexer and/or a multiple output generator, as described further below. As such, independent signals can be transmitted to and through each electrode 6104, 6106, such that each electrode 6104, 6106 can serve a different purpose and/or provide a separate function relative to other electrodes 6104, 6106 in the array. For example, tissue under each electrode 6104, 6106 can be treated individually according to the coagulation needs. However, relevant to the generation of surgical insights, as previously discussed, certain electrodes 6104 of the array can receive signals through the flexible conductor 6108 to generate surgical insights. Other electrodes, such as the electrodes 6106 disposed about a cutline 6026 (FIG. 32), can receive signals through the flexible conductor 6108 to cut tissue that is positioned about the cutline 6026 (FIG. 32). Each electrode 6104, 6106 in the array can be communicably coupled to a surgical hub and/or a control circuit and thus, communicably coupled to an energy source, such that the electrodes 6104, 6106 can receive energy via the flexible conductor 6108. For example, according to one non-limiting aspect, the pairs of active electrodes 6104, 6106 on opposite sides of the channel 6102, may be energized by the energy source at the same time.

According to other non-limiting aspects, different pairs of segmented electrodes 6104, 6106 can be energized or receive different signals via the flexible conductor 6108. Various electrode pairs 6104, 6106 can be energized by the energy source (or generator) to perform certain surgical operations and other electrode pairs 6104, 6106 can be used to generate tissue insights, using the previously discussed techniques. The flexible conductor 6108 can convey various multiplexed signals and distribute them to the corresponding electrodes 6104, 6106 as desired, under the control of the control circuit, which will be discussed in further detail. According to some non-limiting aspects, the energy source, the multiplexer, and the control circuit can be positioned in the nozzle 6017, the shaft 6016, the handle 6020, a housing of a robotic surgical instrument, and/or within a communicably coupled surgical hub of the surgical system. According to some non-limiting aspects, the multiplexer can be similar to those discussed in U.S. patent application Ser. No. 13/795, 205, titled MOTORIZED SURGICAL CUTTING AND FASTENING INSTRUMENT HAVING HANDLE BASED POWER SOURCE, and filed Feb. 14, 2008, which issued as U.S. Pat. No. 9,522,029 on Dec. 20, 2016, the disclosure of which is hereby incorporated by reference in its entirety.

According to the non-limiting aspect of FIG. 33C, a means of integrating the electrodes 6104, 6106 into the end effector 6100 is depicted in accordance with at least on non-limiting aspect of the present disclosure. The flexible conductor can be coupled to conductive tracks $3108_a$, $3108_b$ that traverse each side of the end effector 3100. Similar to the flexible conductor 3108, each conductive track $3108_a$, $3108_b$ can be configured to transmit multiplexed signals to and from the electrodes 3104, 3106. An electrode material 6110, from which the electrodes 6104, 6106 can be formed, can be overmolded with a material from which the sidewalls of $6103_a$, $6103_b$ (FIG. 33A) can be constructed. The overmolding, for example, can include a multi-step injection molding process where two or more components can be molded over top of one another, thereby resulting in a single, solid piece. Of course, according to other non-limiting aspects, other means can be employed to integrate the electrodes 6104, 6106 into the conductive tracks $6108_a$, $6108_b$ and sidewalls of the end effector 6100 (e.g., machining, masking, insert molding, insertion into cavities and adhesion, etc.).

The non-limiting aspect of FIGS. 33A-C illustrate merely one of the aforementioned integration techniques. According to the non-limiting aspect of FIGS. 33A-C, the array of electrodes 6104, 6106 can be integrated into the channel 6102, the flexible conductor 6108 can be configured such that multiplexing takes place within the end effector 6100, and signals, including data signals and power signals, can be routed through the end effector 6100 via tracks on the flexible conductor 6108. The integrated techniques employed by by the end effector 6100 enable signals to be transmitted through the flexible conductor 6108, to and from the array of electrodes 6104, 6106, and through an articulation joint of the surgical instrument, such as the articulation joint 6112 of FIG. 34A. According to the non-limiting aspect of FIG. 34A, the articulation joint 6112 can have one or more supports 6114 that a flexible conductor, such as the flexible conductor 6108 of FIGS. 33A-C, can be routed through, thereby facilitating articulation of an end effector, such as the end effector 6100 of FIGS. 33A-C, without interrupting any signals traversing the flexible conductor to and from the end effector. Of course, similar articulation joints 6112 can be implemented on any of the surgical instruments disclosed herein. FIG. 34B depicts how the flexible conductor 6108 can be further proximally routed after the articulation joint 6112, through a shaft 6116 of the surgical instrument and into a nozzle 6117. FIG. 34C depicts the nozzle 6117 of the surgical instrument in further detail, with the flexible conductor 6108 traversing a housing of the nozzle 6117 and electrically coupled to a control circuit 6119 positioned within the nozzle 6117. However, according to other non-limiting aspects, the control circuit 6119 can be positioned proximal the nozzle 6117, or within a communicably coupled surgical hub. In some non-limiting aspects, the surgical hub can be remotely positioned relative to the surgical instrument itself. Accordingly, end effectors of surgical instruments—and more specifically, arrays of electrodes—can be effectively coupled to a control circuit proximally positioned in the surgical instrument or a communicably coupled surgical hub. The control circuit can subsequently generate insights (e.g., EIS measurements) using the signals via algorithmic implementation, as previously discussed.

Referring now to FIG. 35, another end effector 6200 is depicted in accordance with at least one non-limiting aspect of the present disclosure. According to the non-limiting aspect of FIG. 35, the end effector 6200 can include one or more electrodes 6204 mounted on a separate consumable 6206 configured to be inserted within a channel 6202 defined by the sidewalls $6203_a$, $6203_b$ of the end effector. As such, the channel 6202 and sidewalls $6203_a$, $6203_b$ can be configured to accommodate the separate consumable 6206. For example, the sidewalls $6203_a$, $6203_b$ can include an interior surface composed of a conductive material, such that the conductive material is placed into electrical communication with the electrodes 6204 when the separate consumable is inserted into the channel 6202. Alternately, the channel can include one or more electrical contacts configured to place the electrodes 6204 into electrical communication with a flexible conductor 6208 capable of carrying multiplexed signals, wherein the flexible conductor 6108 traverses through the channel 6202.

In other words, according to the non-limiting aspect of FIG. 35, array of electrodes 3204 can be attached to a separate consumable 6206 and thus, selectively clipped into the channel 6202. In this way, a single end effector 6200 can be configured to accommodate numerous separate consumables 6206, wherein each separate consumable 6206 can include a different array of electrodes 6204 of varying configurations. Furthermore, the separate consumable 6206 can be define a second channel 6212 configured to accommodate a cartridge for the surgical operation (e.g., a staple cartridge, an electrosurgical cartridge, etc.). Accordingly, various combinations of separate consumables 6206 and cartridges can be used by the same end effector 6200. Moreover, the electrodes 6204 can receive and send signals via the flexible conductor 6208, which can be used to generate insights per the previously disclosed techniques, regardless of the cartridge type loaded into the end effector 6200. According to some non-limiting aspects, the flexible conductor 6208 can be routed through the end effector 6200 and surgical instrument in a method similar to those described in reference to the end effector 6100 of FIGS. 33A-C and 34.

Referring now to FIG. 36A-D, another end effector 6300 is depicted in accordance with at least one non-limiting aspect of the present disclosure. According to the non-limiting aspect of FIG. 36, the end effector 6300 can accommodate a cartridge 6306 configured to perform a surgical operation (e.g., a staple cartridge, an electrosurgical cartridge, etc.), and an array of electrodes 6304 can be dispositioned on the cartridge 6306, itself. In specific reference to FIG. 36B, the sidewalls 6303$_a$, 6303$_b$ of the end effector 6300 can once again define a channel 6302, and the channel 6302 can be configured to accommodate the cartridge 6306. The end effector can further include a flexible conductor, such as the flexible conductors 6108, 6208 of FIGS. 33A-C, 34 and 35, capable of carrying multiplexed signals, wherein the flexible conductor 6308 traverses through the channel 6302. The flexible conductor 6308 can be routed through the end effector 6300 and surgical instrument in a method similar to those described in reference to the end effector 6100 of FIGS. 33A-C and 34.

Figure 36A:
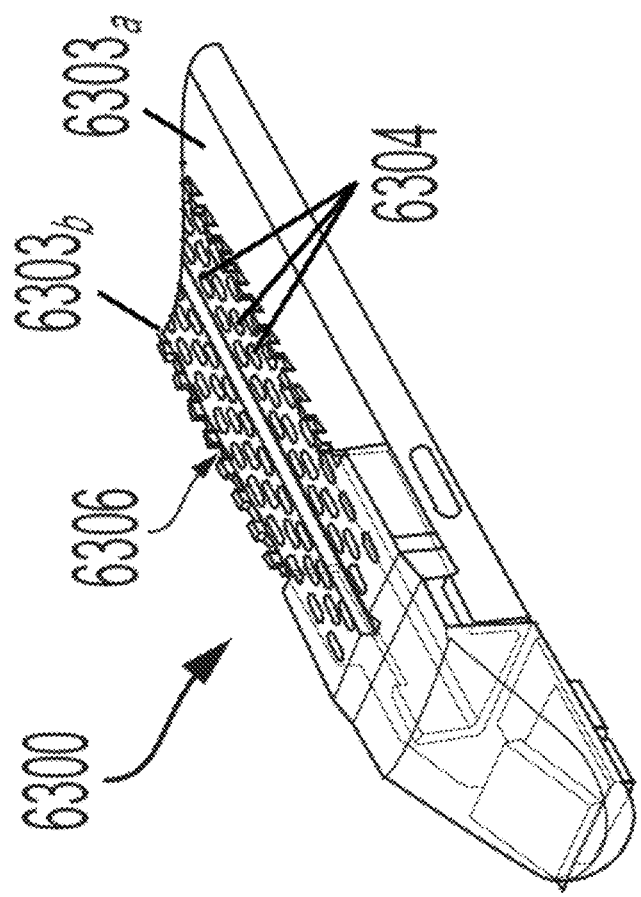
Figure 36B:
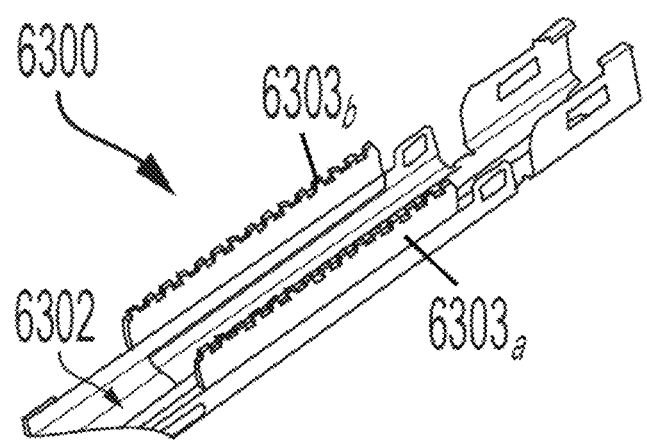
Figure 36C:
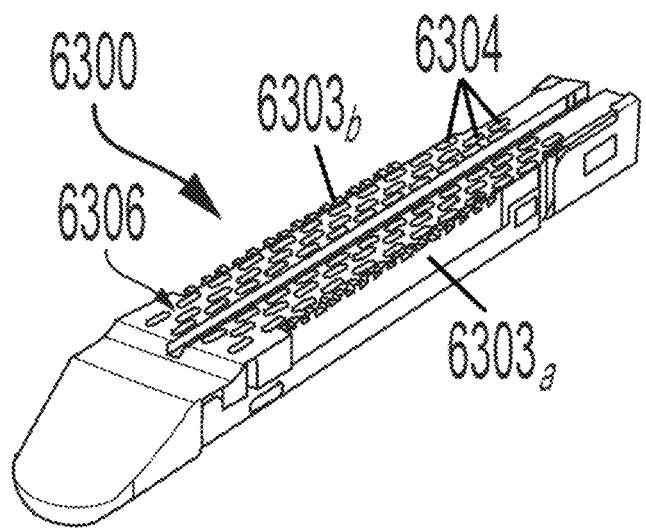

For example, the sidewalls 6303$_a$, 6303$_b$ can include an interior surface composed of a conductive material, such that the conductive material is placed into electrical communication with the electrodes 6304 when the separate consumable is inserted into the channel 6302, as illustrated in FIG. 36C. Alternately, the channel can include one or more electrical contacts configured to place the electrodes 6304 into electrical communication with a flexible conductor 6308 capable of carrying multiplexed signals, wherein the flexible conductor 6308 traverses through the channel 6302.

Figure 36D:
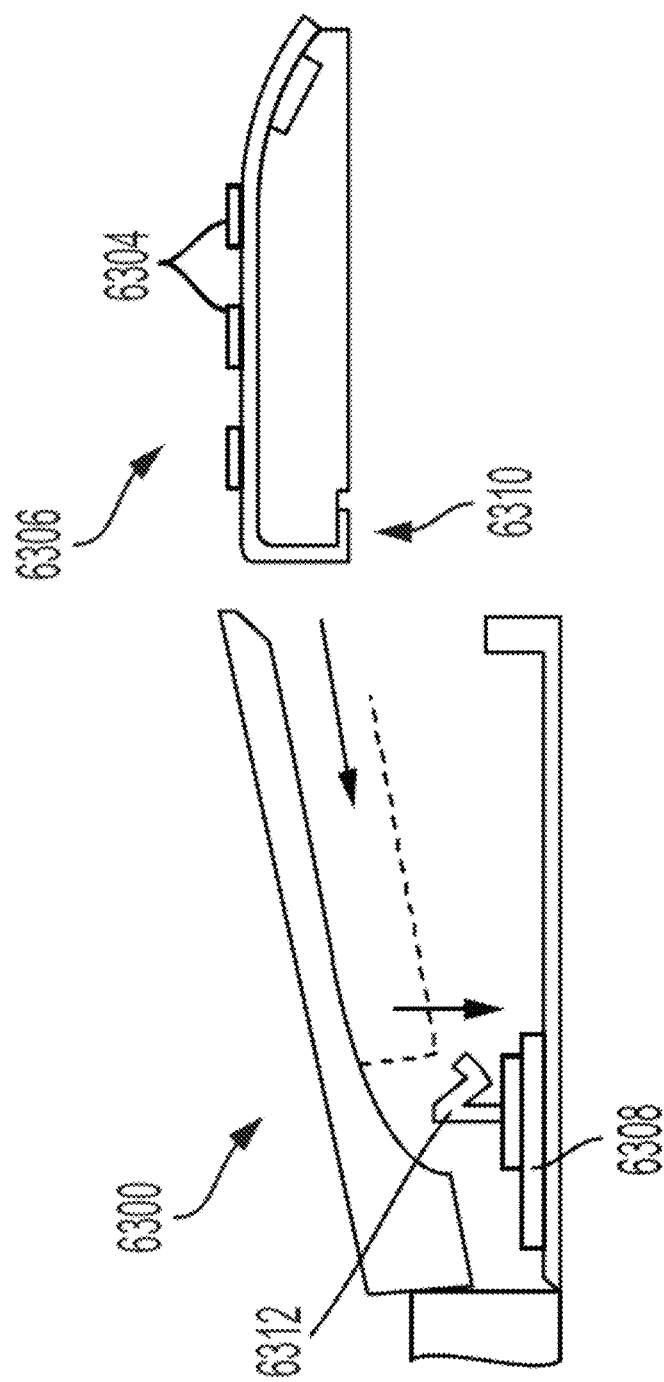

Referring now to FIG. 36D, an insertion of the cartridge 6306 into the end effector 3600 is depicted in accordance with at least one non-limiting aspect of the present disclosure. According to the non-limiting aspect of FIG. 36D, the end effector 6300 can include a conductive element 6312 configured to electrically interface with a corresponding conductive element 6310 on the cartridge 6300. The conductive elements 6310, 6312 can further be configured for multiplexed signal transmission, such that multiplexed signals transmitted through the flexible conductor 6308 of the end effector 6300 can be communicated to and from each electrode 6304 of the array, positioned on the cartridge 6306. According to the non-limiting aspect of FIGS. 36A-D, the array of electrodes 6304 can be integrated onto cartridge 3606, which can be a consumable. The electrodes 6304 can be electrically integrated within the cartridge 3606 via a multiplexing integrated circuit inside the cartridge and electrical connections between the conductive elements 6310, 6312. Because the cartridge 6306 can include the multiplexing electronics, the interfaces 6310, 6312 between the end effector 6300 and the cartridge 6306 can be simplified.

Referring now to FIGS. 37A and 37B, other end effectors 6400$_a$, 6400$_b$, are depicted in accordance with at least one non-limiting aspect of the present disclosure. According to the non-limiting aspects of FIG. 37A the end effector 6400$_a$ can be configured to accommodate a hybrid cartridge 6406$_a$ wherein an array of electrodes 6404$_a$ is positioned on the cartridge 6406$_a$. Each electrode 6404, can be configured for electrical communication with a flexible conductor 6408 capable of carrying multiplexed signals, when the cartridge 6406$_a$ is installed within the end effector 6400$_a$. wherein the flexible conductor 6308 traverses through a channel defined by the end effector 6400$_a$ and can be routed through the end effector 6400 and surgical instrument in a method similar to those described in reference to the end effector 6100 of FIGS. 33A-C and 34.

In reference to FIG. 37B, a similar, albeit subtly different, end effector 6400$_b$ is depicted in accordance with at least one non-limiting aspect of the present disclosure. Notably, the array of electrodes 6404$_b$ is different than the electrodes 6404$_a$ of FIG. 37A. As such, a plurality of conductive elements 6412 that correspond to each electrode 6404$_b$ are dispositioned in each wall 6403$_a$, 6043$_b$ of the end effector 6400$_b$. Accordingly, each electrode 6404$_b$ of the array can receive an intended signal from the multiplexed signals traversing the flexible conductor 6408.

It shall be appreciated that, according to the non-limiting aspects of FIGS. 37A and 37B, the array of electrodes 3404$_a$, 3404$_b$ can be positioned on the cartridge 3406$_a$, 3406$_b$, which can be electrically configured with one or more electrical surfaces (e.g., metal plating, metal pieces bent around the sides, vias through the cartridge, etc.) for an intended connection of each electrode 3404$_a$, 3404$_b$ to an appropriate portion of the flexible conductor 3408. Accordingly, multiplexing takes place in the end effector 3400 but each electrode 3404$_a$, 3404$_b$ still receives the appropriate signal via the electrical connections.

Referring now to FIG. 38, another end effector 3500 is depicted in accordance with at least one non-limiting aspect of the present disclosure. Similar to the end effectors 3400$_a$, 3400$_b$ of FIGS. 37A and 37B, the array of electrodes 3504 can be integrated on the cartridge 3506, itself. Multiplexing, however, can occur either within the cartridge 3506 or end effector 3500 via a flexible conductor 6508 capable of carrying multiplexed signals. Regardless, the end effector 6500 of FIG. 38 can further include a wireless communication module 6514 configured to transmit and receive multiplexed signals to and from a control circuit and/or a surgical hub wirelessly via an infrastructure network (e.g., WiFi®, cellular, etc.) or an ad hoc network (e.g., Bluetooth®, Near Field Communications, RFID, etc.). Accordingly, the wireless communication module 6514 can serve as a communication interface between the end effector 6500 and the surgical hub and/or control circuit, thereby eliminating the need for the routing described in reference to FIGS. 33A-C and 34. It shall be appreciated that a wireless communication module 6514 of FIG. 38 can be similarly applied to any of the surgical instruments and/or end effectors disclosed herein, thereby simplifying—and in some aspects, eliminating—the routing of the flexible conductors disclosed herein.

Referring now to FIGS. 39A-D, another end effector 6600 is depicted in accordance with at least one non-limiting aspect of the present disclosure. According to the non-limiting aspect of FIGS. 39A-D, the end effector 6600 can include a first jaw and a second jaw. For example, the second jaw can be configured as an anvil of the end effector 6600 and a separate consumable 6606 can be configured to be selectively coupled to the second jaw. Whereas the separate consumable 6206 (FIG. 35) was shown as coupled to a bottom jaw of the end effector 6200 of FIG. 35, the separate consumable 6606 can be coupled to the second, or top, jaw 6602 of the end effector 6600 of FIG. 39A. Nonetheless, the array of electrodes 6604 can be coupled to the separate consumable 6606 of FIG. 39A and, when coupled to conductive elements on the second jaw 6602, electrically coupled to a flexible conductor 6608. The flexible conductor 6608 can be capable of carrying multiplexed signals, wherein the flexible conductor 6608 traverses through the end effector 6600 and surgical instrument in a method similar to those described in reference to the end effector 6100 of FIGS. 33A-C and 34. Alternately, the wireless embodiment of FIG. 38 can be employed to transmit signals to and from the array of electrodes 6604.

Figure 39A:
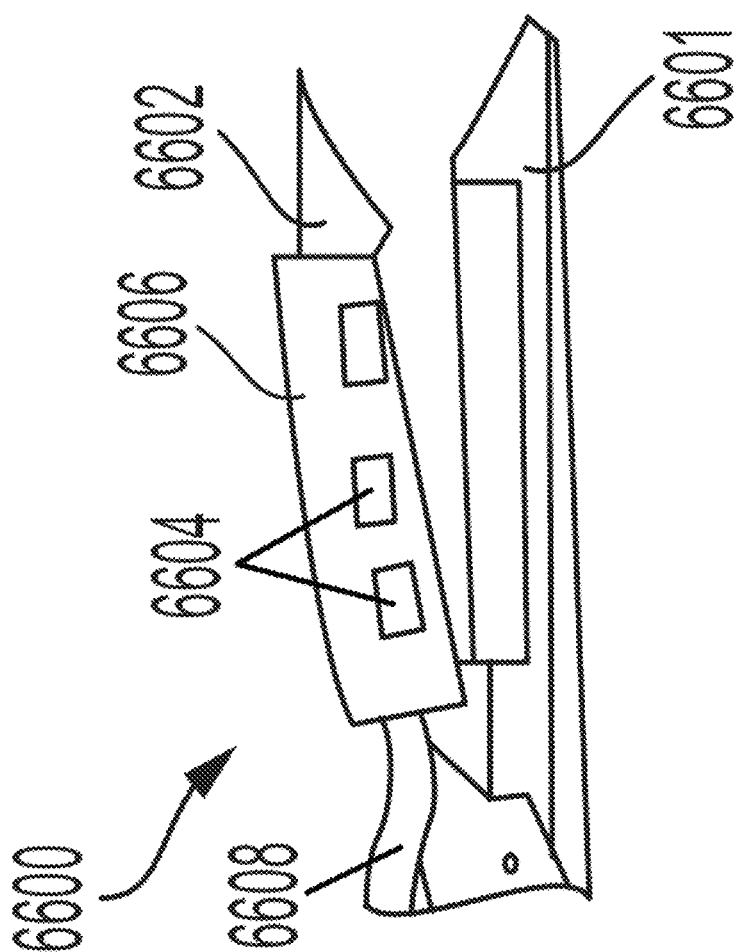
Figure 39B:
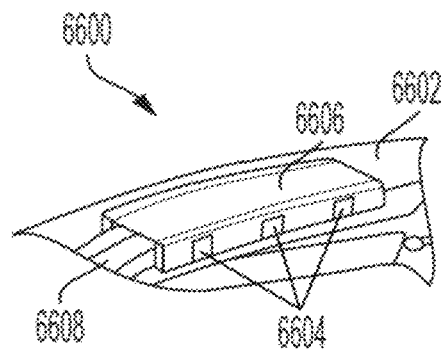
Figure 39C:
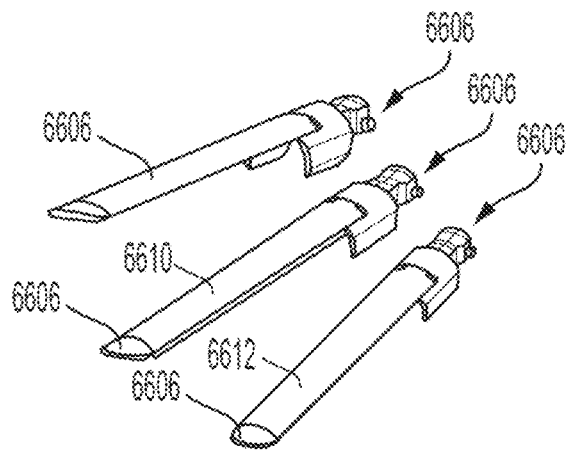
Figure 39D:
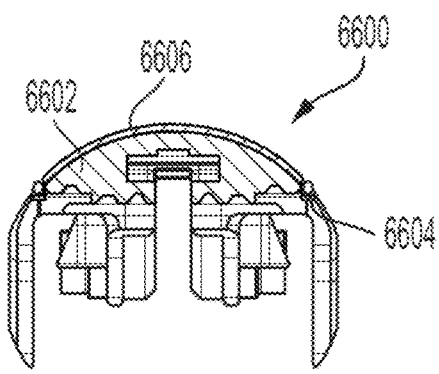

In reference to FIG. 39C, a method of coupling the separate consumable 6606 to the second jaw 6602 of the end effector 6600 of FIGS. 39A and 39B is depicted in accordance with at least one non-limiting aspect of the present disclosure. According to the non-limiting aspect of FIG. 39C, an adhesive layer 6610 can be deposited on a top surface of the second jaw 6602 and the separate consumable 6606 can be deposited on top of the adhesive layer 6610. As such, the separate consumable 6606, including its electrodes 6604 can be coupled to the second jaw 6602, as depicted in the cross-sectioned view of FIG. 39D. Accordingly, the electrodes 6604 can be positioned on the underside of a printed circuit board of the separate consumable 6606, such that they can generate signals for Of course, according to other non-limiting aspects, the separate consumable 6606 can be alternately coupled to the second jaw 6602, for example, via corresponding geometric components, clips, fasteners, and/or a pressure fit.

Referring now to FIG. 40, a flexible circuit 6700 configured for use with any of the end effectors disclosed herein is depicted in accordance with at least one non-limiting aspect of the present disclosure. According to the non-limiting aspect of FIG. 40, the flexible circuit 6700 can be a multiple switching integrated circuit (e.g., a multiplexer) that includes one or more switch circuits 6702 positioned on a flexible printed circuit board 6704 for signal switching and control to and from an end effector. The flexible circuit 6700 can be routed through a shaft of the surgical instrument and integrated into the end effector to provide signal selection and control of electrodes at the end-effector. The flexible circuit 6700 can include a portion that is extended through the articulating joint to the end-effector where electrodes are connected. Another side of the flexible circuit 6700 can extend through the shaft to the proximal side of the tool, where signal conditioning and processing electronics can be placed. The switches 6702 can be configured to turn on/off certain electrodes, thereby resulting in different electrode configurations being activated during impedance measurements.

Referring now to FIG. 41, a system diagram of a system 6800 configured to use the surgical instruments and end effectors disclosed herein is depicted in accordance with at least one non-limiting aspect of the present disclosure. according to the non-limiting aspect of FIG. 41, the system 6800 can utilize a surgical instrument 6801, that includes electronics 6802 for switching and buffering signals to and from a control circuit positioned within the surgical instrument 6801. The surgical instrument 6801 can further include an end effector 6804 configured for a surgical operation (e.g., stapling, sealing, cutting, etc.). An electrode array 6806 can be positioned within the end effector 6804 according to any of the aspects disclosed herein. For example, the electrode array 6806 can include a specifically configured number and arrangement of electrodes (e.g., eight pairs of electrodes, sixteen electrodes in total, etc.). The surgical instrument 6801 can further include electrical connections 6812 routed through the inside of an articulation joint and shaft of the surgical instrument 6801 using any of the flexible conductors and arrangements disclosed herein. A nozzle 6808 of the surgical instrument 6801 can include a control circuit. The nozzle 6808 can be stationary, or further configured to rotate the shaft. The surgical instrument can be further connected to a lab system 6814 or surgical hub configured to display a graphical user interface, which can include a plotting window configured to present the algorithmic insights, as previously described. The system 6800 can be compatible with a plurality of surgical instruments 6816, each configured for use with a plurality of separate consumables and/or cartridges 6818, as disclosed herein. Accordingly, the system 6800 can facilitate the use of numerous, customizable electrode configurations, each capable of performing different surgical operations and generating different insights.

Referring now to FIG. 42, a surgical instrument 6900 is depicted in accordance with at least one non-limiting aspect of the present disclosure. According to the non-limiting aspect of FIG. 42, the surgical instrument 6900 can include a first cable 6902 input and a second cable input 6904 that enter the nozzle 6906 of the surgical instrument 6900. As such, a control circuit 6908 positioned within the nozzle 6906 can process inputs from both the first cable 6902 and the second cable 6904 into a multiplexed signal that can traverse a flexible conductor routed through the surgical instrument 6900 using any of the methods disclosed herein.

Referring now to FIG. 43, a diagram illustrating several non-limiting surgical system configurations 7002, 7004, 7006 is depicted in accordance with at least one non-limiting aspect of the present disclosure. According to the non-limiting aspect of FIG. 43, each of the configurations 7002, 7004, 7006 can employ various electrode configurations, switching circuitry, signal conditioning circuits, signal generators, signal processing circuits, and/or graphical user interfaces to generate and display the insights disclosed herein. For example, a first configuration 7002 employs an electrode array in the end effector, switching circuitry in the tool shaft, and signal conditioning in the tool stage. The signal generator and processor can be located in a surgical hub, and results can be displayed via a graphical user interface on a separate unit. According to the second configuration 7004, an electrode array can be included in the end effector, and switching circuitry as well as signal conditioning can occur in the tool shaft. Once again, the signal generator and processor can be located in a surgical hub, and results can be displayed via a graphical user interface on a separate unit. According to the second configuration 7004, an electrode array can be included in the end effector, and switching circuitry as well as signal conditioning can occur in the tool shaft. Once again, the signal generator and processor can be located in a surgical hub, and results can be displayed via a graphical user interface on a separate unit. According to the third configuration 7006, an electrode array can be included in the end effector, switching circuitry can occur in the tool shaft, and as signal conditioning can occur in the tool stage. However, the signal generator and processor can be located in a surgical instrument, and results can be displayed via a graphical user interface on a separate unit, thereby bypassing the surgical hub altogether.

As previously described, the use of one or more electrodes to generate enhanced insights (e.g., tissue locations, foreign body notifications, critical structure notifications, tissue characterizations, etc.) using a variety of methods, which shall include but shall not be limited to EIS. However, according to some non-limiting aspects, similar devices, systems, and methods can be employed to expand those insights to include the identification of a particular contact and/or a particular timing of contact between the jaws of an end effector and a particular media positioned within those jaws. In other words, certain insights can be used to identify a particular contact of interest between the jaws of an end effector and a media positioned within the jaws of the end effector, which can be used as a point of reference from which other measurements can be taken. For example, such aspects can include the detection of an initial contact with a tissue, which can be subsequently used as a timing mechanism to trigger other sensors that take tissue thickness and/or jaw displacement measurements, as will be disclosed in further detail herein.

Such applications of the aforementioned devices, systems, and methods can be particularly useful as sensing technologies are developed to measure tissue thickness and/or jaw displacement on surgical instruments. Although useful, these enhancements can make it difficult to discern exactly when the required measurements should be taken, as it can be difficult to visually identify when initial contact is made with a tissue sample. In other words, it can be difficult to determine when a sensor begins contacting the tissue while it is simultaneously sensing tissue thickness and/or end effector displacement. These problems can be addressed using the aforementioned devices, systems, and methods in accordance with the following non-limiting aspects of the present disclosure.

Referring now to FIG. 44, a logic flow diagram of a method 4400 of identifying a particular contact between the jaws of an end effector and a media positioned within the jaws of the end effector is depicted in accordance with at least one non-limiting aspect of the present disclosure. Generally, the method 4400 of FIG. 44 utilizes the aforementioned sensing techniques (e.g., electrical impedance sensing techniques, etc.) to enable a sensor—such as a tissue-thickness detecting sensor—to be used as a timing mechanism by which the surgical instrument, or a system communicably coupled to the surgical instrument, knows when to begin taking measurements. Previously, the aforementioned sensing techniques were discussed in reference to detecting a particular media's location within the jaws of an end effector. However, according to the non-limiting aspect of FIG. 44, similar techniques are employed to establish a particular time of contact, such as the identification of when an initial tissue contact is made. Accordingly, the method 4400 of FIG. 44 can enable baseline measurements to be taken immediately when tissue contact is initiated, such that changes in one or more sensed parameters can be tracked over time from the initial point of contact.

For example, according to the non-limiting aspect of FIG. 44, the method 4400 can be specifically employed to perform RF impedance-based sensing to identify an initial point of tissue contact. The identified point of tissue contact can be used as a point of reference for the purposes of timing when other measurements should be taken. According to the non-limiting aspect, the method 4400 can include detecting 4402 a particular contact between the jaws of an end effector and a media positioned within the jaws of the end effector based on the aforementioned sensing techniques. For example, according to the non-limiting aspect of FIG. 44, an initial tissue contact can be detected 4402 via the aforementioned RF impedance sensing techniques. It shall be appreciated that the detection 4402 step of the method 4400 of FIG. 44 can be performed via any of the aforementioned methods, including those discussed in reference to FIGS. 6 and 13-15.

According to the non-limiting aspect of FIG. 44, the method 4400 can further include initiating 4404 a sensing-based characterization process based on the detection 4402 of the particular contact between the jaws of an end effector and a media positioned within the jaws of the end effector. For example, according to the non-limiting aspect of FIG. 44, a tissue-thickness sensing method can be initiated 4404 based on the detected 4402 initial contact between the jaws of the end effector and the tissue. Of course, any number of sensors can be configured to characterize any number of media positioned within the jaws of the end effector in any way and thus, according to other non-limiting aspects, the initiated 4404 characterization can include any other sensing functions of any other sensors.

In further reference to FIG. 44, the method 4400 can further include determining 4406 a tissue characteristic based on sensing method. For example, according to the non-limiting aspect of FIG. 44, the method 4400 can further include determining 4406 a tissue thickness based on thickness sensing method. If the characteristic cannot be determined, the method 4400 can further include continually taking 4408 measurements and comparing the results to an initial baseline. However, if the characteristic can be determined, the method 4400 can further include outputting 4410 the determined characteristic. For example, according to some non-limiting aspects, the determined characteristic can be output to a communicably coupled computing device, such as a surgical hub connected to the surgical instrument. However, according to other non-limiting aspects, the determined characteristic can be output to an on-board display of the surgical instrument, a cloud-computing device, and/or a mobile computing device of the technician, amongst other communicably coupled computing devices.

Likewise, information gained from the aforementioned sensing techniques performed by a first surgical instrument can be alternately applied to a second surgical instrument, illustrating the possibilities of a connected operating room environment. In other words, the present disclosure contemplates non-limiting aspects wherein information from previous firings of different devices could then be used to inform the firing of a second device, regardless of whether the second device is configured to perform the aforementioned sensing techniques. Whereas a fully "smart instrument ecosystem" may require sensors and communication modules installed within each instrument, such systems could result in inefficiencies and might drive costs beyond a point of acceptability where multiple surgical instruments are used in single procedure. Accordingly, it would be extremely beneficial if the aforementioned sensing techniques could be performed by a first surgical instrument and alternately applied to a second surgical instrument.

For example, information gained from the sensing capabilities of a first surgical instrument can be leveraged to inform the firing of one or more separate surgical instruments used during a procedure. This can be accomplished via algorithmic control of the firing sequence of a second device and/or the display of information to the surgeon. As such, the aforementioned sensing techniques can enable an operating clinician to benefit from their use of an entire range of surgical instrument, so long as at least one instrument is configured to generate insights, as previously disclosed. When combined with knowledge of the steps in a surgical procedure, on-screen prompts via a display system, including a heads-up display, could enable the sensed parameters from the first device (e.g., a smart instrument) to inform on-screen recommendations based on the anticipated next step and additional surgical instruments to be used in the procedure, regardless of whether or not those additional instruments are "smart."

Referring now to FIG. 45, a logic flow diagram of a method 4500 of utilized the sensing techniques disclosed herein to inform an operation performed by a second surgical instrument is depicted in accordance with at least one non-limiting aspect of the present disclosure. According to the non-limiting aspect of FIG. 45, the method 4500 can include sensing 4502, via a first surgical instrument, a tissue parameter via the aforementioned sensing techniques. For example, it shall be appreciated that the sensing 4502 step of the method 4500 of FIG. 45 can be performed via any of the aforementioned methods, including those discussed in reference to FIGS. 6 and 13-15. The method 4500 can further include communicating 4504 the sensed parameter to a computing device, such as a central hub, communicably coupled to the first surgical instrument.

Having communicated 4504 the sensed parameter, the method 4500 of FIG. 45 can further include determining 4506 if a second surgical instrument is required by the surgical procedure and whether or not the second surgical instrument is a "smart" instrument, meaning the second instrument is connected and able to receive inputs to inform its operation. Assuming the second surgical instrument is not a "smart" instrument, the method 4500 can further include anticipating 4510 a use of the second instrument based on procedure steps and informing 4512 an operation of the second instrument based on the parameter sensed by the first surgical instrument, and terminating 4518 the process. In other words, the hub itself can provide useful information for the operation of the second surgical instrument that are derived from the parameter sensed by the first surgical instrument via a display, such as a heads-up display, for example. Even though the insights generated by the first surgical instrument cannot be directly implemented via the second surgical instrument, they can be presented to the operating clinician to inform the operation.

However, assuming it is determined that the second surgical instrument is a "smart" instrument, the method 4500 of FIG. 45 can include transmitting 4514 the parameter sensed by the first instrument to the second instrument and performing 4516 the aforementioned sensing techniques via the second instrument. The parameter sensed by the first instrument can be used to supplement or otherwise autonomously influence 4516 operation of the second surgical instrument. For example, the transmission 4514 can include some or all of the insights generated by the first surgical instrument and can inform firing, sensing, or other device functions performed by the second surgical instrument. In other words, because the second surgical instrument is connected, the second surgical instrument can autonomously influence its own operation based on algorithmic inputs provided by the first surgical instrument, without intervention from the operating clinician. Once complete, the method 4500 can include terminating 4518 the process. In other words, the method 4500 of FIG. 45 can be especially valuable if the sensed parameters from the first instrument can be used as inputs to algorithms used for sensing on the second instrument, because the method 4500 can enable the second instrument to have relevant data that it may not have been able to otherwise collect. In other words, only the first surgical instrument need to be configured to sense and generate insights, as previously described, but other devices—including both connected and disconnected device, alike—can benefit from those insights. Thus, a "smart instrument ecosystem" can be both effectively and efficiently achieved via the devices, systems, and methods disclosed herein.

Referring now to FIG. 46, a logic flow diagram of a specific procedure 4600 implementing the method 4500 of FIG. 45 is depicted in accordance with at least one non-limiting aspect of the present disclosure. According to the non-limiting aspect of FIG. 4600, the procedure 4600 can include a colectomy, wherein the first surgical instrument includes an endocutter, for example, and the second surgical instrument includes a circular stapler, for example. Of course, FIG. 46 is merely illustrative of the method 4500 of FIG. 45 and, according to other non-limiting aspects, the procedure can include any number of surgical operations performed by any number of surgical instruments.

Nonetheless, the procedure 4600 of FIG. 46 can include sensing 4602 a tissue thickness and disease state via the aforementioned sensing techniques performed by the endocutter. For example, the sensing 4602 step can be performed via any of the aforementioned methods, including those discussed in reference to FIGS. 6 and 13-15. The procedure can further include communicating 4604 the sensed tissue thickness and disease state to a communicably coupled computing device, such as a central hub. Having communicated 4604 the sensed parameter, the procedure 4600 can further include determining 4606 that the circular stapler is required by the colectomy and whether or not the circular stapler is a "smart" instrument. Assuming the circular stapler is not a "smart" instrument, the procedure 4600 can further include anticipating 4610 a use of the circular stapler based on procedure 4600 steps and informing 4612 an operation of the circular stapler based on the parameter sensed by the first surgical instrument and terminating 4618 the process. Once again, informing 4612 the operation of the circular stapler can include displaying insights generated by the endocutter to the operating clinician to inform the operation.

However, assuming it is determined that the circular stapler is a "smart" instrument, the procedure 4600 of FIG. 46 can include transmitting 4614 the tissue thickness and disease state to the circular stapler for implementation, which can include slowing 4616 the rate of fire and/or limiting a force to fire based on the thickness and disease state. For example, the circular stapler can employ algorithmic intelligence to determine that less speed and/or force to fire may be necessary to cut the diseased tissue. In other words, because the circular stapler is connected, the circular stapler can influence its operation without intervention from the operating clinician. Once complete, the method 4500 can include terminating 4518 the process. In other words, the method 4500 of FIG. 45 can be especially valuable if the sensed parameters from the first instrument can be used as inputs to algorithms used for operating the second instrument, because the method 4500 can enable the second instrument to have relevant data that it may not have been otherwise able to collect.

In other words, in the non-limiting example wherein the procedure 4600 is a colectomy, an endocutter may be used to cut out a portion of the colon, and then a circular stapler could be used for end to end anastomosis. If the circular stapler is a "dumb" device, but the endocutter is a "smart" device, a communicably coupled computing device, such as a central surgical hub, could interpret the insights generated by the endocutter in conjunction with inferred surgical procedure steps to make recommendations for something such as a staple cartridge selection for the circular stapler. If the circular stapler is a "smart" device, it could utilize the insights generated by the endocutter as algorithmic inputs to autonomouslyu influence and/or improve operation of the circular stapler, as previously described.

While the foregoing methods, algorithms, instruments, and systems provided various examples of differentiating media grasped by a surgical end effector mainly based on impedance data, it is understood that the methods, algorithms, instruments, and systems of the present disclosure can be equally applied to other sensed parameters such as current, temperature, and pressure, for example. In at least one instance, for example, methods, algorithms, instruments, and systems can be utilized to differentiate tissue from a foreign object based on detected differences between tissue and a foreign object.

EXAMPLES

Examples of various aspects of end-effectors and surgical instruments of the present disclosure are provided below. An aspect of the end-effector or surgical instrument may include any one or more than one, and any combination of, the examples described below:

Example 1. A surgical instrument, including: an end effector including jaws configured to transition between an opened condition and a closed condition; a plurality of electrodes positioned within the jaws of the end effector, wherein each electrode of the plurality of electrodes is positioned along a longitudinal axis defined by the end effector; a control circuit and a memory configured to store an algorithm configured to cause the control circuit to: receive signals from the plurality of electrodes; determine an impedance signal based on the signals received from the plurality of electrodes; detect a media positioned between the jaws of the end effector based on the determined impedance signal; determine a position of the detected media along the longitudinal axis based on the signals received from the plurality of electrodes; and generate an alert associated with the detected media and the determined position.

Example 2. The surgical instrument of Example 1, wherein the alert includes a digital representation of the end effector, the detected media, and the determined position, and wherein the algorithm is further configured to cause the control circuit to initiate a transmission of the digital representation to a display for visual review by the operating clinician.

Example 3. The surgical instrument of any one of Examples 1-2, wherein the alert includes an audible alert, and wherein the algorithm is further configured to cause the control circuit to cause a speaker communicably coupled to the control circuit for audible transmission to the operating clinician.

Example 4. The surgical instrument of any one of Examples 1-3, wherein the algorithm is further configured to cause the control circuit to: determine a second impedance signal based on the signals received from the plurality of electrodes; detect a second media positioned between the jaws of the end effector based on the determined second impedance signal; determine a second position of the detected second media along the longitudinal axis based on the signals received from the plurality of electrodes; and wherein the alert is also associated with the detected second media and the determined second position.

Example 5. The surgical instrument of any one of Examples 1-4, wherein the algorithm includes a linear support vector machine configured to distinguish the media from the second media based on the determined impedance signal and the determined second impedance signal.

Example 6. The surgical instrument of any one of Examples 1-5, wherein the algorithm detected media includes a tissue sample, and wherein the detected second media includes a foreign object.

Example 7. The surgical instrument of any one of Examples 1-6, wherein the algorithm is further configured to cause the control circuit to characterize the detected media based on the determined impedance signal.

Example 8. The surgical instrument of any one of Examples 1-7, wherein the impedance signal comprises an impedance magnitude.

Example 9. The surgical instrument of any one of Examples 1-8, wherein the impedance signal comprises an phase.

Example 10. The surgical instrument of any one of Examples 1-9, wherein the algorithm is further configured to cause the control circuit to determine a change in the impedance signal across the time domain.

Example 11. The surgical instrument of any one of Examples 1-10, wherein the algorithm is further configured to cause the control circuit to determine a change in the impedance signal across the frequency domain.

Example 12. A surgical system, including a surgical instrument including an end effector including jaws configured to transition between an opened condition and a closed condition, and a plurality of electrodes positioned within the jaws of the end effector, wherein each electrode of the plurality of electrodes is positioned about a longitudinal axis defined by the end effector, and a computer system communicably coupled to the surgical instrument, wherein the computer system includes a control circuit and a memory configured to store an algorithm configured to cause the control circuit to receive signals from the plurality of electrodes, determine an impedance signal based on the signals received from the plurality of electrodes, detect a media positioned between the jaws of the end effector based on the determined impedance signal, determine a position of the detected media along the longitudinal axis based on the signals received from the plurality of electrodes, and generate an alert associated with the detected media and the determined position.

Example 13. The surgical system according to Example 12, wherein the algorithm is further configured to cause the control circuit to determine a second impedance signal based on the signals received from the plurality of electrodes, detect a second media positioned between the jaws of the end effector based on the determined second impedance signal, and determine a second position of the detected second media along the longitudinal axis based on the signals received from the plurality of electrodes, and wherein the alert is also associated with the detected second media and the determined second position.

Example 14. The surgical system according to Example 12 or 13, wherein the algorithm detected media includes a tissue sample, and wherein the detected second media includes a foreign object.

Example 15. The surgical system according to any of Examples 12-14, wherein the algorithm is further configured to cause the control circuit to characterize the detected media based on the determined impedance signal.

Example 16. A method of characterizing media positioned between jaws of an end effector of a surgical instrument, the method including receiving, via a control circuit of the surgical instrument, signals from a plurality of electrodes positioned within the jaws of the end effector, determining, via the control circuit, an impedance signal based on the signals received from the plurality of electrodes, detecting, via the control circuit, the media positioned between the jaws of the end effector based on the determined impedance signal, determining, via the control circuit, a position of the detected media along a longitudinal axis defined by the end effector based on the signals received from the plurality of electrodes, generating, via the control circuit, an alert associated with the detected media and the determined position, and characterizing, via the control circuit, the detected media based on the determined impedance signal.

Example 17. The method according to Example 16, further including determining, via the control circuit, a second impedance signal based on the signals received from the plurality of electrodes, detecting, via the control circuit, a second media positioned between the jaws of the end effector based on the determined second impedance signal, and determining, via the control circuit, a second position of the detected second media along the longitudinal axis based on the signals received from the plurality of electrodes, and wherein the alert is also associated with the detected second media and the determined second position.

Example 18. The method according to Example 16 or 17, further including distinguishing, via the control circuit, the media from the second media based on the determined impedance signal and the determined second impedance signal in accordance with a linear support vector machine.

Example 19. The method according to any of Examples 16-18, The method of claim 16, wherein generating the alert includes generating, via the control circuit, a digital representation of the end effector, the detected media, and the determined position, and initiating, via the control circuit, a transmission of the digital representation to a display for visual review by an operating clinician.

Example 20. The method according to any of Examples 16-19, The method of claim 16, wherein the alert includes an audible alert, and wherein the method further includes causing, via the control circuit, a speaker communicably coupled to the control circuit to play the audible alert.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical instrument, comprising:
   an end effector comprising jaws configured to transition between an opened condition and a closed condition;
   a plurality of electrodes positioned within the jaws of the end effector, wherein each electrode of the plurality of electrodes is positioned about a longitudinal axis defined by the end effector;
   a control circuit and a memory configured to store an algorithm configured to cause the control circuit to:
      receive signals from the plurality of electrodes;
      determine an impedance signal based on the signals received from the plurality of electrodes;
      detect a media positioned between the jaws of the end effector based on the determined impedance signal;
      determine a position of the detected media along the longitudinal axis based on the signals received from the plurality of electrodes; and
      generate an alert associated with the detected media and the determined position.

2. The surgical instrument of claim 1, wherein the alert comprises a digital representation of the end effector, the detected media, and the determined position, and wherein the algorithm is further configured to cause the control circuit to initiate a transmission of the digital representation to a display for visual review by the operating clinician.

3. The surgical instrument of claim 1, wherein the alert comprises an audible alert, and wherein the algorithm is further configured to cause the control circuit to cause a speaker communicably coupled to the control circuit for audible transmission to the operating clinician.

4. The surgical instrument of claim 1, wherein the algorithm is further configured to cause the control circuit to:
   determine a second impedance signal based on the signals received from the plurality of electrodes;
   detect a second media positioned between the jaws of the end effector based on the determined second impedance signal; and
   determine a second position of the detected second media along the longitudinal axis based on the signals received from the plurality of electrodes; and
   wherein the alert is also associated with the detected second media and the determined second position.

5. The surgical instrument of claim 4, wherein the algorithm comprises a linear support vector machine configured to distinguish the media from the second media based on the determined impedance signal and the determined second impedance signal.

6. The surgical instrument of claim 4, wherein the algorithm detected media comprises a tissue sample, and wherein the detected second media comprises a foreign object.

7. The surgical instrument of claim 1, wherein the algorithm is further configured to cause the control circuit to characterize the detected media based on the determined impedance signal.

8. The surgical instrument of claim 1, wherein the impedance signal comprises an impedance magnitude.

9. The surgical instrument of claim 1, wherein the impedance signal comprises an phase.

10. The surgical instrument of claim 1, wherein the algorithm is further configured to cause the control circuit to determine a change in the impedance signal across the time domain.

11. The surgical instrument of claim 1, wherein the algorithm is further configured to cause the control circuit to determine a change in the impedance signal across the frequency domain.

12. A surgical system, comprising:
- a surgical instrument comprising:
  - an end effector comprising jaws configured to transition between an opened condition and a closed condition; and
  - a plurality of electrodes positioned within the jaws of the end effector, wherein each electrode of the plurality of electrodes is positioned about a longitudinal axis defined by the end effector; and
- a computer system communicably coupled to the surgical instrument, wherein the computer system comprises a control circuit and a memory configured to store an algorithm configured to cause the control circuit to:
  - receive signals from the plurality of electrodes;
  - determine an impedance signal based on the signals received from the plurality of electrodes;
  - detect a media positioned between the jaws of the end effector based on the determined impedance signal;
  - determine a position of the detected media along the longitudinal axis based on the signals received from the plurality of electrodes; and
  - generate an alert associated with the detected media and the determined position.

13. The surgical system of claim 12, wherein the algorithm is further configured to cause the control circuit to:
- determine a second impedance signal based on the signals received from the plurality of electrodes;
- detect a second media positioned between the jaws of the end effector based on the determined second impedance signal; and
- determine a second position of the detected second media along the longitudinal axis based on the signals received from the plurality of electrodes; and
- wherein the alert is also associated with the detected second media and the determined second position.

14. The surgical system of claim 13, wherein the algorithm detected media comprises a tissue sample, and wherein the detected second media comprises a foreign object.

15. The surgical system of claim 12, wherein the algorithm is further configured to cause the control circuit to characterize the detected media based on the determined impedance signal.

16. A method of characterizing media positioned between jaws of an end effector of a surgical instrument, the method comprising:
- receiving, via a control circuit of the surgical instrument, signals from a plurality of electrodes positioned within the jaws of the end effector;
- determining, via the control circuit, an impedance signal based on the signals received from the plurality of electrodes;
- detecting, via the control circuit, the media positioned between the jaws of the end effector based on the determined impedance signal;
- determining, via the control circuit, a position of the detected media along a longitudinal axis defined by the end effector based on the signals received from the plurality of electrodes;
- generating, via the control circuit, an alert associated with the detected media and the determined position; and
- characterizing, via the control circuit, the detected media based on the determined impedance signal.

17. The method of claim 16, further comprising:
- determining, via the control circuit, a second impedance signal based on the signals received from the plurality of electrodes;
- detecting, via the control circuit, a second media positioned between the jaws of the end effector based on the determined second impedance signal; and
- determining, via the control circuit, a second position of the detected second media along the longitudinal axis based on the signals received from the plurality of electrodes; and
- wherein the alert is also associated with the detected second media and the determined second position.

18. The method of claim 17, further comprising distinguishing, via the control circuit, the media from the second media based on the determined impedance signal and the determined second impedance signal in accordance with a linear support vector machine.

19. The method of claim 16, wherein generating the alert comprises:
- generating, via the control circuit, a digital representation of the end effector, the detected media, and the determined position; and
- initiating, via the control circuit, a transmission of the digital representation to a display for visual review by an operating clinician.

20. The method of claim 16, wherein the alert comprises an audible alert, and wherein the method further comprises causing, via the control circuit, a speaker communicably coupled to the control circuit to play the audible alert.

* * * * *